(12) United States Patent
Bots et al.

(10) Patent No.: US 10,287,603 B2
(45) Date of Patent: May 14, 2019

(54) BRASSICA PLANTS COMPRISING MUTANT DA1 ALLELES

(71) Applicant: BAYER CROPSCIENCE NV, Diegem (BE)

(72) Inventors: Marc Bots, Ledeberg (BE); Benjamin Laga, Wingene (BE); Celine Mouchel, Gent (BE)

(73) Assignee: BAYER CROPSCIENCE NV, Diegem (BE)

( * ) Notice: Subject to any disclaimer, the term of this patent is extended or adjusted under 35 U.S.C. 154(b) by 361 days.

(21) Appl. No.: 14/782,271

(22) PCT Filed: Apr. 2, 2014

(86) PCT No.: PCT/EP2014/056628
§ 371 (c)(1),
(2) Date: Oct. 2, 2015

(87) PCT Pub. No.: WO2014/161908
PCT Pub. Date: Oct. 9, 2014

(65) Prior Publication Data
US 2016/0040180 A1 Feb. 11, 2016

(30) Foreign Application Priority Data
Apr. 5, 2013 (EP) ..................................... 13162447

(51) Int. Cl.
C12N 15/82 (2006.01)
C07K 14/415 (2006.01)
A01H 1/06 (2006.01)

(52) U.S. Cl.
CPC ........ *C12N 15/8261* (2013.01); *C07K 14/415* (2013.01); *A01H 1/06* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 5,985,557 A | 11/1999 | Prudent et al. | |
| 6,001,567 A | 12/1999 | Brow et al. | |
| 9,624,502 B2 * | 4/2017 | Bevan ................... | C07K 14/415 |
| 2005/0150012 A1 | 7/2005 | Schmulling et al. | |
| 2009/0007295 A1 | 1/2009 | Phillips et al. | |
| 2010/0281576 A1 | 11/2010 | Kim et al. | |
| 2011/0265225 A1 | 10/2011 | Yoshizumi et al. | |
| 2011/0271405 A1 | 11/2011 | Nguyen et al. | |

FOREIGN PATENT DOCUMENTS

| EP | 0242236 A1 | 10/1987 |
|---|---|---|
| EP | 0242246 A1 | 10/1987 |
| EP | 0507698 A1 | 10/1992 |
| EP | 0508909 A1 | 10/1992 |
| WO | WO 01/38551 A1 | 5/2001 |
| WO | WO 03/096797 A2 | 11/2003 |
| WO | WO 2005/085453 A2 | 9/2005 |
| WO | WO 2006/105946 A2 | 10/2006 |
| WO | WO 2007/079353 A2 | 7/2007 |
| WO | WO 2008/144653 A1 | 11/2008 |
| WO | WO 2009/002150 A1 | 12/2008 |
| WO | WO 2009/047525 A1 | 4/2009 |
| WO | WO 2010/039750 A2 | 4/2010 |
| WO | WO 2012/100682 A1 | 8/2012 |
| WO | WO 2012/119152 A1 | 9/2012 |

OTHER PUBLICATIONS

Li Yunhai et al. Control of final seed and organ size by the DA1 gene family in *Arabidopsis thaliana*. Genes and Development. May 1, 2008, vol. 22, No. 10, pp. 1331-1336.*
Hill M.A. et al Functional analysis of conserved histidines in ADP-glucose pyrophosphorylase from *Escherichia coli*. Biochem Biophys Res Commun. Mar. 17, 1998;244(2):573-7.*
Gottwald et al. Tilling in the two-rowed barley cultivar 'Barke' reveals preferred sites of functional diversity in the gene HvHox1. BMC Res. Notes. Dec. 17, 2009;2:258.*
Stephenson et al. A rich Tilling resource for studying gene function in Brassica rapa. BMC Plant Biol. Apr. 9, 2010;10:62.*
Harloff et al. A mutation screening platform for rapeseed (*Brassica napus* L.) and the detection of sinapine biosynthesis mutants. Theor. Appl. Genet. Mar. 2012;124(5):957-69. Epub Dec. 24, 2011.*
Altschul et al., "Basic Local Alignment Search Tool," Journal of Molecular Biology, 1990, vol. 2015, pp. 403-410.
Azpiroz-Leehan et al., "T-DNA insertion mutagenesis in *Arabidopsis*: going back and forth," Trends Genet, 1997, vol. 13, pp. 152-156.
Cai et al., "Identification of candidate genes of QTLs for seed weight in Brassica napus through comparative mapping among *Arabidopsis* and *Brassica* species," BMC Genetics, 2012, 13: 105, pp. 1-17.
Fan et al., "Mapping of quantitative trait loci and development of allele-specific markers for seed weight in *Brassica napus*," Theor. Appl. Genet., 2010, vol. 121, pp. 1289-1301.
Gonzalez et al., "David and Goliath: what can the tiny weed *Arabidopsis* teach us to improve biomass production in crops?" Current Opinion in Plant Biology, 2009, vol. 12, pp. 157-164.
Henikoff et al., "Tilling. Traditional Mutagenesis Meets Functional Genomics," Plant Physiology, 2004, vol. 135, pp. 630-636.
International Search Report issued in International Application No. PCT/EP2014/056628 dated Jun. 27, 2014.
Krizek, "Making bigger plants: key regulators of final organ size," Current Opinion in Plant Biology, 2009, vol. 12, pp. 17-22.

(Continued)

*Primary Examiner* — Cynthia E Collins
(74) *Attorney, Agent, or Firm* — Arent Fox LLP

(57) ABSTRACT

The present invention relates to methods and means to increase seed weight in *Brassica*. More specifically, the invention relates to mutant DA1 genes in *Brassica* plants and the use thereof to seed weight.

15 Claims, 9 Drawing Sheets

Specification includes a Sequence Listing.

(56) References Cited

OTHER PUBLICATIONS

Li et al., "A fast neutron deletion mutagenesis-based reverse genetics system for plants," The Plant Journal, 2001, vol. 27, pp. 235-242.
Li et al., "Control of final seed and organ size by the DA1 gene family in *Arabidopsis thaliana*," Genes Dev, 2008, pp. 1331-1336.
Li et al., "Reverse genetics by fast neutron mutagenesis in higher plants," Funct Integr. Genomics, 2002, vol. 2, pp. 254-258.
Liu et al., "Increasing seed mass and oil content in transgenic *Arabidopsis* by the overexpression of wri 1-like gene from *Brassica napus*," Pant Physiology and Biochemistry, 2010, vol. 48, pp. 9-15.
McCallum et al., "Targeted Screening for induced mutations," Nat. Biotechnol, 2000, vol. 18, pp. 455-457.
McCallum et al., "Targeting Induced Local Lesions In Genomes (Tilling) for Plant Functional Genomics," Plant Physiol., 2000, vol. 123, pp. 439-442.
McKenzie et al., "Tissue-culture enhanced transposition of the maize transposable element Dissociation in *Brassica oleracea* var. *italica*," Theor Appl Genet, 2002, vol. 105, pp. 23-33.
Needleman et al., "A General Method Applicable to the Search for Similarities in the Amino Acid Sequence of Two Proteins," J. Mol. Biol., 1970, vol. 48, pp. 443-453.
Rice et al., "EMBOSS: The European Molecular Biology Open Software Suite," Trends in Genetics, 2000, vol. 16, pp. 276-277.
Thompson et al., "CLUSTAL W: improving the sensitivity of progressive multiple sequence alignment through sequence weighting, position-specific gap penalties and weight matrix choice," Nucleic Acid Research, 1994, vol. 22, pp. 4673-4680.
Zhang et al., "Genetic and correlation analysis of silique-traits in *Brassica napus* L. by quantitative trait locus mapping," Theor Appl. Genet, 2011, vol. 122, pp. 21-31.

* cited by examiner

```
SEQ
ID NO
2     1  MGWFNKIFKGS-NQRLRVGNNKHNHNV-YYDNYPTASHD-DEPSAADTDA
5     1  MGWLNKIFKGS-NQRHPMGNEHYHHNGGYYENYP---HEHSEP----TDA
8     1  MGWFNKIFKGS-TQRFRLGND-HDHNG-YYQSYP----H-DEPS-ADTDP
11    1  MGWLNKIFKGS-NQRPPVGNEYYHHNGGYYENYP---HE-HSEPSAETDA
14    1  MGWFNKIFKGS-TQRFRLGND-HDHNG-YYQSYP----H-DEPS-ADTDP
56    1  MGWLNKIFKGS-NQRHPMGNEHYHHNGGYYDNYP---HEHSEP----TDA
59    1  MGWFNKIFKGS-TQRFRLGND-HDHNG-YYQSYP----H-DEPS-ADTDP
62    1  MGWLNKIFKGS-NQRPPVGNEHYHHNGGYYENYP---HE-HSEPSAETDA
65    1  MGWFNKIFKGS-TQRFRLGND-HDHNG-YYQSYP----H-DEPS-ADTDP
69    1  MGWFNKIFKGS-TQRFRLGND-HDHNG-YYQSYP----H-DEPS-ADTDP
72    1  MGWFNKIFKGSSNQRFPVGN-EHYHNYGYYD--PNA--H-SEPS-ADTDA
75    1  MGWFNKIFKGS-TQRFRLGND-HGHSG-YYQSYPHSSH--DEPSA-DTDP

UIM1
2    48  DND-EPHHTQEPSTSEDNTSND**QENEDIDRAIALSLLEE-NQE**QTS--I-
5    43  D------HTQEPSTSEEETWNGKENEEVDRALALSILEEENQGPET--N-
8    42  DPDPDETHTQEPSTSEEDTSG-QENEDIDRAIALSLIEN-SQGQTNNTC-
11   46  D------HTQEPSTSEEETWNGQENEEVDRAIALSILEEENQGPET--N-
14   42  DPDPDETHTQEPSTSEEDTSG-QENDDIDRAIALSLIEN-SQGHTN--TG
56   43  D------HTQEPSTSEEETWNGKENEEVDRVIALSILEEENQRPET--N-
59   42  DPDPDETHTQEPSTSEEDTSG-QENEDIDRAIALSLIEN-SQGQTNNTC-
62   46  D------HTQEPSTSEEETWNGKENEEVDRAIALSILEEENQGPET--N-
65   42  DPDPDETHTQEPSTSEEDTSG-QENEDIDRAIALSLIEN-SQGHTN--TG
69   42  DPDPDETHTQEPSTSEEDTSG-QENEDIDRAIALSLIEN-SQGHTN--TG
72   44  D------HTQEPSTSED-TWNGQENEEVDRAIAMSLLEE-NQGQTN----
75   45  DPDPDETHTQEPSTSEEDTSNDQENEEIDRAIALSLLEE-SQGQTN--TG

UIM2
2    93  ---SG--KYSMPVDEDEQLARALQESMVVGNSPRHKSGSTYDNGNAYGAG
5    84  ---TGAWKHAM-MDDDEQLARAIQESMIARN------GTTYDFGNA----
8    89  ---AG--KYAM-VDEDEQLARAIQESMVVGNTPRQKHGSSYDIGNAYGAG
11   87  ---TGAWKHAM-MDDDEQLARAIQESMIVRN------GTTYDFGNA----
14   88  ---AG--KYAM-VDEDEQLARAIQESMVVGNTPRQKHGSSYDIGNAYGAG
56   84  ---TGAWKHAM-MDDDEQLARAIQESMIARN------GTTYDFGNA----
59   89  ---AG--KYAM-VDEDEQLARAIQESMVVGNTPRQKHGSSYDIGNAYGAG
62   87  ---TGAWKHAM-MDDDEQLARAIQESMIVRN------GTTYDFGNA----
65   88  AVNAG--KYAM-VDEDEQLARAIQESMVVGNTPRQKHGSSYDIGNAYGSG
69   88  AVNAG--KYAM-VDEDEQLARAIQESMVVGNTPRQKHGSSYDIGNAYGSG
72   82  ---KG--KYAM-VDDDEQLARAIQESMIARN------GATYDN---IGAG
75   92  ---AG--KYAM-VDDDEQLARAIQESMVVGNTPRQKHGSSYDIGNAYGAG
```

Figure 1

```
SEQ
ID NO                                                         LIM
  2   138  DLYGNGHMYGGG---NVYANGDIYYPRPITFQMDFRICAGCNMEIGHGRF
  5   120  --YGNGHMHGGG---NVYANGDIYYPRPIAFSMDFRICAGCNMEIGQGRY
  8   133  DVYGNGHMHGGG---NVYANGDIYYPRPTAFPMDFRICAGCNMEIGHGRY
 11   123  --YGNGHMHGGG---NVYDSGDIYYPRPIAFSMDFRICAGCNMEIGHGRY
 14   132  DVYGNGHMHGGG---NVYANGDIYYPRPTAFPMDFRICAGCNMEIGHGRY
 56   120  --YGNGHMHGGG---NVYDNGDIYYPRPIAFSMDFRICAGCNMEIGHGRY
 59   133  DVYGNGHMHGGG---NVYANGDIYYPRPTAFPMDFRICAGCNMEIGHGRY
 62   123  --YGNGHMHGGG---NVYDSGDIYYPRPIAFSMDFRICAGCNMEIGHGRY
 65   135  DVYGNGHMHGGG---NVYANGDIYYPRPTAFPMDFRICAGCNMEIGHGRY
 69   135  DVYGNGHMHGGG---NVYANGDIYYPRPTAFPMDFRICAGCNMEIGHGRY
 72   117  DFYGNGPMHGGGGGGNVYANGDIYYPKPIAFSMDFRICAGCNMEIGHGRY
 75   136  DVYGNGHMHGGGG--NVYANGDIYYPRPTAFPMDFRICAGCNMEIGHGRY
                                     LIM
  2   185  LNCLNSLWHPECFRCYGCSQPISEYEFSTSGNYPFHKACYRERYHPKCDV
  5   165  LNCLNALWHPQCFRCYGCSHPISEYEFSTSGNYPFHKACYRERFHPKCDV
  8   180  LNCLNALWHPECFRCYGCRHPISEYEFSTSGNYPFHKACYRERYHPKCDV
 11   168  LNCINALWHPQCFRCHGCSHPISEYEFSTSGNYPFHKACYRERFHPKCDV
 14   179  LNCLNALWHPECFRCYGCRHPISEYEFSTSGNYPFHKACYRERYHPKCDV
 56   165  LNCLNALWHPQCFRCYGCSHPISEYEFSTSGNYPFHKACYRERFHPKCDV
 59   180  LNCLNALWHPECFRCYGCRHPISEYEFSTSGNYPFHKACYRERYHPKCDV
 62   168  LNCLNALWHPQCFRCYGCSHPISEYEFSTSGNYPFHKACYRERFHPKCDV
 65   182  LNCLNALWHPECFRCYGCRHPISEYEFSTSGNYPFHKACYRERYHPKCDV
 69   182  LNCLNALWHPECFRCYGCRHPISEYEFSTSGNYPFHKACYRERYHPKCDV
 72   167  LNCLNALWHPECFRCYGCSHPISEYEFSTSGNYPFHKACYRERFHPKCDV
 75   184  LNCLNALWHPECFRCYGCRHPISEYEFSTSGNYPFHKACYRERYHPKCDV 2   235  CSHFIPTNHAGLIEYRAHPFWVQKYCPSHEHDATPRCCSCERMEPRNTRY
  5   215  CSLFISTNHAGLIEYRAHPFWVQKYCPSHEHDATPRCCSCERMEPRNTGY
  8   230  CSLFIPTNHAGLIEYRAHPFWVQKYCPSHEHDATPRCCSCERMEPRNTGY
 11   218  CSLFIPTNHAGLIEYRAHPFWVQKYCPSHEHDATPRCCSCERMESRNTGY
 14   229  CSLFIPTNHAGLIEYRAHPFWVQKYCPSHEHDATPRCCSCERMEPRNTGY
 56   215  CSLFISTNHAGLIEYRAHPFWVQKYCPSHEHDATPRCCSCERMEPRNTGY
 59   230  CSLFIPTNHAGLIEYRAHPFWVQKYCPSHEHDATPRCCSCERMEPRNTGY
 62   218  CSLFIPTNRAGLIEYRAHPFWVQKYCPSHEHDATPRCCSCERMESRNTGY
 65   232  CSLFIPTNHAGLIEYRAHPFWVQKYCPSHEHDATPRCCSCERMEPRNTGY
 69   232  CSLFIPTNHAGLIEYRAHPFWVQKYCPSHEHDATPRCCSCERMEPRNTGY
 72   217  CSHFIPTNLAGLIEYRAHPFWVQKYCPSHEHDATPRCCSCERMEPRNTGY
 75   234  CSHFIPTNHAGLIEYRAHPFWVQKYCPSHEHDATPRCCSCERMEPRNTGY
```

Figure 1, continued

SEQ
ID NO
| | | |
|---|---|---|
| 2 | 285 | VELNDGRKLCLECLDSAVMDTMQCQPLYLQIQNFYEGLNMKVEQEVPLLL |
| 5 | 265 | FELNDGRKLCLECLDSSVMDTFQCQPLYLQIQEFYEGLNMTVEQEVPLLL |
| 8 | 280 | VELNDGRKLCLECLDSAVMDTFQCQPLYLQIQEFYEGLFMKVEQDVPLLL |
| 11 | 268 | FELNDGRKLCLECLDSSVMDTFQCQPLYLQIQEFYEGLNMTVEQEVPLLL |
| 14 | 279 | VELNDGRKLCLECLDSAVMDTFQCQPLYLQIQEFYEGLFMKVEQDVPLLL |
| 56 | 265 | FELNDGRKLCLECLDSSVMDTFQCQPLYLQIQEFYEGLNMTVEQEVPLLL |
| 59 | 280 | VELNDGRKLCLECLDSAVMDTFQCQPLYLQIQEFYEGLFMKVEQDVPLLL |
| 62 | 268 | FELNDGRKLCLECLDSSVMDTFQCQPLYLQIQEFYEGLNMTVEQEVPLLL |
| 65 | 282 | VELNDGRKLCLECLDSAVMDTFQCQPLYLQIQEFYEGLFMKVEQDVPLLL |
| 69 | 282 | VELNDGRKLCLECLDSAVMDTFQCQPLYLQIQEFYEGLFMKVEQDVPLLL |
| 72 | 267 | VELNDGRKLCLECLDSAVMDTFQCQPLYLQIQEFYEGLNMKVEQEVPLLL |
| 75 | 284 | VELNDGRKLCLECLDSAVMDTFQCQPLYLQIQAFYEGLFMKVEQDVPLLL |

| | | |
|---|---|---|
| 2 | 335 | VERQALNEAREGEKNGHYHMPETRGLCLSEEQTVSTVRKRSKHGTGKWAG |
| 5 | 315 | VERQALNEAREGERNGHYHMPETRGLCLSEEQTVRTVRKRSK---GNWSG |
| 8 | 330 | VERQALNEAREGEKNGHYHMPETRGLCLSEEQTVSTVRKRSKHGTGNWAG |
| 11 | 318 | VERQALNEAREGERNGHYHMPETRGLCLSEEQTVRTVRKRSK---GNWSG |
| 14 | 329 | VERQALNEAREGEKNGHYHMPETRGLCLSEEQTVSTVRKRSKHGTGNWAG |
| 56 | 315 | VERQALNEAREGERNGHYHMPETRGLCLSEEQTVRTVRKRSK---GNWSG |
| 59 | 330 | VERQALNEAREGEKNGHYHMPETRGLCLSEEQTVSTVRKRSKHGTGNWAG |
| 62 | 318 | VERQALNEAREGERNGHYHMPETRGLCLSEEQTVRTVRKRSK---GNWSG |
| 65 | 332 | VERQALNEAREGEKNGHYHMPETRGLCLSEEQTVSTVRKRSKHGTGNWAG |
| 69 | 332 | VERQALNEAREGEKNGHYHMPETRGLCLSEEQTVSTVRKRSKHGTGNWAG |
| 72 | 317 | VERQALNEAREGEKNGHYHMPETRGLCLSEEQTVRTVRKRSKHSTGNWAG |
| 75 | 334 | VERQALNEAREGEKNGHYHMPETRGLCLSEEQTVSTVRKRSKHGTGNWGG |

| | | |
|---|---|---|
| 2 | 385 | N-ITEPYKLTRQCEVTAILILFGLPRLLTGSILAHEMMHAWMRLKGFRTL |
| 5 | 362 | NMITEQFKLTRRCEVTAILILFGLPRLLTGSILAHEMMHAWMRLKGFRPL |
| 8 | 380 | NMITEPYKLTRQCEVTAILILFGLPRLLTGSILAHEMMHAWMRLKGFRTL |
| 11 | 365 | NMITEQFKLTRRCEVTAILILFGLPRLLTGSILAHEMMHAWMRLKGFRTL |
| 14 | 379 | NMITEPYKLTRQCEVTAILILFGLPRLLTGSILAHEMMHAWMRLKGFRTL |
| 56 | 362 | NMITEQFKLTRRCEVTAILILFGLPRLLTGSILAHEMMHAWMRLKGFRPL |
| 59 | 380 | NMITEPYKLTRQCEVTAILILFGLPRLLTGSILAHEMMHAWMRLKGFRTL |
| 62 | 365 | NMITEQFKLTRRCEVTAILILFGLPRLLTGSILAHEMMHAWMRLKGFRTL |
| 65 | 382 | NMITEPYKLTRQCEVTAILILFGLPRLLTGSILAHEMMHAWMRLKGFRTL |
| 69 | 382 | NMITEPYKLTRQCEVTAILILFGLPRLLTGSILAHEMMHAWMRLKGFRTL |
| 72 | 367 | NMITEPFKLTRRCEVTAILILFGLPRLLTGSILAHEMMHAWMRLNGFRTL |
| 75 | 384 | NMITEPYKLTRQCEVTAILILFGLPRLLTGSILAHEMMHAWMRLKGFRTL |

Figure 1, continued

```
SEQ
ID NO
 2    434  SQDVEEGICQVMAHKWLDAELAAGSTNSNAASSSSSSQG-LKKGPRSQYE
 5    412  SQDVEEGICQVMAHKWLEAELAAGSRNSNAASSSSSSYGGVKKGPRSQYE
 8    430  SQDVEEGICQVMAHKWLEAELAAGSRNSNVA-SSSSSRG-VKKGPRSQYE
11    415  SQDVEEGICQVMAHKWLEVELAAGSRNSNAASSSYG--G-VKKGPKSQYE
14    429  SQDVEEGICQVMAHKWLEAELAAGSRNSNVASSSSSSGGLKKGPRSQYE
56    412  SQDVEEGICQVMAHKWLEAELAAGSRNSNAASSSSSSYGGVKKGPRSQYE
59    430  SQDVEEGICQVMAHKWLEAELAAGSRNSNVA-SSSSSRG-VKKGPRSQYE
62    415  SQDVEEGICQVMAHKWLEVELAAGSRNSNAASSSYG--G-VKKGPKSQYE
65    432  SQDVEEGICQVMAHKWLEAELAAGSRNSNVASSSSSSSGGLKKGPRSQYE
69    432  SQDVEEGICQVMAHKWLEAELAAGSRNSNVASSSSSSSGGLKKGPRSQYE
72    417  SQDVEEGICQVMAHKWLEAELDAGSGNSNAASSSSSSRG-VKKGPRSQYE
75    434  SQDVEEGICQVMAHKWLEAELAAGSRNSNVASSSSSSGGGLKKGPRSQYE 2    483  RKLGEFFKHQIESDASPVYGDGFRAGRLAVHKYGLRKTLEHIQMTGRFPV
 5    462  RKLGEFFKHQIEADASPVYGDGFRAGRLAVNKYGLRRTLEHIQMTGRFPV
 8    478  RKLGEFFKHQIESDASPVYGDGFRAGRLAVNKYGLPKTLEHIQMTGRFPV
11    462  RKLGEFFKHQIESDASPVYGDGFRAGRLAVSKYGLRRTLEHIQMTGRFPV
14    479  RKLGEFFKHQIESDASPVYGDGFRAGRLAVNKYGLPKTLEHIHMTGRFPV
56    462  RKLGEFFKHQIEADASPVYGDGFRAGRLAVNKYGLRRTLEHIQMTGRFPV
59    478  RKLGEFFKHQIESDASPVYGDGFRAGRLAVNKYGLPKTLEHIQMTGRFPV
62    462  RKLGEFFKHQIESDASPVYGDGFRAGRLAVSKYGLRRTLEHIQMTGRFPV
65    482  RKLGEFFKHQIESDASPVYGDGFRAGRLAVNKFRDGPT-----------
69    482  RKLGEFFKHQIESDASPVYGDGFRAGRLAVNKYGLPKTLEHIHMTGRFPV
72    466  RKLGEFFKHQIESDASPVYGDGFRAGKLAVNKYGLRRTLEHIQMTGRFPV
75    484  RKLGEFFKHQIESDASPVYGDGFRAGRLAVNKYGLGKTLEHIQMTGRFPV
```

Figure 1, continued

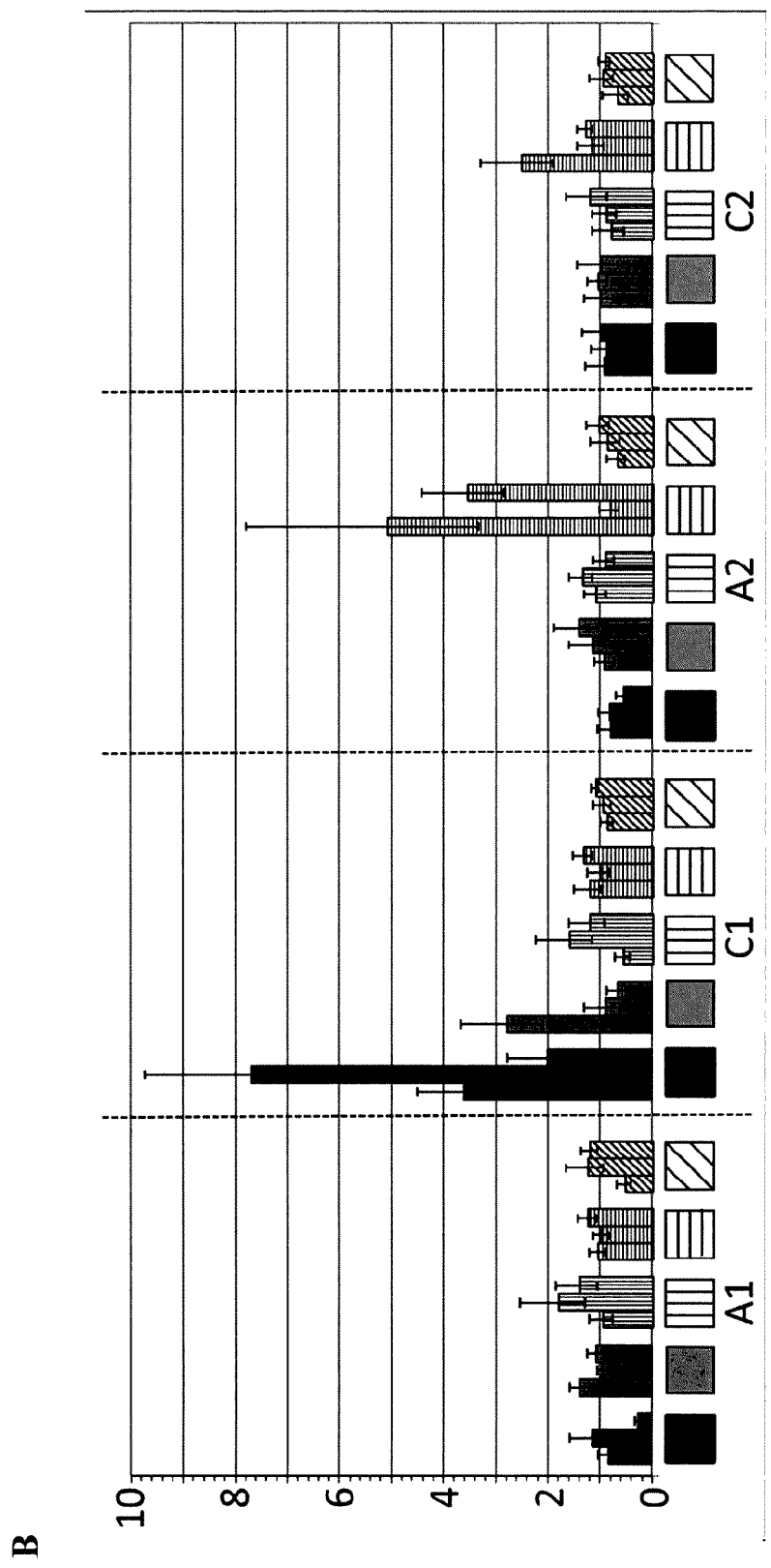
Figure 3, continued

SEQUENCE LISTING

<160> NUMBER OF SEQ ID NOS: 75

<210> SEQ ID NO 1
<211> LENGTH: 1599
<212> TYPE: DNA
<213> ORGANISM: Arabidopsis thaliana
<220> FEATURE:
<221> NAME/KEY: CDS
<222> LOCATION: (1)..(1599)

<400> SEQUENCE: 1

```
atg ggt tgg ttt aac aag atc ttt aaa ggc tct aac caa agg ctc cgg      48
Met Gly Trp Phe Asn Lys Ile Phe Lys Gly Ser Asn Gln Arg Leu Arg
1               5                   10                  15 gtt ggg aat aat aag cac aat cac aat gtt tat tac gat aat tat ccg      96
Val Gly Asn Asn Lys His Asn His Asn Val Tyr Tyr Asp Asn Tyr Pro
            20                  25                  30
```

```
act gct tca cat gat gat gag cct agt gcg gcg gat aca gat gct gat      144
Thr Ala Ser His Asp Asp Glu Pro Ser Ala Ala Asp Thr Asp Ala Asp
        35                  40                  45 aat gat gaa cct cat cat act cag gaa cca tct aca tct gag gat aat      192
Asn Asp Glu Pro His His Thr Gln Glu Pro Ser Thr Ser Glu Asp Asn
 50                  55                  60 aca tcg aat gac cag gaa aat gaa gac ata gac cgt gca att gca ttg      240
Thr Ser Asn Asp Gln Glu Asn Glu Asp Ile Asp Arg Ala Ile Ala Leu
 65                  70                  75                  80 tcg ctt tta gaa gag aat caa gaa cag aca agt ata agc ggg aaa tac      288
Ser Leu Leu Glu Glu Asn Gln Glu Gln Thr Ser Ile Ser Gly Lys Tyr
                 85                  90                  95 tcg atg ccg gtg gat gaa gat gag caa ctt gct aga gcc cta caa gaa      336
Ser Met Pro Val Asp Glu Asp Glu Gln Leu Ala Arg Ala Leu Gln Glu
            100                 105                 110 agt atg gta gtt ggg aat tca ccc cgt cac aaa agt gga agt aca tat      384
Ser Met Val Val Gly Asn Ser Pro Arg His Lys Ser Gly Ser Thr Tyr
            115                 120                 125 gat aat ggg aat gca tat gga gct gga gat tta tat ggg aat gga cat      432
Asp Asn Gly Asn Ala Tyr Gly Ala Gly Asp Leu Tyr Gly Asn Gly His
        130                 135                 140 atg tat gga gga gga aat gta tat gca aat gga gat att tat tat cca      480
Met Tyr Gly Gly Gly Asn Val Tyr Ala Asn Gly Asp Ile Tyr Tyr Pro
145                 150                 155                 160 aga cct att act ttt caa atg gat ttc agg att tgt gct ggc tgt aat      528
Arg Pro Ile Thr Phe Gln Met Asp Phe Arg Ile Cys Ala Gly Cys Asn
                165                 170                 175 atg gag att ggc cat gga aga ttt ctg aat tgc ctt aat tca cta tgg      576
Met Glu Ile Gly His Gly Arg Phe Leu Asn Cys Leu Asn Ser Leu Trp
            180                 185                 190 cat cca gaa tgt ttt cga tgt tat ggc tgc agt cag ccg att tct gag      624
His Pro Glu Cys Phe Arg Cys Tyr Gly Cys Ser Gln Pro Ile Ser Glu
            195                 200                 205 tac gag ttt tca aca tca ggg aac tac cct ttt cac aag gct tgt tac      672
Tyr Glu Phe Ser Thr Ser Gly Asn Tyr Pro Phe His Lys Ala Cys Tyr
210                 215                 220 agg gag aga tat cat cct aaa tgt gat gtc tgc agc cac ttt ata cca      720
Arg Glu Arg Tyr His Pro Lys Cys Asp Val Cys Ser His Phe Ile Pro
225                 230                 235                 240 aca aat cat gct ggt ctt att gaa tat agg gca cat cct ttt tgg gtt      768
Thr Asn His Ala Gly Leu Ile Glu Tyr Arg Ala His Pro Phe Trp Val
                245                 250                 255 cag aag tat tgt cct tct cac gaa cac gat gct acc ccg aga tgt tgc      816
Gln Lys Tyr Cys Pro Ser His Glu His Asp Ala Thr Pro Arg Cys Cys
            260                 265                 270 agt tgt gaa aga atg gag cca cgg aat acg aga tat gtt gaa ctt aac      864
Ser Cys Glu Arg Met Glu Pro Arg Asn Thr Arg Tyr Val Glu Leu Asn
            275                 280                 285 gat gga cgg aaa ctt tgc ctt gag tgt ttg gac tcg gcg gtc atg gac      912
Asp Gly Arg Lys Leu Cys Leu Glu Cys Leu Asp Ser Ala Val Met Asp
        290                 295                 300 acc atg caa tgc caa cct ctg tac ttg caa ata caa aat ttc tat gaa      960
Thr Met Gln Cys Gln Pro Leu Tyr Leu Gln Ile Gln Asn Phe Tyr Glu
305                 310                 315                 320 gga ctc aac atg aag gta gag cag gaa gtt cca ctc ctc ttg gtt gag     1008
Gly Leu Asn Met Lys Val Glu Gln Glu Val Pro Leu Leu Leu Val Glu
                325                 330                 335 aga caa gca ctt aac gaa gcc aga gaa ggt gaa aag aat ggt cac tat     1056
Arg Gln Ala Leu Asn Glu Ala Arg Glu Gly Glu Lys Asn Gly His Tyr
```

```
                340             345             350
cac atg cca gaa aca aga gga ctc tgc ctt tca gaa gaa caa act gtt   1104
His Met Pro Glu Thr Arg Gly Leu Cys Leu Ser Glu Glu Gln Thr Val
    355             360             365 agt act gta aga aag cga tca aag cat ggc aca gga aaa tgg gcc ggg   1152
Ser Thr Val Arg Lys Arg Ser Lys His Gly Thr Gly Lys Trp Ala Gly
370             375             380 aat att aca gaa cct tac aag tta aca cgg caa tgt gaa gtt acc gcc   1200
Asn Ile Thr Glu Pro Tyr Lys Leu Thr Arg Gln Cys Glu Val Thr Ala
385             390             395             400 att ctc atc tta ttc ggg ctc cct agg tta ctt act ggt tcg att cta   1248
Ile Leu Ile Leu Phe Gly Leu Pro Arg Leu Leu Thr Gly Ser Ile Leu
            405             410             415 gct cat gag atg atg cat gcg tgg atg agg ctc aaa gga ttc cga aca   1296
Ala His Glu Met Met His Ala Trp Met Arg Leu Lys Gly Phe Arg Thr
        420             425             430 ctg agc caa gat gtt gaa gaa ggt ata tgt caa gtg atg gct cat aaa   1344
Leu Ser Gln Asp Val Glu Glu Gly Ile Cys Gln Val Met Ala His Lys
    435             440             445 tgg tta gat gct gag tta gct gct ggt tca aca aat agc aat gct gca   1392
Trp Leu Asp Ala Glu Leu Ala Ala Gly Ser Thr Asn Ser Asn Ala Ala
450             455             460 tca tca tcc tcc tct tct caa gga ctg aaa aag gga ccg aga tct cag   1440
Ser Ser Ser Ser Ser Ser Gln Gly Leu Lys Lys Gly Pro Arg Ser Gln
465             470             475             480 tac gag aga aag ctt ggt gag ttt ttc aag cac caa atc gag tct gat   1488
Tyr Glu Arg Lys Leu Gly Glu Phe Phe Lys His Gln Ile Glu Ser Asp
            485             490             495 gct tct ccg gtt tat gga gac ggg ttc aga gct ggg agg tta gct gtt   1536
Ala Ser Pro Val Tyr Gly Asp Gly Phe Arg Ala Gly Arg Leu Ala Val
        500             505             510 cac aag tac ggt ttg cga aaa aca ctt gag cat ata cag atg acc ggt   1584
His Lys Tyr Gly Leu Arg Lys Thr Leu Glu His Ile Gln Met Thr Gly
    515             520             525 aga ttc ccg gtt taa                                               1599
Arg Phe Pro Val
530

<210> SEQ ID NO 2
<211> LENGTH: 532
<212> TYPE: PRT
<213> ORGANISM: Arabidopsis thaliana

<400> SEQUENCE: 2

Met Gly Trp Phe Asn Lys Ile Phe Lys Gly Ser Asn Gln Arg Leu Arg
1               5                   10                  15

Val Gly Asn Asn Lys His Asn His Asn Val Tyr Tyr Asp Asn Tyr Pro
            20                  25                  30

Thr Ala Ser His Asp Asp Glu Pro Ser Ala Ala Asp Thr Asp Ala Asp
        35                  40                  45

Asn Asp Glu Pro His His Thr Gln Glu Pro Ser Thr Ser Glu Asp Asn
    50                  55                  60

Thr Ser Asn Asp Gln Glu Asn Glu Asp Ile Asp Arg Ala Ile Ala Leu
65                  70                  75                  80

Ser Leu Leu Glu Glu Asn Gln Glu Gln Thr Ser Ile Ser Gly Lys Tyr
                85                  90                  95

Ser Met Pro Val Asp Glu Asp Glu Gln Leu Ala Arg Ala Leu Gln Glu
            100                 105                 110
```

```
Ser Met Val Val Gly Asn Ser Pro Arg His Lys Ser Gly Ser Thr Tyr
            115                 120                 125
Asp Asn Gly Asn Ala Tyr Gly Ala Gly Asp Leu Tyr Gly Asn Gly His
        130                 135                 140
Met Tyr Gly Gly Gly Asn Val Tyr Ala Asn Gly Asp Ile Tyr Tyr Pro
145                 150                 155                 160
Arg Pro Ile Thr Phe Gln Met Asp Phe Arg Ile Cys Ala Gly Cys Asn
                165                 170                 175
Met Glu Ile Gly His Gly Arg Phe Leu Asn Cys Leu Asn Ser Leu Trp
            180                 185                 190
His Pro Glu Cys Phe Arg Cys Tyr Gly Cys Ser Gln Pro Ile Ser Glu
        195                 200                 205
Tyr Glu Phe Ser Thr Ser Gly Asn Tyr Pro Phe His Lys Ala Cys Tyr
    210                 215                 220
Arg Glu Arg Tyr His Pro Lys Cys Asp Val Cys Ser His Phe Ile Pro
225                 230                 235                 240
Thr Asn His Ala Gly Leu Ile Glu Tyr Arg Ala His Pro Phe Trp Val
                245                 250                 255
Gln Lys Tyr Cys Pro Ser His Glu His Asp Ala Thr Pro Arg Cys Cys
            260                 265                 270
Ser Cys Glu Arg Met Glu Pro Arg Asn Thr Arg Tyr Val Glu Leu Asn
        275                 280                 285
Asp Gly Arg Lys Leu Cys Leu Glu Cys Leu Asp Ser Ala Val Met Asp
    290                 295                 300
Thr Met Gln Cys Gln Pro Leu Tyr Leu Gln Ile Gln Asn Phe Tyr Glu
305                 310                 315                 320
Gly Leu Asn Met Lys Val Glu Gln Glu Val Pro Leu Leu Val Glu
                325                 330                 335
Arg Gln Ala Leu Asn Glu Ala Arg Glu Gly Glu Lys Asn Gly His Tyr
            340                 345                 350
His Met Pro Glu Thr Arg Gly Leu Cys Leu Ser Glu Glu Gln Thr Val
        355                 360                 365
Ser Thr Val Arg Lys Arg Ser Lys His Gly Thr Gly Lys Trp Ala Gly
    370                 375                 380
Asn Ile Thr Glu Pro Tyr Lys Leu Thr Arg Gln Cys Glu Val Thr Ala
385                 390                 395                 400
Ile Leu Ile Leu Phe Gly Leu Pro Arg Leu Leu Thr Gly Ser Ile Leu
                405                 410                 415
Ala His Glu Met Met His Ala Trp Met Arg Leu Lys Gly Phe Arg Thr
            420                 425                 430
Leu Ser Gln Asp Val Glu Glu Gly Ile Cys Gln Val Met Ala His Lys
        435                 440                 445
Trp Leu Asp Ala Glu Leu Ala Ala Gly Ser Thr Asn Ser Asn Ala Ala
    450                 455                 460
Ser Ser Ser Ser Ser Ser Gln Gly Leu Lys Lys Gly Pro Arg Ser Gln
465                 470                 475                 480
Tyr Glu Arg Lys Leu Gly Glu Phe Phe Lys His Gln Ile Glu Ser Asp
                485                 490                 495
Ala Ser Pro Val Tyr Gly Asp Gly Phe Arg Ala Gly Arg Leu Ala Val
            500                 505                 510
His Lys Tyr Gly Leu Arg Lys Thr Leu Glu His Ile Gln Met Thr Gly
        515                 520                 525
Arg Phe Pro Val
```

```
<210> SEQ ID NO 3
<211> LENGTH: 2231
<212> TYPE: DNA
<213> ORGANISM: Brassica napus
<220> FEATURE:
<221> NAME/KEY: exon
<222> LOCATION: (1)..(156)
<223> OTHER INFORMATION: Exon 1
<220> FEATURE:
<221> NAME/KEY: exon
<222> LOCATION: (325)..(427)
<223> OTHER INFORMATION: Exon 2
<220> FEATURE:
<221> NAME/KEY: exon
<222> LOCATION: (529)..(718)
<223> OTHER INFORMATION: Exon 3
<220> FEATURE:
<221> NAME/KEY: exon
<222> LOCATION: (808)..(928)
<223> OTHER INFORMATION: Exon 4
<220> FEATURE:
<221> NAME/KEY: exon
<222> LOCATION: (1015)..(1098)
<223> OTHER INFORMATION: Exon 5
<220> FEATURE:
<221> NAME/KEY: exon
<222> LOCATION: (1175)..(1294)
<223> OTHER INFORMATION: Exon 6
<220> FEATURE:
<221> NAME/KEY: exon
<222> LOCATION: (1295)..(1507)
<223> OTHER INFORMATION: Exon 7
<220> FEATURE:
<221> NAME/KEY: mutation
<222> LOCATION: (1385)..(1385)
<223> OTHER INFORMATION: C=>T in YIIN601/602
<220> FEATURE:
<221> NAME/KEY: exon
<222> LOCATION: (1594)..(1825)
<223> OTHER INFORMATION: Exon 8-9
<220> FEATURE:
<221> NAME/KEY: mutation
<222> LOCATION: (1683)..(1683)
<223> OTHER INFORMATION: G=>A in YIIN603
<220> FEATURE:
<221> NAME/KEY: exon
<222> LOCATION: (1915)..(2231)
<223> OTHER INFORMATION: Exon 10
<220> FEATURE:
<221> NAME/KEY: mutation
<222> LOCATION: (1932)..(1932)
<223> OTHER INFORMATION: C=>T in YIIN604

<400> SEQUENCE: 3 atg ggt tgg tta aac aag atc ttc aaa ggc tct aac caa agg cac ccc      48
Met Gly Trp Leu Asn Lys Ile Phe Lys Gly Ser Asn Gln Arg His Pro
1               5                   10                  15 atg ggg aat gaa cac tat cat cat aat ggc ggc tat tac gag aac tac      96
Met Gly Asn Glu His Tyr His His Asn Gly Gly Tyr Tyr Glu Asn Tyr
            20                  25                  30 ccg cac gaa cat tct gag cct act gat gct gat cat acg cag gaa cca     144
Pro His Glu His Ser Glu Pro Thr Asp Ala Asp His Thr Gln Glu Pro
        35                  40                  45 tct act tct gag gtgttactat atgctgattg aatattgata gctttgcttt         196
Ser Thr Ser Glu
            50 tatagttttt ttgttttctg atttaggaga tctcaaaaat agtcaaataa atcatattag    256 tctccattta tcagataatg gtttgtagtg taacctcaaa attttgttgt ttttttttact  316 tttactag gag gag aca tgg aat ggg aag gaa aat gag gaa gta gac cgt    366
```

```
                Glu Glu Thr Trp Asn Gly Lys Glu Asn Glu Glu Val Asp Arg
                 55                  60                  65 gca ctt gca ttg tct att tta gaa gaa gag aat caa gga cca gag act         414
Ala Leu Ala Leu Ser Ile Leu Glu Glu Glu Asn Gln Gly Pro Glu Thr
         70                  75                  80 aat aca ggc gcc t gtgagttaca ttttactgat ttgtttcagc ccaaaacagt           467
Asn Thr Gly Ala
         85 aatatgaaaa atacagtttt gttatacatt tgaaaaaata aaaataaaaa atgaaaagca       527 ggg aaa cac gca atg atg gat gac gat gag caa ctt gct aga gcc ata         575
Trp Lys His Ala Met Met Asp Asp Asp Glu Gln Leu Ala Arg Ala Ile
             90                  95                 100 caa gag agt atg ata gct agg aat gga act act tat gac ttt ggg aat         623
Gln Glu Ser Met Ile Ala Arg Asn Gly Thr Thr Tyr Asp Phe Gly Asn
            105                 110                 115 gca tat ggg aat gga cat atg cat gga gga ggc aat gta tat gcc aac         671
Ala Tyr Gly Asn Gly His Met His Gly Gly Gly Asn Val Tyr Ala Asn
            120                 125                 130 ggt gat att tat tat cca aga cct att gct ttc tca atg gac ttc ag          718
Gly Asp Ile Tyr Tyr Pro Arg Pro Ile Ala Phe Ser Met Asp Phe Arg
135                 140                 145                 150 gtttcactta gatggccttt taatttgggt tgatgtgtta tagtttcttt tagctttttt       778
atcaacaact tgtcactact gcataatag g atc tgt gct ggc tgc aat atg gag       832
                                 Ile Cys Ala Gly Cys Asn Met Glu
                                                             155 att ggc cag gga aga tat ctg aat tgc ctc aat gca tta tgg cat cca         880
Ile Gly Gln Gly Arg Tyr Leu Asn Cys Leu Asn Ala Leu Trp His Pro
            160                 165                 170 caa tgt ttt cga tgc tat ggc tgc agt cac cca atc tct gag tac gag         928
Gln Cys Phe Arg Cys Tyr Gly Cys Ser His Pro Ile Ser Glu Tyr Glu
175                 180                 185                 190 gtgaactcaa actcattctt tccgttgtag tttaaccttt gaatcaatgt aataacatgt       988
tttccttttt ttttggtctt aaatag ttc tca acg tct ggg aac tac cct ttt      1041
                             Phe Ser Thr Ser Gly Asn Tyr Pro Phe
                                             195 cac aaa gct tgt tac agg gag agg ttc cat cca aaa tgt gat gtc tgc        1089
His Lys Ala Cys Tyr Arg Glu Arg Phe His Pro Lys Cys Asp Val Cys
200                 205                 210                 215 agc ctc ttt gtatgtaaaa tctttagcat tttcagttgt tttctttcgg                1138
Ser Leu Phe atattccact tatgttattt tcttttcttg tgacag att tca aca aac cat gct        1192
                                       Ile Ser Thr Asn His Ala
                                                           220 ggt ctt att gag tat aga gca cat cct ttc tgg gtc cag aag tat tgt        1240
Gly Leu Ile Glu Tyr Arg Ala His Pro Phe Trp Val Gln Lys Tyr Cys
225                 230                 235                 240 cca tct cac gaa cac gat gct act cct aga tgt tgc agt tgt gaa aga        1288
Pro Ser His Glu His Asp Ala Thr Pro Arg Cys Cys Ser Cys Glu Arg
            245                 250                 255 atg gag cca cgg aat aca gga tat ttt gaa ctc aac gat gga cgg aag        1336
Met Glu Pro Arg Asn Thr Gly Tyr Phe Glu Leu Asn Asp Gly Arg Lys
            260                 265                 270 ctt tgc ctg gag tgt cta gac tca tcg gtg atg gac act ttt caa tgc        1384
Leu Cys Leu Glu Cys Leu Asp Ser Ser Val Met Asp Thr Phe Gln Cys
        275                 280                 285 caa cct ctg tac tta cag ata caa gag ttc tac gaa gga ctt aac atg        1432
Gln Pro Leu Tyr Leu Gln Ile Gln Glu Phe Tyr Glu Gly Leu Asn Met
        290                 295                 300
```

```
acg gta gag cag gag gtt cca ctt ctc tta gtt gag cgg cag gca ctt      1480
Thr Val Glu Gln Glu Val Pro Leu Leu Leu Val Glu Arg Gln Ala Leu
305                 310                 315                 320 aac gaa gcc aga gaa ggt gaa agg aat gtgagtagaa caaaaaatac             1527
Asn Glu Ala Arg Glu Gly Glu Arg Asn
                325 aaatttactt tagtaactat ttgagaatgt gtcacattta tattgtgtca ctgtgtgctt      1587 tcttag ggt cac tat cac atg cca gag aca aga gga ctc tgt ctg tcg        1635
       Gly His Tyr His Met Pro Glu Thr Arg Gly Leu Cys Leu Ser
           330                 335                 340 gaa gaa caa act gtt aga act gtg aga aag aga tcg aag gga aac tgg       1683
Glu Glu Gln Thr Val Arg Thr Val Arg Lys Arg Ser Lys Gly Asn Trp
345                 350                 355 agt ggg aat atg atc aca gag caa ttc aag cta act cgc cga tgc gag       1731
Ser Gly Asn Met Ile Thr Glu Gln Phe Lys Leu Thr Arg Arg Cys Glu
    360                 365                 370                 375 gtt acc gcc att ctc atc tta ttt ggt ctc cct agg cta ctc act ggt       1779
Val Thr Ala Ile Leu Ile Leu Phe Gly Leu Pro Arg Leu Leu Thr Gly
                380                 385                 390 tca att cta gct cat gag atg atg cac gcg tgg atg cgg ctc aaa g         1825
Ser Ile Leu Ala His Glu Met Met His Ala Trp Met Arg Leu Lys
                395                 400                 405 gtgagtttct tgcttcttgt ttcttatcta actgcttctc ttgtttcaca tttgttgaac     1885
cgttactaca atgtgtggtc ttgaaaaag gg  ttc cgg cca ctt agc caa gat       1937
                                    Gly Phe Arg Pro Leu Ser Gln Asp
                                                    410 gtt gaa gag ggg ata tgt caa gtg atg gct cat aag tgg tta gaa gct       1985
Val Glu Glu Gly Ile Cys Gln Val Met Ala His Lys Trp Leu Glu Ala
415                 420                 425                 430 gag tta gct gct ggt tca aga aat agc aat gct gca tca tct tca tca      2033
Glu Leu Ala Ala Gly Ser Arg Asn Ser Asn Ala Ala Ser Ser Ser Ser
                435                 440                 445 tct tct tat gga gga gtg aag aag gga cca agg tct cag tac gag agg       2081
Ser Ser Tyr Gly Gly Val Lys Lys Gly Pro Arg Ser Gln Tyr Glu Arg
            450                 455                 460 aag ctt ggt gag ttt ttc aag cac cag ata gag gct gat gct tct ccg       2129
Lys Leu Gly Glu Phe Phe Lys His Gln Ile Glu Ala Asp Ala Ser Pro
                465                 470                 475 gtt tat gga gat ggg ttc aga gcc ggg agg cta gca gtt aac aag tat       2177
Val Tyr Gly Asp Gly Phe Arg Ala Gly Arg Leu Ala Val Asn Lys Tyr
            480                 485                 490 ggt ttg agg aga aca ctt gag cat ata cag atg act ggg aga ttc ccg       2225
Gly Leu Arg Arg Thr Leu Glu His Ile Gln Met Thr Gly Arg Phe Pro
495                 500                 505                 510 gtt taa                                                               2231
Val

<210> SEQ ID NO 4
<211> LENGTH: 1536
<212> TYPE: DNA
<213> ORGANISM: Brassica napus
<220> FEATURE:
<221> NAME/KEY: CDS
<222> LOCATION: (1)..(1536)
<220> FEATURE:
<221> NAME/KEY: mutation
<222> LOCATION: (865)..(865)
<223> OTHER INFORMATION: C=>T in YIIN601/602
<220> FEATURE:
<221> NAME/KEY: mutation
<222> LOCATION: (1077)..(1077)
```

<223> OTHER INFORMATION: G=>A in YIIN603
<220> FEATURE:
<221> NAME/KEY: mutation
<222> LOCATION: (1237)..(1237)
<223> OTHER INFORMATION: C=>T in YIIN604

<400> SEQUENCE: 4

```
atg ggt tgg tta aac aag atc ttc aaa ggc tct aac caa agg cac ccc      48
Met Gly Trp Leu Asn Lys Ile Phe Lys Gly Ser Asn Gln Arg His Pro
 1               5                  10                  15 atg ggg aat gaa cac tat cat cat aat ggc ggc tat tac gag aac tac      96
Met Gly Asn Glu His Tyr His His Asn Gly Gly Tyr Tyr Glu Asn Tyr
             20                  25                  30 ccg cac gaa cat tct gag cct act gat gct gat cat acg cag gaa cca     144
Pro His Glu His Ser Glu Pro Thr Asp Ala Asp His Thr Gln Glu Pro
         35                  40                  45 tct act tct gag gag gag aca tgg aat ggg aag gaa aat gag gaa gta     192
Ser Thr Ser Glu Glu Glu Thr Trp Asn Gly Lys Glu Asn Glu Glu Val
     50                  55                  60 gac cgt gca ctt gca ttg tct att tta gaa gaa gag aat caa gga cca     240
Asp Arg Ala Leu Ala Leu Ser Ile Leu Glu Glu Glu Asn Gln Gly Pro
 65                  70                  75                  80 gag act aat aca ggc gcc tgg aaa cac gca atg atg gat gac gat gag     288
Glu Thr Asn Thr Gly Ala Trp Lys His Ala Met Met Asp Asp Asp Glu
                 85                  90                  95 caa ctt gct aga gcc ata caa gag agt atg ata gct agg aat gga act     336
Gln Leu Ala Arg Ala Ile Gln Glu Ser Met Ile Ala Arg Asn Gly Thr
            100                 105                 110 act tat gac ttt ggg aat gca tat ggg aat gga cat atg cat gga gga     384
Thr Tyr Asp Phe Gly Asn Ala Tyr Gly Asn Gly His Met His Gly Gly
        115                 120                 125 ggc aat gta tat gcc aac ggt gat att tat tat cca aga cct att gct     432
Gly Asn Val Tyr Ala Asn Gly Asp Ile Tyr Tyr Pro Arg Pro Ile Ala
    130                 135                 140 ttc tca atg gac ttc agg atc tgt gct ggc tgc aat atg gag att ggc     480
Phe Ser Met Asp Phe Arg Ile Cys Ala Gly Cys Asn Met Glu Ile Gly
145                 150                 155                 160 cag gga aga tat ctg aat tgc ctc aat gca tta tgg cat cca caa tgt     528
Gln Gly Arg Tyr Leu Asn Cys Leu Asn Ala Leu Trp His Pro Gln Cys
                165                 170                 175 ttt cga tgc tat ggc tgc agt cac cca atc tct gag tac gag ttc tca     576
Phe Arg Cys Tyr Gly Cys Ser His Pro Ile Ser Glu Tyr Glu Phe Ser
            180                 185                 190 acg tct ggg aac tac cct ttt cac aaa gct tgt tac agg gag agg ttc     624
Thr Ser Gly Asn Tyr Pro Phe His Lys Ala Cys Tyr Arg Glu Arg Phe
        195                 200                 205 cat cca aaa tgt gat gtc tgc agc ctc ttt att tca aca aac cat gct     672
His Pro Lys Cys Asp Val Cys Ser Leu Phe Ile Ser Thr Asn His Ala
    210                 215                 220 ggt ctt att gag tat aga gca cat cct ttc tgg gtc cag aag tat tgt     720
Gly Leu Ile Glu Tyr Arg Ala His Pro Phe Trp Val Gln Lys Tyr Cys
225                 230                 235                 240 cca tct cac gaa cac gat gct act cct aga tgt tgc agt tgt gaa aga     768
Pro Ser His Glu His Asp Ala Thr Pro Arg Cys Cys Ser Cys Glu Arg
                245                 250                 255 atg gag cca cgg aat aca gga tat ttt gaa ctc aac gat gga cgg aag     816
Met Glu Pro Arg Asn Thr Gly Tyr Phe Glu Leu Asn Asp Gly Arg Lys
            260                 265                 270 ctt tgc ctg gag tgt cta gac tca tcg gtg atg gac act ttt caa tgc     864
Leu Cys Leu Glu Cys Leu Asp Ser Ser Val Met Asp Thr Phe Gln Cys
        275                 280                 285
```

```
caa cct ctg tac tta cag ata caa gag ttc tac gaa gga ctt aac atg      912
Gln Pro Leu Tyr Leu Gln Ile Gln Glu Phe Tyr Glu Gly Leu Asn Met
    290                 295                 300 acg gta gag cag gag gtt cca ctt ctc tta gtt gag cgg cag gca ctt      960
Thr Val Glu Gln Glu Val Pro Leu Leu Leu Val Glu Arg Gln Ala Leu
305                 310                 315                 320 aac gaa gcc aga gaa ggt gaa agg aat ggt cac tat cac atg cca gag     1008
Asn Glu Ala Arg Glu Gly Glu Arg Asn Gly His Tyr His Met Pro Glu
                325                 330                 335 aca aga gga ctc tgt ctg tcg gaa gaa caa act gtt aga act gtg aga     1056
Thr Arg Gly Leu Cys Leu Ser Glu Glu Gln Thr Val Arg Thr Val Arg
            340                 345                 350 aag aga tcg aag gga aac tgg agt ggg aat atg atc aca gag caa ttc     1104
Lys Arg Ser Lys Gly Asn Trp Ser Gly Asn Met Ile Thr Glu Gln Phe
        355                 360                 365 aag cta act cgc cga tgc gag gtt acc gcc att ctc atc tta ttt ggt     1152
Lys Leu Thr Arg Arg Cys Glu Val Thr Ala Ile Leu Ile Leu Phe Gly
    370                 375                 380 ctc cct agg cta ctc act ggt tca att cta gct cat gag atg atg cac     1200
Leu Pro Arg Leu Leu Thr Gly Ser Ile Leu Ala His Glu Met Met His
385                 390                 395                 400 gcg tgg atg cgg ctc aaa ggg ttc cgg cca ctt agc caa gat gtt gaa     1248
Ala Trp Met Arg Leu Lys Gly Phe Arg Pro Leu Ser Gln Asp Val Glu
                405                 410                 415 gag ggg ata tgt caa gtg atg gct cat aag tgg tta gaa gct gag tta     1296
Glu Gly Ile Cys Gln Val Met Ala His Lys Trp Leu Glu Ala Glu Leu
            420                 425                 430 gct gct ggt tca aga aat agc aat gct gca tca tct tca tca tct tct     1344
Ala Ala Gly Ser Arg Asn Ser Asn Ala Ala Ser Ser Ser Ser Ser Ser
        435                 440                 445 tat gga gga gtg aag aag gga cca agg tct cag tac gag agg aag ctt     1392
Tyr Gly Gly Val Lys Lys Gly Pro Arg Ser Gln Tyr Glu Arg Lys Leu
    450                 455                 460 ggt gag ttt ttc aag cac cag ata gag gct gat gct tct ccg gtt tat     1440
Gly Glu Phe Phe Lys His Gln Ile Glu Ala Asp Ala Ser Pro Val Tyr
465                 470                 475                 480 gga gat ggg ttc aga gcc ggg agg cta gca gtt aac aag tat ggt ttg     1488
Gly Asp Gly Phe Arg Ala Gly Arg Leu Ala Val Asn Lys Tyr Gly Leu
                485                 490                 495 agg aga aca ctt gag cat ata cag atg act ggg aga ttc ccg gtt taa     1536
Arg Arg Thr Leu Glu His Ile Gln Met Thr Gly Arg Phe Pro Val
            500                 505                 510

<210> SEQ ID NO 5
<211> LENGTH: 511
<212> TYPE: PRT
<213> ORGANISM: Brassica napus

<400> SEQUENCE: 5

Met Gly Trp Leu Asn Lys Ile Phe Lys Gly Ser Asn Gln Arg His Pro
1               5                   10                  15

Met Gly Asn Glu His Tyr His His Asn Gly Gly Tyr Tyr Glu Asn Tyr
            20                  25                  30

Pro His Glu His Ser Glu Pro Thr Asp Ala Asp His Thr Gln Glu Pro
        35                  40                  45

Ser Thr Ser Glu Glu Glu Thr Trp Asn Gly Lys Glu Asn Glu Glu Val
    50                  55                  60

Asp Arg Ala Leu Ala Leu Ser Ile Leu Glu Glu Glu Asn Gln Gly Pro
65                  70                  75                  80
```

Glu Thr Asn Thr Gly Ala Trp Lys His Ala Met Met Asp Asp Glu
                85                  90                  95

Gln Leu Ala Arg Ala Ile Gln Glu Ser Met Ile Ala Arg Asn Gly Thr
            100                 105                 110

Thr Tyr Asp Phe Gly Asn Ala Tyr Gly Asn Gly His Met His Gly Gly
        115                 120                 125

Gly Asn Val Tyr Ala Asn Gly Asp Ile Tyr Tyr Pro Arg Pro Ile Ala
    130                 135                 140

Phe Ser Met Asp Phe Arg Ile Cys Ala Gly Cys Asn Met Glu Ile Gly
145                 150                 155                 160

Gln Gly Arg Tyr Leu Asn Cys Leu Asn Ala Leu Trp His Pro Gln Cys
                165                 170                 175

Phe Arg Cys Tyr Gly Cys Ser His Pro Ile Ser Glu Tyr Glu Phe Ser
            180                 185                 190

Thr Ser Gly Asn Tyr Pro Phe His Lys Ala Cys Tyr Arg Glu Arg Phe
        195                 200                 205

His Pro Lys Cys Asp Val Cys Ser Leu Phe Ile Ser Thr Asn His Ala
    210                 215                 220

Gly Leu Ile Glu Tyr Arg Ala His Pro Phe Trp Val Gln Lys Tyr Cys
225                 230                 235                 240

Pro Ser His Glu His Asp Ala Thr Pro Arg Cys Cys Ser Cys Glu Arg
                245                 250                 255

Met Glu Pro Arg Asn Thr Gly Tyr Phe Glu Leu Asn Asp Gly Arg Lys
            260                 265                 270

Leu Cys Leu Glu Cys Leu Asp Ser Ser Val Met Asp Thr Phe Gln Cys
        275                 280                 285

Gln Pro Leu Tyr Leu Gln Ile Gln Glu Phe Tyr Glu Gly Leu Asn Met
    290                 295                 300

Thr Val Glu Gln Glu Val Pro Leu Leu Val Glu Arg Gln Ala Leu
305                 310                 315                 320

Asn Glu Ala Arg Glu Gly Glu Arg Asn Gly His Tyr His Met Pro Glu
                325                 330                 335

Thr Arg Gly Leu Cys Leu Ser Glu Glu Gln Thr Val Arg Thr Val Arg
            340                 345                 350

Lys Arg Ser Lys Gly Asn Trp Ser Gly Asn Met Ile Thr Glu Gln Phe
        355                 360                 365

Lys Leu Thr Arg Arg Cys Glu Val Thr Ala Ile Leu Ile Phe Gly
    370                 375                 380

Leu Pro Arg Leu Leu Thr Gly Ser Ile Leu Ala His Glu Met Met His
385                 390                 395                 400

Ala Trp Met Arg Leu Lys Gly Phe Arg Pro Leu Ser Gln Asp Val Glu
                405                 410                 415

Glu Gly Ile Cys Gln Val Met Ala His Lys Trp Leu Glu Ala Glu Leu
            420                 425                 430

Ala Ala Gly Ser Arg Asn Ser Asn Ala Ala Ser Ser Ser Ser Ser Ser
        435                 440                 445

Tyr Gly Gly Val Lys Lys Gly Pro Arg Ser Gln Tyr Glu Arg Lys Leu
    450                 455                 460

Gly Glu Phe Phe Lys His Gln Ile Glu Ala Asp Ala Ser Pro Val Tyr
465                 470                 475                 480

Gly Asp Gly Phe Arg Ala Gly Arg Leu Ala Val Asn Lys Tyr Gly Leu
                485                 490                 495

Arg Arg Thr Leu Glu His Ile Gln Met Thr Gly Arg Phe Pro Val
            500                 505                 510

<210> SEQ ID NO 6
<211> LENGTH: 2267
<212> TYPE: DNA
<213> ORGANISM: Brassica napus
<220> FEATURE:
<221> NAME/KEY: exon
<222> LOCATION: (1)..(171)
<223> OTHER INFORMATION: Exon 1
<220> FEATURE:
<221> NAME/KEY: exon
<222> LOCATION: (244)..(340)
<223> OTHER INFORMATION: Exon 2
<220> FEATURE:
<221> NAME/KEY: exon
<222> LOCATION: (421)..(646)
<223> OTHER INFORMATION: Exon 3
<220> FEATURE:
<221> NAME/KEY: exon
<222> LOCATION: (737)..(857)
<223> OTHER INFORMATION: Exon 4
<220> FEATURE:
<221> NAME/KEY: exon
<222> LOCATION: (933)..(1016)
<223> OTHER INFORMATION: Exon 5
<220> FEATURE:
<221> NAME/KEY: exon
<222> LOCATION: (1129)..(1248)
<223> OTHER INFORMATION: Exon 6
<220> FEATURE:
<221> NAME/KEY: exon
<222> LOCATION: (1333)..(1545)
<223> OTHER INFORMATION: Exon 7
<220> FEATURE:
<221> NAME/KEY: exon
<222> LOCATION: (1647)..(1828)
<223> OTHER INFORMATION: Exon 8
<220> FEATURE:
<221> NAME/KEY: mutation
<222> LOCATION: (1672)..(1672)
<223> OTHER INFORMATION: G=>A in YIIN609
<220> FEATURE:
<221> NAME/KEY: mutation
<222> LOCATION: (1744)..(1744)
<223> OTHER INFORMATION: G=>A in YIIN605
<220> FEATURE:
<221> NAME/KEY: exon
<222> LOCATION: (1829)..(1887)
<223> OTHER INFORMATION: Exon 9
<220> FEATURE:
<221> NAME/KEY: mutation
<222> LOCATION: (1874)..(1874)
<223> OTHER INFORMATION: G=>A in YIIN608
<220> FEATURE:
<221> NAME/KEY: exon
<222> LOCATION: (1957)..(2267)
<223> OTHER INFORMATION: Exon 10
<220> FEATURE:
<221> NAME/KEY: mutation
<222> LOCATION: (1974)..(1974)
<223> OTHER INFORMATION: C=>T in YIIN607
<220> FEATURE:
<221> NAME/KEY: mutation
<222> LOCATION: (1998)..(1998)
<223> OTHER INFORMATION: C=>T in YIIN606

<400> SEQUENCE: 6 atg ggt tgg ttt aac aag atc ttc aaa ggc tct acc caa agg ttc cgg       48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat       96
Leu Gly Asn Asp His Asp His Asn Gly Tyr Tyr Gln Ser Tyr Pro His
            20                  25                  30

| | |
|---|---|
| gat gag cct agt gct gat act gat cct gat cct gat cct gat gaa act<br>Asp Glu Pro Ser Ala Asp Thr Asp Pro Asp Pro Asp Pro Asp Glu Thr<br>     35                       40                      45 | 144 |
| cat act cag gaa cca tct acc tct gag gttactataa ctctctttac<br>His Thr Gln Glu Pro Ser Thr Ser Glu<br>     50                  55 | 191 |
| atatctctgg tttgtactat tgcttcaaca ttttgttgtt tcccttttact ag gag gat<br>                                                                          Glu Asp | 249 |
| aca tcc ggc cag gaa aac gaa gac ata gat cgt gca atc gca ttg tct<br>Thr Ser Gly Gln Glu Asn Glu Asp Ile Asp Arg Ala Ile Ala Leu Ser<br>60                     65                     70                       75 | 297 |
| ctt ata gaa aac agt caa gga cag act aat aat aca tgc gct g<br>Leu Ile Glu Asn Ser Gln Gly Gln Thr Asn Asn Thr Cys Ala<br>                   80                     85 | 340 |
| gtgagtcctt tttccttgcc aaactagaaa tatgaattat gaaactcggt ttgttacatt | 400 |
| taaaagaata gccaacgcag gg  aag tac gca atg gtg gat gaa gat gag caa<br>                                     Gly Lys Tyr Ala Met Val Asp Glu Asp Glu Gln<br>                                       90                     95                           100 | 452 |
| ctt gct aga gcc ata caa gag agc atg gta gtt ggg aat aca ccg cgt<br>Leu Ala Arg Ala Ile Gln Glu Ser Met Val Val Gly Asn Thr Pro Arg<br>         105                     110                     115 | 500 |
| cag aag cat gga agt agt tat gat att ggg aat gca tat ggg gct gga<br>Gln Lys His Gly Ser Ser Tyr Asp Ile Gly Asn Ala Tyr Gly Ala Gly<br>         120                     125                     130 | 548 |
| gac gtt tac ggg aat gga cat atg cat gga ggt gga aat gta tat gcc<br>Asp Val Tyr Gly Asn Gly His Met His Gly Gly Gly Asn Val Tyr Ala<br>135                     140                     145 | 596 |
| aat gga gat att tat tat cca aga cct act gct ttc cca atg gat ttc<br>Asn Gly Asp Ile Tyr Tyr Pro Arg Pro Thr Ala Phe Pro Met Asp Phe<br>150                     155                     160 | 644 |
| ag  gttcactttg atactcaatc aatcatctgt agcctgtttg ttaagtttct<br>Arg<br>165 | 696 |
| ttccagttaa gtaactcacc aacaacgtgt cactacctag g att tgt gct ggc tgc<br>                                                                         Ile Cys Ala Gly Cys<br>                                                                                            170 | 752 |
| aat atg gag att gga cat gga aga tat ctg aat tgc ttg aat gca cta<br>Asn Met Glu Ile Gly His Gly Arg Tyr Leu Asn Cys Leu Asn Ala Leu<br>         175                     180                     185 | 800 |
| tgg cat cca gaa tgt ttt cga tgt tat ggc tgt agg cat ccc atc tct<br>Trp His Pro Glu Cys Phe Arg Cys Tyr Gly Cys Arg His Pro Ile Ser<br>                   190                     195                     200 | 848 |
| gag tac gag gtgaagtcaa gctttcttat tcttttgatt gtagataacc<br>Glu Tyr Glu<br>205 | 897 |
| ttcaaaatta acgcataaca tgttttcctt tatag ttc tca acg tct ggg aac<br>                                                        Phe Ser Thr Ser Gly Asn<br>                                                                        210 | 950 |
| tac cct ttt cac aaa gct tgt tat agg gag aga tac cat cca aaa tgt<br>Tyr Pro Phe His Lys Ala Cys Tyr Arg Glu Arg Tyr His Pro Lys Cys<br>         215                     220                     225 | 998 |
| gat gtc tgc agc ctc ttt gtatgtaaat ctttagcctt ttttcattt<br>Asp Val Cys Ser Leu Phe<br>230 | 1046 |
| ttaaagtgcc tatatatgcc ttgtttcctt cggatattgc acttatcttc tgttgatttt | 1106 |
| cttgtttcga atgttgtgac ag att cca aca aac cat gct ggt ctt att gaa<br>                                    Ile Pro Thr Asn His Ala Gly Leu Ile Glu<br>                                            235                     240 | 1158 |

| | |
|---|---|
| tat agg gca cat cct ttt tgg gtc cag aag tat tgc cct tct cac gaa<br>Tyr Arg Ala His Pro Phe Trp Val Gln Lys Tyr Cys Pro Ser His Glu<br>245                        250                        255 | 1206 |
| cac gat gct acc cca aga tgt tgc agt tgc gaa aga atg gag<br>His Asp Ala Thr Pro Arg Cys Cys Ser Cys Glu Arg Met Glu<br>260                      265                      270 | 1248 |
| gttgagtttt tctcccccta agtgtcctac aacaaacatc ttcccaaagt caatactaat | 1308 |
| ttgccagctt tcgtttatgt gcag cca cgc aat aca gga tat gtt gaa ctt<br>                               Pro Arg Asn Thr Gly Tyr Val Glu Leu<br>                                     275                      280 | 1359 |
| aac gat gga cgg aaa ctt tgc ctt gaa tgt ctg gac tca gcg gtg atg<br>Asn Asp Gly Arg Lys Leu Cys Leu Glu Cys Leu Asp Ser Ala Val Met<br>                 285                      290                      295 | 1407 |
| gac act ttt caa tgc caa cct ctg tat ctg cag ata caa gaa ttc tac<br>Asp Thr Phe Gln Cys Gln Pro Leu Tyr Leu Gln Ile Gln Glu Phe Tyr<br>300                        305                      310 | 1455 |
| gaa ggt ctt ttc atg aag gtt gag cag gac gtt cca ctt ctt tta gtt<br>Glu Gly Leu Phe Met Lys Val Glu Gln Asp Val Pro Leu Leu Leu Val<br>315                      320                      325                      330 | 1503 |
| gag agg caa gca ctc aac gaa gcc aga gaa ggt gaa aag aat<br>Glu Arg Gln Ala Leu Asn Glu Ala Arg Glu Gly Glu Lys Asn<br>                 335                      340 | 1545 |
| gtgagtaaac aacatacagt tgtcaagtaa tttatttgaa tatatcacat ttatttttgt | 1605 |
| tttatccgaa gtgttttaac ttttggttgt gttcttctta g ggt cac tat cac atg<br>                                                    Gly His Tyr His Met<br>                                                                345 | 1661 |
| cca gag aca aga gga ctc tgc ctt tca gaa gaa caa act gtt agc act<br>Pro Glu Thr Arg Gly Leu Cys Leu Ser Glu Glu Gln Thr Val Ser Thr<br>350                        355                      360                      365 | 1709 |
| gta aga aag aga tcg aag cat ggc aca gga aac tgg gct ggg aat atg<br>Val Arg Lys Arg Ser Lys His Gly Thr Gly Asn Trp Ala Gly Asn Met<br>                 370                      375                      380 | 1757 |
| att aca gag cct tac aag tta aca cgt caa tgc gag gtc act gcc att<br>Ile Thr Glu Pro Tyr Lys Leu Thr Arg Gln Cys Glu Val Thr Ala Ile<br>                 385                      390                      395 | 1805 |
| ctc atc ttg ttt ggg ctc cct agg cta ctc acc ggt tcg att cta gct<br>Leu Ile Leu Phe Gly Leu Pro Arg Leu Leu Thr Gly Ser Ile Leu Ala<br>                 400                      405                      410 | 1853 |
| cat gag atg atg cac gcg tgg atg cgg ctc aag g gtgagtttct<br>His Glu Met Met His Ala Trp Met Arg Leu Lys<br>               415                      420 | 1897 |
| tagttcactg cttctctttt tttttcacat tgttgaatct ctattgtggt cttgaaaag | 1956 |
| ga ttc cgg acg ctg agc caa gac gtt gaa gaa gga ata tgt caa gtg<br>Gly Phe Arg Thr Leu Ser Gln Asp Val Glu Glu Gly Ile Cys Gln Val<br>425                        430                      435                      440 | 2003 |
| atg gct cat aag tgg ttg gaa gca gag tta gct gct ggt tca aga aac<br>Met Ala His Lys Trp Leu Glu Ala Glu Leu Ala Ala Gly Ser Arg Asn<br>                 445                      450                      455 | 2051 |
| agc aat gtt gcg tca tct tca tct tct aga gga gtg aag aag gga cca<br>Ser Asn Val Ala Ser Ser Ser Ser Ser Arg Gly Val Lys Lys Gly Pro<br>                 460                      465                      470 | 2099 |
| aga tcg cag tac gag agg aag ctt ggt gag ttt ttc aag cac caa atc<br>Arg Ser Gln Tyr Glu Arg Lys Leu Gly Glu Phe Phe Lys His Gln Ile<br>                 475                      480                      485 | 2147 |
| gag tct gat gct tct ccg gtt tat gga gac ggg ttc agg gct ggg agg<br>Glu Ser Asp Ala Ser Pro Val Tyr Gly Asp Gly Phe Arg Ala Gly Arg<br>                 490                      495                      500 | 2195 |
| tta gcg gtt aac aag tat ggt ttg cca aaa aca ctt gag cat ata cag | 2243 |

```
Leu Ala Val Asn Lys Tyr Gly Leu Pro Lys Thr Leu Glu His Ile Gln
505                 510                 515                 520 atg acc ggt aga ttc ccg gtt taa                                      2267
Met Thr Gly Arg Phe Pro Val
                525

<210> SEQ ID NO 7
<211> LENGTH: 1584
<212> TYPE: DNA
<213> ORGANISM: Brassica napus
<220> FEATURE:
<221> NAME/KEY: CDS
<222> LOCATION: (1)..(1584)
<220> FEATURE:
<221> NAME/KEY: mutation
<222> LOCATION: (1058)..(1058)
<223> OTHER INFORMATION: G=>A in  YIIN609
<220> FEATURE:
<221> NAME/KEY: mutation
<222> LOCATION: (1130)..(1130)
<223> OTHER INFORMATION: G=>A in  YIIN605
<220> FEATURE:
<221> NAME/KEY: mutation
<222> LOCATION: (1260)..(1260)
<223> OTHER INFORMATION: G=>A in  YIIN608
<220> FEATURE:
<221> NAME/KEY: mutation
<222> LOCATION: (1291)..(1291)
<223> OTHER INFORMATION: C=>T in  YIIN607
<220> FEATURE:
<221> NAME/KEY: mutation
<222> LOCATION: (1315)..(1315)
<223> OTHER INFORMATION: C=>T in  YIIN606

<400> SEQUENCE: 7 atg ggt tgg ttt aac aag atc ttc aaa ggc tct acc caa agg ttc cgg    48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat    96
Leu Gly Asn Asp His Asp His Asn Gly Tyr Tyr Gln Ser Tyr Pro His
            20                  25                  30 gat gag cct agt gct gat act gat cct gat cct gat cct gat gaa act   144
Asp Glu Pro Ser Ala Asp Thr Asp Pro Asp Pro Asp Pro Asp Glu Thr
        35                  40                  45 cat act cag gaa cca tct acc tct gag gag gat aca tcc ggc cag gaa   192
His Thr Gln Glu Pro Ser Thr Ser Glu Glu Asp Thr Ser Gly Gln Glu
    50                  55                  60 aac gaa gac ata gat cgt gca atc gca ttg tct ctt ata gaa aac agt   240
Asn Glu Asp Ile Asp Arg Ala Ile Ala Leu Ser Leu Ile Glu Asn Ser
65                  70                  75                  80 caa gga cag act aat aat aca tgc gct ggg aag tac gca atg gtg gat   288
Gln Gly Gln Thr Asn Asn Thr Cys Ala Gly Lys Tyr Ala Met Val Asp
                85                  90                  95 gaa gat gag caa ctt gct aga gcc ata caa gag agc atg gta gtt ggg   336
Glu Asp Glu Gln Leu Ala Arg Ala Ile Gln Glu Ser Met Val Val Gly
            100                 105                 110 aat aca ccg cgt cag aag cat gga agt agt tat gat att ggg aat gca   384
Asn Thr Pro Arg Gln Lys His Gly Ser Ser Tyr Asp Ile Gly Asn Ala
        115                 120                 125 tat ggg gct gga gac gtt tac ggg aat gga cat atg cat gga ggt gga   432
Tyr Gly Ala Gly Asp Val Tyr Gly Asn Gly His Met His Gly Gly Gly
    130                 135                 140 aat gta tat gcc aat gga gat att tat tat cca aga cct act gct ttc   480
Asn Val Tyr Ala Asn Gly Asp Ile Tyr Tyr Pro Arg Pro Thr Ala Phe
145                 150                 155                 160 cca atg gat ttc agg att tgt gct ggc tgc aat atg gag att gga cat   528
```

-continued

```
                Pro Met Asp Phe Arg Ile Cys Ala Gly Cys Asn Met Glu Ile Gly His
                                165                 170                 175 gga aga tat ctg aat tgc ttg aat gca cta tgg cat cca gaa tgt ttt         576
Gly Arg Tyr Leu Asn Cys Leu Asn Ala Leu Trp His Pro Glu Cys Phe
            180                 185                 190 cga tgt tat ggc tgt agg cat ccc atc tct gag tac gag ttc tca acg         624
Arg Cys Tyr Gly Cys Arg His Pro Ile Ser Glu Tyr Glu Phe Ser Thr
        195                 200                 205 tct ggg aac tac cct ttt cac aaa gct tgt tat agg gag aga tac cat         672
Ser Gly Asn Tyr Pro Phe His Lys Ala Cys Tyr Arg Glu Arg Tyr His
    210                 215                 220 cca aaa tgt gat gtc tgc agc ctc ttt att cca aca aac cat gct ggt         720
Pro Lys Cys Asp Val Cys Ser Leu Phe Ile Pro Thr Asn His Ala Gly
225                 230                 235                 240 ctt att gaa tat agg gca cat cct ttt tgg gtc cag aag tat tgc cct         768
Leu Ile Glu Tyr Arg Ala His Pro Phe Trp Val Gln Lys Tyr Cys Pro
                245                 250                 255 tct cac gaa cac gat gct acc cca aga tgt tgc agt tgc gaa aga atg         816
Ser His Glu His Asp Ala Thr Pro Arg Cys Cys Ser Cys Glu Arg Met
            260                 265                 270 gag cca cgc aat aca gga tat gtt gaa ctt aac gat gga cgg aaa ctt         864
Glu Pro Arg Asn Thr Gly Tyr Val Glu Leu Asn Asp Gly Arg Lys Leu
        275                 280                 285 tgc ctt gaa tgt ctg gac tca gcg gtg atg gac act ttt caa tgc caa         912
Cys Leu Glu Cys Leu Asp Ser Ala Val Met Asp Thr Phe Gln Cys Gln
    290                 295                 300 cct ctg tat ctg cag ata caa gaa ttc tac gaa ggt ctt ttc atg aag         960
Pro Leu Tyr Leu Gln Ile Gln Glu Phe Tyr Glu Gly Leu Phe Met Lys
305                 310                 315                 320 gtt gag cag gac gtt cca ctt ctt tta gtt gag agg caa gca ctc aac        1008
Val Glu Gln Asp Val Pro Leu Leu Leu Val Glu Arg Gln Ala Leu Asn
                325                 330                 335 gaa gcc aga gaa ggt gaa aag aat ggt cac tat cac atg cca gag aca        1056
Glu Ala Arg Glu Gly Glu Lys Asn Gly His Tyr His Met Pro Glu Thr
            340                 345                 350 aga gga ctc tgc ctt tca gaa gaa caa act gtt agc act gta aga aag        1104
Arg Gly Leu Cys Leu Ser Glu Glu Gln Thr Val Ser Thr Val Arg Lys
        355                 360                 365 aga tcg aag cat ggc aca gga aac tgg gct ggg aat atg att aca gag        1152
Arg Ser Lys His Gly Thr Gly Asn Trp Ala Gly Asn Met Ile Thr Glu
    370                 375                 380 cct tac aag tta aca cgt caa tgc gag gtc act gcc att ctc atc ttg        1200
Pro Tyr Lys Leu Thr Arg Gln Cys Glu Val Thr Ala Ile Leu Ile Leu
385                 390                 395                 400 ttt ggg ctc cct agg cta ctc acc ggt tcg att cta gct cat gag atg        1248
Phe Gly Leu Pro Arg Leu Leu Thr Gly Ser Ile Leu Ala His Glu Met
                405                 410                 415 atg cac gcg tgg atg cgg ctc aag gga ttc cgg acg ctg agc caa gac        1296
Met His Ala Trp Met Arg Leu Lys Gly Phe Arg Thr Leu Ser Gln Asp
            420                 425                 430 gtt gaa gaa gga ata tgt caa gtg atg gct cat aag tgg ttg gaa gca        1344
Val Glu Glu Gly Ile Cys Gln Val Met Ala His Lys Trp Leu Glu Ala
        435                 440                 445 gag tta gct gct ggt tca aga aac agc aat gtt gcg tca tct tca tct        1392
Glu Leu Ala Ala Gly Ser Arg Asn Ser Asn Val Ala Ser Ser Ser Ser
    450                 455                 460 tct aga gga gtg aag aag gga cca aga tcg cag tac gag agg aag ctt        1440
Ser Arg Gly Val Lys Lys Gly Pro Arg Ser Gln Tyr Glu Arg Lys Leu
465                 470                 475                 480
```

```
ggt gag ttt ttc aag cac caa atc gag tct gat gct tct ccg gtt tat    1488
Gly Glu Phe Phe Lys His Gln Ile Glu Ser Asp Ala Ser Pro Val Tyr
            485                 490                 495 gga gac ggg ttc agg gct ggg agg tta gcg gtt aac aag tat ggt ttg    1536
Gly Asp Gly Phe Arg Ala Gly Arg Leu Ala Val Asn Lys Tyr Gly Leu
        500                 505                 510 cca aaa aca ctt gag cat ata cag atg acc ggt aga ttc ccg gtt taa   1584
Pro Lys Thr Leu Glu His Ile Gln Met Thr Gly Arg Phe Pro Val
            515                 520                 525
```

<210> SEQ ID NO 8
<211> LENGTH: 527
<212> TYPE: PRT
<213> ORGANISM: Brassica napus

<400> SEQUENCE: 8

```
Met Gly Trp Phe Asn Lys Ile Phe Lys Gly Ser Thr Gln Arg Phe Arg
1               5                   10                  15

Leu Gly Asn Asp His Asp His Asn Gly Tyr Tyr Gln Ser Tyr Pro His
            20                  25                  30

Asp Glu Pro Ser Ala Asp Thr Asp Pro Asp Pro Asp Pro Asp Glu Thr
        35                  40                  45

His Thr Gln Glu Pro Ser Thr Ser Glu Glu Asp Thr Ser Gly Gln Glu
    50                  55                  60

Asn Glu Asp Ile Asp Arg Ala Ile Ala Leu Ser Leu Ile Glu Asn Ser
65                  70                  75                  80

Gln Gly Gln Thr Asn Asn Thr Cys Ala Gly Lys Tyr Ala Met Val Asp
                85                  90                  95

Glu Asp Glu Gln Leu Ala Arg Ala Ile Gln Glu Ser Met Val Val Gly
            100                 105                 110

Asn Thr Pro Arg Gln Lys His Gly Ser Ser Tyr Asp Ile Gly Asn Ala
        115                 120                 125

Tyr Gly Ala Gly Asp Val Tyr Gly Asn Gly His Met His Gly Gly Gly
    130                 135                 140

Asn Val Tyr Ala Asn Gly Asp Ile Tyr Tyr Pro Arg Pro Thr Ala Phe
145                 150                 155                 160

Pro Met Asp Phe Arg Ile Cys Ala Gly Cys Asn Met Glu Ile Gly His
                165                 170                 175

Gly Arg Tyr Leu Asn Cys Leu Asn Ala Leu Trp His Pro Glu Cys Phe
            180                 185                 190

Arg Cys Tyr Gly Cys Arg His Pro Ile Ser Glu Tyr Glu Phe Ser Thr
        195                 200                 205

Ser Gly Asn Tyr Pro Phe His Lys Ala Cys Tyr Arg Glu Arg Tyr His
    210                 215                 220

Pro Lys Cys Asp Val Cys Ser Leu Phe Ile Pro Thr Asn His Ala Gly
225                 230                 235                 240

Leu Ile Glu Tyr Arg Ala His Pro Phe Trp Val Gln Lys Tyr Cys Pro
                245                 250                 255

Ser His Glu His Asp Ala Thr Pro Arg Cys Cys Ser Cys Glu Arg Met
            260                 265                 270

Glu Pro Arg Asn Thr Gly Tyr Val Glu Leu Asn Asp Gly Arg Lys Leu
        275                 280                 285

Cys Leu Glu Cys Leu Asp Ser Ala Val Met Asp Thr Phe Gln Cys Gln
    290                 295                 300

Pro Leu Tyr Leu Gln Ile Gln Glu Phe Tyr Glu Gly Leu Phe Met Lys
305                 310                 315                 320
```

```
Val Glu Gln Asp Val Pro Leu Leu Leu Val Glu Arg Gln Ala Leu Asn
                325                 330                 335

Glu Ala Arg Glu Gly Glu Lys Asn Gly His Tyr His Met Pro Glu Thr
            340                 345                 350

Arg Gly Leu Cys Leu Ser Glu Glu Gln Thr Val Ser Thr Val Arg Lys
        355                 360                 365

Arg Ser Lys His Gly Thr Gly Asn Trp Ala Gly Asn Met Ile Thr Glu
370                 375                 380

Pro Tyr Lys Leu Thr Arg Gln Cys Glu Val Thr Ala Ile Leu Ile Leu
385                 390                 395                 400

Phe Gly Leu Pro Arg Leu Leu Thr Gly Ser Ile Leu Ala His Glu Met
                405                 410                 415

Met His Ala Trp Met Arg Leu Lys Gly Phe Arg Thr Leu Ser Gln Asp
            420                 425                 430

Val Glu Glu Gly Ile Cys Gln Val Met Ala His Lys Trp Leu Glu Ala
        435                 440                 445

Glu Leu Ala Ala Gly Ser Arg Asn Ser Asn Val Ala Ser Ser Ser Ser
    450                 455                 460

Ser Arg Gly Val Lys Lys Gly Pro Arg Ser Gln Tyr Glu Arg Lys Leu
465                 470                 475                 480

Gly Glu Phe Phe Lys His Gln Ile Glu Ser Asp Ala Ser Pro Val Tyr
                485                 490                 495

Gly Asp Gly Phe Arg Ala Gly Arg Leu Ala Val Asn Lys Tyr Gly Leu
            500                 505                 510

Pro Lys Thr Leu Glu His Ile Gln Met Thr Gly Arg Phe Pro Val
        515                 520                 525

<210> SEQ ID NO 9
<211> LENGTH: 2250
<212> TYPE: DNA
<213> ORGANISM: Brassica napus
<220> FEATURE:
<221> NAME/KEY: exon
<222> LOCATION: (1)..(165)
<223> OTHER INFORMATION: Exon 1
<220> FEATURE:
<221> NAME/KEY: exon
<222> LOCATION: (333)..(435)
<223> OTHER INFORMATION: Exon 2
<220> FEATURE:
<221> NAME/KEY: exon
<222> LOCATION: (547)..(736)
<223> OTHER INFORMATION: Exon 3
<220> FEATURE:
<221> NAME/KEY: exon
<222> LOCATION: (823)..(943)
<223> OTHER INFORMATION: Exon 4
<220> FEATURE:
<221> NAME/KEY: exon
<222> LOCATION: (1034)..(1117)
<223> OTHER INFORMATION: Exon 5
<220> FEATURE:
<221> NAME/KEY: exon
<222> LOCATION: (1200)..(1532)
<223> OTHER INFORMATION: Exon 6-7
<220> FEATURE:
<221> NAME/KEY: mutation
<222> LOCATION: (1425)..(1425)
<223> OTHER INFORMATION: C=>T in YIIN 610
<220> FEATURE:
<221> NAME/KEY: exon
<222> LOCATION: (1622)..(1853)
<223> OTHER INFORMATION: Exon 8-9
<220> FEATURE:
<221> NAME/KEY: mutation
```

<222> LOCATION: (1670)..(1670)
<223> OTHER INFORMATION: C=>T in YIIN 612
<220> FEATURE:
<221> NAME/KEY: exon
<222> LOCATION: (1943)..(2250)
<223> OTHER INFORMATION: Exon 10
<220> FEATURE:
<221> NAME/KEY: mutation
<222> LOCATION: (1960)..(1960)
<223> OTHER INFORMATION: C=>T in YIIN 611
<220> FEATURE:
<221> NAME/KEY: mutation
<222> LOCATION: (2004)..(2004)
<223> OTHER INFORMATION: G=>A in YIIN 613

<400> SEQUENCE: 9

```
atg ggt tgg tta aac aag atc ttc aaa ggc tct aac caa agg ccc ccc        48
Met Gly Trp Leu Asn Lys Ile Phe Lys Gly Ser Asn Gln Arg Pro Pro
1               5                   10                  15 gtg ggg aat gag tac tat cat cat aat ggc ggc tat tac gag aac tac        96
Val Gly Asn Glu Tyr Tyr His His Asn Gly Gly Tyr Tyr Glu Asn Tyr
            20                  25                  30 ccg cac gaa cat tct gag cct agt gca gag aca gat gct gat cat acg       144
Pro His Glu His Ser Glu Pro Ser Ala Glu Thr Asp Ala Asp His Thr
        35                  40                  45 cag gaa cca tct act tct gag gttactatat gctgattgaa tatttgatag          195
Gln Glu Pro Ser Thr Ser Glu
    50                  55 cttttgtttt atagtttttt tttctgattt aggagatctc aaaaatagtc aaataaatca     255
tattagtctc catttatcag ataatggttt gtagtgtaac ctcaaaattt tgttgttttt     315 tttttttactt ttactag gaa gag aca tgg aat ggg cag gaa aat gaa gaa       365
                    Glu Glu Thr Trp Asn Gly Gln Glu Asn Glu Glu
                                60                  65 gta gac cgt gca att gca ttg tct att tta gaa gaa gag aat caa gga       413
Val Asp Arg Ala Ile Ala Leu Ser Ile Leu Glu Glu Glu Asn Gln Gly
            70                  75                  80 cca gag act aat aca ggc gcc t gtgagttaca ttttactgat tgttttagcc       465
Pro Glu Thr Asn Thr Gly Ala
        85 caaaacagaa taatatgaaa gaaaaaaaga tagttttgtt tcatacattt tgaaaaaaat     525 aaaataaaaa atgaaaagca g gg aaa cac gca atg atg gat gac gat gag        575
                        Trp Lys His Ala Met Met Asp Asp Asp Glu
                            90                  95 cag ctt gct aga gcc ata caa gag agt atg ata gtt agg aat gga act       623
Gln Leu Ala Arg Ala Ile Gln Glu Ser Met Ile Val Arg Asn Gly Thr
100                 105                 110                 115 act tat gac ttt ggg aat gca tat ggg aat gga cat atg cat gga gga       671
Thr Tyr Asp Phe Gly Asn Ala Tyr Gly Asn Gly His Met His Gly Gly
                120                 125                 130 ggc aat gta tat gac agt ggt gat att tat tat cca aga cct att gct       719
Gly Asn Val Tyr Asp Ser Gly Asp Ile Tyr Tyr Pro Arg Pro Ile Ala
            135                 140                 145 ttc tca atg gac ttc ag gtttcactta gatggccttt taattttggt              766
Phe Ser Met Asp Phe Arg
            150 tgatgtgtta tagtttcttt tagctttta tcaacaactt gtcactactg gcatag g        823 att tgt gct ggc tgc aat atg gag att ggc cat gga aga tat ctg aat      871
Ile Cys Ala Gly Cys Asn Met Glu Ile Gly His Gly Arg Tyr Leu Asn
    155                 160                 165 tgc atc aac gca cta tgg cat cca caa tgt ttt cga tgt cat ggc tgc      919
Cys Ile Asn Ala Leu Trp His Pro Gln Cys Phe Arg Cys His Gly Cys
```

```
                170              175              180              185
agt cac cca atc tct gag tac gag gtgaactcaa attcattctt tccgttgtag     973
Ser His Pro Ile Ser Glu Tyr Glu
                190 tttaaccttt gaatcaatgt aataacatgt tttccttctt ttcttttgg tcttaaatag    1033 ttc tca acg tct ggg aac tac cct ttt cac aaa gct tgt tac agg gag     1081
Phe Ser Thr Ser Gly Asn Tyr Pro Phe His Lys Ala Cys Tyr Arg Glu
    195              200              205 agg ttt cat cca aaa tgt gat gtc tgc agc ctc ttt gtatgtaaaa          1127
Arg Phe His Pro Lys Cys Asp Val Cys Ser Leu Phe
210              215              220 tctttacccc ttttccgttg ttttcttcg gatattgcac ttatcttatg ttactttctt    1187
ttcttgtgac ag att cca acg aac cat gct ggt ctt ata gag tat aga gca   1238
             Ile Pro Thr Asn His Ala Gly Leu Ile Glu Tyr Arg Ala
                           225              230 cat cct ttc tgg gtc cag aag tat tgc cca tct cac gaa cac gat gct     1286
His Pro Phe Trp Val Gln Lys Tyr Cys Pro Ser His Glu His Asp Ala
235              240              245              250 act cct aga tgt tgc agt tgt gaa aga atg gag tca cgg aat aca gga     1334
Thr Pro Arg Cys Cys Ser Cys Glu Arg Met Glu Ser Arg Asn Thr Gly
             255              260              265 tat ttt gaa ctc aac gat gga cgg aag ctt tgc ctt gag tgt cta gac     1382
Tyr Phe Glu Leu Asn Asp Gly Arg Lys Leu Cys Leu Glu Cys Leu Asp
             270              275              280 tca tcg gtg atg gac act ttt caa tgc cag cct ctg tac ttg cag ata     1430
Ser Ser Val Met Asp Thr Phe Gln Cys Gln Pro Leu Tyr Leu Gln Ile
             285              290              295 caa gag ttc tac gaa gga ctt aac atg acg gta gag cag gag gtt cca     1478
Gln Glu Phe Tyr Glu Gly Leu Asn Met Thr Val Glu Gln Glu Val Pro
    300              305              310 ctt ctc ttg gtt gag agg caa gca ctt aac gaa gcc aga gaa ggt gaa     1526
Leu Leu Leu Val Glu Arg Gln Ala Leu Asn Glu Ala Arg Glu Gly Glu
315              320              325              330 agg aat gtgagtagaa caaaaaaaat acaaatttac tttagtaact atttgagaat      1582
Arg Asn gtgtcacatt tatattgtgt cattgtgtgc tttctttag ggt cac tat cac atg      1636
                                           Gly His Tyr His Met
                                                       335 cca gag aca aga gga ctc tgc ctt tca gag gaa caa act gtt aga act     1684
Pro Glu Thr Arg Gly Leu Cys Leu Ser Glu Glu Gln Thr Val Arg Thr
             340              345              350 gtg aga aag aga tcg aag gga aac tgg agt ggg aat atg att aca gag     1732
Val Arg Lys Arg Ser Lys Gly Asn Trp Ser Gly Asn Met Ile Thr Glu
355              360              365 caa ttc aag cta act cgc cgg tgc gag gtt act gcc att ctc atc tta     1780
Gln Phe Lys Leu Thr Arg Arg Cys Glu Val Thr Ala Ile Leu Ile Leu
370              375              380              385 ttt ggt ctc cct agg cta ctc acc ggt tcg att cta gct cat gag atg     1828
Phe Gly Leu Pro Arg Leu Leu Thr Gly Ser Ile Leu Ala His Glu Met
             390              395              400 atg cac gcg tgg atg cgg ctc aaa g gtgagtttct tgcttcttgt             1873
Met His Ala Trp Met Arg Leu Lys
             405 ttcttatcta actgcttctc ttgtttcacg tttgttgaac cgttactaca atgtgtggtc   1933 ttgaaaaag gg ttc cgg aca ctg agc caa gat gtt gaa gag ggg ata tgt    1983
            Gly Phe Arg Thr Leu Ser Gln Asp Val Glu Glu Gly Ile Cys
                410              415              420
```

| | | |
|---|---|---|
| caa gtg atg gct cat aag tgg tta gaa gtt gag ttg gct gct ggg tct<br>Gln Val Met Ala His Lys Trp Leu Glu Val Glu Leu Ala Ala Gly Ser<br>425                430                435 | | 2031 |
| aga aac agc aac gct gca tca tct tct tat gga gga gtg aag aag gga<br>Arg Asn Ser Asn Ala Ala Ser Ser Ser Tyr Gly Gly Val Lys Lys Gly<br>440                445               450               455 | | 2079 |
| cca aag tcg cag tac gag agg aag ctt ggt gag ttt ttc aag cac cag<br>Pro Lys Ser Gln Tyr Glu Arg Lys Leu Gly Glu Phe Phe Lys His Gln<br>             460               465               470 | | 2127 |
| ata gag tct gat gct tct ccg gtt tat gga gat ggg ttc agg gcc ggg<br>Ile Glu Ser Asp Ala Ser Pro Val Tyr Gly Asp Gly Phe Arg Ala Gly<br>475               480              485 | | 2175 |
| agg tta gca gtt agc aag tat ggt ttg agg aga aca ctt gag cat ata<br>Arg Leu Ala Val Ser Lys Tyr Gly Leu Arg Arg Thr Leu Glu His Ile<br>490               495               500 | | 2223 |
| caa atg act ggg aga ttc ccg gtt taa<br>Gln Met Thr Gly Arg Phe Pro Val<br>505               510 | | 2250 |

<210> SEQ ID NO 10
<211> LENGTH: 1536
<212> TYPE: DNA
<213> ORGANISM: Brassica napus
<220> FEATURE:
<221> NAME/KEY: CDS
<222> LOCATION: (1)..(1536)
<220> FEATURE:
<221> NAME/KEY: mutation
<222> LOCATION: (889)..(889)
<223> OTHER INFORMATION: C=>T in YIIN610
<220> FEATURE:
<221> NAME/KEY: mutation
<222> LOCATION: (1045)..(1045)
<223> OTHER INFORMATION: C=>T in YIIN612
<220> FEATURE:
<221> NAME/KEY: mutation
<222> LOCATION: (1246)..(1246)
<223> OTHER INFORMATION: C=>T in YIIN611
<220> FEATURE:
<221> NAME/KEY: mutation
<222> LOCATION: (1290)..(1290)
<223> OTHER INFORMATION: C=>T in YIIN613

<400> SEQUENCE: 10

| | | |
|---|---|---|
| atg ggt tgg tta aac aag atc ttc aaa ggc tct aac caa agg ccc ccc<br>Met Gly Trp Leu Asn Lys Ile Phe Lys Gly Ser Asn Gln Arg Pro Pro<br>1                 5                 10                15 | | 48 |
| gtg ggg aat gag tac tat cat cat aat ggc ggc tat tac gag aac tac<br>Val Gly Asn Glu Tyr Tyr His His Asn Gly Gly Tyr Tyr Glu Asn Tyr<br>             20               25               30 | | 96 |
| ccg cac gaa cat tct gag cct agt gca gag aca gat gct gat cat acg<br>Pro His Glu His Ser Glu Pro Ser Ala Glu Thr Asp Ala Asp His Thr<br>                 35               40               45 | | 144 |
| cag gaa cca tct act tct gag gaa gag aca tgg aat ggg cag gaa aat<br>Gln Glu Pro Ser Thr Ser Glu Glu Glu Thr Trp Asn Gly Gln Glu Asn<br>50               55               60 | | 192 |
| gaa gaa gta gac cgt gca att gca ttg tct att tta gaa gaa gag aat<br>Glu Glu Val Asp Arg Ala Ile Ala Leu Ser Ile Leu Glu Glu Glu Asn<br>65               70               75               80 | | 240 |
| caa gga cca gag act aat aca ggc gcc tgg aaa cac gca atg atg gat<br>Gln Gly Pro Glu Thr Asn Thr Gly Ala Trp Lys His Ala Met Met Asp<br>              85               90               95 | | 288 |
| gac gat gag cag ctt gct aga gcc ata caa gag agt atg ata gtt agg<br>Asp Asp Glu Gln Leu Ala Arg Ala Ile Gln Glu Ser Met Ile Val Arg<br>               100              105              110 | | 336 |

-continued

| | | |
|---|---|---|
| aat gga act act tat gac ttt ggg aat gca tat ggg aat gga cat atg<br>Asn Gly Thr Thr Tyr Asp Phe Gly Asn Ala Tyr Gly Asn Gly His Met<br>115                    120                   125 | 384 |
| cat gga gga ggc aat gta tat gac agt ggt gat att tat tat cca aga<br>His Gly Gly Gly Asn Val Tyr Asp Ser Gly Asp Ile Tyr Tyr Pro Arg<br>130                    135                   140 | 432 |
| cct att gct ttc tca atg gac ttc agg att tgt gct ggc tgc aat atg<br>Pro Ile Ala Phe Ser Met Asp Phe Arg Ile Cys Ala Gly Cys Asn Met<br>145                      150                   155                   160 | 480 |
| gag att ggc cat gga aga tat ctg aat tgc atc aac gca cta tgg cat<br>Glu Ile Gly His Gly Arg Tyr Leu Asn Cys Ile Asn Ala Leu Trp His<br>                   165                   170                   175 | 528 |
| cca caa tgt ttt cga tgt cat ggc tgc agt cac cca atc tct gag tac<br>Pro Gln Cys Phe Arg Cys His Gly Cys Ser His Pro Ile Ser Glu Tyr<br>                   180                   185                   190 | 576 |
| gag ttc tca acg tct ggg aac tac cct ttt cac aaa gct tgt tac agg<br>Glu Phe Ser Thr Ser Gly Asn Tyr Pro Phe His Lys Ala Cys Tyr Arg<br>                   195                   200                   205 | 624 |
| gag agg ttt cat cca aaa tgt gat gtc tgc agc ctc ttt att cca acg<br>Glu Arg Phe His Pro Lys Cys Asp Val Cys Ser Leu Phe Ile Pro Thr<br>210                    215                   220 | 672 |
| aac cat gct ggt ctt ata gag tat aga gca cat cct ttc tgg gtc cag<br>Asn His Ala Gly Leu Ile Glu Tyr Arg Ala His Pro Phe Trp Val Gln<br>225                      230                   235                   240 | 720 |
| aag tat tgc cca tct cac gaa cac gat gct act cct aga tgt tgc agt<br>Lys Tyr Cys Pro Ser His Glu His Asp Ala Thr Pro Arg Cys Cys Ser<br>                   245                   250                   255 | 768 |
| tgt gaa aga atg gag tca cgg aat aca gga tat ttt gaa ctc aac gat<br>Cys Glu Arg Met Glu Ser Arg Asn Thr Gly Tyr Phe Glu Leu Asn Asp<br>                   260                   265                   270 | 816 |
| gga cgg aag ctt tgc ctt gag tgt cta gac tca tcg gtg atg gac act<br>Gly Arg Lys Leu Cys Leu Glu Cys Leu Asp Ser Ser Val Met Asp Thr<br>                   275                   280                   285 | 864 |
| ttt caa tgc cag cct ctg tac ttg cag ata caa gag ttc tac gaa gga<br>Phe Gln Cys Gln Pro Leu Tyr Leu Gln Ile Gln Glu Phe Tyr Glu Gly<br>290                    295                   300 | 912 |
| ctt aac atg acg gta gag cag gag gtt cca ctt ctc ttg gtt gag agg<br>Leu Asn Met Thr Val Glu Gln Glu Val Pro Leu Leu Leu Val Glu Arg<br>305                    310                   315                   320 | 960 |
| caa gca ctt aac gaa gcc aga gaa ggt gaa agg aat ggt cac tat cac<br>Gln Ala Leu Asn Glu Ala Arg Glu Gly Glu Arg Asn Gly His Tyr His<br>                   325                   330                   335 | 1008 |
| atg cca gag aca aga gga ctc tgc ctt tca gag gaa caa act gtt aga<br>Met Pro Glu Thr Arg Gly Leu Cys Leu Ser Glu Glu Gln Thr Val Arg<br>                   340                   345                   350 | 1056 |
| act gtg aga aag aga tcg aag gga aac tgg agt ggg aat atg att aca<br>Thr Val Arg Lys Arg Ser Lys Gly Asn Trp Ser Gly Asn Met Ile Thr<br>355                    360                   365 | 1104 |
| gag caa ttc aag cta act cgc cgg tgc gag gtt act gcc att ctc atc<br>Glu Gln Phe Lys Leu Thr Arg Arg Cys Glu Val Thr Ala Ile Leu Ile<br>370                    375                   380 | 1152 |
| tta ttt ggt ctc cct agg cta ctc acc ggt tcg att cta gct cat gag<br>Leu Phe Gly Leu Pro Arg Leu Leu Thr Gly Ser Ile Leu Ala His Glu<br>385                    390                   395                   400 | 1200 |
| atg atg cac gcg tgg atg cgg ctc aaa ggg ttc cgg aca ctg agc caa<br>Met Met His Ala Trp Met Arg Leu Lys Gly Phe Arg Thr Leu Ser Gln<br>                   405                   410                   415 | 1248 |
| gat gtt gaa gag ggg ata tgt caa gtg atg gct cat aag tgg tta gaa<br>Asp Val Glu Glu Gly Ile Cys Gln Val Met Ala His Lys Trp Leu Glu<br>420                    425                   430 | 1296 |

```
gtt gag ttg gct gct ggg tct aga aac agc aac gct gca tca tct tct    1344
Val Glu Leu Ala Ala Gly Ser Arg Asn Ser Asn Ala Ala Ser Ser Ser
            435                 440                 445 tat gga gga gtg aag aag gga cca aag tcg cag tac gag agg aag ctt    1392
Tyr Gly Gly Val Lys Lys Gly Pro Lys Ser Gln Tyr Glu Arg Lys Leu
        450                 455                 460 ggt gag ttt ttc aag cac cag ata gag tct gat gct tct ccg gtt tat    1440
Gly Glu Phe Phe Lys His Gln Ile Glu Ser Asp Ala Ser Pro Val Tyr
465                 470                 475                 480 gga gat ggg ttc agg gcc ggg agg tta gca gtt agc aag tat ggt ttg    1488
Gly Asp Gly Phe Arg Ala Gly Arg Leu Ala Val Ser Lys Tyr Gly Leu
                485                 490                 495 agg aga aca ctt gag cat ata caa atg act ggg aga ttc ccg gtt taa    1536
Arg Arg Thr Leu Glu His Ile Gln Met Thr Gly Arg Phe Pro Val
            500                 505                 510

<210> SEQ ID NO 11
<211> LENGTH: 511
<212> TYPE: PRT
<213> ORGANISM: Brassica napus

<400> SEQUENCE: 11

Met Gly Trp Leu Asn Lys Ile Phe Lys Gly Ser Asn Gln Arg Pro Pro
1               5                   10                  15

Val Gly Asn Glu Tyr Tyr His His Asn Gly Tyr Tyr Glu Asn Tyr
            20                  25                  30

Pro His Glu His Ser Glu Pro Ser Ala Glu Thr Asp Ala Asp His Thr
        35                  40                  45

Gln Glu Pro Ser Thr Ser Glu Glu Thr Trp Asn Gly Gln Glu Asn
    50                  55                  60

Glu Glu Val Asp Arg Ala Ile Ala Leu Ser Ile Leu Glu Glu Asn
65                  70                  75                  80

Gln Gly Pro Glu Thr Asn Thr Gly Ala Trp Lys His Ala Met Met Asp
                85                  90                  95

Asp Asp Glu Gln Leu Ala Arg Ala Ile Gln Glu Ser Met Ile Val Arg
            100                 105                 110

Asn Gly Thr Thr Tyr Asp Phe Gly Asn Ala Tyr Gly Asn Gly His Met
        115                 120                 125

His Gly Gly Asn Val Tyr Asp Ser Gly Asp Ile Tyr Tyr Pro Arg
    130                 135                 140

Pro Ile Ala Phe Ser Met Asp Phe Arg Ile Cys Ala Gly Cys Asn Met
145                 150                 155                 160

Glu Ile Gly His Gly Arg Tyr Leu Asn Cys Ile Asn Ala Leu Trp His
                165                 170                 175

Pro Gln Cys Phe Arg Cys His Gly Cys Ser His Pro Ile Ser Glu Tyr
            180                 185                 190

Glu Phe Ser Thr Ser Gly Asn Tyr Pro Phe His Lys Ala Cys Tyr Arg
        195                 200                 205

Glu Arg Phe His Pro Lys Cys Asp Val Cys Ser Leu Phe Ile Pro Thr
    210                 215                 220

Asn His Ala Gly Leu Ile Glu Tyr Arg Ala His Pro Phe Trp Val Gln
225                 230                 235                 240

Lys Tyr Cys Pro Ser His Glu His Asp Ala Thr Pro Arg Cys Cys Ser
                245                 250                 255

Cys Glu Arg Met Glu Ser Arg Asn Thr Gly Tyr Phe Glu Leu Asn Asp
            260                 265                 270
```

```
Gly Arg Lys Leu Cys Leu Glu Cys Leu Asp Ser Ser Val Met Asp Thr
            275                 280                 285

Phe Gln Cys Gln Pro Leu Tyr Leu Gln Ile Gln Glu Phe Tyr Glu Gly
            290                 295                 300

Leu Asn Met Thr Val Glu Gln Glu Val Pro Leu Leu Leu Val Glu Arg
305                 310                 315                 320

Gln Ala Leu Asn Glu Ala Arg Glu Gly Glu Arg Asn Gly His Tyr His
            325                 330                 335

Met Pro Glu Thr Arg Gly Leu Cys Leu Ser Glu Gln Thr Val Arg
            340                 345                 350

Thr Val Arg Lys Arg Ser Lys Gly Asn Trp Ser Gly Asn Met Ile Thr
            355                 360                 365

Glu Gln Phe Lys Leu Thr Arg Arg Cys Glu Val Thr Ala Ile Leu Ile
            370                 375                 380

Leu Phe Gly Leu Pro Arg Leu Leu Thr Gly Ser Ile Leu Ala His Glu
385                 390                 395                 400

Met Met His Ala Trp Met Arg Leu Lys Gly Phe Arg Thr Leu Ser Gln
            405                 410                 415

Asp Val Glu Glu Gly Ile Cys Gln Val Met Ala His Lys Trp Leu Glu
            420                 425                 430

Val Glu Leu Ala Ala Gly Ser Arg Asn Ser Asn Ala Ala Ser Ser Ser
            435                 440                 445

Tyr Gly Gly Val Lys Lys Gly Pro Lys Ser Gln Tyr Glu Arg Lys Leu
            450                 455                 460

Gly Glu Phe Phe Lys His Gln Ile Glu Ser Asp Ala Ser Pro Val Tyr
465                 470                 475                 480

Gly Asp Gly Phe Arg Ala Gly Arg Leu Ala Val Ser Lys Tyr Gly Leu
            485                 490                 495

Arg Arg Thr Leu Glu His Ile Gln Met Thr Gly Arg Phe Pro Val
            500                 505                 510

<210> SEQ ID NO 12
<211> LENGTH: 2286
<212> TYPE: DNA
<213> ORGANISM: Brassica napus
<220> FEATURE:
<221> NAME/KEY: exon
<222> LOCATION: (1)..(171)
<223> OTHER INFORMATION: Exon 1
<220> FEATURE:
<221> NAME/KEY: exon
<222> LOCATION: (247)..(340)
<223> OTHER INFORMATION: Exon 2
<220> FEATURE:
<221> NAME/KEY: exon
<222> LOCATION: (425)..(650)
<223> OTHER INFORMATION: Exon 3
<220> FEATURE:
<221> NAME/KEY: exon
<222> LOCATION: (735)..(855)
<223> OTHER INFORMATION: Exon 4
<220> FEATURE:
<221> NAME/KEY: exon
<222> LOCATION: (939)..(1022)
<223> OTHER INFORMATION: Exon 5
<220> FEATURE:
<221> NAME/KEY: exon
<222> LOCATION: (1151)..(1270)
<223> OTHER INFORMATION: Exon 6
<220> FEATURE:
<221> NAME/KEY: exon
<222> LOCATION: (1356)..(1568)
<223> OTHER INFORMATION: Exon 7
```

```
<220> FEATURE:
<221> NAME/KEY: exon
<222> LOCATION: (1662)..(1902)
<223> OTHER INFORMATION: Exon 8-9
<220> FEATURE:
<221> NAME/KEY: exon
<222> LOCATION: (1970)..(2286)
<223> OTHER INFORMATION: Exon 10
<220> FEATURE:
<221> NAME/KEY: mutation
<222> LOCATION: (2011)..(2011)
<223> OTHER INFORMATION: C=>T in YIIN614/YIIN615

<400> SEQUENCE: 12
```

```
atg ggt tgg ttt aac aag atc ttc aaa ggc tct acc caa agg ttc cgg       48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat       96
Leu Gly Asn Asp His Asp His Asn Gly Tyr Tyr Gln Ser Tyr Pro His
            20                  25                  30 gat gag cct agt gct gat act gat cct gat cct gat cct gat gaa act      144
Asp Glu Pro Ser Ala Asp Thr Asp Pro Asp Pro Asp Pro Asp Glu Thr
        35                  40                  45 cat act cag gaa cca tct acc tct gag gttactataa ctgtctttac            191
His Thr Gln Glu Pro Ser Thr Ser Glu
    50                  55 atatctctgg ctgcttgtac tgttgcttca acattttttt gtttcccttt actag gag     249
                                                              Glu gat aca tcc ggc cag gag aat gac gac att gac cgt gct atc gca ttg      297
Asp Thr Ser Gly Gln Glu Asn Asp Asp Ile Asp Arg Ala Ile Ala Leu
        60                  65                  70 tct ctt ata gaa aac agt caa gga cat act aac aca ggc gcc g            340
Ser Leu Ile Glu Asn Ser Gln Gly His Thr Asn Thr Gly Ala
75                  80                  85 gtgagtcctt tttccttgcc aaactagaaa gaaatatgaa ttatgaaact cggtttgtta    400
catttaacag aatagtgaac gcag gg  aag tac gca atg gtg gat gaa gat       450
                             Gly Lys Tyr Ala Met Val Asp Glu Asp
                                             90                  95 gag cag ctt gct aga gcc ata caa gag agc atg gta gtt ggg aat aca      498
Glu Gln Leu Ala Arg Ala Ile Gln Glu Ser Met Val Val Gly Asn Thr
        100                 105                 110 ccg cgt cag aag cat gga agc agt tat gat att ggg aac gca tat ggt      546
Pro Arg Gln Lys His Gly Ser Ser Tyr Asp Ile Gly Asn Ala Tyr Gly
    115                 120                 125 gct gga gac gta tac ggg aat gga cat atg cat gga ggt gga aat gtt      594
Ala Gly Asp Val Tyr Gly Asn Gly His Met His Gly Gly Gly Asn Val
130                 135                 140                 145 tat gcc aat gga gac att tat tat cca aga cct act gct ttt cct atg      642
Tyr Ala Asn Gly Asp Ile Tyr Tyr Pro Arg Pro Thr Ala Phe Pro Met
            150                 155                 160 gat ttc ag  gttcactttt gatactcaat taatcatctg tagcctgttt              690
Asp Phe Arg aacttggttg agatgtgtta ataaacttat caagaacacc ttag g att tgt gct       744
                                                 Ile Cys Ala
                                                     165 ggc tgc aat atg gag att ggg cat gga aga tat ctg aat tgc ttg aat      792
Gly Cys Asn Met Glu Ile Gly His Gly Arg Tyr Leu Asn Cys Leu Asn
            170                 175                 180 gca ctg tgg cat ccg gaa tgt ttt cga tgc tat ggc tgt agg cac ccc      840
Ala Leu Trp His Pro Glu Cys Phe Arg Cys Tyr Gly Cys Arg His Pro
        185                 190                 195
```

```
att tct gag tac gag gtgaaatcaa gctttctcat tctttctttt gtagttaacc      895
Ile Ser Glu Tyr Glu
200 tttgatgtaa tgaataacat gttttccttt tttttcttaa tag ttc tca aca tct      950
                                             Phe Ser Thr Ser
                                                 205 ggg aac tac cct ttc cac aaa gct tgt tat agg gag aga tac cat cca      998
Gly Asn Tyr Pro Phe His Lys Ala Cys Tyr Arg Glu Arg Tyr His Pro
210             215                 220 aaa tgt gat gtc tgc agc ctc ttt gtatgtaaat ctttagtctt tgttttccat    1052
Lys Cys Asp Val Cys Ser Leu Phe
225             230 cattaaagtg cctatttatg cgttgtttct ttcggatagt gcacttatta tatcttctgt   1112
tgattttctt gttttcgaat gtaaatttgt tgtgacag att cca aca aac cat gct   1168
                                         Ile Pro Thr Asn His Ala
                                                         235 ggt ctt att gaa tat agg gca cat cct ttt tgg gtc cag aag tac tgc     1216
Gly Leu Ile Glu Tyr Arg Ala His Pro Phe Trp Val Gln Lys Tyr Cys
        240                 245                 250 cct tct cac gaa cac gat gct acc cca aga tgt tgc agt tgc gaa aga    1264
Pro Ser His Glu His Asp Ala Thr Pro Arg Cys Cys Ser Cys Glu Arg
255             260                 265                 270 atg gag gtgagttttt ctccccaaaa tgtgtcccac aacaaacatc tgctcaaagt     1320
Met Glu cgaaatgtca actttcgttt tttttttctt tgtag cca cgg aat aca gga tat     1373
                                       Pro Arg Asn Thr Gly Tyr
                                                       275 gtt gaa ctt aac gat gga cgg aaa ctt tgc ctg gag tgt ctg gac tca    1421
Val Glu Leu Asn Asp Gly Arg Lys Leu Cys Leu Glu Cys Leu Asp Ser
280             285                 290 gca gtc atg gac act ttt caa tgc caa cct ctg tat ctg cag ata caa    1469
Ala Val Met Asp Thr Phe Gln Cys Gln Pro Leu Tyr Leu Gln Ile Gln
295             300                 305                 310 gaa ttc tat gaa ggg ctt ttc atg aag gta gag cag gac gtt cca ctt    1517
Glu Phe Tyr Glu Gly Leu Phe Met Lys Val Glu Gln Asp Val Pro Leu
            315                 320                 325 ctt tta gtt gag agg caa gca ctc aac gaa gcc aga gaa ggt gaa aag    1565
Leu Leu Val Glu Arg Gln Ala Leu Asn Glu Ala Arg Glu Gly Glu Lys
        330                 335                 340 aat gtgagtagca aaagaaaaa cacaattata cttcagtaca tatatcacct          1618
Asn tttttcacaa gtgttttaag cttttcattg tgtgcttcct tag ggt cac tat cac    1673
                                                Gly His Tyr His
                                                        345 atg cca gag acg aga gga ctc tgc ctt tca gaa gaa caa act gtt agc    1721
Met Pro Glu Thr Arg Gly Leu Cys Leu Ser Glu Glu Gln Thr Val Ser
        350                 355                 360 act gtg aga aag aga tcg aag cat ggc aca gga aac tgg gct ggg aat    1769
Thr Val Arg Lys Arg Ser Lys His Gly Thr Gly Asn Trp Ala Gly Asn
365             370                 375 atg att aca gag cct tac aag tta aca cgt caa tgc gag gtt act gcc    1817
Met Ile Thr Glu Pro Tyr Lys Leu Thr Arg Gln Cys Glu Val Thr Ala
380             385                 390                 395 att ctc atc ttg ttt ggg ctc cct agg cta ctc acc ggt tcg att cta    1865
Ile Leu Ile Leu Phe Gly Leu Pro Arg Leu Leu Thr Gly Ser Ile Leu
            400                 405                 410 gct cat gag atg atg cac gcg tgg atg cgg ctc aaa g gtgagtttct       1912
Ala His Glu Met Met His Ala Trp Met Arg Leu Lys
            415                 420
```

```
tagttcactg cttctctttt tttcacattg ttgaatctct attgtggtct tgaaaag       1969 ga  ttc cgg acg ctg agc caa gac gtt gaa gaa gga ata tgt caa gta      2016
Gly Phe Arg Thr Leu Ser Gln Asp Val Glu Glu Gly Ile Cys Gln Val
        425                 430                 435 atg gct cat aag tgg ttg gaa gca gag tta gct gct ggt tca aga aac      2064
Met Ala His Lys Trp Leu Glu Ala Glu Leu Ala Ala Gly Ser Arg Asn
440                 445                 450                 455 agc aat gtt gca tca tca tca tct tct tct tct gga gga ttg aag aag      2112
Ser Asn Val Ala Ser Ser Ser Ser Ser Ser Ser Gly Gly Leu Lys Lys
                460                 465                 470 gga cca aga tcg caa tac gag agg aag ctt ggt gag ttt ttc aag cac      2160
Gly Pro Arg Ser Gln Tyr Glu Arg Lys Leu Gly Glu Phe Phe Lys His
        475                 480                 485 caa atc gag tct gat gct tct ccg gtt tat gga gac ggg ttc agg gct      2208
Gln Ile Glu Ser Asp Ala Ser Pro Val Tyr Gly Asp Gly Phe Arg Ala
                490                 495                 500 ggg agg tta gcg gtt aac aag tat ggt ttg ccg aaa aca ctt gag cat      2256
Gly Arg Leu Ala Val Asn Lys Tyr Gly Leu Pro Lys Thr Leu Glu His
        505                 510                 515 ata cat atg acc ggt aga ttc ccg gtt taa                              2286
Ile His Met Thr Gly Arg Phe Pro Val
520                 525

<210> SEQ ID NO 13
<211> LENGTH: 1587
<212> TYPE: DNA
<213> ORGANISM: Brassica napus
<220> FEATURE:
<221> NAME/KEY: CDS
<222> LOCATION: (1)..(1587)
<220> FEATURE:
<221> NAME/KEY: mutation
<222> LOCATION: (1312)..(1312)
<223> OTHER INFORMATION: C=>T in YIIN614/YIIN615

<400> SEQUENCE: 13 atg ggt tgg ttt aac aag atc ttc aaa ggc tct acc caa agg ttc cgg       48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat       96
Leu Gly Asn Asp His Asp His Asn Gly Tyr Tyr Gln Ser Tyr Pro His
                20                  25                  30 gat gag cct agt gct gat act gat cct gat cct gat cct gat gaa act      144
Asp Glu Pro Ser Ala Asp Thr Asp Pro Asp Pro Asp Pro Asp Glu Thr
            35                  40                  45 cat act cag gaa cca tct acc tct gag gag gat aca tcc ggc cag gag      192
His Thr Gln Glu Pro Ser Thr Ser Glu Glu Asp Thr Ser Gly Gln Glu
        50                  55                  60 aat gac gac att gac cgt gct atc gca ttg tct ctt ata gaa aac agt      240
Asn Asp Asp Ile Asp Arg Ala Ile Ala Leu Ser Leu Ile Glu Asn Ser
65                  70                  75                  80 caa gga cat act aac aca ggc gcc ggg aag tac gca atg gtg gat gaa      288
Gln Gly His Thr Asn Thr Gly Ala Gly Lys Tyr Ala Met Val Asp Glu
                85                  90                  95 gat gag cag ctt gct aga gcc ata caa gag agc atg gta gtt ggg aat      336
Asp Glu Gln Leu Ala Arg Ala Ile Gln Glu Ser Met Val Val Gly Asn
            100                 105                 110 aca ccg cgt cag aag cat gga agc agt tat gat att ggg aac gca tat      384
Thr Pro Arg Gln Lys His Gly Ser Ser Tyr Asp Ile Gly Asn Ala Tyr
        115                 120                 125 ggt gct gga gac gta tac ggg aat gga cat atg cat gga ggt gga aat      432
```

|  |  |  |  |  |  |  |  |  |  |  |  |  |
|---|---|---|---|---|---|---|---|---|---|---|---|---|
| Gly | Ala<br>130 | Gly | Asp | Val | Tyr<br>135 | Gly | Asn | Gly | His<br>140 | Met | His | Gly | Gly | Asn |

| gtt | tat | gcc | aat | gga | gac | att | tat | tat | cca | aga | cct | act | gct | ttt | cct | 480 |
|---|---|---|---|---|---|---|---|---|---|---|---|---|---|---|---|---|
| Val<br>145 | Tyr | Ala | Asn | Gly<br>150 | Asp | Ile | Tyr | Tyr<br>155 | Pro | Arg | Pro | Thr<br>160 | Ala | Phe | Pro | |

| atg | gat | ttc | agg | att | tgt | gct | ggc | tgc | aat | atg | gag | att | ggg | cat | gga | 528 |
|---|---|---|---|---|---|---|---|---|---|---|---|---|---|---|---|---|
| Met | Asp | Phe | Arg<br>165 | Ile | Cys | Ala | Gly | Cys<br>170 | Asn | Met | Glu | Ile<br>175 | Gly | His | Gly | |

| aga | tat | ctg | aat | tgc | ttg | aat | gca | ctg | tgg | cat | ccg | gaa | tgt | ttt | cga | 576 |
|---|---|---|---|---|---|---|---|---|---|---|---|---|---|---|---|---|
| Arg | Tyr | Leu | Asn<br>180 | Cys | Leu | Asn | Ala | Leu<br>185 | Trp | His | Pro | Glu<br>190 | Cys | Phe | Arg | |

| tgc | tat | ggc | tgt | agg | cac | ccc | att | tct | gag | tac | gag | ttc | tca | aca | tct | 624 |
|---|---|---|---|---|---|---|---|---|---|---|---|---|---|---|---|---|
| Cys | Tyr | Gly | Cys<br>195 | Arg | His | Pro | Ile | Ser<br>200 | Glu | Tyr | Glu | Phe<br>205 | Ser | Thr | Ser | |

| ggg | aac | tac | cct | ttc | cac | aaa | gct | tgt | tat | agg | gag | aga | tac | cat | cca | 672 |
|---|---|---|---|---|---|---|---|---|---|---|---|---|---|---|---|---|
| Gly | Asn<br>210 | Tyr | Pro | Phe | His<br>215 | Lys | Ala | Cys | Tyr<br>220 | Arg | Glu | Arg | Tyr | His | Pro | |

| aaa | tgt | gat | gtc | tgc | agc | ctc | ttt | att | cca | aca | aac | cat | gct | ggt | ctt | 720 |
|---|---|---|---|---|---|---|---|---|---|---|---|---|---|---|---|---|
| Lys<br>225 | Cys | Asp | Val | Cys<br>230 | Ser | Leu | Phe | Ile<br>235 | Pro | Thr | Asn | His<br>240 | Ala | Gly | Leu | |

| att | gaa | tat | agg | gca | cat | cct | ttt | tgg | gtc | cag | aag | tac | tgc | cct | tct | 768 |
|---|---|---|---|---|---|---|---|---|---|---|---|---|---|---|---|---|
| Ile | Glu | Tyr | Arg | Ala<br>245 | His | Pro | Phe | Trp<br>250 | Val | Gln | Lys | Tyr<br>255 | Cys | Pro | Ser | |

| cac | gaa | cac | gat | gct | acc | cca | aga | tgt | tgc | agt | tgc | gaa | aga | atg | gag | 816 |
|---|---|---|---|---|---|---|---|---|---|---|---|---|---|---|---|---|
| His | Glu | His | Asp<br>260 | Ala | Thr | Pro | Arg<br>265 | Cys | Cys | Ser | Cys<br>270 | Glu | Arg | Met | Glu | |

| cca | cgg | aat | aca | gga | tat | gtt | gaa | ctt | aac | gat | gga | cgg | aaa | ctt | tgc | 864 |
|---|---|---|---|---|---|---|---|---|---|---|---|---|---|---|---|---|
| Pro | Arg | Asn<br>275 | Thr | Gly | Tyr | Val<br>280 | Glu | Leu | Asn | Asp<br>285 | Gly | Arg | Lys | Leu | Cys | |

| ctg | gag | tgt | ctg | gac | tca | gca | gtc | atg | gac | act | ttt | caa | tgc | caa | cct | 912 |
|---|---|---|---|---|---|---|---|---|---|---|---|---|---|---|---|---|
| Leu | Glu<br>290 | Cys | Leu | Asp | Ser<br>295 | Ala | Val | Met | Asp<br>300 | Thr | Phe | Gln | Cys | Gln | Pro | |

| ctg | tat | ctg | cag | ata | caa | gaa | ttc | tat | gaa | ggg | ctt | ttc | atg | aag | gta | 960 |
|---|---|---|---|---|---|---|---|---|---|---|---|---|---|---|---|---|
| Leu<br>305 | Tyr | Leu | Gln | Ile<br>310 | Gln | Glu | Phe | Tyr<br>315 | Glu | Gly | Leu | Phe<br>320 | Met | Lys | Val | |

| gag | cag | gac | gtt | cca | ctt | ctt | tta | gtt | gag | agg | caa | gca | ctc | aac | gaa | 1008 |
|---|---|---|---|---|---|---|---|---|---|---|---|---|---|---|---|---|
| Glu | Gln | Asp | Val | Pro<br>325 | Leu | Leu | Leu | Val<br>330 | Glu | Arg | Gln | Ala<br>335 | Leu | Asn | Glu | |

| gcc | aga | gaa | ggt | gaa | aag | aat | ggt | cac | tat | cac | atg | cca | gag | acg | aga | 1056 |
|---|---|---|---|---|---|---|---|---|---|---|---|---|---|---|---|---|
| Ala | Arg | Glu | Gly<br>340 | Glu | Lys | Asn | Gly<br>345 | His | Tyr | His | Met<br>350 | Pro | Glu | Thr | Arg | |

| gga | ctc | tgc | ctt | tca | gaa | gaa | caa | act | gtt | agc | act | gtg | aga | aag | aga | 1104 |
|---|---|---|---|---|---|---|---|---|---|---|---|---|---|---|---|---|
| Gly | Leu | Cys<br>355 | Leu | Ser | Glu | Glu<br>360 | Gln | Thr | Val | Ser<br>365 | Thr | Val | Arg | Lys | Arg | |

| tcg | aag | cat | ggc | aca | gga | aac | tgg | gct | ggg | aat | atg | att | aca | gag | cct | 1152 |
|---|---|---|---|---|---|---|---|---|---|---|---|---|---|---|---|---|
| Ser | Lys | His<br>370 | Gly | Thr | Gly | Asn<br>375 | Trp | Ala | Gly | Asn<br>380 | Met | Ile | Thr | Glu | Pro | |

| tac | aag | tta | aca | cgt | caa | tgc | gag | gtt | act | gcc | att | ctc | atc | ttg | ttt | 1200 |
|---|---|---|---|---|---|---|---|---|---|---|---|---|---|---|---|---|
| Tyr<br>385 | Lys | Leu | Thr | Arg<br>390 | Gln | Cys | Glu | Val<br>395 | Thr | Ala | Ile | Leu<br>400 | Ile | Leu | Phe | |

| ggg | ctc | cct | agg | cta | ctc | acc | ggt | tcg | att | cta | gct | cat | gag | atg | atg | 1248 |
|---|---|---|---|---|---|---|---|---|---|---|---|---|---|---|---|---|
| Gly | Leu | Pro | Arg | Leu<br>405 | Leu | Thr | Gly | Ser<br>410 | Ile | Leu | Ala | His<br>415 | Glu | Met | Met | |

| cac | gcg | tgg | atg | cgg | ctc | aaa | gga | ttc | cgg | acg | ctg | agc | caa | gac | gtt | 1296 |
|---|---|---|---|---|---|---|---|---|---|---|---|---|---|---|---|---|
| His | Ala | Trp | Met<br>420 | Arg | Leu | Lys | Gly<br>425 | Phe | Arg | Thr | Leu<br>430 | Ser | Gln | Asp | Val | |

| gaa | gaa | gga | ata | tgt | caa | gta | atg | gct | cat | aag | tgg | ttg | gaa | gca | gag | 1344 |
|---|---|---|---|---|---|---|---|---|---|---|---|---|---|---|---|---|
| Glu | Glu | Gly | Ile<br>435 | Cys | Gln | Val | Met<br>440 | Ala | His | Lys | Trp<br>445 | Leu | Glu | Ala | Glu | |

| | | | | | | | | | | | | | | | |
|---|---|---|---|---|---|---|---|---|---|---|---|---|---|---|---|
| tta | gct | gct | ggt | tca | aga | aac | agc | aat | gtt | gca | tca | tca | tct | tct | 1392 |
| Leu | Ala | Ala | Gly | Ser | Arg | Asn | Ser | Asn | Val | Ala | Ser | Ser | Ser | Ser | |
| | 450 | | | | 455 | | | | | 460 | | | | | |
| tct | tct | gga | gga | ttg | aag | aag | gga | cca | aga | tcg | caa | tac | gag | agg | aag | 1440 |
| Ser | Ser | Gly | Gly | Leu | Lys | Lys | Gly | Pro | Arg | Ser | Gln | Tyr | Glu | Arg | Lys |
| 465 | | | | | 470 | | | | | 475 | | | | | 480 |
| ctt | ggt | gag | ttt | ttc | aag | cac | caa | atc | gag | tct | gat | gct | tct | ccg | gtt | 1488 |
| Leu | Gly | Glu | Phe | Phe | Lys | His | Gln | Ile | Glu | Ser | Asp | Ala | Ser | Pro | Val |
| | | | | 485 | | | | | 490 | | | | | 495 | |
| tat | gga | gac | ggg | ttc | agg | gct | ggg | agg | tta | gcg | gtt | aac | aag | tat | ggt | 1536 |
| Tyr | Gly | Asp | Gly | Phe | Arg | Ala | Gly | Arg | Leu | Ala | Val | Asn | Lys | Tyr | Gly |
| | | 500 | | | | | 505 | | | | | 510 | | | |
| ttg | ccg | aaa | aca | ctt | gag | cat | ata | cat | atg | acc | ggt | aga | ttc | ccg | gtt | 1584 |
| Leu | Pro | Lys | Thr | Leu | Glu | His | Ile | His | Met | Thr | Gly | Arg | Phe | Pro | Val |
| | 515 | | | | | 520 | | | | | 525 | | | | |
| taa | | | | | | | | | | | | | | | 1587 |

<210> SEQ ID NO 14
<211> LENGTH: 528
<212> TYPE: PRT
<213> ORGANISM: Brassica napus

<400> SEQUENCE: 14

Met Gly Trp Phe Asn Lys Ile Phe Lys Gly Ser Thr Gln Arg Phe Arg
1               5                   10                  15

Leu Gly Asn Asp His Asp His Asn Gly Tyr Tyr Gln Ser Tyr Pro His
                20                  25                  30

Asp Glu Pro Ser Ala Asp Thr Asp Pro Asp Pro Asp Pro Asp Glu Thr
            35                  40                  45

His Thr Gln Glu Pro Ser Thr Ser Glu Glu Asp Thr Ser Gly Gln Glu
        50                  55                  60

Asn Asp Asp Ile Asp Arg Ala Ile Ala Leu Ser Leu Ile Glu Asn Ser
65                  70                  75                  80

Gln Gly His Thr Asn Thr Gly Ala Gly Lys Tyr Ala Met Val Asp Glu
                85                  90                  95

Asp Glu Gln Leu Ala Arg Ala Ile Gln Glu Ser Met Val Val Gly Asn
            100                 105                 110

Thr Pro Arg Gln Lys His Gly Ser Ser Tyr Asp Ile Gly Asn Ala Tyr
        115                 120                 125

Gly Ala Gly Asp Val Tyr Gly Asn Gly His Met His Gly Gly Asn
    130                 135                 140

Val Tyr Ala Asn Gly Asp Ile Tyr Tyr Pro Arg Pro Thr Ala Phe Pro
145                 150                 155                 160

Met Asp Phe Arg Ile Cys Ala Gly Cys Asn Met Glu Ile Gly His Gly
                165                 170                 175

Arg Tyr Leu Asn Cys Leu Asn Ala Leu Trp His Pro Glu Cys Phe Arg
            180                 185                 190

Cys Tyr Gly Cys Arg His Pro Ile Ser Glu Tyr Glu Phe Ser Thr Ser
        195                 200                 205

Gly Asn Tyr Pro Phe His Lys Ala Cys Tyr Arg Glu Arg Tyr His Pro
    210                 215                 220

Lys Cys Asp Val Cys Ser Leu Phe Ile Pro Thr Asn His Ala Gly Leu
225                 230                 235                 240

Ile Glu Tyr Arg Ala His Pro Phe Trp Val Gln Lys Tyr Cys Pro Ser
                245                 250                 255

His Glu His Asp Ala Thr Pro Arg Cys Cys Ser Cys Glu Arg Met Glu

```
                    260             265             270
Pro Arg Asn Thr Gly Tyr Val Glu Leu Asn Asp Gly Arg Lys Leu Cys
            275             280             285
Leu Glu Cys Leu Asp Ser Ala Val Met Asp Thr Phe Gln Cys Gln Pro
        290             295             300
Leu Tyr Leu Gln Ile Gln Glu Phe Tyr Glu Gly Leu Phe Met Lys Val
305             310             315             320
Glu Gln Asp Val Pro Leu Leu Leu Val Glu Arg Gln Ala Leu Asn Glu
                325             330             335
Ala Arg Glu Gly Glu Lys Asn Gly His Tyr His Met Pro Glu Thr Arg
            340             345             350
Gly Leu Cys Leu Ser Glu Glu Gln Thr Val Ser Thr Val Arg Lys Arg
        355             360             365
Ser Lys His Gly Thr Gly Asn Trp Ala Gly Asn Met Ile Thr Glu Pro
    370             375             380
Tyr Lys Leu Thr Arg Gln Cys Glu Val Thr Ala Ile Leu Ile Leu Phe
385             390             395             400
Gly Leu Pro Arg Leu Leu Thr Gly Ser Ile Leu Ala His Glu Met Met
                405             410             415
His Ala Trp Met Arg Leu Lys Gly Phe Arg Thr Leu Ser Gln Asp Val
            420             425             430
Glu Glu Gly Ile Cys Gln Val Met Ala His Lys Trp Leu Glu Ala Glu
        435             440             445
Leu Ala Ala Gly Ser Arg Asn Ser Asn Val Ala Ser Ser Ser Ser Ser
    450             455             460
Ser Ser Gly Gly Leu Lys Lys Gly Pro Arg Ser Gln Tyr Glu Arg Lys
465             470             475             480
Leu Gly Glu Phe Phe Lys His Gln Ile Glu Ser Asp Ala Ser Pro Val
                485             490             495
Tyr Gly Asp Gly Phe Arg Ala Gly Arg Leu Ala Val Asn Lys Tyr Gly
            500             505             510
Leu Pro Lys Thr Leu Glu His Ile His Met Thr Gly Arg Phe Pro Val
        515             520             525

<210> SEQ ID NO 15
<211> LENGTH: 2267
<212> TYPE: DNA
<213> ORGANISM: Brassica napus
<220> FEATURE:
<221> NAME/KEY: exon
<222> LOCATION: (1)..(171)
<223> OTHER INFORMATION: Exon 1
<220> FEATURE:
<221> NAME/KEY: exon
<222> LOCATION: (244)..(340)
<223> OTHER INFORMATION: Exon 2
<220> FEATURE:
<221> NAME/KEY: exon
<222> LOCATION: (421)..(646)
<223> OTHER INFORMATION: Exon 3
<220> FEATURE:
<221> NAME/KEY: exon
<222> LOCATION: (737)..(857)
<223> OTHER INFORMATION: Exon 4
<220> FEATURE:
<221> NAME/KEY: exon
<222> LOCATION: (933)..(1016)
<223> OTHER INFORMATION: Exon 5
<220> FEATURE:
<221> NAME/KEY: exon
<222> LOCATION: (1129)..(1248)
<223> OTHER INFORMATION: Exon 6
```

```
<220> FEATURE:
<221> NAME/KEY: exon
<222> LOCATION: (1333)..(1545)
<223> OTHER INFORMATION: Exon 7
<220> FEATURE:
<221> NAME/KEY: exon
<222> LOCATION: (1647)..(1828)
<223> OTHER INFORMATION: Exon 8
<220> FEATURE:
<221> NAME/KEY: exon
<222> LOCATION: (1829)..(1887)
<223> OTHER INFORMATION: Exon 9
<220> FEATURE:
<221> NAME/KEY: exon
<222> LOCATION: (1957)..(2267)
<223> OTHER INFORMATION: Exon 10

<400> SEQUENCE: 15 atg ggt tgg ttt aac aag atc ttc aaa ggc tct acc caa agg ttc cgg      48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat      96
Leu Gly Asn Asp His Asp His Asn Gly Tyr Tyr Gln Ser Tyr Pro His
            20                  25                  30 gat gag cct agt gct gat act gat cct gat cct gat cct gat gaa act     144
Asp Glu Pro Ser Ala Asp Thr Asp Pro Asp Pro Asp Pro Asp Glu Thr
        35                  40                  45 cat act cag gaa cca tct acc tct gag gttactataa ctctctttac           191
His Thr Gln Glu Pro Ser Thr Ser Glu
50                  55 atatctctgg tttgtactat tgcttcaaca ttttgttgtt tcccttact ag gag gat    249
                                                        Glu Asp aca tcc ggc cag gaa aac gaa gac ata gat cgt gca atc gca ttg tct     297
Thr Ser Gly Gln Glu Asn Glu Asp Ile Asp Arg Ala Ile Ala Leu Ser
60                  65                  70                  75 ctt ata gaa aac agt caa gga cag act aat aat aca tgc gct g           340
Leu Ile Glu Asn Ser Gln Gly Gln Thr Asn Asn Thr Cys Ala
                80                  85 gtgagtcctt tttccttgcc aaactagaaa tatgaattat gaaactcggt tgttacatt    400 taaaagaata gccaacgcag gg  aag tac gca atg gtg gat gaa gat gag caa   452
                         Gly Lys Tyr Ala Met Val Asp Glu Asp Glu Gln
                                90                  95                  100 ctt gct aga gcc ata caa gag agc atg gta gtt ggg aat aca ccg cgt     500
Leu Ala Arg Ala Ile Gln Glu Ser Met Val Val Gly Asn Thr Pro Arg
                105                 110                 115 cag aag cat gga agt agt tat gat att ggg aat gca tat ggg gct gga     548
Gln Lys His Gly Ser Ser Tyr Asp Ile Gly Asn Ala Tyr Gly Ala Gly
        120                 125                 130 gac gtt tac ggg aat gga cat atg cat gga ggt gga aat gta tat gcc     596
Asp Val Tyr Gly Asn Gly His Met His Gly Gly Gly Asn Val Tyr Ala
    135                 140                 145 aat gga gat att tat tat cca aga cct act gct ttc cca atg gat ttc     644
Asn Gly Asp Ile Tyr Tyr Pro Arg Pro Thr Ala Phe Pro Met Asp Phe
150                 155                 160 ag gttcactttg atactcaatc aatcatctgt agcctgtttg ttaagtttct           696
Arg
165 ttccagttaa gtaactcacc aacaacgtgt cactacctag g att tgt gct ggc tgc   752
                                              Ile Cys Ala Gly Cys
                                                              170 aat atg gag att gga cat gga aga tat ctg aat tgc ttg aat gca cta     800
Asn Met Glu Ile Gly His Gly Arg Tyr Leu Asn Cys Leu Asn Ala Leu
            175                 180                 185
```

```
tgg cat cca gaa tgt ttt cga tgt tat ggc tgt agg cat ccc atc tct        848
Trp His Pro Glu Cys Phe Arg Cys Tyr Gly Cys Arg His Pro Ile Ser
        190                 195                 200 gag tac gag gtgaagtcaa gctttcttat tcttttgatt gtagataacc                897
Glu Tyr Glu
        205 ttcaaaatta acgcataaca tgttttcctt tatag ttc tca acg tct ggg aac         950
                                     Phe Ser Thr Ser Gly Asn
                                                         210 tac cct ttt cac aaa gct tgt tat agg gag aga tac cat cca aaa tgt        998
Tyr Pro Phe His Lys Ala Cys Tyr Arg Glu Arg Tyr His Pro Lys Cys
        215                 220                 225 gat gtc tgc agc ctc ttt gtatgtaaat ctttagcctt tttttcattt               1046
Asp Val Cys Ser Leu Phe
        230 ttaaagtgcc tatatatgcc ttgtttcctt cggatattgc acttatcttc tgttgatttt      1106 cttgtttcga atgttgtgac ag att cca aca aac cat gct ggt ctt att gaa       1158
                          Ile Pro Thr Asn His Ala Gly Leu Ile Glu
                                      235                 240 tat agg gca cat cct ttt tgg gtc cag aag tat tgc cct tct cac gaa        1206
Tyr Arg Ala His Pro Phe Trp Val Gln Lys Tyr Cys Pro Ser His Glu
        245                 250                 255 cac gat gct acc cca aga tgt tgc agt tgc gaa aga atg gag                1248
His Asp Ala Thr Pro Arg Cys Cys Ser Cys Glu Arg Met Glu
260                 265                 270 gttgagtttt tctcccccta agtgtcctac aacaaacatc ttcccaaagt caatactaat      1308
ttgccagctt tcgtttatgt gcag cca cgc aat aca gga tat gtt gaa ctt         1359
                           Pro Arg Asn Thr Gly Tyr Val Glu Leu
                                   275                 280 aac gat gga cgg aaa ctt tgc ctt gaa tgt ctg gac tca gcg gtg atg        1407
Asn Asp Gly Arg Lys Leu Cys Leu Glu Cys Leu Asp Ser Ala Val Met
        285                 290                 295 gac act ttt caa tgc caa cct ctg tat ctg cag ata caa gaa ttc tac        1455
Asp Thr Phe Gln Cys Gln Pro Leu Tyr Leu Gln Ile Gln Glu Phe Tyr
        300                 305                 310 gaa ggt ctt ttc atg aag gtt gag cag gac gtt cca ctt ctt tta gtt        1503
Glu Gly Leu Phe Met Lys Val Glu Gln Asp Val Pro Leu Leu Leu Val
315                 320                 325                 330 gag agg caa gca ctc aac gaa gcc aga gaa ggt gaa aag aat                1545
Glu Arg Gln Ala Leu Asn Glu Ala Arg Glu Gly Glu Lys Asn
                    335                 340 gtgagtaaac aacatacagt tgtcaagtaa tttatttgaa tatatcacat ttattttgt       1605 tttatccgaa gtgttttaac ttttggttgt gttcttctta g ggt cac tat cac atg      1661
                                              Gly His Tyr His Met
                                                          345 cca gag aca aaa gga ctc tgc ctt tca gaa gaa caa act gtt agc act        1709
Pro Glu Thr Lys Gly Leu Cys Leu Ser Glu Glu Gln Thr Val Ser Thr
350                 355                 360                 365 gta aga aag aga tcg aag cat ggc aca gga aac tgg gct ggg aat atg        1757
Val Arg Lys Arg Ser Lys His Gly Thr Gly Asn Trp Ala Gly Asn Met
        370                 375                 380 att aca gag cct tac aag tta aca cgt caa tgc gag gtc act gcc att        1805
Ile Thr Glu Pro Tyr Lys Leu Thr Arg Gln Cys Glu Val Thr Ala Ile
        385                 390                 395 ctc atc ttg ttt ggg ctc cct agg cta ctc acc ggt tcg att cta gct        1853
Leu Ile Leu Phe Gly Leu Pro Arg Leu Leu Thr Gly Ser Ile Leu Ala
        400                 405                 410
```

| | | |
|---|---|---|
| cat gag atg atg cac gcg tgg atg cgg ctc aag g gtgagtttct<br>His Glu Met Met His Ala Trp Met Arg Leu Lys<br>       415                       420 | | 1897 |
| tagttcactg cttctctttt ttttcacat tgttgaatct ctattgtggt cttgaaaag | | 1956 |
| ga ttc cgg acg ctg agc caa gac gtt gaa gaa gga ata tgt caa gtg<br>   Gly Phe Arg Thr Leu Ser Gln Asp Val Glu Glu Gly Ile Cys Gln Val<br>   425                   430                 435                440 | | 2003 |
| atg gct cat aag tgg ttg gaa gca gag tta gct gct ggt tca aga aac<br>Met Ala His Lys Trp Leu Glu Ala Glu Leu Ala Ala Gly Ser Arg Asn<br>                        445                 450                 455 | | 2051 |
| agc aat gtt gcg tca tct tca tct aga gga gtg aag aag gga cca<br>Ser Asn Val Ala Ser Ser Ser Ser Arg Gly Val Lys Lys Gly Pro<br>            460                 465                 470 | | 2099 |
| aga tcg cag tac gag agg aag ctt ggt gag ttt ttc aag cac caa atc<br>Arg Ser Gln Tyr Glu Arg Lys Leu Gly Glu Phe Phe Lys His Gln Ile<br>                475                 480                 485 | | 2147 |
| gag tct gat gct tct ccg gtt tat gga gac ggg ttc agg gct ggg agg<br>Glu Ser Asp Ala Ser Pro Val Tyr Gly Asp Gly Phe Arg Ala Gly Arg<br>490                       495                 500 | | 2195 |
| tta gcg gtt aac aag tat ggt ttg cca aaa aca ctt gag cat ata cag<br>Leu Ala Val Asn Lys Tyr Gly Leu Pro Lys Thr Leu Glu His Ile Gln<br>505                       510                 515                 520 | | 2243 |
| atg acc ggt aga ttc ccg gtt taa<br>Met Thr Gly Arg Phe Pro Val<br>                  525 | | 2267 |

<210> SEQ ID NO 16
<211> LENGTH: 1584
<212> TYPE: DNA
<213> ORGANISM: Brassica napus
<220> FEATURE:
<221> NAME/KEY: CDS
<222> LOCATION: (1)..(1584)

<400> SEQUENCE: 16

| | | |
|---|---|---|
| atg ggt tgg ttt aac aag atc ttc aaa ggc tct acc caa agg ttc cgg<br>Met Gly Trp Phe Asn Lys Ile Phe Lys Gly Ser Thr Gln Arg Phe Arg<br>1                    5                    10                  15 | | 48 |
| ctt ggg aat gac cat gac cac aat ggc tat tac cag agt tat cca cat<br>Leu Gly Asn Asp His Asp His Asn Gly Tyr Tyr Gln Ser Tyr Pro His<br>             20                     25                    30 | | 96 |
| gat gag cct agt gct gat act gat cct gat cct gat cct gat gaa act<br>Asp Glu Pro Ser Ala Asp Thr Asp Pro Asp Pro Asp Pro Asp Glu Thr<br>                35                 40                 45 | | 144 |
| cat act cag gaa cca tct acc tct gag gag gat aca tcc ggc cag gaa<br>His Thr Gln Glu Pro Ser Thr Ser Glu Glu Asp Thr Ser Gly Gln Glu<br> 50                    55                 60 | | 192 |
| aac gaa gac ata gat cgt gca atc gca ttg tct ctt ata gaa aac agt<br>Asn Glu Asp Ile Asp Arg Ala Ile Ala Leu Ser Leu Ile Glu Asn Ser<br>65                    70                 75                 80 | | 240 |
| caa gga cag act aat aat aca tgc gct ggg aag tac gca atg gtg gat<br>Gln Gly Gln Thr Asn Asn Thr Cys Ala Gly Lys Tyr Ala Met Val Asp<br>                    85                 90                 95 | | 288 |
| gaa gat gag caa ctt gct aga gcc ata caa gag agc atg gta gtt ggg<br>Glu Asp Glu Gln Leu Ala Arg Ala Ile Gln Glu Ser Met Val Val Gly<br>                    100                105               110 | | 336 |
| aat aca ccg cgt cag aag cat gga agt agt tat gat att ggg aat gca<br>Asn Thr Pro Arg Gln Lys His Gly Ser Ser Tyr Asp Ile Gly Asn Ala<br>            115                 120                125 | | 384 |
| tat ggg gct gga gac gtt tac ggg aat gga cat atg cat gga ggt gga<br>Tyr Gly Ala Gly Asp Val Tyr Gly Asn Gly His Met His Gly Gly Gly | | 432 |

```
                130                 135                 140
aat gta tat gcc aat gga gat att tat tat cca aga cct act gct ttc      480
Asn Val Tyr Ala Asn Gly Asp Ile Tyr Tyr Pro Arg Pro Thr Ala Phe
145                 150                 155                 160 cca atg gat ttc agg att tgt gct ggc tgc aat atg gag att gga cat      528
Pro Met Asp Phe Arg Ile Cys Ala Gly Cys Asn Met Glu Ile Gly His
                165                 170                 175 gga aga tat ctg aat tgc ttg aat gca cta tgg cat cca gaa tgt ttt      576
Gly Arg Tyr Leu Asn Cys Leu Asn Ala Leu Trp His Pro Glu Cys Phe
            180                 185                 190 cga tgt tat ggc tgt agg cat ccc atc tct gag tac gag ttc tca acg      624
Arg Cys Tyr Gly Cys Arg His Pro Ile Ser Glu Tyr Glu Phe Ser Thr
        195                 200                 205 tct ggg aac tac cct ttt cac aaa gct tgt tat agg gag aga tac cat      672
Ser Gly Asn Tyr Pro Phe His Lys Ala Cys Tyr Arg Glu Arg Tyr His
    210                 215                 220 cca aaa tgt gat gtc tgc agc ctc ttt att cca aca aac cat gct ggt      720
Pro Lys Cys Asp Val Cys Ser Leu Phe Ile Pro Thr Asn His Ala Gly
225                 230                 235                 240 ctt att gaa tat agg gca cat cct ttt tgg gtc cag aag tat tgc cct      768
Leu Ile Glu Tyr Arg Ala His Pro Phe Trp Val Gln Lys Tyr Cys Pro
                245                 250                 255 tct cac gaa cac gat gct acc cca aga tgt tgc agt tgc gaa aga atg      816
Ser His Glu His Asp Ala Thr Pro Arg Cys Cys Ser Cys Glu Arg Met
            260                 265                 270 gag cca cgc aat aca gga tat gtt gaa ctt aac gat gga cgg aaa ctt      864
Glu Pro Arg Asn Thr Gly Tyr Val Glu Leu Asn Asp Gly Arg Lys Leu
        275                 280                 285 tgc ctt gaa tgt ctg gac tca gcg gtg atg gac act ttt caa tgc caa      912
Cys Leu Glu Cys Leu Asp Ser Ala Val Met Asp Thr Phe Gln Cys Gln
    290                 295                 300 cct ctg tat ctg cag ata caa gaa ttc tac gaa ggt ctt ttc atg aag      960
Pro Leu Tyr Leu Gln Ile Gln Glu Phe Tyr Glu Gly Leu Phe Met Lys
305                 310                 315                 320 gtt gag cag gac gtt cca ctt ctt tta gtt gag agg caa gca ctc aac     1008
Val Glu Gln Asp Val Pro Leu Leu Leu Val Glu Arg Gln Ala Leu Asn
                325                 330                 335 gaa gcc aga gaa ggt gaa aag aat ggt cac tat cac atg cca gag aca     1056
Glu Ala Arg Glu Gly Glu Lys Asn Gly His Tyr His Met Pro Glu Thr
            340                 345                 350 aaa gga ctc tgc ctt tca gaa gaa caa act gtt agc act gta aga aag     1104
Lys Gly Leu Cys Leu Ser Glu Glu Gln Thr Val Ser Thr Val Arg Lys
        355                 360                 365 aga tcg aag cat ggc aca gga aac tgg gct ggg aat atg att aca gag     1152
Arg Ser Lys His Gly Thr Gly Asn Trp Ala Gly Asn Met Ile Thr Glu
    370                 375                 380 cct tac aag tta aca cgt caa tgc gag gtc act gcc att ctc atc ttg     1200
Pro Tyr Lys Leu Thr Arg Gln Cys Glu Val Thr Ala Ile Leu Ile Leu
385                 390                 395                 400 ttt ggg ctc cct agg cta ctc acc ggt tcg att cta gct cat gag atg     1248
Phe Gly Leu Pro Arg Leu Leu Thr Gly Ser Ile Leu Ala His Glu Met
                405                 410                 415 atg cac gcg tgg atg cgg ctc aag gga ttc cgg acg ctg agc caa gac     1296
Met His Ala Trp Met Arg Leu Lys Gly Phe Arg Thr Leu Ser Gln Asp
            420                 425                 430 gtt gaa gaa gga ata tgt caa gtg atg gct cat aag tgg ttg gaa gca     1344
Val Glu Glu Gly Ile Cys Gln Val Met Ala His Lys Trp Leu Glu Ala
        435                 440                 445 gag tta gct gct ggt tca aga aac agc aat gtt gcg tca tct tca tct     1392
```

```
Glu Leu Ala Ala Gly Ser Arg Asn Ser Asn Val Ala Ser Ser Ser Ser
            450                 455                 460 tct aga gga gtg aag aag gga cca aga tcg cag tac gag agg aag ctt      1440
Ser Arg Gly Val Lys Lys Gly Pro Arg Ser Gln Tyr Glu Arg Lys Leu
465                 470                 475                 480 ggt gag ttt ttc aag cac caa atc gag tct gat gct tct ccg gtt tat      1488
Gly Glu Phe Phe Lys His Gln Ile Glu Ser Asp Ala Ser Pro Val Tyr
                    485                 490                 495 gga gac ggg ttc agg gct ggg agg tta gcg gtt aac aag tat ggt ttg      1536
Gly Asp Gly Phe Arg Ala Gly Arg Leu Ala Val Asn Lys Tyr Gly Leu
                500                 505                 510 cca aaa aca ctt gag cat ata cag atg acc ggt aga ttc ccg gtt taa      1584
Pro Lys Thr Leu Glu His Ile Gln Met Thr Gly Arg Phe Pro Val
            515                 520                 525

<210> SEQ ID NO 17
<211> LENGTH: 527
<212> TYPE: PRT
<213> ORGANISM: Brassica napus

<400> SEQUENCE: 17

Met Gly Trp Phe Asn Lys Ile Phe Lys Gly Ser Thr Gln Arg Phe Arg
1               5                   10                  15

Leu Gly Asn Asp His Asp His Asn Gly Tyr Tyr Gln Ser Tyr Pro His
            20                  25                  30

Asp Glu Pro Ser Ala Asp Thr Asp Pro Asp Pro Asp Pro Asp Glu Thr
        35                  40                  45

His Thr Gln Glu Pro Ser Thr Ser Glu Glu Asp Thr Ser Gly Gln Glu
    50                  55                  60

Asn Glu Asp Ile Asp Arg Ala Ile Ala Leu Ser Leu Ile Glu Asn Ser
65                  70                  75                  80

Gln Gly Gln Thr Asn Asn Thr Cys Ala Gly Lys Tyr Ala Met Val Asp
                85                  90                  95

Glu Asp Glu Gln Leu Ala Arg Ala Ile Gln Glu Ser Met Val Val Gly
            100                 105                 110

Asn Thr Pro Arg Gln Lys His Gly Ser Ser Tyr Asp Ile Gly Asn Ala
        115                 120                 125

Tyr Gly Ala Gly Asp Val Tyr Gly Asn Gly His Met His Gly Gly Gly
    130                 135                 140

Asn Val Tyr Ala Asn Gly Asp Ile Tyr Tyr Pro Arg Pro Thr Ala Phe
145                 150                 155                 160

Pro Met Asp Phe Arg Ile Cys Ala Gly Cys Asn Met Glu Ile Gly His
                165                 170                 175

Gly Arg Tyr Leu Asn Cys Leu Asn Ala Leu Trp His Pro Glu Cys Phe
            180                 185                 190

Arg Cys Tyr Gly Cys Arg His Pro Ile Ser Glu Tyr Glu Phe Ser Thr
        195                 200                 205

Ser Gly Asn Tyr Pro Phe His Lys Ala Cys Tyr Arg Glu Arg Tyr His
    210                 215                 220

Pro Lys Cys Asp Val Cys Ser Leu Phe Ile Pro Thr Asn His Ala Gly
225                 230                 235                 240

Leu Ile Glu Tyr Arg Ala His Pro Phe Trp Val Gln Lys Tyr Cys Pro
                245                 250                 255

Ser His Glu His Asp Ala Thr Pro Arg Cys Cys Ser Cys Glu Arg Met
            260                 265                 270

Glu Pro Arg Asn Thr Gly Tyr Val Glu Leu Asn Asp Gly Arg Lys Leu
```

```
            275                 280                 285
Cys Leu Glu Cys Leu Asp Ser Ala Val Met Asp Thr Phe Gln Cys Gln
290                 295                 300
Pro Leu Tyr Leu Gln Ile Gln Glu Phe Tyr Glu Gly Leu Phe Met Lys
305                 310                 315                 320
Val Glu Gln Asp Val Pro Leu Leu Leu Val Glu Arg Gln Ala Leu Asn
                    325                 330                 335
Glu Ala Arg Glu Gly Glu Lys Asn Gly His Tyr His Met Pro Glu Thr
                340                 345                 350
Lys Gly Leu Cys Leu Ser Glu Glu Gln Thr Val Ser Thr Val Arg Lys
            355                 360                 365
Arg Ser Lys His Gly Thr Gly Asn Trp Ala Gly Asn Met Ile Thr Glu
        370                 375                 380
Pro Tyr Lys Leu Thr Arg Gln Cys Glu Val Thr Ala Ile Leu Ile Leu
385                 390                 395                 400
Phe Gly Leu Pro Arg Leu Leu Thr Gly Ser Ile Leu Ala His Glu Met
                    405                 410                 415
Met His Ala Trp Met Arg Leu Lys Gly Phe Arg Thr Leu Ser Gln Asp
                420                 425                 430
Val Glu Glu Gly Ile Cys Gln Val Met Ala His Lys Trp Leu Glu Ala
            435                 440                 445
Glu Leu Ala Ala Gly Ser Arg Asn Ser Asn Val Ala Ser Ser Ser Ser
        450                 455                 460
Ser Arg Gly Val Lys Lys Gly Pro Arg Ser Gln Tyr Glu Arg Lys Leu
465                 470                 475                 480
Gly Glu Phe Phe Lys His Gln Ile Glu Ser Asp Ala Ser Pro Val Tyr
                    485                 490                 495
Gly Asp Gly Phe Arg Ala Gly Arg Leu Ala Val Asn Lys Tyr Gly Leu
                500                 505                 510
Pro Lys Thr Leu Glu His Ile Gln Met Thr Gly Arg Phe Pro Val
            515                 520                 525

<210> SEQ ID NO 18
<211> LENGTH: 26
<212> TYPE: DNA
<213> ORGANISM: artificial
<220> FEATURE:
<223> OTHER INFORMATION: Primer 1 for DA1-A1-EMS03

<400> SEQUENCE: 18
acgagttagc ttgaattgct ctgtaa                                        26

<210> SEQ ID NO 19
<211> LENGTH: 25
<212> TYPE: DNA
<213> ORGANISM: artificial
<220> FEATURE:
<223> OTHER INFORMATION: Primer 2 for DA1-A1-EMS03

<400> SEQUENCE: 19
tctgtcggaa gaacaaactg ttaga                                         25

<210> SEQ ID NO 20
<211> LENGTH: 14
<212> TYPE: DNA
<213> ORGANISM: Artificial
<220> FEATURE:
<223> OTHER INFORMATION: FAM probe for DA1-A1-EMS03
```

<400> SEQUENCE: 20
cccacttcag tttc                                                            14

<210> SEQ ID NO 21
<211> LENGTH: 18
<212> TYPE: DNA
<213> ORGANISM: artificial
<220> FEATURE:
<223> OTHER INFORMATION: DA1-A1-EMS03

<400> SEQUENCE: 21
atattcccac tccagttt                                                        18

<210> SEQ ID NO 22
<211> LENGTH: 28
<212> TYPE: DNA
<213> ORGANISM: artificial
<220> FEATURE:
<223> OTHER INFORMATION: Primer 1 for DA1-A2-EMS01

<400> SEQUENCE: 22
gagcaaactg ttagcactgt aagaaaga                                             28

<210> SEQ ID NO 23
<211> LENGTH: 21
<212> TYPE: DNA
<213> ORGANISM: artificial
<220> FEATURE:
<223> OTHER INFORMATION: Primer 2 for DA1-A2-EMS01

<400> SEQUENCE: 23
cctcgcattg acgtgtcaac t                                                    21

<210> SEQ ID NO 24
<211> LENGTH: 17
<212> TYPE: DNA
<213> ORGANISM: artificial
<220> FEATURE:
<223> OTHER INFORMATION: FAM probe for DA1-A2-EMS01

<400> SEQUENCE: 24
cacaggaaac taggctg                                                         17

<210> SEQ ID NO 25
<211> LENGTH: 16
<212> TYPE: DNA
<213> ORGANISM: artificial
<220> FEATURE:
<223> OTHER INFORMATION: VIC probe for DA1-A2-EMS01

<400> SEQUENCE: 25
acaggaaact gggctg                                                          16

<210> SEQ ID NO 26
<211> LENGTH: 25
<212> TYPE: DNA
<213> ORGANISM: artificial
<220> FEATURE:
<223> OTHER INFORMATION: Primer 1 for DA1-A2-EMS05

<400> SEQUENCE: 26
ccatgcttcg atctctttct tacag                                                25

<210> SEQ ID NO 27
<211> LENGTH: 24

-continued

```
<212> TYPE: DNA
<213> ORGANISM: artificial
<220> FEATURE:
<223> OTHER INFORMATION: Primer 2 for DA1-A2-EMS05

<400> SEQUENCE: 27
tagggtcact atcacatgcc agag                                           24

<210> SEQ ID NO 28
<211> LENGTH: 16
<212> TYPE: DNA
<213> ORGANISM: artificial
<220> FEATURE:
<223> OTHER INFORMATION: FAM probe for DA1-A2-EMS05

<400> SEQUENCE: 28
aaggcagagt cctttt                                                    16

<210> SEQ ID NO 29
<211> LENGTH: 15
<212> TYPE: DNA
<213> ORGANISM: artificial
<220> FEATURE:
<223> OTHER INFORMATION: VIC probe for DA1-A2-EMS05

<400> SEQUENCE: 29
aggcagagtc ctctt                                                     15

<210> SEQ ID NO 30
<211> LENGTH: 24
<212> TYPE: DNA
<213> ORGANISM: artificial
<220> FEATURE:
<223> OTHER INFORMATION: Primer 1 for DA1-C1-EMS02

<400> SEQUENCE: 30
ccatcacttg acatatcccc tctt                                           24

<210> SEQ ID NO 31
<211> LENGTH: 26
<212> TYPE: DNA
<213> ORGANISM: artificial
<220> FEATURE:
<223> OTHER INFORMATION: Primer 2 for DA1-C1-EMS02

<400> SEQUENCE: 31
actacaatgt gtggtcttga aaaagg                                         26

<210> SEQ ID NO 32
<211> LENGTH: 18
<212> TYPE: DNA
<213> ORGANISM: artificial
<220> FEATURE:
<223> OTHER INFORMATION: FAM probe for DA1-C1-EMS02

<400> SEQUENCE: 32
aacatcttag ctcagtgt                                                  18

<210> SEQ ID NO 33
<211> LENGTH: 18
<212> TYPE: DNA
<213> ORGANISM: artificial
<220> FEATURE:
<223> OTHER INFORMATION: VIC probe for DA1-C1-EMS02

<400> SEQUENCE: 33
```

-continued

| acatcttggc tcagtgtc | 18 |

<210> SEQ ID NO 34
<211> LENGTH: 24
<212> TYPE: DNA
<213> ORGANISM: artificial
<220> FEATURE:
<223> OTHER INFORMATION: Primer 1 for DA1-C1-EMS03

<400> SEQUENCE: 34

| ctttagggtc actatcacat gcca | 24 |

<210> SEQ ID NO 35
<211> LENGTH: 22
<212> TYPE: DNA
<213> ORGANISM: artificial
<220> FEATURE:
<223> OTHER INFORMATION: Primer 2 for DA1-C1-EMS03

<400> SEQUENCE: 35

| attcccactc cagtttccct tc | 22 |

<210> SEQ ID NO 36
<211> LENGTH: 16
<212> TYPE: DNA
<213> ORGANISM: artificial
<220> FEATURE:
<223> OTHER INFORMATION: FAM probe for DA1-C1-EMS03

<400> SEQUENCE: 36

| tttcagagga ataaac | 16 |

<210> SEQ ID NO 37
<211> LENGTH: 16
<212> TYPE: DNA
<213> ORGANISM: artificial
<220> FEATURE:
<223> OTHER INFORMATION: VIC probe for DA1-C1-EMS03

<400> SEQUENCE: 37

| tttcagagga acaaac | 16 |

<210> SEQ ID NO 38
<211> LENGTH: 19
<212> TYPE: DNA
<213> ORGANISM: artificial
<220> FEATURE:
<223> OTHER INFORMATION: Primer 1 for DA1-C2-EMS02

<400> SEQUENCE: 38

| cgctgagcca agacgttga | 19 |

<210> SEQ ID NO 39
<211> LENGTH: 23
<212> TYPE: DNA
<213> ORGANISM: artificial
<220> FEATURE:
<223> OTHER INFORMATION: Primer 2 for DA1-C2-EMS02

<400> SEQUENCE: 39

| caacattgct gtttcttgaa cca | 23 |

<210> SEQ ID NO 40
<211> LENGTH: 20
<212> TYPE: DNA
<213> ORGANISM: artificial

```
<220> FEATURE:
<223> OTHER INFORMATION: FAM probe for DA1-C2-EMS02

<400> SEQUENCE: 40
aggaatatgt taagtaatgg                                                  20

<210> SEQ ID NO 41
<211> LENGTH: 19
<212> TYPE: DNA
<213> ORGANISM: artificial
<220> FEATURE:
<223> OTHER INFORMATION: VIC probe for DA1-C2-EMS02

<400> SEQUENCE: 41
aggaatatgt caagtaatg                                                   19

<210> SEQ ID NO 42
<211> LENGTH: 24
<212> TYPE: DNA
<213> ORGANISM: artificial
<220> FEATURE:
<223> OTHER INFORMATION: Primer 1 for DA1-C1-EMS04

<400> SEQUENCE: 42
acactgagcc aagatgttga agag                                             24

<210> SEQ ID NO 43
<211> LENGTH: 21
<212> TYPE: DNA
<213> ORGANISM: artificial
<220> FEATURE:
<223> OTHER INFORMATION: Primer 2 for DA1-C1-EMS04

<400> SEQUENCE: 43
tgcagcgttg ctgtttctag a                                                21

<210> SEQ ID NO 44
<211> LENGTH: 17
<212> TYPE: DNA
<213> ORGANISM: artificial
<220> FEATURE:
<223> OTHER INFORMATION: FAM probe for DA1-C1-EMS04

<400> SEQUENCE: 44
atggctcata agtgatt                                                     17

<210> SEQ ID NO 45
<211> LENGTH: 22
<212> TYPE: DNA
<213> ORGANISM: artificial
<220> FEATURE:
<223> OTHER INFORMATION: VIC probe for DA1-C1-EMS04

<400> SEQUENCE: 45
tcataagtgg ttagaagttg ag                                               22

<210> SEQ ID NO 46
<211> LENGTH: 16
<212> TYPE: DNA
<213> ORGANISM: artificial
<220> FEATURE:
<223> OTHER INFORMATION: Primer 1 for DA1-A2-EMS02

<400> SEQUENCE: 46
ccggacgctg agccaa                                                      16
```

<210> SEQ ID NO 47
<211> LENGTH: 23
<212> TYPE: DNA
<213> ORGANISM: artificial
<220> FEATURE:
<223> OTHER INFORMATION: Primer 2 for DA1-A2-EMS02

<400> SEQUENCE: 47
cttgaaccag cagctaactc tgc                                          23

<210> SEQ ID NO 48
<211> LENGTH: 22
<212> TYPE: DNA
<213> ORGANISM: artificial
<220> FEATURE:
<223> OTHER INFORMATION: FAM probe for DA1-A2-EMS02

<400> SEQUENCE: 48
agaaggaata tgttaagtga tg                                           22

<210> SEQ ID NO 49
<211> LENGTH: 20
<212> TYPE: DNA
<213> ORGANISM: artificial
<220> FEATURE:
<223> OTHER INFORMATION: VIC probe for DA1-A2-EMS02

<400> SEQUENCE: 49
agaaggaata tgtcaagtga                                              20

<210> SEQ ID NO 50
<211> LENGTH: 25
<212> TYPE: DNA
<213> ORGANISM: artificial
<220> FEATURE:
<223> OTHER INFORMATION: Primer 1 for DA1-A2-EMS03

<400> SEQUENCE: 50
ctattgtggt cttgaaaagg attcc                                        25

<210> SEQ ID NO 51
<211> LENGTH: 24
<212> TYPE: DNA
<213> ORGANISM: artificial
<220> FEATURE:
<223> OTHER INFORMATION: Primer 2 for DA1-A2-EMS03

<400> SEQUENCE: 51
atgagccatc acttgacata ttcc                                         24

<210> SEQ ID NO 52
<211> LENGTH: 14
<212> TYPE: DNA
<213> ORGANISM: artificial
<220> FEATURE:
<223> OTHER INFORMATION: FAM probe for DA1-A2-EMS03

<400> SEQUENCE: 52
cgctgagcta agac                                                    14

<210> SEQ ID NO 53
<211> LENGTH: 14
<212> TYPE: DNA
<213> ORGANISM: artificial
<220> FEATURE:
<223> OTHER INFORMATION: VIC probe for DA1-A2-EMS03

```
<400> SEQUENCE: 53
acgctgagcc aaga                                                         14

<210> SEQ ID NO 54
<211> LENGTH: 2234
<212> TYPE: DNA
<213> ORGANISM: Brassica rapa
<220> FEATURE:
<221> NAME/KEY: exon
<222> LOCATION: (1)..(156)
<223> OTHER INFORMATION: Exon 1
<220> FEATURE:
<221> NAME/KEY: exon
<222> LOCATION: (322)..(424)
<223> OTHER INFORMATION: Exon 2
<220> FEATURE:
<221> NAME/KEY: exon
<222> LOCATION: (537)..(726)
<223> OTHER INFORMATION: Exon 3
<220> FEATURE:
<221> NAME/KEY: exon
<222> LOCATION: (813)..(933)
<223> OTHER INFORMATION: Exon 4
<220> FEATURE:
<221> NAME/KEY: exon
<222> LOCATION: (1022)..(1105)
<223> OTHER INFORMATION: Exon 5
<220> FEATURE:
<221> NAME/KEY: exon
<222> LOCATION: (1182)..(1514)
<223> OTHER INFORMATION: Exon 6-7
<220> FEATURE:
<221> NAME/KEY: exon
<222> LOCATION: (1597)..(1828)
<223> OTHER INFORMATION: Exon 8-9
<220> FEATURE:
<221> NAME/KEY: exon
<222> LOCATION: (1918)..(2234)
<223> OTHER INFORMATION: Exon 10

<400> SEQUENCE: 54 atg ggt tgg tta aac aag atc ttc aaa ggc tct aac caa agg cac ccc         48
Met Gly Trp Leu Asn Lys Ile Phe Lys Gly Ser Asn Gln Arg His Pro
1               5                   10                  15 atg ggg aat gaa cac tat cat cat aat ggc ggc tat tac gat aac tac         96
Met Gly Asn Glu His Tyr His His Asn Gly Gly Tyr Tyr Asp Asn Tyr
            20                  25                  30 ccg cac gaa cat tct gag cct act gat gct gat cat acg cag gaa cca        144
Pro His Glu His Ser Glu Pro Thr Asp Ala Asp His Thr Gln Glu Pro
        35                  40                  45 tct act tct gag gtgttactat atgctgattg aatattgata gctttgcttt            196
Ser Thr Ser Glu
        50 tatagttttt tttctgattt aggagatctc aaaaatagtc aaataaatca tattagtctc      256 catttatcag ataatggttt gtagtgtaac ctcaaaattt tgttgttttt ttttacttt       316 actag gag gag aca tgg aat ggg aag gaa aat gaa gaa gta gac cgt gta      366
      Glu Glu Thr Trp Asn Gly Lys Glu Asn Glu Glu Val Asp Arg Val
          55                  60                  65 att gca ttg tct att tta gaa gaa gag aat caa aga cca gag act aat        414
Ile Ala Leu Ser Ile Leu Glu Glu Glu Asn Gln Arg Pro Glu Thr Asn
    70                  75                  80 aca ggc gcc t gtgagtttat acattttact gattgtttta gcccaaaaca              464
Thr Gly Ala
    85 gaataatatg aagaaaaaaa gatggttttg tttcatacat ttaaaaaaaa taaaataaaa       524
```

| | |
|---|---|
| aatgaaaagc ag gg aaa cac gca atg atg gat gac gat gag caa ctt gct<br>                 Trp Lys His Ala Met Met Asp Asp Asp Glu Gln Leu Ala<br>                               90                          95 | 574 |
| aga gcc ata caa gag agt atg ata gct agg aat gga act act tat gac<br>Arg Ala Ile Gln Glu Ser Met Ile Ala Arg Asn Gly Thr Thr Tyr Asp<br>100                  105                110                115 | 622 |
| ttt ggg aat gca tat ggg aat gga cat atg cat gga gga ggc aat gta<br>Phe Gly Asn Ala Tyr Gly Asn Gly His Met His Gly Gly Gly Asn Val<br>                 120                125                130 | 670 |
| tat gac aat ggt gat att tat tat cca aga cct att gct ttc tca atg<br>Tyr Asp Asn Gly Asp Ile Tyr Tyr Pro Arg Pro Ile Ala Phe Ser Met<br>                 135                140                145 | 718 |
| gac ttc ag gtttcactta gatagccttt taattttggg ttgatgtgtt<br>Asp Phe Arg<br>          150 | 766 |
| atagtttctt ttaactttt atcaacaact tgtcactgca aatag g atc tgt gct<br>                                                                    Ile Cys Ala | 822 |
| ggc tgc aat atg gag att ggc cat gga aga tat ctg aat tgc ctc aat<br>Gly Cys Asn Met Glu Ile Gly His Gly Arg Tyr Leu Asn Cys Leu Asn<br>                 155                160                165 | 870 |
| gca ctt tgg cat cca caa tgt ttt cga tgc tat ggc tgc agt cac cca<br>Ala Leu Trp His Pro Gln Cys Phe Arg Cys Tyr Gly Cys Ser His Pro<br>170                  175                180                185 | 918 |
| atc tct gag tac gag gtgaactcaa actcattctt tccgttgtag tttaaccttt<br>Ile Ser Glu Tyr Glu<br>                 190 | 973 |
| gaatcaatgt aataacatgt tttccttttt tttttggtc ttaaatag ttc tca acg<br>                                                                  Phe Ser Thr | 1030 |
| tct ggg aac tac cct ttt cac aaa gca tgt tac agg gag agg ttc cat<br>Ser Gly Asn Tyr Pro Phe His Lys Ala Cys Tyr Arg Glu Arg Phe His<br>                 195                200                205 | 1078 |
| cca aaa tgt gat gtc tgc agc ctc ttt gtatgtaaaa tctttagcat<br>Pro Lys Cys Asp Val Cys Ser Leu Phe<br>210                  215 | 1125 |
| tttcagttgt tttctttcgg atattccact tatgttattt tcttttcttg tgacag att<br>                                                                      Ile | 1184 |
| tca aca aac cat gct ggt ctt att gag tat aga gca cat cct ttc tgg<br>Ser Thr Asn His Ala Gly Leu Ile Glu Tyr Arg Ala His Pro Phe Trp<br>220                  225                230                235 | 1232 |
| gtc cag aag tat tgc cct tct cac gaa cac gat gct acg cca aga tgt<br>Val Gln Lys Tyr Cys Pro Ser His Glu His Asp Ala Thr Pro Arg Cys<br>                 240                245                250 | 1280 |
| tgc agc tgt gaa aga atg gag ccg cgt aat aca gga tat ttt gaa ctc<br>Cys Ser Cys Glu Arg Met Glu Pro Arg Asn Thr Gly Tyr Phe Glu Leu<br>255                  260                265 | 1328 |
| aac gat gga cgg aag ctt tgc ctt gag tgt cta gac tca tcg gtg atg<br>Asn Asp Gly Arg Lys Leu Cys Leu Glu Cys Leu Asp Ser Ser Val Met<br>                 270                275                280 | 1376 |
| gac act ttt caa tgc cag cct ctg tac ttg cag ata caa gag ttc tat<br>Asp Thr Phe Gln Cys Gln Pro Leu Tyr Leu Gln Ile Gln Glu Phe Tyr<br>285                  290                295 | 1424 |
| gaa gga ctt aac atg acg gta gag cag gag gtt cca ctt ctc tta gtt<br>Glu Gly Leu Asn Met Thr Val Glu Gln Glu Val Pro Leu Leu Leu Val<br>300                  305                310                315 | 1472 |
| gag agg cag gca ctt aac gaa gcc aga gaa ggt gaa agg aat<br>Glu Arg Gln Ala Leu Asn Glu Ala Arg Glu Gly Glu Arg Asn<br>                 320                325 | 1514 |
| gtgagtaaaa aaatacaaat ttactttagt aactatttga gaatgtgtca catttatatt | 1574 |

```
gtgtcattgt gtgctttctt ag ggt cac tat cac atg cca gag aca aga gga      1626
                        Gly His Tyr His Met Pro Glu Thr Arg Gly
                                        330             335 ctc tgt ctg tcg gaa gaa caa act gtt aga act gtg aga aag aga tcg       1674
Leu Cys Leu Ser Glu Glu Gln Thr Val Arg Thr Val Arg Lys Arg Ser
340             345                 350                 355 aag gga aac tgg agt ggg aat atg att aca gag caa ttc aag cta act       1722
Lys Gly Asn Trp Ser Gly Asn Met Ile Thr Glu Gln Phe Lys Leu Thr
                360                 365                 370 cgt cga tgc gag gtt act gcc att ctc atc ttg ttt ggt ctc cct agg       1770
Arg Arg Cys Glu Val Thr Ala Ile Leu Ile Leu Phe Gly Leu Pro Arg
            375                 380                 385 cta ctc act ggt tca att cta gct cat gag atg atg cac gcg tgg atg       1818
Leu Leu Thr Gly Ser Ile Leu Ala His Glu Met Met His Ala Trp Met
        390                 395                 400 cgg ctc aaa g gtgagtttct tgcttcttgt ttcttatcta actgcttctc             1868
Arg Leu Lys
        405 ttgtttcaca tttgttgaac cgttactaca atgtgtggtc ttgaaaaag gg  ttc cgg     1925
                                                         Gly Phe Arg cca ctt agc caa gat gtt gaa gag ggg ata tgt caa gtg atg gct cat       1973
Pro Leu Ser Gln Asp Val Glu Glu Gly Ile Cys Gln Val Met Ala His
410             415                 420                 425 aag tgg tta gaa gct gag tta gct gct ggt tca aga aat agc aat gct       2021
Lys Trp Leu Glu Ala Glu Leu Ala Ala Gly Ser Arg Asn Ser Asn Ala
                430                 435                 440 gca tca tct tca tca tct tct tat gga gga gtg aag aag gga cca agg       2069
Ala Ser Ser Ser Ser Ser Ser Tyr Gly Gly Val Lys Lys Gly Pro Arg
            445                 450                 455 tct cag tac gag agg aag ctt ggt gag ttt ttc aag cac cag ata gag       2117
Ser Gln Tyr Glu Arg Lys Leu Gly Glu Phe Phe Lys His Gln Ile Glu
        460                 465                 470 gct gat gct tct ccg gtt tat gga gat ggg ttc aga gcc ggg agg cta       2165
Ala Asp Ala Ser Pro Val Tyr Gly Asp Gly Phe Arg Ala Gly Arg Leu
475                 480                 485 gca gtt aac aag tat ggt ttg agg aga aca ctt gag cat ata cag atg       2213
Ala Val Asn Lys Tyr Gly Leu Arg Arg Thr Leu Glu His Ile Gln Met
490             495                 500                 505 act ggg aga ttc ccg gtt taa                                           2234
Thr Gly Arg Phe Pro Val
                510

<210> SEQ ID NO 55
<211> LENGTH: 1536
<212> TYPE: DNA
<213> ORGANISM: Brassica rapa
<220> FEATURE:
<221> NAME/KEY: CDS
<222> LOCATION: (1)..(1536)

<400> SEQUENCE: 55 atg ggt tgg tta aac aag atc ttc aaa ggc tct aac caa agg cac ccc       48
Met Gly Trp Leu Asn Lys Ile Phe Lys Gly Ser Asn Gln Arg His Pro
1               5                   10                  15 atg ggg aat gaa cac tat cat cat aat ggc ggc tat tac gat aac tac       96
Met Gly Asn Glu His Tyr His His Asn Gly Gly Tyr Tyr Asp Asn Tyr
                20                  25                  30 ccg cac gaa cat tct gag cct act gat gct gat cat acg cag gaa cca      144
Pro His Glu His Ser Glu Pro Thr Asp Ala Asp His Thr Gln Glu Pro
            35                  40                  45 tct act tct gag gag gag aca tgg aat ggg aag gaa aat gaa gaa gta      192
```

```
                Ser Thr Ser Glu Glu Thr Trp Asn Gly Lys Glu Asn Glu Val
                    50              55                  60 gac cgt gta att gca ttg tct att tta gaa gaa gag aat caa aga cca         240
Asp Arg Val Ile Ala Leu Ser Ile Leu Glu Glu Glu Asn Gln Arg Pro
65              70                  75                  80 gag act aat aca ggc gcc tgg aaa cac gca atg atg gat gac gat gag         288
Glu Thr Asn Thr Gly Ala Trp Lys His Ala Met Met Asp Asp Asp Glu
                    85                  90                  95 caa ctt gct aga gcc ata caa gag agt atg ata gct agg aat gga act         336
Gln Leu Ala Arg Ala Ile Gln Glu Ser Met Ile Ala Arg Asn Gly Thr
                100                 105                 110 act tat gac ttt ggg aat gca tat ggg aat gga cat atg cat gga gga         384
Thr Tyr Asp Phe Gly Asn Ala Tyr Gly Asn Gly His Met His Gly Gly
                115                 120                 125 ggc aat gta tat gac aat ggt gat att tat tat cca aga cct att gct         432
Gly Asn Val Tyr Asp Asn Gly Asp Ile Tyr Tyr Pro Arg Pro Ile Ala
130                 135                 140 ttc tca atg gac ttc agg atc tgt gct ggc tgc aat atg gag att ggc         480
Phe Ser Met Asp Phe Arg Ile Cys Ala Gly Cys Asn Met Glu Ile Gly
145                 150                 155                 160 cat gga aga tat ctg aat tgc ctc aat gca ctt tgg cat cca caa tgt         528
His Gly Arg Tyr Leu Asn Cys Leu Asn Ala Leu Trp His Pro Gln Cys
                165                 170                 175 ttt cga tgc tat ggc tgc agt cac cca atc tct gag tac gag ttc tca         576
Phe Arg Cys Tyr Gly Cys Ser His Pro Ile Ser Glu Tyr Glu Phe Ser
                180                 185                 190 acg tct ggg aac tac cct ttt cac aaa gca tgt tac agg gag agg ttc         624
Thr Ser Gly Asn Tyr Pro Phe His Lys Ala Cys Tyr Arg Glu Arg Phe
                195                 200                 205 cat cca aaa tgt gat gtc tgc agc ctc ttt att tca aca aac cat gct         672
His Pro Lys Cys Asp Val Cys Ser Leu Phe Ile Ser Thr Asn His Ala
210                 215                 220 ggt ctt att gag tat aga gca cat cct ttc tgg gtc cag aag tat tgc         720
Gly Leu Ile Glu Tyr Arg Ala His Pro Phe Trp Val Gln Lys Tyr Cys
225                 230                 235                 240 cct tct cac gaa cac gat gct acg cca aga tgt tgc agc tgt gaa aga         768
Pro Ser His Glu His Asp Ala Thr Pro Arg Cys Cys Ser Cys Glu Arg
                245                 250                 255 atg gag ccg cgt aat aca gga tat ttt gaa ctc aac gat gga cgg aag         816
Met Glu Pro Arg Asn Thr Gly Tyr Phe Glu Leu Asn Asp Gly Arg Lys
                260                 265                 270 ctt tgc ctt gag tgt cta gac tca tcg gtg atg gac act ttt caa tgc         864
Leu Cys Leu Glu Cys Leu Asp Ser Ser Val Met Asp Thr Phe Gln Cys
                275                 280                 285 cag cct ctg tac ttg cag ata caa gag ttc tat gaa gga ctt aac atg         912
Gln Pro Leu Tyr Leu Gln Ile Gln Glu Phe Tyr Glu Gly Leu Asn Met
290                 295                 300 acg gta gag cag gag gtt cca ctt ctc tta gtt gag agg cag gca ctt         960
Thr Val Glu Gln Glu Val Pro Leu Leu Leu Val Glu Arg Gln Ala Leu
305                 310                 315                 320 aac gaa gcc aga gaa ggt gaa agg aat ggt cac tat cac atg cca gag        1008
Asn Glu Ala Arg Glu Gly Glu Arg Asn Gly His Tyr His Met Pro Glu
                325                 330                 335 aca aga gga ctc tgt ctg tcg gaa gaa caa act gtt aga act gtg aga        1056
Thr Arg Gly Leu Cys Leu Ser Glu Glu Gln Thr Val Arg Thr Val Arg
                340                 345                 350 aag aga tcg aag gga aac tgg agt ggg aat atg att aca gag caa ttc        1104
Lys Arg Ser Lys Gly Asn Trp Ser Gly Asn Met Ile Thr Glu Gln Phe
                355                 360                 365
```

```
aag cta act cgt cga tgc gag gtt act gcc att ctc atc ttg ttt ggt     1152
Lys Leu Thr Arg Arg Cys Glu Val Thr Ala Ile Leu Ile Leu Phe Gly
370                 375                 380 ctc cct agg cta ctc act ggt tca att cta gct cat gag atg atg cac     1200
Leu Pro Arg Leu Leu Thr Gly Ser Ile Leu Ala His Glu Met Met His
385                 390                 395                 400 gcg tgg atg cgg ctc aaa ggg ttc cgg cca ctt agc caa gat gtt gaa     1248
Ala Trp Met Arg Leu Lys Gly Phe Arg Pro Leu Ser Gln Asp Val Glu
                405                 410                 415 gag ggg ata tgt caa gtg atg gct cat aag tgg tta gaa gct gag tta     1296
Glu Gly Ile Cys Gln Val Met Ala His Lys Trp Leu Glu Ala Glu Leu
            420                 425                 430 gct gct ggt tca aga aat agc aat gct gca tct tca tca tct tct         1344
Ala Ala Gly Ser Arg Asn Ser Asn Ala Ala Ser Ser Ser Ser Ser
        435                 440                 445 tat gga gga gtg aag aag gga cca agg tct cag tac gag agg aag ctt     1392
Tyr Gly Gly Val Lys Lys Gly Pro Arg Ser Gln Tyr Glu Arg Lys Leu
    450                 455                 460 ggt gag ttt ttc aag cac cag ata gag gct gat gct tct ccg gtt tat     1440
Gly Glu Phe Phe Lys His Gln Ile Glu Ala Asp Ala Ser Pro Val Tyr
465                 470                 475                 480 gga gat ggg ttc aga gcc ggg agg cta gca gtt aac aag tat ggt ttg     1488
Gly Asp Gly Phe Arg Ala Gly Arg Leu Ala Val Asn Lys Tyr Gly Leu
                485                 490                 495 agg aga aca ctt gag cat ata cag atg act ggg aga ttc ccg gtt taa     1536
Arg Arg Thr Leu Glu His Ile Gln Met Thr Gly Arg Phe Pro Val
            500                 505                 510

<210> SEQ ID NO 56
<211> LENGTH: 511
<212> TYPE: PRT
<213> ORGANISM: Brassica rapa

<400> SEQUENCE: 56

Met Gly Trp Leu Asn Lys Ile Phe Lys Gly Ser Asn Gln Arg His Pro
1               5                   10                  15

Met Gly Asn Glu His Tyr His His Asn Gly Gly Tyr Tyr Asp Asn Tyr
            20                  25                  30

Pro His Glu His Ser Glu Pro Thr Asp Ala Asp His Thr Gln Glu Pro
        35                  40                  45

Ser Thr Ser Glu Glu Glu Thr Trp Asn Gly Lys Glu Asn Glu Glu Val
    50                  55                  60

Asp Arg Val Ile Ala Leu Ser Ile Leu Glu Glu Asn Gln Arg Pro
65                  70                  75                  80

Glu Thr Asn Thr Gly Ala Trp Lys His Ala Met Met Asp Asp Asp Glu
                85                  90                  95

Gln Leu Ala Arg Ala Ile Gln Glu Ser Met Ile Ala Arg Asn Gly Thr
            100                 105                 110

Thr Tyr Asp Phe Gly Asn Ala Tyr Gly Asn Gly His Met His Gly Gly
        115                 120                 125

Gly Asn Val Tyr Asp Asn Gly Asp Ile Tyr Tyr Pro Arg Pro Ile Ala
    130                 135                 140

Phe Ser Met Asp Phe Arg Ile Cys Ala Gly Cys Asn Met Glu Ile Gly
145                 150                 155                 160

His Gly Arg Tyr Leu Asn Cys Leu Asn Ala Leu Trp His Pro Gln Cys
                165                 170                 175

Phe Arg Cys Tyr Gly Cys Ser His Pro Ile Ser Glu Tyr Glu Phe Ser
            180                 185                 190
```

```
Thr Ser Gly Asn Tyr Pro Phe His Lys Ala Cys Tyr Arg Glu Arg Phe
        195                 200                 205

His Pro Lys Cys Asp Val Cys Ser Leu Phe Ile Ser Thr Asn His Ala
    210                 215                 220

Gly Leu Ile Glu Tyr Arg Ala His Pro Phe Trp Val Gln Lys Tyr Cys
225                 230                 235                 240

Pro Ser His Glu His Asp Ala Thr Pro Arg Cys Cys Ser Cys Glu Arg
                245                 250                 255

Met Glu Pro Arg Asn Thr Gly Tyr Phe Glu Leu Asn Asp Gly Arg Lys
                260                 265                 270

Leu Cys Leu Glu Cys Leu Asp Ser Ser Val Met Asp Thr Phe Gln Cys
            275                 280                 285

Gln Pro Leu Tyr Leu Gln Ile Gln Glu Phe Tyr Glu Gly Leu Asn Met
        290                 295                 300

Thr Val Glu Gln Glu Val Pro Leu Leu Val Glu Arg Gln Ala Leu
305                 310                 315                 320

Asn Glu Ala Arg Glu Gly Arg Asn Gly His Tyr His Met Pro Glu
                325                 330                 335

Thr Arg Gly Leu Cys Leu Ser Glu Gln Thr Val Arg Thr Val Arg
                340                 345                 350

Lys Arg Ser Lys Gly Asn Trp Ser Gly Asn Met Ile Thr Glu Gln Phe
            355                 360                 365

Lys Leu Thr Arg Arg Cys Glu Val Thr Ala Ile Leu Ile Leu Phe Gly
        370                 375                 380

Leu Pro Arg Leu Leu Thr Gly Ser Ile Leu Ala His Glu Met Met His
385                 390                 395                 400

Ala Trp Met Arg Leu Lys Gly Phe Arg Pro Leu Ser Gln Asp Val Glu
                405                 410                 415

Glu Gly Ile Cys Gln Val Met Ala His Lys Trp Leu Glu Ala Glu Leu
                420                 425                 430

Ala Ala Gly Ser Arg Asn Ser Asn Ala Ala Ser Ser Ser Ser Ser
            435                 440                 445

Tyr Gly Gly Val Lys Lys Gly Pro Arg Ser Gln Tyr Glu Arg Lys Leu
        450                 455                 460

Gly Glu Phe Phe Lys His Gln Ile Glu Ala Asp Ala Ser Pro Val Tyr
465                 470                 475                 480

Gly Asp Gly Phe Arg Ala Gly Arg Leu Ala Val Asn Lys Tyr Gly Leu
                485                 490                 495

Arg Arg Thr Leu Glu His Ile Gln Met Thr Gly Arg Phe Pro Val
                500                 505                 510

<210> SEQ ID NO 57
<211> LENGTH: 2278
<212> TYPE: DNA
<213> ORGANISM: Brassica rapa
<220> FEATURE:
<221> NAME/KEY: exon
<222> LOCATION: (1)..(171)
<223> OTHER INFORMATION: Exon 1
<220> FEATURE:
<221> NAME/KEY: exon
<222> LOCATION: (244)..(340)
<223> OTHER INFORMATION: Exon 2
<220> FEATURE:
<221> NAME/KEY: exon
<222> LOCATION: (421)..(646)
<223> OTHER INFORMATION: Exon 3
<220> FEATURE:
```

<220> FEATURE:
<221> NAME/KEY: exon
<222> LOCATION: (737)..(857)
<223> OTHER INFORMATION: Exon 4
<220> FEATURE:
<221> NAME/KEY: exon
<222> LOCATION: (933)..(1016)
<223> OTHER INFORMATION: Exon 5
<220> FEATURE:
<221> NAME/KEY: exon
<222> LOCATION: (1136)..(1255)
<223> OTHER INFORMATION: Exon 6
<220> FEATURE:
<221> NAME/KEY: exon
<222> LOCATION: (1339)..(1551)
<223> OTHER INFORMATION: Exon 7
<220> FEATURE:
<221> NAME/KEY: exon
<222> LOCATION: (1658)..(1839)
<223> OTHER INFORMATION: Exon 8
<220> FEATURE:
<221> NAME/KEY: exon
<222> LOCATION: (1840)..(1898)
<223> OTHER INFORMATION: Exon 9
<220> FEATURE:
<221> NAME/KEY: exon
<222> LOCATION: (1968)..(2278)
<223> OTHER INFORMATION: Exon 10

<400> SEQUENCE: 57

```
atg ggt tgg ttt aac aag atc ttc aaa ggc tct acc caa agg ttc cgg      48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat      96
Leu Gly Asn Asp His Asp His Asn Gly Tyr Tyr Gln Ser Tyr Pro His
            20                  25                  30 gat gag cct agt gct gat act gat cct gat cct gat cct gat gaa act     144
Asp Glu Pro Ser Ala Asp Thr Asp Pro Asp Pro Asp Pro Asp Glu Thr
        35                  40                  45 cat act cag gaa cca tct acc tct gag gttactataa ctctctttac            191
His Thr Gln Glu Pro Ser Thr Ser Glu
    50                  55 atatctctgg tttgtactat tgcttcaaca ttttgttgtt tcccttact ag gag gat     249
                                                         Glu Asp aca tcc ggc cag gaa aac gaa gac ata gat cgt gca atc gca ttg tct     297
Thr Ser Gly Gln Glu Asn Glu Asp Ile Asp Arg Ala Ile Ala Leu Ser
60                  65                  70                  75 ctt ata gaa aac agt caa gga cag act aat aat aca tgc gct g           340
Leu Ile Glu Asn Ser Gln Gly Gln Thr Asn Asn Thr Cys Ala
                80                  85 gtgagtcctt tttccttgcc aaactagaaa tatgaattat gaaactcggt ttgttacatt   400
taaaagaata gccaacgcag gg  aag tac gca atg gtg gat gaa gat gag caa   452
                         Gly Lys Tyr Ala Met Val Asp Glu Asp Glu Gln
                                 90                  95                 100 ctt gct aga gcc ata caa gag agc atg gta gtt ggg aat aca ccg cgt     500
Leu Ala Arg Ala Ile Gln Glu Ser Met Val Val Gly Asn Thr Pro Arg
            105                 110                 115 cag aag cat gga agt agt tat gat att ggg aat gca tat ggg gct gga     548
Gln Lys His Gly Ser Ser Tyr Asp Ile Gly Asn Ala Tyr Gly Ala Gly
        120                 125                 130 gac gtt tac ggg aat gga cat atg cat gga ggt gga aat gta tat gcc     596
Asp Val Tyr Gly Asn Gly His Met His Gly Gly Gly Asn Val Tyr Ala
    135                 140                 145 aat gga gat att tat tat cca aga cct act gct ttc cca atg gat ttc     644
Asn Gly Asp Ile Tyr Tyr Pro Arg Pro Thr Ala Phe Pro Met Asp Phe
150                 155                 160
```

```
ag  gttcactttg atactcaatc aatcatctgt agcctgtttg ttaagtttct          696
Arg
165 ttccagttaa gtaactcacc aacaacgtgt cactacctag g att tgt gct ggc tgc   752
                                              Ile Cys Ala Gly Cys
                                                              170 aat atg gag att gga cat gga aga tat ctg aat tgc ttg aat gca cta    800
Asn Met Glu Ile Gly His Gly Arg Tyr Leu Asn Cys Leu Asn Ala Leu
            175                 180                 185 tgg cat cca gaa tgt ttt cga tgt tat ggc tgt agg cac ccc att tct    848
Trp His Pro Glu Cys Phe Arg Cys Tyr Gly Cys Arg His Pro Ile Ser
            190                 195                 200 gag tac gag gtgaagtcaa gctttcttat tcttttgatt gtagataacc             897
Glu Tyr Glu
        205 ttcaaaacta acgcataaca tgttttcctt tatag ttc tca acg tct ggg aac      950
                                      Phe Ser Thr Ser Gly Asn
                                                          210 tac cct ttt cac aaa gct tgt tat agg gag aga tac cat cca aaa tgt    998
Tyr Pro Phe His Lys Ala Cys Tyr Arg Glu Arg Tyr His Pro Lys Cys
            215                 220                 225 gat gtc tgc agc ctc ttt gtatgtaaat ctttagcctt ttttcatttt            1046
Asp Val Cys Ser Leu Phe
                230 taaagtgcct atatatgcct tgtttccttc ggatattgca cttatctttt gttgattttc   1106 ttgtttcgaa tgcaaatttg ttgtgacag att cca aca aac cat gct ggt ctt    1159
                                Ile Pro Thr Asn His Ala Gly Leu
                                            235                 240 att gaa tat agg gca cat cct ttt tgg gtc cag aag tat tgc cct tct    1207
Ile Glu Tyr Arg Ala His Pro Phe Trp Val Gln Lys Tyr Cys Pro Ser
            245                 250                 255 cac gaa cac gat gct acc cca aga tgt tgc agt tgc gaa aga atg gag    1255
His Glu His Asp Ala Thr Pro Arg Cys Cys Ser Cys Glu Arg Met Glu
            260                 265                 270 gttgagtttt tctcccctaa gtgtcccaca acaaacatct tcccaaagtc aatactaatt   1315
tgccaacttt cgtttatgtg cag cca cgc aat aca gga tat gtt gaa ctt aac  1368
                        Pro Arg Asn Thr Gly Tyr Val Glu Leu Asn
                                    275                 280 gat gga cgg aaa ctt tgc ctt gaa tgt ctg gac tca gcg gtg atg gac    1416
Asp Gly Arg Lys Leu Cys Leu Glu Cys Leu Asp Ser Ala Val Met Asp
            285                 290                 295 act ttt caa tgc caa cct ctg tat ctg cag ata caa gaa ttc tac gaa    1464
Thr Phe Gln Cys Gln Pro Leu Tyr Leu Gln Ile Gln Glu Phe Tyr Glu
300                 305                 310                 315 ggt ctt ttc atg aag gta gag cag gac gtt cca ctt ctt tta gtt gag    1512
Gly Leu Phe Met Lys Val Glu Gln Asp Val Pro Leu Leu Leu Val Glu
            320                 325                 330 agg caa gca ctc aac gaa gcc aga gaa ggt gaa aag aat gtgagtaaac     1561
Arg Gln Ala Leu Asn Glu Ala Arg Glu Gly Glu Lys Asn
            335                 340 aacatacagt tgtcaagtaa tttatttgaa tatatcactt ttttttttgt tttatccgaa  1621
gtgttttaac ttttggttgt gttcttctct tcttag ggt cac tat cac atg cca    1675
                                        Gly His Tyr His Met Pro
                                        345                 350 gag aca aga gga ctc tgc ctt tca gaa gag caa act gtt agc act gta    1723
Glu Thr Arg Gly Leu Cys Leu Ser Glu Glu Gln Thr Val Ser Thr Val
            355                 360                 365 aga aag aga tcg aag cat ggc aca gga aac tgg gct ggg aat atg att    1771
```

```
                Arg Lys Arg Ser Lys His Gly Thr Gly Asn Trp Ala Gly Asn Met Ile
                                370                 375                 380 aca gag cct tac aag ttg aca cgt caa tgc gag gtt act gcc att ctc          1819
Thr Glu Pro Tyr Lys Leu Thr Arg Gln Cys Glu Val Thr Ala Ile Leu
        385                 390                 395 atc ttg ttt ggg ctc cct agg cta ctc acc ggt tcg att cta gct cat          1867
Ile Leu Phe Gly Leu Pro Arg Leu Leu Thr Gly Ser Ile Leu Ala His
400                 405                 410 gag atg atg cac gcg tgg atg cgg ctc aag g gtgagtttct tagttcactg          1918
Glu Met Met His Ala Trp Met Arg Leu Lys
415                 420 cttctctttt tttttcacat tgttgaatct ctattgtggt cttgaaaag ga  ttc cgg        1975
                                                        Gly Phe Arg
                                                            425 acg ctg agc caa gac gtt gaa gaa gga ata tgt caa gtg atg gct cat          2023
Thr Leu Ser Gln Asp Val Glu Glu Gly Ile Cys Gln Val Met Ala His
        430                 435                 440 aag tgg ttg gaa gca gag tta gct gct ggt tca aga aac agc aat gtt          2071
Lys Trp Leu Glu Ala Glu Leu Ala Ala Gly Ser Arg Asn Ser Asn Val
445                 450                 455 gcg tca tct tca tct tct aga gga gtg aag aag gga cca aga tcg cag          2119
Ala Ser Ser Ser Ser Ser Arg Gly Val Lys Lys Gly Pro Arg Ser Gln
460                 465                 470                 475 tac gag agg aag ctt ggt gag ttt ttc aag cac caa atc gag tct gat          2167
Tyr Glu Arg Lys Leu Gly Glu Phe Phe Lys His Gln Ile Glu Ser Asp
                480                 485                 490 gct tct ccg gtt tat gga gac ggg ttc agg gct ggg agg tta gcg gtt          2215
Ala Ser Pro Val Tyr Gly Asp Gly Phe Arg Ala Gly Arg Leu Ala Val
        495                 500                 505 aac aag tat ggt ttg cca aaa aca ctt gag cat ata cag atg acc ggt          2263
Asn Lys Tyr Gly Leu Pro Lys Thr Leu Glu His Ile Gln Met Thr Gly
510                 515                 520 aga ttc ccg gtt taa                                                      2278
Arg Phe Pro Val
    525

<210> SEQ ID NO 58
<211> LENGTH: 1584
<212> TYPE: DNA
<213> ORGANISM: Brassica rapa
<220> FEATURE:
<221> NAME/KEY: CDS
<222> LOCATION: (1)..(1584)

<400> SEQUENCE: 58 atg ggt tgg ttt aac aag atc ttc aaa ggc tct acc caa agg ttc cgg           48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat           96
Leu Gly Asn Asp His Asp His Asn Gly Tyr Tyr Gln Ser Tyr Pro His
            20                  25                  30 gat gag cct agt gct gat act gat cct gat cct gat cct gat gaa act          144
Asp Glu Pro Ser Ala Asp Thr Asp Pro Asp Pro Asp Pro Asp Glu Thr
        35                  40                  45 cat act cag gaa cca tct acc tct gag gag gat aca tcc ggc cag gaa          192
His Thr Gln Glu Pro Ser Thr Ser Glu Glu Asp Thr Ser Gly Gln Glu
    50                  55                  60 aac gaa gac ata gat cgt gca atc gca ttg tct ctt ata gaa aac agt          240
Asn Glu Asp Ile Asp Arg Ala Ile Ala Leu Ser Leu Ile Glu Asn Ser
65                  70                  75                  80 caa gga cag act aat aat aca tgc gct ggg aag tac gca atg gtg gat          288
```

```
                Gln Gly Gln Thr Asn Asn Thr Cys Ala Gly Lys Tyr Ala Met Val Asp
                                85                  90                  95 gaa gat gag caa ctt gct aga gcc ata caa gag agc atg gta gtt ggg         336
Glu Asp Glu Gln Leu Ala Arg Ala Ile Gln Glu Ser Met Val Val Gly
            100                 105                 110 aat aca ccg cgt cag aag cat gga agt agt tat gat att ggg aat gca         384
Asn Thr Pro Arg Gln Lys His Gly Ser Ser Tyr Asp Ile Gly Asn Ala
            115                 120                 125 tat ggg gct gga gac gtt tac ggg aat gga cat atg cat gga ggt gga         432
Tyr Gly Ala Gly Asp Val Tyr Gly Asn Gly His Met His Gly Gly Gly
            130                 135                 140 aat gta tat gcc aat gga gat att tat tat cca aga cct act gct ttc         480
Asn Val Tyr Ala Asn Gly Asp Ile Tyr Tyr Pro Arg Pro Thr Ala Phe
145                 150                 155                 160 cca atg gat ttc agg att tgt gct ggc tgc aat atg gag att gga cat         528
Pro Met Asp Phe Arg Ile Cys Ala Gly Cys Asn Met Glu Ile Gly His
                165                 170                 175 gga aga tat ctg aat tgc ttg aat gca cta tgg cat cca gaa tgt ttt         576
Gly Arg Tyr Leu Asn Cys Leu Asn Ala Leu Trp His Pro Glu Cys Phe
            180                 185                 190 cga tgt tat ggc tgt agg cac ccc att tct gag tac gag ttc tca acg         624
Arg Cys Tyr Gly Cys Arg His Pro Ile Ser Glu Tyr Glu Phe Ser Thr
        195                 200                 205 tct ggg aac tac cct ttt cac aaa gct tgt tat agg gag aga tac cat         672
Ser Gly Asn Tyr Pro Phe His Lys Ala Cys Tyr Arg Glu Arg Tyr His
210                 215                 220 cca aaa tgt gat gtc tgc agc ctc ttt att cca aca aac cat gct ggt         720
Pro Lys Cys Asp Val Cys Ser Leu Phe Ile Pro Thr Asn His Ala Gly
225                 230                 235                 240 ctt att gaa tat agg gca cat cct ttt tgg gtc cag aag tat tgc cct         768
Leu Ile Glu Tyr Arg Ala His Pro Phe Trp Val Gln Lys Tyr Cys Pro
                245                 250                 255 tct cac gaa cac gat gct acc cca aga tgt tgc agt tgc gaa aga atg         816
Ser His Glu His Asp Ala Thr Pro Arg Cys Cys Ser Cys Glu Arg Met
            260                 265                 270 gag cca cgc aat aca gga tat gtt gaa ctt aac gat gga cgg aaa ctt         864
Glu Pro Arg Asn Thr Gly Tyr Val Glu Leu Asn Asp Gly Arg Lys Leu
        275                 280                 285 tgc ctt gaa tgt ctg gac tca gcg gtg atg gac act ttt caa tgc caa         912
Cys Leu Glu Cys Leu Asp Ser Ala Val Met Asp Thr Phe Gln Cys Gln
    290                 295                 300 cct ctg tat ctg cag ata caa gaa ttc tac gaa ggt ctt ttc atg aag         960
Pro Leu Tyr Leu Gln Ile Gln Glu Phe Tyr Glu Gly Leu Phe Met Lys
305                 310                 315                 320 gta gag cag gac gtt cca ctt ctt tta gtt gag agg caa gca ctc aac        1008
Val Glu Gln Asp Val Pro Leu Leu Leu Val Glu Arg Gln Ala Leu Asn
                325                 330                 335 gaa gcc aga gaa ggt gaa aag aat ggt cac tat cac atg cca gag aca        1056
Glu Ala Arg Glu Gly Glu Lys Asn Gly His Tyr His Met Pro Glu Thr
            340                 345                 350 aga gga ctc tgc ctt tca gaa gag caa act gtt agc act gta aga aag        1104
Arg Gly Leu Cys Leu Ser Glu Glu Gln Thr Val Ser Thr Val Arg Lys
        355                 360                 365 aga tcg aag cat ggc aca gga aac tgg gct ggg aat atg att aca gag        1152
Arg Ser Lys His Gly Thr Gly Asn Trp Ala Gly Asn Met Ile Thr Glu
    370                 375                 380 cct tac aag ttg aca cgt caa tgc gag gtt act gcc att ctc atc ttg        1200
Pro Tyr Lys Leu Thr Arg Gln Cys Glu Val Thr Ala Ile Leu Ile Leu
385                 390                 395                 400
```

| | | | | | | | | | | | | | | |
|---|---|---|---|---|---|---|---|---|---|---|---|---|---|---|
| ttt | ggg | ctc | cct | agg | cta | ctc | acc | ggt | tcg | att | cta | gct | cat | gag | atg | 1248 |
| Phe | Gly | Leu | Pro | Arg | Leu | Leu | Thr | Gly | Ser | Ile | Leu | Ala | His | Glu | Met |
| | | | 405 | | | | | 410 | | | | | 415 | | |

| | | | | | | | | | | | | | | |
|---|---|---|---|---|---|---|---|---|---|---|---|---|---|---|
| atg | cac | gcg | tgg | atg | cgg | ctc | aag | gga | ttc | cgg | acg | ctg | agc | caa | gac | 1296 |
| Met | His | Ala | Trp | Met | Arg | Leu | Lys | Gly | Phe | Arg | Thr | Leu | Ser | Gln | Asp |
| | | | 420 | | | | | 425 | | | | | 430 | | |

| | | | | | | | | | | | | | | |
|---|---|---|---|---|---|---|---|---|---|---|---|---|---|---|
| gtt | gaa | gaa | gga | ata | tgt | caa | gtg | atg | gct | cat | aag | tgg | ttg | gaa | gca | 1344 |
| Val | Glu | Glu | Gly | Ile | Cys | Gln | Val | Met | Ala | His | Lys | Trp | Leu | Glu | Ala |
| | | 435 | | | | | 440 | | | | | 445 | | | |

| | | | | | | | | | | | | | | |
|---|---|---|---|---|---|---|---|---|---|---|---|---|---|---|
| gag | tta | gct | gct | ggt | tca | aga | aac | agc | aat | gtt | gcg | tca | tct | tca | tct | 1392 |
| Glu | Leu | Ala | Ala | Gly | Ser | Arg | Asn | Ser | Asn | Val | Ala | Ser | Ser | Ser | Ser |
| | 450 | | | | | 455 | | | | | 460 | | | | |

| | | | | | | | | | | | | | | |
|---|---|---|---|---|---|---|---|---|---|---|---|---|---|---|
| tct | aga | gga | gtg | aag | aag | gga | cca | aga | tcg | cag | tac | gag | agg | aag | ctt | 1440 |
| Ser | Arg | Gly | Val | Lys | Lys | Gly | Pro | Arg | Ser | Gln | Tyr | Glu | Arg | Lys | Leu |
| 465 | | | | 470 | | | | | 475 | | | | | 480 | |

| | | | | | | | | | | | | | | |
|---|---|---|---|---|---|---|---|---|---|---|---|---|---|---|
| ggt | gag | ttt | ttc | aag | cac | caa | atc | gag | tct | gat | gct | tct | ccg | gtt | tat | 1488 |
| Gly | Glu | Phe | Phe | Lys | His | Gln | Ile | Glu | Ser | Asp | Ala | Ser | Pro | Val | Tyr |
| | | | | 485 | | | | | 490 | | | | | 495 | |

| | | | | | | | | | | | | | | |
|---|---|---|---|---|---|---|---|---|---|---|---|---|---|---|
| gga | gac | ggg | ttc | agg | gct | ggg | agg | tta | gcg | gtt | aac | aag | tat | ggt | ttg | 1536 |
| Gly | Asp | Gly | Phe | Arg | Ala | Gly | Arg | Leu | Ala | Val | Asn | Lys | Tyr | Gly | Leu |
| | | | 500 | | | | | 505 | | | | | 510 | | |

| | | | | | | | | | | | | | |
|---|---|---|---|---|---|---|---|---|---|---|---|---|---|
| cca | aaa | aca | ctt | gag | cat | ata | cag | atg | acc | ggt | aga | ttc | ccg | gtt | taa | 1584 |
| Pro | Lys | Thr | Leu | Glu | His | Ile | Gln | Met | Thr | Gly | Arg | Phe | Pro | Val |
| | | | 515 | | | | | 520 | | | | | 525 | |

<210> SEQ ID NO 59
<211> LENGTH: 527
<212> TYPE: PRT
<213> ORGANISM: Brassica rapa

<400> SEQUENCE: 59

| Met | Gly | Trp | Phe | Asn | Lys | Ile | Phe | Lys | Gly | Ser | Thr | Gln | Arg | Phe | Arg |
|---|---|---|---|---|---|---|---|---|---|---|---|---|---|---|---|
| 1 | | | | 5 | | | | | 10 | | | | | 15 | |

| Leu | Gly | Asn | Asp | His | Asp | His | Asn | Gly | Tyr | Tyr | Gln | Ser | Tyr | Pro | His |
|---|---|---|---|---|---|---|---|---|---|---|---|---|---|---|---|
| | | | 20 | | | | | 25 | | | | | 30 | | |

| Asp | Glu | Pro | Ser | Ala | Asp | Thr | Asp | Pro | Asp | Pro | Asp | Glu | Thr |
|---|---|---|---|---|---|---|---|---|---|---|---|---|---|
| | | 35 | | | | | 40 | | | | | 45 | |

| His | Thr | Gln | Glu | Pro | Ser | Thr | Ser | Glu | Glu | Asp | Thr | Ser | Gly | Gln | Glu |
|---|---|---|---|---|---|---|---|---|---|---|---|---|---|---|---|
| | 50 | | | | | 55 | | | | | 60 | | | | |

| Asn | Glu | Asp | Ile | Asp | Arg | Ala | Ile | Ala | Leu | Ser | Leu | Ile | Glu | Asn | Ser |
|---|---|---|---|---|---|---|---|---|---|---|---|---|---|---|---|
| 65 | | | | | 70 | | | | | 75 | | | | | 80 |

| Gln | Gly | Gln | Thr | Asn | Asn | Thr | Cys | Ala | Gly | Lys | Tyr | Ala | Met | Val | Asp |
|---|---|---|---|---|---|---|---|---|---|---|---|---|---|---|---|
| | | | | 85 | | | | | 90 | | | | | 95 | |

| Glu | Asp | Glu | Gln | Leu | Ala | Arg | Ala | Ile | Gln | Glu | Ser | Met | Val | Val | Gly |
|---|---|---|---|---|---|---|---|---|---|---|---|---|---|---|---|
| | | | 100 | | | | | 105 | | | | | 110 | | |

| Asn | Thr | Pro | Arg | Gln | Lys | His | Gly | Ser | Ser | Tyr | Asp | Ile | Gly | Asn | Ala |
|---|---|---|---|---|---|---|---|---|---|---|---|---|---|---|---|
| | | | 115 | | | | | 120 | | | | | 125 | | |

| Tyr | Gly | Ala | Gly | Asp | Val | Tyr | Gly | Asn | Gly | His | Met | His | Gly | Gly |
|---|---|---|---|---|---|---|---|---|---|---|---|---|---|---|
| | 130 | | | | | 135 | | | | | 140 | | | |

| Asn | Val | Tyr | Ala | Asn | Gly | Asp | Ile | Tyr | Tyr | Pro | Arg | Pro | Thr | Ala | Phe |
|---|---|---|---|---|---|---|---|---|---|---|---|---|---|---|---|
| 145 | | | | | 150 | | | | | 155 | | | | | 160 |

| Pro | Met | Asp | Phe | Arg | Ile | Cys | Ala | Gly | Cys | Asn | Met | Glu | Ile | Gly | His |
|---|---|---|---|---|---|---|---|---|---|---|---|---|---|---|---|
| | | | | 165 | | | | | 170 | | | | | 175 | |

| Gly | Arg | Tyr | Leu | Asn | Cys | Leu | Asn | Ala | Leu | Trp | His | Pro | Glu | Cys | Phe |
|---|---|---|---|---|---|---|---|---|---|---|---|---|---|---|---|
| | | | 180 | | | | | 185 | | | | | 190 | | |

| Arg | Cys | Tyr | Gly | Cys | Arg | His | Pro | Ile | Ser | Glu | Tyr | Glu | Phe | Ser | Thr |
|---|---|---|---|---|---|---|---|---|---|---|---|---|---|---|---|
| | | | 195 | | | | | 200 | | | | | 205 | | |

Ser Gly Asn Tyr Pro Phe His Lys Ala Cys Tyr Arg Glu Arg Tyr His
    210                 215                 220

Pro Lys Cys Asp Val Cys Ser Leu Phe Ile Pro Thr Asn His Ala Gly
225                 230                 235                 240

Leu Ile Glu Tyr Arg Ala His Pro Phe Trp Val Gln Lys Tyr Cys Pro
                245                 250                 255

Ser His Glu His Asp Ala Thr Pro Arg Cys Cys Ser Cys Glu Arg Met
            260                 265                 270

Glu Pro Arg Asn Thr Gly Tyr Val Glu Leu Asn Asp Gly Arg Lys Leu
        275                 280                 285

Cys Leu Glu Cys Leu Asp Ser Ala Val Met Asp Thr Phe Gln Cys Gln
290                 295                 300

Pro Leu Tyr Leu Gln Ile Gln Glu Phe Tyr Glu Gly Leu Phe Met Lys
305                 310                 315                 320

Val Glu Gln Asp Val Pro Leu Leu Leu Val Glu Arg Gln Ala Leu Asn
                325                 330                 335

Glu Ala Arg Glu Gly Leu Lys Asn Gly His Tyr His Met Pro Glu Thr
            340                 345                 350

Arg Gly Leu Cys Leu Ser Glu Glu Gln Thr Val Ser Thr Val Arg Lys
        355                 360                 365

Arg Ser Lys His Gly Thr Gly Asn Trp Ala Gly Asn Met Ile Thr Glu
370                 375                 380

Pro Tyr Lys Leu Thr Arg Gln Cys Glu Val Thr Ala Ile Leu Ile Leu
385                 390                 395                 400

Phe Gly Leu Pro Arg Leu Leu Thr Gly Ser Ile Leu Ala His Glu Met
                405                 410                 415

Met His Ala Trp Met Arg Leu Lys Gly Phe Arg Thr Leu Ser Gln Asp
            420                 425                 430

Val Glu Glu Gly Ile Cys Gln Val Met Ala His Lys Trp Leu Glu Ala
        435                 440                 445

Glu Leu Ala Ala Gly Ser Arg Asn Ser Asn Val Ala Ser Ser Ser Ser
450                 455                 460

Ser Arg Gly Val Lys Lys Gly Pro Arg Ser Gln Tyr Glu Arg Lys Leu
465                 470                 475                 480

Gly Glu Phe Phe Lys His Gln Ile Glu Ser Asp Ala Ser Pro Val Tyr
                485                 490                 495

Gly Asp Gly Phe Arg Ala Gly Arg Leu Ala Val Asn Lys Tyr Gly Leu
            500                 505                 510

Pro Lys Thr Leu Glu His Ile Gln Met Thr Gly Arg Phe Pro Val
        515                 520                 525

<210> SEQ ID NO 60
<211> LENGTH: 2250
<212> TYPE: DNA
<213> ORGANISM: Brassica oleracea
<220> FEATURE:
<221> NAME/KEY: exon
<222> LOCATION: (1)..(165)
<223> OTHER INFORMATION: Exon 1
<220> FEATURE:
<221> NAME/KEY: exon
<222> LOCATION: (333)..(435)
<223> OTHER INFORMATION: Exon 2
<220> FEATURE:
<221> NAME/KEY: exon
<222> LOCATION: (547)..(736)
<223> OTHER INFORMATION: Exon 3
<220> FEATURE:
<221> NAME/KEY: exon

```
<222> LOCATION: (823)..(943)
<223> OTHER INFORMATION: Exon 4
<220> FEATURE:
<221> NAME/KEY: exon
<222> LOCATION: (1034)..(1117)
<223> OTHER INFORMATION: Exon 5
<220> FEATURE:
<221> NAME/KEY: exon
<222> LOCATION: (1200)..(1532)
<223> OTHER INFORMATION: Exon 6-7
<220> FEATURE:
<221> NAME/KEY: exon
<222> LOCATION: (1622)..(1853)
<223> OTHER INFORMATION: Exon 8-9
<220> FEATURE:
<221> NAME/KEY: exon
<222> LOCATION: (1943)..(2250)
<223> OTHER INFORMATION: Exon 10

<400> SEQUENCE: 60 atg ggt tgg tta aac aag atc ttc aaa ggc tct aac caa agg ccc ccc      48
Met Gly Trp Leu Asn Lys Ile Phe Lys Gly Ser Asn Gln Arg Pro Pro
1               5                   10                  15 gtg ggg aat gag cac tat cat cat aat ggc ggc tat tac gag aac tac      96
Val Gly Asn Glu His Tyr His His Asn Gly Gly Tyr Tyr Glu Asn Tyr
            20                  25                  30 ccg cac gaa cat tct gag cct agt gca gag aca gat gct gat cat acg     144
Pro His Glu His Ser Glu Pro Ser Ala Glu Thr Asp Ala Asp His Thr
        35                  40                  45 cag gaa cca tct act tct gag gttactatat gctgattgag tatttgatag        195
Gln Glu Pro Ser Thr Ser Glu
    50                  55 cttttgtttt atagtttttt ttttctgatt taggagatct caaaaatagt caaataaatc   255
atattagtct ccatttatca gataatggtt tgtagtgtaa cctcaaaatt ttgttgttgt   315 tttttactt ttactag gaa gag aca tgg aat ggg aag gaa aat gaa gaa       365
                Glu Glu Thr Trp Asn Gly Lys Glu Asn Glu Glu
                                60                  65 gta gac cgt gca att gca ttg tct att tta gaa gaa gag aat caa gga    413
Val Asp Arg Ala Ile Ala Leu Ser Ile Leu Glu Glu Glu Asn Gln Gly
                70                  75                  80 cca gag act aat aca ggc gcc t gtgagttaca ttttactgat tgttttagcc    465
Pro Glu Thr Asn Thr Gly Ala
            85 caaaacagaa taatatgaag aaaaaaaaga tagttttgtt tcatacattt tgaaaaaaat   525 aaaataaaaa atgaaaagca g gg aaa cac gca atg atg gat gac gat gag     575
                        Trp Lys His Ala Met Met Asp Asp Asp Glu
                                    90                  95 caa ctt gct aga gcc ata caa gag agt atg ata gtt agg aat gga act    623
Gln Leu Ala Arg Ala Ile Gln Glu Ser Met Ile Val Arg Asn Gly Thr
100                 105                 110                 115 act tat gac ttt ggg aat gca tat ggg aat gga cat atg cat gga gga   671
Thr Tyr Asp Phe Gly Asn Ala Tyr Gly Asn Gly His Met His Gly Gly
                120                 125                 130 ggc aat gta tat gac agt ggt gat att tat tat cca aga cct att gct   719
Gly Asn Val Tyr Asp Ser Gly Asp Ile Tyr Tyr Pro Arg Pro Ile Ala
            135                 140                 145 ttc tca atg gac ttc ag gtttcactta gatggccttt taattttggt            766
Phe Ser Met Asp Phe Arg
                150 tgatctgtta tagtttcttt tagcttttta tcaacaactt gtcactgctg gcatag g    823 att tgt gct ggc tgc aat atg gag att ggc cat gga aga tat ctg aat   871
Ile Cys Ala Gly Cys Asn Met Glu Ile Gly His Gly Arg Tyr Leu Asn
```

-continued

```
                  155                 160                 165
tgc ctc aac gca cta tgg cat cca caa tgt ttt cga tgt tat ggc tgc        919
Cys Leu Asn Ala Leu Trp His Pro Gln Cys Phe Arg Cys Tyr Gly Cys
170                 175                 180                 185 agt cac cca atc tct gag tac gag gtgaactcaa attcattctt tccgttgtag       973
Ser His Pro Ile Ser Glu Tyr Glu
                190 tttaacctttt gaatcaatgt ataacatgt tttccttctt tttttttttgg tcttaaatag    1033 ttc tca acg tct ggg aac tac cct ttt cac aaa gct tgt tac agg gag       1081
Phe Ser Thr Ser Gly Asn Tyr Pro Phe His Lys Ala Cys Tyr Arg Glu
    195                 200                 205 agg ttt cat cca aaa tgt gat gtc tgc agc ctc ttt gtatgtaaaa            1127
Arg Phe His Pro Lys Cys Asp Val Cys Ser Leu Phe
210                 215                 220 tctttacccc ttttccgttg tttttcttcg gatattgcac ttatcttatg ttactttctt     1187
ttcttgtgac ag att cca acg aac cgt gct ggt ctt ata gag tat aga gca    1238
              Ile Pro Thr Asn Arg Ala Gly Leu Ile Glu Tyr Arg Ala
                                 225                 230 cat cct ttc tgg gtc cag aag tat tgc cca tct cac gaa cac gat gct       1286
His Pro Phe Trp Val Gln Lys Tyr Cys Pro Ser His Glu His Asp Ala
235                 240                 245                 250 act cct aga tgt tgc agt tgt gaa aga atg gag tca cgg aat aca gga       1334
Thr Pro Arg Cys Cys Ser Cys Glu Arg Met Glu Ser Arg Asn Thr Gly
                255                 260                 265 tat ttt gaa ctc aac gat gga cgg aag ctt tgc ctt gag tgt cta gac       1382
Tyr Phe Glu Leu Asn Asp Gly Arg Lys Leu Cys Leu Glu Cys Leu Asp
            270                 275                 280 tca tcg gtg atg gac act ttt caa tgc cag cct ctg tac ttg cag ata       1430
Ser Ser Val Met Asp Thr Phe Gln Cys Gln Pro Leu Tyr Leu Gln Ile
        285                 290                 295 caa gag ttc tac gaa gga ctt aac atg acg gta gag cag gag gtt cca       1478
Gln Glu Phe Tyr Glu Gly Leu Asn Met Thr Val Glu Gln Glu Val Pro
    300                 305                 310 ctt ctc ttg gtt gag agg caa gca ctt aac gaa gcc aga gaa ggt gaa       1526
Leu Leu Leu Val Glu Arg Gln Ala Leu Asn Glu Ala Arg Glu Gly Glu
315                 320                 325                 330 agg aat gtgagtagaa caaaaaaaat acaaatttac tttagtaact atttgagaat        1582
Arg Asn gtgtcacatt tatattgtgt cattgtgtgc tttctttag ggt cac tat cac atg        1636
                                           Gly His Tyr His Met
                                                          335 cca gag aca aga gga ctc tgc ctt tca gag gaa caa act gtt aga act       1684
Pro Glu Thr Arg Gly Leu Cys Leu Ser Glu Glu Gln Thr Val Arg Thr
                340                 345                 350 gtg aga aag aga tcg aag gga aac tgg agt ggg aat atg att aca gag       1732
Val Arg Lys Arg Ser Lys Gly Asn Trp Ser Gly Asn Met Ile Thr Glu
    355                 360                 365 caa ttc aag cta act cgc cgg tgc gag gtt act gcc att ctc atc tta       1780
Gln Phe Lys Leu Thr Arg Arg Cys Glu Val Thr Ala Ile Leu Ile Leu
370                 375                 380                 385 ttt ggt ctc cct agg cta ctc acc ggt tcg att cta gct cat gag atg       1828
Phe Gly Leu Pro Arg Leu Leu Thr Gly Ser Ile Leu Ala His Glu Met
                390                 395                 400 atg cac gcg tgg atg cgg ctc aaa g gtgagtttct tgcttcttgt               1873
Met His Ala Trp Met Arg Leu Lys
                405 ttcttatcta actgcttctc ttgtttcacg tttgttgaac cgttactaca atgtgtggtc     1933
```

```
ttgaaaaag gg  ttc cgg aca ctg agc caa gat gtt gaa gag ggg ata tgt        1983
            Gly Phe Arg Thr Leu Ser Gln Asp Val Glu Glu Gly Ile Cys
                410                 415                 420 caa gtg atg gct cat aag tgg tta gaa gtt gag ttg gct gct ggg tct          2031
Gln Val Met Ala His Lys Trp Leu Glu Val Glu Leu Ala Ala Gly Ser
    425                 430                 435 aga aac agc aac gct gca tca tct tct tat gga gga gtg aag aag gga          2079
Arg Asn Ser Asn Ala Ala Ser Ser Ser Tyr Gly Gly Val Lys Lys Gly
440                 445                 450                 455 cca aag tcg cag tac gag agg aag ctt ggt gag ttt ttc aag cac cag          2127
Pro Lys Ser Gln Tyr Glu Arg Lys Leu Gly Glu Phe Phe Lys His Gln
                460                 465                 470 ata gag tct gat gct tct ccg gtt tat gga gat ggg ttc agg gcc ggg          2175
Ile Glu Ser Asp Ala Ser Pro Val Tyr Gly Asp Gly Phe Arg Ala Gly
            475                 480                 485 agg tta gca gtt agc aag tat ggt ttg agg aga aca ctt gag cat ata          2223
Arg Leu Ala Val Ser Lys Tyr Gly Leu Arg Arg Thr Leu Glu His Ile
        490                 495                 500 caa atg act ggg aga ttc ccg gtt taa                                      2250
Gln Met Thr Gly Arg Phe Pro Val
    505                 510

<210> SEQ ID NO 61
<211> LENGTH: 1536
<212> TYPE: DNA
<213> ORGANISM: Brassica oleracea
<220> FEATURE:
<221> NAME/KEY: CDS
<222> LOCATION: (1)..(1536)

<400> SEQUENCE: 61 atg ggt tgg tta aac aag atc ttc aaa ggc tct aac caa agg ccc ccc          48
Met Gly Trp Leu Asn Lys Ile Phe Lys Gly Ser Asn Gln Arg Pro Pro
1               5                   10                  15 gtg ggg aat gag cac tat cat cat aat ggc ggc tat tac gag aac tac         96
Val Gly Asn Glu His Tyr His His Asn Gly Gly Tyr Tyr Glu Asn Tyr
            20                  25                  30 ccg cac gaa cat tct gag cct agt gca gag aca gat gct gat cat acg        144
Pro His Glu His Ser Glu Pro Ser Ala Glu Thr Asp Ala Asp His Thr
        35                  40                  45 cag gaa cca tct act tct gag gaa gag aca tgg aat ggg aag gaa aat        192
Gln Glu Pro Ser Thr Ser Glu Glu Glu Thr Trp Asn Gly Lys Glu Asn
    50                  55                  60 gaa gaa gta gac cgt gca att gca ttg tct att tta gaa gaa gag aat        240
Glu Glu Val Asp Arg Ala Ile Ala Leu Ser Ile Leu Glu Glu Glu Asn
65                  70                  75                  80 caa gga cca gag act aat aca ggc gcc tgg aaa cac gca atg atg gat        288
Gln Gly Pro Glu Thr Asn Thr Gly Ala Trp Lys His Ala Met Met Asp
                85                  90                  95 gac gat gag caa ctt gct aga gcc ata caa gag agt atg ata gtt agg        336
Asp Asp Glu Gln Leu Ala Arg Ala Ile Gln Glu Ser Met Ile Val Arg
            100                 105                 110 aat gga act act tat gac ttt ggg aat gca tat ggg aat gga cat atg        384
Asn Gly Thr Thr Tyr Asp Phe Gly Asn Ala Tyr Gly Asn Gly His Met
        115                 120                 125 cat gga gga ggc aat gta tat gac agt ggt gat att tat tat cca aga        432
His Gly Gly Gly Asn Val Tyr Asp Ser Gly Asp Ile Tyr Tyr Pro Arg
    130                 135                 140 cct att gct ttc tca atg gac ttc agg att tgt gct ggc tgc aat atg        480
Pro Ile Ala Phe Ser Met Asp Phe Arg Ile Cys Ala Gly Cys Asn Met
145                 150                 155                 160
```

```
gag att ggc cat gga aga tat ctg aat tgc ctc aac gca cta tgg cat      528
Glu Ile Gly His Gly Arg Tyr Leu Asn Cys Leu Asn Ala Leu Trp His
            165                 170                 175 cca caa tgt ttt cga tgt tat ggc tgc agt cac cca atc tct gag tac      576
Pro Gln Cys Phe Arg Cys Tyr Gly Cys Ser His Pro Ile Ser Glu Tyr
            180                 185                 190 gag ttc tca acg tct ggg aac tac cct ttt cac aaa gct tgt tac agg      624
Glu Phe Ser Thr Ser Gly Asn Tyr Pro Phe His Lys Ala Cys Tyr Arg
            195                 200                 205 gag agg ttt cat cca aaa tgt gat gtc tgc agc ctc ttt att cca acg      672
Glu Arg Phe His Pro Lys Cys Asp Val Cys Ser Leu Phe Ile Pro Thr
            210                 215                 220 aac cgt gct ggt ctt ata gag tat aga gca cat cct ttc tgg gtc cag      720
Asn Arg Ala Gly Leu Ile Glu Tyr Arg Ala His Pro Phe Trp Val Gln
225                 230                 235                 240 aag tat tgc cca tct cac gaa cac gat gct act cct aga tgt tgc agt      768
Lys Tyr Cys Pro Ser His Glu His Asp Ala Thr Pro Arg Cys Cys Ser
            245                 250                 255 tgt gaa aga atg gag tca cgg aat aca gga tat ttt gaa ctc aac gat      816
Cys Glu Arg Met Glu Ser Arg Asn Thr Gly Tyr Phe Glu Leu Asn Asp
            260                 265                 270 gga cgg aag ctt tgc ctt gag tgt cta gac tca tcg gtg atg gac act      864
Gly Arg Lys Leu Cys Leu Glu Cys Leu Asp Ser Ser Val Met Asp Thr
            275                 280                 285 ttt caa tgc cag cct ctg tac ttg cag ata caa gag ttc tac gaa gga      912
Phe Gln Cys Gln Pro Leu Tyr Leu Gln Ile Gln Glu Phe Tyr Glu Gly
            290                 295                 300 ctt aac atg acg gta gag cag gag gtt cca ctc ctc ttg gtt gag agg      960
Leu Asn Met Thr Val Glu Gln Glu Val Pro Leu Leu Leu Val Glu Arg
305                 310                 315                 320 caa gca ctt aac gaa gcc aga gaa ggt gaa agg aat ggt cac tat cac     1008
Gln Ala Leu Asn Glu Ala Arg Glu Gly Glu Arg Asn Gly His Tyr His
            325                 330                 335 atg cca gag aca aga gga ctc tgc ctt tca gag gaa caa act gtt aga     1056
Met Pro Glu Thr Arg Gly Leu Cys Leu Ser Glu Glu Gln Thr Val Arg
            340                 345                 350 act gtg aga aag aga tcg aag gga aac tgg agt ggg aat atg att aca     1104
Thr Val Arg Lys Arg Ser Lys Gly Asn Trp Ser Gly Asn Met Ile Thr
            355                 360                 365 gag caa ttc aag cta act cgc cgg tgc gag gtt act gcc att ctc atc     1152
Glu Gln Phe Lys Leu Thr Arg Arg Cys Glu Val Thr Ala Ile Leu Ile
            370                 375                 380 tta ttt ggt ctc cct agg cta ctc acc ggt tcg att cta gct cat gag     1200
Leu Phe Gly Leu Pro Arg Leu Leu Thr Gly Ser Ile Leu Ala His Glu
385                 390                 395                 400 atg atg cac gcg tgg atg cgg ctc aaa ggg ttc cgg aca ctg agc caa     1248
Met Met His Ala Trp Met Arg Leu Lys Gly Phe Arg Thr Leu Ser Gln
            405                 410                 415 gat gtt gaa gag ggg ata tgt caa gtg atg gct cat aag tgg tta gaa     1296
Asp Val Glu Glu Gly Ile Cys Gln Val Met Ala His Lys Trp Leu Glu
            420                 425                 430 gtt gag ttg gct gct ggg tct aga aac agc aac gct gca tca tct tct     1344
Val Glu Leu Ala Ala Gly Ser Arg Asn Ser Asn Ala Ala Ser Ser Ser
            435                 440                 445 tat gga gga gtg aag aag gga cca aag tcg cag tac gag agg aag ctt     1392
Tyr Gly Gly Val Lys Lys Gly Pro Lys Ser Gln Tyr Glu Arg Lys Leu
            450                 455                 460 ggt gag ttt ttc aag cac cag ata gag tct gat gct tct ccg gtt tat     1440
Gly Glu Phe Phe Lys His Gln Ile Glu Ser Asp Ala Ser Pro Val Tyr
465                 470                 475                 480
```

-continued

```
gga gat ggg ttc agg gcc ggg agg tta gca gtt agc aag tat ggt ttg      1488
Gly Asp Gly Phe Arg Ala Gly Arg Leu Ala Val Ser Lys Tyr Gly Leu
            485                 490                 495 agg aga aca ctt gag cat ata caa atg act ggg aga ttc ccg gtt taa      1536
Arg Arg Thr Leu Glu His Ile Gln Met Thr Gly Arg Phe Pro Val
        500                 505                 510
```

<210> SEQ ID NO 62
<211> LENGTH: 511
<212> TYPE: PRT
<213> ORGANISM: Brassica oleracea

<400> SEQUENCE: 62

```
Met Gly Trp Leu Asn Lys Ile Phe Lys Gly Ser Asn Gln Arg Pro Pro
1               5                   10                  15

Val Gly Asn Glu His Tyr His His Asn Gly Gly Tyr Tyr Glu Asn Tyr
            20                  25                  30

Pro His Glu His Ser Glu Pro Ser Ala Glu Thr Asp Ala Asp His Thr
        35                  40                  45

Gln Glu Pro Ser Thr Ser Glu Glu Thr Trp Asn Gly Lys Glu Asn
    50                  55                  60

Glu Glu Val Asp Arg Ala Ile Ala Leu Ser Ile Leu Glu Glu Glu Asn
65                  70                  75                  80

Gln Gly Pro Glu Thr Asn Thr Gly Ala Trp Lys His Ala Met Met Asp
                85                  90                  95

Asp Asp Glu Gln Leu Ala Arg Ala Ile Gln Glu Ser Met Ile Val Arg
            100                 105                 110

Asn Gly Thr Thr Tyr Asp Phe Gly Asn Ala Tyr Gly Asn Gly His Met
        115                 120                 125

His Gly Gly Gly Asn Val Tyr Asp Ser Gly Asp Ile Tyr Tyr Pro Arg
    130                 135                 140

Pro Ile Ala Phe Ser Met Asp Phe Arg Ile Cys Ala Gly Cys Asn Met
145                 150                 155                 160

Glu Ile Gly His Gly Arg Tyr Leu Asn Cys Leu Asn Ala Leu Trp His
                165                 170                 175

Pro Gln Cys Phe Arg Cys Tyr Gly Cys Ser His Pro Ile Ser Glu Tyr
            180                 185                 190

Glu Phe Ser Thr Ser Gly Asn Tyr Pro Phe His Lys Ala Cys Tyr Arg
        195                 200                 205

Glu Arg Phe His Pro Lys Cys Asp Val Cys Ser Leu Phe Ile Pro Thr
    210                 215                 220

Asn Arg Ala Gly Leu Ile Glu Tyr Arg Ala His Pro Phe Trp Val Gln
225                 230                 235                 240

Lys Tyr Cys Pro Ser His Glu His Asp Ala Thr Pro Arg Cys Cys Ser
                245                 250                 255

Cys Glu Arg Met Glu Ser Arg Asn Thr Gly Tyr Phe Glu Leu Asn Asp
            260                 265                 270

Gly Arg Lys Leu Cys Leu Glu Cys Leu Asp Ser Ser Val Met Asp Thr
        275                 280                 285

Phe Gln Cys Gln Pro Leu Tyr Leu Gln Ile Glu Phe Tyr Glu Gly
    290                 295                 300

Leu Asn Met Thr Val Glu Gln Glu Val Pro Leu Leu Val Glu Arg
305                 310                 315                 320

Gln Ala Leu Asn Glu Ala Arg Glu Gly Glu Arg Asn Gly His Tyr His
                325                 330                 335
```

```
Met Pro Glu Thr Arg Gly Leu Cys Leu Ser Glu Gln Thr Val Arg
            340                 345                 350

Thr Val Arg Lys Arg Ser Lys Gly Asn Trp Ser Gly Asn Met Ile Thr
            355                 360                 365

Glu Gln Phe Lys Leu Thr Arg Arg Cys Glu Val Thr Ala Ile Leu Ile
370                 375                 380

Leu Phe Gly Leu Pro Arg Leu Leu Thr Gly Ser Ile Leu Ala His Glu
385                 390                 395                 400

Met Met His Ala Trp Met Arg Leu Lys Gly Phe Arg Thr Leu Ser Gln
                405                 410                 415

Asp Val Glu Glu Gly Ile Cys Gln Val Met Ala His Lys Trp Leu Glu
            420                 425                 430

Val Glu Leu Ala Ala Gly Ser Arg Asn Ser Asn Ala Ala Ser Ser Ser
            435                 440                 445

Tyr Gly Gly Val Lys Lys Gly Pro Lys Ser Gln Tyr Glu Arg Lys Leu
        450                 455                 460

Gly Glu Phe Phe Lys His Gln Ile Glu Ser Asp Ala Ser Pro Val Tyr
465                 470                 475                 480

Gly Asp Gly Phe Arg Ala Gly Arg Leu Ala Val Ser Lys Tyr Gly Leu
                485                 490                 495

Arg Arg Thr Leu Glu His Ile Gln Met Thr Gly Arg Phe Pro Val
            500                 505                 510

<210> SEQ ID NO 63
<211> LENGTH: 2258
<212> TYPE: DNA
<213> ORGANISM: Brassica oleracea
<220> FEATURE:
<221> NAME/KEY: exon
<222> LOCATION: (1)..(171)
<223> OTHER INFORMATION: Exon 1
<220> FEATURE:
<221> NAME/KEY: exon
<222> LOCATION: (247)..(340)
<223> OTHER INFORMATION: Exon 2
<220> FEATURE:
<221> NAME/KEY: exon
<222> LOCATION: (416)..(650)
<223> OTHER INFORMATION: Exon 3
<220> FEATURE:
<221> NAME/KEY: exon
<222> LOCATION: (735)..(855)
<223> OTHER INFORMATION: Exon 4
<220> FEATURE:
<221> NAME/KEY: exon
<222> LOCATION: (939)..(1022)
<223> OTHER INFORMATION: Exon 5 isoform 1 and 3
<220> FEATURE:
<221> NAME/KEY: variation
<222> LOCATION: (939)..(1002)
<223> OTHER INFORMATION: Exon 5 isoform 2
<220> FEATURE:
<221> NAME/KEY: exon
<222> LOCATION: (1122)..(1241)
<223> OTHER INFORMATION: Exon 6 isoform 1 and 3
<220> FEATURE:
<221> NAME/KEY: variation
<222> LOCATION: (1157)..(1241)
<223> OTHER INFORMATION: Exon 6 isoform 2
<220> FEATURE:
<221> NAME/KEY: exon
<222> LOCATION: (1328)..(1540)
<223> OTHER INFORMATION: Exon 7
<220> FEATURE:
<221> NAME/KEY: exon
<222> LOCATION: (1634)..(1874)
<223> OTHER INFORMATION: Exon 8-9
```

```
<220> FEATURE:
<221> NAME/KEY: exon
<222> LOCATION: (1942)..(2197)
<223> OTHER INFORMATION: Exon 10 isoform 1
<220> FEATURE:
<221> NAME/KEY: variation
<222> LOCATION: (1942)..(2258)
<223> OTHER INFORMATION: Exon 10 isoform 2 and 3

<400> SEQUENCE: 63 atg ggt tgg ttt aac aag atc ttc aaa ggc tct acc caa agg ttc cgg      48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat      96
Leu Gly Asn Asp His Asp His Asn Gly Tyr Tyr Gln Ser Tyr Pro His
            20                  25                  30 gat gag cct agt gct gat act gat cct gat cct gat cct gat gaa act     144
Asp Glu Pro Ser Ala Asp Thr Asp Pro Asp Pro Asp Pro Asp Glu Thr
        35                  40                  45 cat act cag gaa cca tct acc tct gag gttactataa ctgtctttac           191
His Thr Gln Glu Pro Ser Thr Ser Glu
    50                  55 atatctctgg ctgcttgtac tgttgcttca acatttttt gtttcccttt actag gag     249
                                                                Glu gat aca tcc ggc cag gag aat gaa gac att gac cgt gca atc gca ttg     297
Asp Thr Ser Gly Gln Glu Asn Glu Asp Ile Asp Arg Ala Ile Ala Leu
        60                  65                  70 tct ctt ata gaa aac agt caa gga cat act aac aca ggc gcc g           340
Ser Leu Ile Glu Asn Ser Gln Gly His Thr Asn Thr Gly Ala
75                  80                  85 gtgagtcctt tttccttgcc aaactagaaa gaaatatgaa ttatgaaact cggtttgtta   400
catttaacag aatag tg  aac gca ggg aag tac gca atg gtg gat gaa gat   450
                    Val Asn Ala Gly Lys Tyr Ala Met Val Asp Glu Asp
                                90                  95                 100 gag cag ctt gct aga gcc ata caa gag agc atg gta gtt ggg aat aca     498
Glu Gln Leu Ala Arg Ala Ile Gln Glu Ser Met Val Val Gly Asn Thr
            105                 110                 115 ccg cgt cag aag cat gga agc agt tat gat att ggg aac gca tat ggg     546
Pro Arg Gln Lys His Gly Ser Ser Tyr Asp Ile Gly Asn Ala Tyr Gly
        120                 125                 130 tct gga gac gta tac ggg aat gga cat atg cat gga ggt gga aat gtt     594
Ser Gly Asp Val Tyr Gly Asn Gly His Met His Gly Gly Asn Val
    135                 140                 145 tat gcc aat gga gac att tat tat cca aga cct act gct ttt cct atg     642
Tyr Ala Asn Gly Asp Ile Tyr Tyr Pro Arg Pro Thr Ala Phe Pro Met
150                 155                 160 gat ttc ag  gttcactttt gatactcaat taatcatctg tagcctgttt             690
Asp Phe Arg
165 aacttggttg agatgtgtta ataacttat caagaacacc ttag g att tgt gct       744
                                                  Ile Cys Ala
                                                          170 ggc tgc aat atg gag att ggg cat gga aga tat ctg aat tgc ttg aat     792
Gly Cys Asn Met Glu Ile Gly His Gly Arg Tyr Leu Asn Cys Leu Asn
            175                 180                 185 gca ctg tgg cat ccg gaa tgt ttt cga tgt tat ggc tgt agg cac ccc     840
Ala Leu Trp His Pro Glu Cys Phe Arg Cys Tyr Gly Cys Arg His Pro
        190                 195                 200 att tct gag tac gag gtgaaatcaa gctttctcat tctttctatt gtagttaacc    895
Ile Ser Glu Tyr Glu
        205
```

```
tttgatgtaa tgaataacat gttttccttt tttttcttaa tag ttc tca aca tct      950
                                                 Phe Ser Thr Ser
                                                             210 ggt aac tac cct ttt cac aaa gct tgt tat agg gag aga tac cat cca      998
Gly Asn Tyr Pro Phe His Lys Ala Cys Tyr Arg Glu Arg Tyr His Pro
            215                 220                 225 aaa tgt gat gtc tgc agc ctc ttt gtatgtaaat ctttagtctt ttttttccat    1052
Lys Cys Asp Val Cys Ser Leu Phe
230                 235 cattaaagtg cctatttatt atatcttctg ttgattttct tgtttcgaa tgtaaatttg    1112 ttgtgacag att cca aca aac cat gct ggt ctt att gaa tat agg gca cat   1163
         Ile Pro Thr Asn His Ala Gly Leu Ile Glu Tyr Arg Ala His
                 240                 245 cct ttt tgg gtc cag aag tac tgc cct tct cac gaa cac gat gct acc     1211
Pro Phe Trp Val Gln Lys Tyr Cys Pro Ser His Glu His Asp Ala Thr
250                 255                 260                 265 cca aga tgt tgc agt tgc gaa aga atg gag gtgagttttt ctccccaaaa       1261
Pro Arg Cys Cys Ser Cys Glu Arg Met Glu
                270                 275 tgtgtcccac aacaaacatc tgctcaaagt cgaaatgtca actttcgctt ttttttttct   1321 ttgtag cca cgg aat aca gga tat gtt gaa ctt aac gat gga cgg aaa      1369
       Pro Arg Asn Thr Gly Tyr Val Glu Leu Asn Asp Gly Arg Lys
                       280                 285 ctt tgc ctg gag tgt ctg gac tca gcg gtc atg gac act ttt caa tgc     1417
Leu Cys Leu Glu Cys Leu Asp Ser Ala Val Met Asp Thr Phe Gln Cys
290                 295                 300                 305 caa cct ctg tat ctg cag ata caa gaa ttc tat gaa ggg ctt ttc atg     1465
Gln Pro Leu Tyr Leu Gln Ile Gln Glu Phe Tyr Glu Gly Leu Phe Met
                310                 315                 320 aag gta gag cag gac gtt cca ctt ctt tta gtt gag agg caa gca ctc     1513
Lys Val Glu Gln Asp Val Pro Leu Leu Leu Val Glu Arg Gln Ala Leu
            325                 330                 335 aac gaa gcc aga gaa ggt gaa aag aat gtgagtagca aaaataaaaa           1560
Asn Glu Ala Arg Glu Gly Glu Lys Asn
340                 345 cacaattata cttcagtaaa tatatctcct tttttcacaa gtgttttaag cttttcattg   1620
tgtgcttcct tag ggt cac tat cac atg cca gag acg aga gga ctc tgc      1669
               Gly His Tyr His Met Pro Glu Thr Arg Gly Leu Cys
                   350                 355 ctt tca gaa gaa caa act gtt agc act gtg aga aag aga tcg aag cat     1717
Leu Ser Glu Glu Gln Thr Val Ser Thr Val Arg Lys Arg Ser Lys His
360                 365                 370 ggc aca gga aac tgg gct ggg aat atg att aca gag cct tac aag tta     1765
Gly Thr Gly Asn Trp Ala Gly Asn Met Ile Thr Glu Pro Tyr Lys Leu
375                 380                 385                 390 aca cgt caa tgc gag gtt act gcc att ctc atc ttg ttt ggg ctc cct     1813
Thr Arg Gln Cys Glu Val Thr Ala Ile Leu Ile Leu Phe Gly Leu Pro
                395                 400                 405 agg cta ctc acc ggt tcg att cta gct cat gag atg atg cac gcg tgg     1861
Arg Leu Leu Thr Gly Ser Ile Leu Ala His Glu Met Met His Ala Trp
            410                 415                 420 atg cgg ctc aaa g gtgagtttct tagttcactg cttctctttt tttcacattg       1914
Met Arg Leu Lys
425 ttgaatctct attgtggtct tgaaaag ga  ttc cgg acg ctg agc caa gac gtt   1967
                                 Gly Phe Arg Thr Leu Ser Gln Asp Val
                                                 430                 435
```

-continued

| | |
|---|---|
| gaa gaa gga ata tgt caa gta atg gct cat aag tgg ttg gaa gca gag<br>Glu Glu Gly Ile Cys Gln Val Met Ala His Lys Trp Leu Glu Ala Glu<br>440 445 450 | 2015 |
| tta gct gct ggt tca aga aac agc aat gtt gca tca tca tct tct<br>Leu Ala Ala Gly Ser Arg Asn Ser Asn Val Ala Ser Ser Ser Ser Ser<br>455 460 465 | 2063 |
| tct tct gga gga ttg aag aag gga cca aga tcg caa tac gag agg aag<br>Ser Ser Gly Gly Leu Lys Lys Gly Pro Arg Ser Gln Tyr Glu Arg Lys<br>470 475 480 | 2111 |
| ctt ggt gag ttt ttc aag cac caa atc gag tct gat gct tct ccg gtt<br>Leu Gly Glu Phe Phe Lys His Gln Ile Glu Ser Asp Ala Ser Pro Val<br>485 490 495 | 2159 |
| tat gga gac ggg ttc agg gct ggg agg tta gcg gtt aa caagtatggt<br>Tyr Gly Asp Gly Phe Arg Ala Gly Arg Leu Ala Val<br>500 505 510 | 2207 |
| ttgccgaaaa cacttgagca tatacatatg accggtagat tcccggttta a | 2258 |

<210> SEQ ID NO 64
<211> LENGTH: 1571
<212> TYPE: DNA
<213> ORGANISM: Brassica oleracea
<220> FEATURE:
<221> NAME/KEY: CDS
<222> LOCATION: (1)..(1560)

<400> SEQUENCE: 64

| | |
|---|---|
| atg ggt tgg ttt aac aag atc ttc aaa ggc tct acc caa agg ttc cgg<br>Met Gly Trp Phe Asn Lys Ile Phe Lys Gly Ser Thr Gln Arg Phe Arg<br>1 5 10 15 | 48 |
| ctt ggg aat gac cat gac cac aat ggc tat tac cag agt tat cca cat<br>Leu Gly Asn Asp His Asp His Asn Gly Tyr Tyr Gln Ser Tyr Pro His<br>20 25 30 | 96 |
| gat gag cct agt gct gat act gat cct gat cct gat cct gat gaa act<br>Asp Glu Pro Ser Ala Asp Thr Asp Pro Asp Pro Asp Pro Asp Glu Thr<br>35 40 45 | 144 |
| cat act cag gaa cca tct acc tct gag gag gat aca tcc ggc cag gag<br>His Thr Gln Glu Pro Ser Thr Ser Glu Glu Asp Thr Ser Gly Gln Glu<br>50 55 60 | 192 |
| aat gaa gac att gac cgt gca atc gca ttg tct ctt ata gaa aac agt<br>Asn Glu Asp Ile Asp Arg Ala Ile Ala Leu Ser Leu Ile Glu Asn Ser<br>65 70 75 80 | 240 |
| caa gga cat act aac aca ggc gcc gtg aac gca ggg aag tac gca atg<br>Gln Gly His Thr Asn Thr Gly Ala Val Asn Ala Gly Lys Tyr Ala Met<br>85 90 95 | 288 |
| gtg gat gaa gat gag cag ctt gct aga gcc ata caa gag agc atg gta<br>Val Asp Glu Asp Glu Gln Leu Ala Arg Ala Ile Gln Glu Ser Met Val<br>100 105 110 | 336 |
| gtt ggg aat aca ccg cgt cag aag cat gga agc agt tat gat att ggg<br>Val Gly Asn Thr Pro Arg Gln Lys His Gly Ser Ser Tyr Asp Ile Gly<br>115 120 125 | 384 |
| aac gca tat ggg tct gga gac gta tac ggg aat gga cat atg cat gga<br>Asn Ala Tyr Gly Ser Gly Asp Val Tyr Gly Asn Gly His Met His Gly<br>130 135 140 | 432 |
| ggt gga aat gtt tat gcc aat gga gac att tat tat cca aga cct act<br>Gly Gly Asn Val Tyr Ala Asn Gly Asp Ile Tyr Tyr Pro Arg Pro Thr<br>145 150 155 160 | 480 |
| gct ttt cct atg gat ttc agg att tgt gct ggc tgc aat atg gag att<br>Ala Phe Pro Met Asp Phe Arg Ile Cys Ala Gly Cys Asn Met Glu Ile<br>165 170 175 | 528 |
| ggg cat gga aga tat ctg aat tgc ttg aat gca ctg tgg cat ccg gaa<br>Gly His Gly Arg Tyr Leu Asn Cys Leu Asn Ala Leu Trp His Pro Glu | 576 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 180 |     |     |     | 185 |     |     |     |     | 190 |     |     |     |     |     |      |
| tgt | ttt | cga | tgt | tat | ggc | tgt | agg | cac | ccc | att | tct | gag | tac | gag | ttc | 624  |
| Cys | Phe | Arg | Cys | Tyr | Gly | Cys | Arg | His | Pro | Ile | Ser | Glu | Tyr | Glu | Phe |      |
|     |     | 195 |     |     |     |     | 200 |     |     |     |     | 205 |     |     |     |      |
| tca | aca | tct | ggt | aac | tac | cct | ttt | cac | aaa | gct | tgt | tat | agg | gag | aga | 672  |
| Ser | Thr | Ser | Gly | Asn | Tyr | Pro | Phe | His | Lys | Ala | Cys | Tyr | Arg | Glu | Arg |      |
|     | 210 |     |     |     |     | 215 |     |     |     |     | 220 |     |     |     |     |      |
| tac | cat | cca | aaa | tgt | gat | gtc | tgc | agc | ctc | ttt | att | cca | aca | aac | cat | 720  |
| Tyr | His | Pro | Lys | Cys | Asp | Val | Cys | Ser | Leu | Phe | Ile | Pro | Thr | Asn | His |      |
| 225 |     |     |     |     | 230 |     |     |     |     | 235 |     |     |     |     | 240 |      |
| gct | ggt | ctt | att | gaa | tat | agg | gca | cat | cct | ttt | tgg | gtc | cag | aag | tac | 768  |
| Ala | Gly | Leu | Ile | Glu | Tyr | Arg | Ala | His | Pro | Phe | Trp | Val | Gln | Lys | Tyr |      |
|     |     |     |     | 245 |     |     |     |     | 250 |     |     |     |     | 255 |     |      |
| tgc | cct | tct | cac | gaa | cac | gat | gct | acc | cca | aga | tgt | tgc | agt | tgc | gaa | 816  |
| Cys | Pro | Ser | His | Glu | His | Asp | Ala | Thr | Pro | Arg | Cys | Cys | Ser | Cys | Glu |      |
|     |     |     | 260 |     |     |     |     | 265 |     |     |     |     | 270 |     |     |      |
| aga | atg | gag | cca | cgg | aat | aca | gga | tat | gtt | gaa | ctt | aac | gat | gga | cgg | 864  |
| Arg | Met | Glu | Pro | Arg | Asn | Thr | Gly | Tyr | Val | Glu | Leu | Asn | Asp | Gly | Arg |      |
|     |     | 275 |     |     |     |     | 280 |     |     |     |     | 285 |     |     |     |      |
| aaa | ctt | tgc | ctg | gag | tgt | ctg | gac | tca | gcg | gtc | atg | gac | act | ttt | caa | 912  |
| Lys | Leu | Cys | Leu | Glu | Cys | Leu | Asp | Ser | Ala | Val | Met | Asp | Thr | Phe | Gln |      |
|     | 290 |     |     |     |     | 295 |     |     |     |     | 300 |     |     |     |     |      |
| tgc | caa | cct | ctg | tat | ctg | cag | ata | caa | gaa | ttc | tat | gaa | ggg | ctt | ttc | 960  |
| Cys | Gln | Pro | Leu | Tyr | Leu | Gln | Ile | Gln | Glu | Phe | Tyr | Glu | Gly | Leu | Phe |      |
| 305 |     |     |     |     | 310 |     |     |     |     | 315 |     |     |     |     | 320 |      |
| atg | aag | gta | gag | cag | gac | gtt | cca | ctt | ctt | tta | gtt | gag | agg | caa | gca | 1008 |
| Met | Lys | Val | Glu | Gln | Asp | Val | Pro | Leu | Leu | Leu | Val | Glu | Arg | Gln | Ala |      |
|     |     |     |     | 325 |     |     |     |     | 330 |     |     |     |     | 335 |     |      |
| ctc | aac | gaa | gcc | aga | gaa | ggt | gaa | aag | aat | ggt | cac | tat | cac | atg | cca | 1056 |
| Leu | Asn | Glu | Ala | Arg | Glu | Gly | Glu | Lys | Asn | Gly | His | Tyr | His | Met | Pro |      |
|     |     |     | 340 |     |     |     |     | 345 |     |     |     |     | 350 |     |     |      |
| gag | acg | aga | gga | ctc | tgc | ctt | tca | gaa | gaa | caa | act | gtt | agc | act | gtg | 1104 |
| Glu | Thr | Arg | Gly | Leu | Cys | Leu | Ser | Glu | Glu | Gln | Thr | Val | Ser | Thr | Val |      |
|     |     | 355 |     |     |     |     | 360 |     |     |     |     | 365 |     |     |     |      |
| aga | aag | aga | tcg | aag | cat | ggc | aca | gga | aac | tgg | gct | ggg | aat | atg | att | 1152 |
| Arg | Lys | Arg | Ser | Lys | His | Gly | Thr | Gly | Asn | Trp | Ala | Gly | Asn | Met | Ile |      |
|     | 370 |     |     |     |     | 375 |     |     |     |     | 380 |     |     |     |     |      |
| aca | gag | cct | tac | aag | tta | aca | cgt | caa | tgc | gag | gtt | act | gcc | att | ctc | 1200 |
| Thr | Glu | Pro | Tyr | Lys | Leu | Thr | Arg | Gln | Cys | Glu | Val | Thr | Ala | Ile | Leu |      |
| 385 |     |     |     |     | 390 |     |     |     |     | 395 |     |     |     |     | 400 |      |
| atc | ttg | ttt | ggg | ctc | cct | agg | cta | ctc | acc | ggt | tcg | att | cta | gct | cat | 1248 |
| Ile | Leu | Phe | Gly | Leu | Pro | Arg | Leu | Leu | Thr | Gly | Ser | Ile | Leu | Ala | His |      |
|     |     |     |     | 405 |     |     |     |     | 410 |     |     |     |     | 415 |     |      |
| gag | atg | atg | cac | gcg | tgg | atg | cgg | ctc | aaa | gga | ttc | cgg | acg | ctg | agc | 1296 |
| Glu | Met | Met | His | Ala | Trp | Met | Arg | Leu | Lys | Gly | Phe | Arg | Thr | Leu | Ser |      |
|     |     |     | 420 |     |     |     |     | 425 |     |     |     |     | 430 |     |     |      |
| caa | gac | gtt | gaa | gaa | gga | ata | tgt | caa | gta | atg | gct | cat | aag | tgg | ttg | 1344 |
| Gln | Asp | Val | Glu | Glu | Gly | Ile | Cys | Gln | Val | Met | Ala | His | Lys | Trp | Leu |      |
|     |     | 435 |     |     |     |     | 440 |     |     |     |     | 445 |     |     |     |      |
| gaa | gca | gag | tta | gct | gct | ggt | tca | aga | aac | agc | aat | gtt | gca | tca | tca | 1392 |
| Glu | Ala | Glu | Leu | Ala | Ala | Gly | Ser | Arg | Asn | Ser | Asn | Val | Ala | Ser | Ser |      |
|     | 450 |     |     |     |     | 455 |     |     |     |     | 460 |     |     |     |     |      |
| tca | tct | tct | tct | tct | gga | gga | ttg | aag | aag | gga | cca | aga | tcg | caa | tac | 1440 |
| Ser | Ser | Ser | Ser | Ser | Gly | Gly | Leu | Lys | Lys | Gly | Pro | Arg | Ser | Gln | Tyr |      |
| 465 |     |     |     |     | 470 |     |     |     |     | 475 |     |     |     |     | 480 |      |
| gag | agg | aag | ctt | ggt | gag | ttt | ttc | aag | cac | caa | atc | gag | tct | gat | gct | 1488 |
| Glu | Arg | Lys | Leu | Gly | Glu | Phe | Phe | Lys | His | Gln | Ile | Glu | Ser | Asp | Ala |      |
|     |     |     |     | 485 |     |     |     |     | 490 |     |     |     |     | 495 |     |      |
| tct | ccg | gtt | tat | gga | gac | ggg | ttc | agg | gct | ggg | agg | tta | gcg | gtt | aac | 1536 |

```
Ser Pro Val Tyr Gly Asp Gly Phe Arg Ala Gly Arg Leu Ala Val Asn
            500                 505                 510 aaa ttc aga gat ggt cca acc taa atcgaaccgt a                        1571
Lys Phe Arg Asp Gly Pro Thr
        515

<210> SEQ ID NO 65
<211> LENGTH: 519
<212> TYPE: PRT
<213> ORGANISM: Brassica oleracea

<400> SEQUENCE: 65

Met Gly Trp Phe Asn Lys Ile Phe Lys Gly Ser Thr Gln Arg Phe Arg
1               5                   10                  15

Leu Gly Asn Asp His Asp His Asn Gly Tyr Tyr Gln Ser Tyr Pro His
            20                  25                  30

Asp Glu Pro Ser Ala Asp Thr Asp Pro Asp Pro Asp Pro Asp Glu Thr
        35                  40                  45

His Thr Gln Glu Pro Ser Thr Ser Glu Glu Asp Thr Ser Gly Gln Glu
    50                  55                  60

Asn Glu Asp Ile Asp Arg Ala Ile Ala Leu Ser Leu Ile Glu Asn Ser
65                  70                  75                  80

Gln Gly His Thr Asn Thr Gly Ala Val Asn Ala Gly Lys Tyr Ala Met
                85                  90                  95

Val Asp Glu Asp Glu Gln Leu Ala Arg Ala Ile Gln Glu Ser Met Val
            100                 105                 110

Val Gly Asn Thr Pro Arg Gln Lys His Gly Ser Ser Tyr Asp Ile Gly
        115                 120                 125

Asn Ala Tyr Gly Ser Gly Asp Val Tyr Gly Asn Gly His Met His Gly
    130                 135                 140

Gly Gly Asn Val Tyr Ala Asn Gly Asp Ile Tyr Tyr Pro Arg Pro Thr
145                 150                 155                 160

Ala Phe Pro Met Asp Phe Arg Ile Cys Ala Gly Cys Asn Met Glu Ile
                165                 170                 175

Gly His Gly Arg Tyr Leu Asn Cys Leu Asn Ala Leu Trp His Pro Glu
            180                 185                 190

Cys Phe Arg Cys Tyr Gly Cys Arg His Pro Ile Ser Glu Tyr Glu Phe
        195                 200                 205

Ser Thr Ser Gly Asn Tyr Pro Phe His Lys Ala Cys Tyr Arg Glu Arg
    210                 215                 220

Tyr His Pro Lys Cys Asp Val Cys Ser Leu Phe Ile Pro Thr Asn His
225                 230                 235                 240

Ala Gly Leu Ile Glu Tyr Arg Ala His Pro Phe Trp Val Gln Lys Tyr
                245                 250                 255

Cys Pro Ser His Glu His Asp Ala Thr Pro Arg Cys Cys Ser Cys Glu
            260                 265                 270

Arg Met Glu Pro Arg Asn Thr Gly Tyr Val Glu Leu Asn Asp Gly Arg
        275                 280                 285

Lys Leu Cys Leu Glu Cys Leu Asp Ser Ala Val Met Asp Thr Phe Gln
    290                 295                 300

Cys Gln Pro Leu Tyr Leu Gln Ile Gln Glu Phe Tyr Glu Gly Leu Phe
305                 310                 315                 320

Met Lys Val Glu Gln Asp Val Pro Leu Leu Leu Val Glu Arg Gln Ala
                325                 330                 335

Leu Asn Glu Ala Arg Glu Gly Glu Lys Asn Gly His Tyr His Met Pro
```

```
                    340                 345                 350
Glu Thr Arg Gly Leu Cys Leu Ser Glu Glu Gln Thr Val Ser Thr Val
            355                 360                 365

Arg Lys Arg Ser Lys His Gly Thr Gly Asn Trp Ala Gly Asn Met Ile
        370                 375                 380

Thr Glu Pro Tyr Lys Leu Thr Arg Gln Cys Glu Val Thr Ala Ile Leu
385                 390                 395                 400

Ile Leu Phe Gly Leu Pro Arg Leu Leu Thr Gly Ser Ile Leu Ala His
                405                 410                 415

Glu Met Met His Ala Trp Met Arg Leu Lys Gly Phe Arg Thr Leu Ser
            420                 425                 430

Gln Asp Val Glu Glu Gly Ile Cys Gln Val Met Ala His Lys Trp Leu
        435                 440                 445

Glu Ala Glu Leu Ala Ala Gly Ser Arg Asn Ser Asn Val Ala Ser Ser
    450                 455                 460

Ser Ser Ser Ser Gly Gly Leu Lys Lys Gly Pro Arg Ser Gln Tyr
465                 470                 475                 480

Glu Arg Lys Leu Gly Glu Phe Phe Lys His Gln Ile Glu Ser Asp Ala
                485                 490                 495

Ser Pro Val Tyr Gly Asp Gly Phe Arg Ala Gly Arg Leu Ala Val Asn
            500                 505                 510

Lys Phe Arg Asp Gly Pro Thr
        515

<210> SEQ ID NO 66
<211> LENGTH: 1541
<212> TYPE: DNA
<213> ORGANISM: Brassica oleracea
<220> FEATURE:
<221> NAME/KEY: CDS
<222> LOCATION: (1)..(909)

<400> SEQUENCE: 66 atg ggt tgg ttt aac aag atc ttc aaa ggc tct acc caa agg ttc cgg      48
Met Gly Trp Phe Asn Lys Ile Phe Lys Gly Ser Thr Gln Arg Phe Arg
1               5                   10                  15 ctt ggg aat gac cat gac cac aat ggc tat tac cag agt tat cca cat      96
Leu Gly Asn Asp His Asp His Asn Gly Tyr Tyr Gln Ser Tyr Pro His
            20                  25                  30 gat gag cct agt gct gat act gat cct gat cct gat cct gat gaa act     144
Asp Glu Pro Ser Ala Asp Thr Asp Pro Asp Pro Asp Pro Asp Glu Thr
        35                  40                  45 cat act cag gaa cca tct acc tct gag gag gat aca tcc ggc cag gag     192
His Thr Gln Glu Pro Ser Thr Ser Glu Glu Asp Thr Ser Gly Gln Glu
    50                  55                  60 aat gaa gac att gac cgt gca atc gca ttg tct ctt ata gaa aac agt     240
Asn Glu Asp Ile Asp Arg Ala Ile Ala Leu Ser Leu Ile Glu Asn Ser
65                  70                  75                  80 caa gga cat act aac aca ggc gcc gtg aac gca ggg aag tac gca atg     288
Gln Gly His Thr Asn Thr Gly Ala Val Asn Ala Gly Lys Tyr Ala Met
                85                  90                  95 gtg gat gaa gat gag cag ctt gct aga gcc ata caa gag agc atg gta     336
Val Asp Glu Asp Glu Gln Leu Ala Arg Ala Ile Gln Glu Ser Met Val
            100                 105                 110 gtt ggg aat aca ccg cgt cag aag cat gga agc agt tat gat att ggg     384
Val Gly Asn Thr Pro Arg Gln Lys His Gly Ser Ser Tyr Asp Ile Gly
        115                 120                 125 aac gca tat ggg tct gga gac gta tac ggg aat gga cat atg cat gga     432
```

|   |   |   |   |   |   |   |   |   |   |   |   |   |   |   |   |
|---|---|---|---|---|---|---|---|---|---|---|---|---|---|---|---|
| Asn | Ala | Tyr | Gly | Ser | Gly | Asp | Val | Tyr | Gly | Asn | Gly | His | Met | His | Gly |
|   | 130 |   |   |   | 135 |   |   |   | 140 |   |   |   |   |   |   |

```
ggt gga aat gtt tat gcc aat gga gac att tat tat cca aga cct act       480
Gly Gly Asn Val Tyr Ala Asn Gly Asp Ile Tyr Tyr Pro Arg Pro Thr
145             150                 155                 160 gct ttt cct atg gat ttc agg att tgt gct ggc tgc aat atg gag att       528
Ala Phe Pro Met Asp Phe Arg Ile Cys Ala Gly Cys Asn Met Glu Ile
                165                 170                 175 ggg cat gga aga tat ctg aat tgc ttg aat gca ctg tgg cat ccg gaa       576
Gly His Gly Arg Tyr Leu Asn Cys Leu Asn Ala Leu Trp His Pro Glu
            180                 185                 190 tgt ttt cga tgt tat ggc tgt agg cac ccc att tct gag tac gag ttc       624
Cys Phe Arg Cys Tyr Gly Cys Arg His Pro Ile Ser Glu Tyr Glu Phe
        195                 200                 205 tca aca tct ggt aac tac cct ttt cac aaa gct tgt tat agg gag aga       672
Ser Thr Ser Gly Asn Tyr Pro Phe His Lys Ala Cys Tyr Arg Glu Arg
    210                 215                 220 tac cat cca aaa tgg cac atc ctt ttt ggg tcc aga agt act gcc ctt       720
Tyr His Pro Lys Trp His Ile Leu Phe Gly Ser Arg Ser Thr Ala Leu
225             230                 235                 240 ctc acg aac acg atg cta ccc caa gat gtt gca gtt gcg aaa gaa tgg       768
Leu Thr Asn Thr Met Leu Pro Gln Asp Val Ala Val Ala Lys Glu Trp
                245                 250                 255 agc cac gga ata cag gat atg ttg aac tta acg atg gac gga aac ttt       816
Ser His Gly Ile Gln Asp Met Leu Asn Leu Thr Met Asp Gly Asn Phe
                260                 265                 270 gcc tgg agt gtc tgg act cag cgg tca tgg aca ctt ttc aat gcc aac       864
Ala Trp Ser Val Trp Thr Gln Arg Ser Trp Thr Leu Phe Asn Ala Asn
            275                 280                 285 ctc tgt atc tgc aga tac aag aat tct atg aag ggc ttt tca tga           909
Leu Cys Ile Cys Arg Tyr Lys Asn Ser Met Lys Gly Phe Ser
        290                 295                 300 aggtagagca ggacgttcca cttcttttag ttgagaggca agcactcaac gaagccagag     969
aaggtgaaaa gaatggtcac tatcacatgc agagacgag aggactctgc ctttcagaag     1029
aacaaactgt tagcactgtg agaaagagat cgaagcatgg cacaggaaac tgggctggga     1089
atatgattac agagccttac aagttaacac gtcaatgcga ggttactgcc attctcatct    1149
tgtttgggct ccctaggcta ctcaccggtt cgattctagc tcatgagatg atgcacgcgt    1209
ggatgcggct caaaggattc cggacgctga gccaagacgt tgaagaagga atatgtcaag    1269
taatggctca taagtggttg gaagcagagt tagctgctgg ttcaagaaac agcaatgttg    1329
catcatcatc atcttcttct tctggaggat tgaagaaggg accaagatcg caatacgaga    1389
ggaagcttgg tgagttttc aagcaccaaa tcgagtctga tgcttctccg gtttatggag     1449
acgggttcag ggctgggagg ttagcggtta acaagtatgg tttgccgaaa acacttgagc    1509
atatacatat gaccggtaga ttcccggttt aa                                  1541
```

```
<210> SEQ ID NO 67
<211> LENGTH: 302
<212> TYPE: PRT
<213> ORGANISM: Brassica oleracea

<400> SEQUENCE: 67
```

|   |   |   |   |   |   |   |   |   |   |   |   |   |   |   |
|---|---|---|---|---|---|---|---|---|---|---|---|---|---|---|
| Met | Gly | Trp | Phe | Asn | Lys | Ile | Phe | Lys | Gly | Ser | Thr | Gln | Arg | Phe | Arg |
| 1 |   |   |   | 5 |   |   |   |   | 10 |   |   |   |   | 15 |   |

|   |   |   |   |   |   |   |   |   |   |   |   |   |   |
|---|---|---|---|---|---|---|---|---|---|---|---|---|---|
| Leu | Gly | Asn | Asp | His | Asp | His | Asn | Gly | Tyr | Tyr | Gln | Ser | Tyr | Pro | His |
|   |   |   | 20 |   |   |   |   | 25 |   |   |   |   | 30 |   |   |

```
Asp Glu Pro Ser Ala Asp Thr Asp Pro Asp Pro Asp Glu Thr
         35                  40                  45

His Thr Gln Glu Pro Ser Thr Ser Glu Glu Asp Thr Ser Gly Gln Glu
 50                      55                  60

Asn Glu Asp Ile Asp Arg Ala Ile Ala Leu Ser Leu Ile Glu Asn Ser
 65                  70                  75                  80

Gln Gly His Thr Asn Thr Gly Ala Val Asn Ala Gly Lys Tyr Ala Met
                 85                  90                  95

Val Asp Glu Asp Glu Gln Leu Ala Arg Ala Ile Gln Glu Ser Met Val
            100                 105                 110

Val Gly Asn Thr Pro Arg Gln Lys His Gly Ser Ser Tyr Asp Ile Gly
        115                 120                 125

Asn Ala Tyr Gly Ser Gly Asp Val Tyr Gly Asn Gly His Met His Gly
130                 135                 140

Gly Gly Asn Val Tyr Ala Asn Gly Asp Ile Tyr Tyr Pro Arg Pro Thr
145                 150                 155                 160

Ala Phe Pro Met Asp Phe Arg Ile Cys Ala Gly Cys Asn Met Glu Ile
                165                 170                 175

Gly His Gly Arg Tyr Leu Asn Cys Leu Asn Ala Leu Trp His Pro Glu
            180                 185                 190

Cys Phe Arg Cys Tyr Gly Cys Arg His Pro Ile Ser Glu Tyr Glu Phe
        195                 200                 205

Ser Thr Ser Gly Asn Tyr Pro Phe His Lys Ala Cys Tyr Arg Glu Arg
    210                 215                 220

Tyr His Pro Lys Trp His Ile Leu Phe Gly Ser Arg Ser Thr Ala Leu
225                 230                 235                 240

Leu Thr Asn Thr Met Leu Pro Gln Asp Val Ala Val Ala Lys Glu Trp
                245                 250                 255

Ser His Gly Ile Gln Asp Met Leu Asn Leu Thr Met Asp Gly Asn Phe
            260                 265                 270

Ala Trp Ser Val Trp Thr Gln Arg Ser Trp Thr Leu Phe Asn Ala Asn
        275                 280                 285

Leu Cys Ile Cys Arg Tyr Lys Asn Ser Met Lys Gly Phe Ser
    290                 295                 300

<210> SEQ ID NO 68
<211> LENGTH: 1596
<212> TYPE: DNA
<213> ORGANISM: Brassica oleracea
<220> FEATURE:
<221> NAME/KEY: CDS
<222> LOCATION: (1)..(1596)

<400> SEQUENCE: 68 atg ggt tgg ttt aac aag atc ttc aaa ggc tct acc caa agg ttc cgg     48
Met Gly Trp Phe Asn Lys Ile Phe Lys Gly Ser Thr Gln Arg Phe Arg
 1               5                  10                  15 ctt ggg aat gac cat gac cac aat ggc tat tac cag agt tat cca cat     96
Leu Gly Asn Asp His Asp His Asn Gly Tyr Tyr Gln Ser Tyr Pro His
             20                  25                  30 gat gag cct agt gct gat act gat cct gat cct gat cct gat gaa act    144
Asp Glu Pro Ser Ala Asp Thr Asp Pro Asp Pro Asp Pro Asp Glu Thr
         35                  40                  45 cat act cag gaa cca tct acc tct gag gag gat aca tcc ggc cag gag    192
His Thr Gln Glu Pro Ser Thr Ser Glu Glu Asp Thr Ser Gly Gln Glu
 50                      55                  60 aat gaa gac att gac cgt gca atc gca ttg tct ctt ata gaa aac agt    240
```

-continued

```
                Asn Glu Asp Ile Asp Arg Ala Ile Ala Leu Ser Leu Ile Glu Asn Ser
                 65                  70                  75                  80 caa gga cat act aac aca ggc gcc gtg aac gca ggg aag tac gca atg              288
Gln Gly His Thr Asn Thr Gly Ala Val Asn Ala Gly Lys Tyr Ala Met
                 85                  90                  95 gtg gat gaa gat gag cag ctt gct aga gcc ata caa gag agc atg gta              336
Val Asp Glu Asp Glu Gln Leu Ala Arg Ala Ile Gln Glu Ser Met Val
                100                 105                 110 gtt ggg aat aca ccg cgt cag aag cat gga agc agt tat gat att ggg              384
Val Gly Asn Thr Pro Arg Gln Lys His Gly Ser Ser Tyr Asp Ile Gly
                115                 120                 125 aac gca tat ggg tct gga gac gta tac ggg aat gga cat atg cat gga              432
Asn Ala Tyr Gly Ser Gly Asp Val Tyr Gly Asn Gly His Met His Gly
            130                 135                 140 ggt gga aat gtt tat gcc aat gga gac att tat tat cca aga cct act              480
Gly Gly Asn Val Tyr Ala Asn Gly Asp Ile Tyr Tyr Pro Arg Pro Thr
145                 150                 155                 160 gct ttt cct atg gat ttc agg att tgt gct ggc tgc aat atg gag att              528
Ala Phe Pro Met Asp Phe Arg Ile Cys Ala Gly Cys Asn Met Glu Ile
                165                 170                 175 ggg cat gga aga tat ctg aat tgc ttg aat gca ctg tgg cat ccg gaa              576
Gly His Gly Arg Tyr Leu Asn Cys Leu Asn Ala Leu Trp His Pro Glu
                180                 185                 190 tgt ttt cga tgt tat ggc tgt agg cac ccc att tct gag tac gag ttc              624
Cys Phe Arg Cys Tyr Gly Cys Arg His Pro Ile Ser Glu Tyr Glu Phe
                195                 200                 205 tca aca tct ggt aac tac cct ttt cac aaa gct tgt tat agg gag aga              672
Ser Thr Ser Gly Asn Tyr Pro Phe His Lys Ala Cys Tyr Arg Glu Arg
            210                 215                 220 tac cat cca aaa tgt gat gtc tgc agc ctc ttt att cca aca aac cat              720
Tyr His Pro Lys Cys Asp Val Cys Ser Leu Phe Ile Pro Thr Asn His
225                 230                 235                 240 gct ggt ctt att gaa tat agg gca cat cct ttt tgg gtc cag aag tac              768
Ala Gly Leu Ile Glu Tyr Arg Ala His Pro Phe Trp Val Gln Lys Tyr
                245                 250                 255 tgc cct tct cac gaa cac gat gct acc cca aga tgt tgc agt tgc gaa              816
Cys Pro Ser His Glu His Asp Ala Thr Pro Arg Cys Cys Ser Cys Glu
                260                 265                 270 aga atg gag cca cgg aat aca gga tat gtt gaa ctt aac gat gga cgg              864
Arg Met Glu Pro Arg Asn Thr Gly Tyr Val Glu Leu Asn Asp Gly Arg
                275                 280                 285 aaa ctt tgc ctg gag tgt ctg gac tca gcg gtc atg gac act ttt caa              912
Lys Leu Cys Leu Glu Cys Leu Asp Ser Ala Val Met Asp Thr Phe Gln
            290                 295                 300 tgc caa cct ctg tat ctg cag ata caa gaa ttc tat gaa ggg ctt ttc              960
Cys Gln Pro Leu Tyr Leu Gln Ile Gln Glu Phe Tyr Glu Gly Leu Phe
305                 310                 315                 320 atg aag gta gag cag gac gtt cca ctt ctt tta gtt gag agg caa gca             1008
Met Lys Val Glu Gln Asp Val Pro Leu Leu Leu Val Glu Arg Gln Ala
                325                 330                 335 ctc aac gaa gcc aga gaa ggt gaa aag aat ggt cac tat cac atg cca             1056
Leu Asn Glu Ala Arg Glu Gly Glu Lys Asn Gly His Tyr His Met Pro
                340                 345                 350 gag acg aga gga ctc tgc ctt tca gaa gaa caa act gtt agc act gtg             1104
Glu Thr Arg Gly Leu Cys Leu Ser Glu Glu Gln Thr Val Ser Thr Val
                355                 360                 365 aga aag aga tcg aag cat ggc aca gga aac tgg gct ggg aat atg att             1152
Arg Lys Arg Ser Lys His Gly Thr Gly Asn Trp Ala Gly Asn Met Ile
                370                 375                 380
```

```
aca gag cct tac aag tta aca cgt caa tgc gag gtt act gcc att ctc    1200
Thr Glu Pro Tyr Lys Leu Thr Arg Gln Cys Glu Val Thr Ala Ile Leu
385                 390                 395                 400 atc ttg ttt ggg ctc cct agg cta ctc acc ggt tcg att cta gct cat    1248
Ile Leu Phe Gly Leu Pro Arg Leu Leu Thr Gly Ser Ile Leu Ala His
            405                 410                 415 gag atg atg cac gcg tgg atg cgg ctc aaa gga ttc cgg acg ctg agc    1296
Glu Met Met His Ala Trp Met Arg Leu Lys Gly Phe Arg Thr Leu Ser
        420                 425                 430 caa gac gtt gaa gaa gga ata tgt caa gta atg gct cat aag tgg ttg    1344
Gln Asp Val Glu Glu Gly Ile Cys Gln Val Met Ala His Lys Trp Leu
    435                 440                 445 gaa gca gag tta gct gct ggt tca aga aac agc aat gtt gca tca tca    1392
Glu Ala Glu Leu Ala Ala Gly Ser Arg Asn Ser Asn Val Ala Ser Ser
450                 455                 460 tca tct tct tct tct gga gga ttg aag aag gga cca aga tcg caa tac    1440
Ser Ser Ser Ser Ser Gly Gly Leu Lys Lys Gly Pro Arg Ser Gln Tyr
465                 470                 475                 480 gag agg aag ctt ggt gag ttt ttc aag cac caa atc gag tct gat gct    1488
Glu Arg Lys Leu Gly Glu Phe Phe Lys His Gln Ile Glu Ser Asp Ala
            485                 490                 495 tct ccg gtt tat gga gac ggg ttc agg gct ggg agg tta gcg gtt aac    1536
Ser Pro Val Tyr Gly Asp Gly Phe Arg Ala Gly Arg Leu Ala Val Asn
        500                 505                 510 aag tat ggt ttg ccg aaa aca ctt gag cat ata cat atg acc ggt aga    1584
Lys Tyr Gly Leu Pro Lys Thr Leu Glu His Ile His Met Thr Gly Arg
    515                 520                 525 ttc ccg gtt taa                                                    1596
Phe Pro Val
    530

<210> SEQ ID NO 69
<211> LENGTH: 531
<212> TYPE: PRT
<213> ORGANISM: Brassica oleracea

<400> SEQUENCE: 69

Met Gly Trp Phe Asn Lys Ile Phe Lys Gly Ser Thr Gln Arg Phe Arg
1               5                   10                  15

Leu Gly Asn Asp His Asp His Asn Gly Tyr Tyr Gln Ser Tyr Pro His
            20                  25                  30

Asp Glu Pro Ser Ala Asp Thr Asp Pro Asp Pro Asp Pro Asp Glu Thr
        35                  40                  45

His Thr Gln Glu Pro Ser Thr Ser Glu Glu Asp Thr Ser Gly Gln Glu
    50                  55                  60

Asn Glu Asp Ile Asp Arg Ala Ile Ala Leu Ser Leu Ile Glu Asn Ser
65                  70                  75                  80

Gln Gly His Thr Asn Thr Gly Ala Val Asn Ala Gly Lys Tyr Ala Met
                85                  90                  95

Val Asp Glu Asp Glu Gln Leu Ala Arg Ala Ile Gln Glu Ser Met Val
            100                 105                 110

Val Gly Asn Thr Pro Arg Gln Lys His Gly Ser Ser Tyr Asp Ile Gly
        115                 120                 125

Asn Ala Tyr Gly Ser Gly Asp Val Tyr Gly Asn Gly His Met His Gly
    130                 135                 140

Gly Gly Asn Val Tyr Ala Asn Gly Asp Ile Tyr Tyr Pro Arg Pro Thr
145                 150                 155                 160

Ala Phe Pro Met Asp Phe Arg Ile Cys Ala Gly Cys Asn Met Glu Ile
```

```
              165                 170                 175
Gly His Gly Arg Tyr Leu Asn Cys Leu Asn Ala Leu Trp His Pro Glu
            180                 185                 190

Cys Phe Arg Cys Tyr Gly Cys Arg His Pro Ile Ser Glu Tyr Glu Phe
            195                 200                 205

Ser Thr Ser Gly Asn Tyr Pro Phe His Lys Ala Cys Tyr Arg Glu Arg
    210                 215                 220

Tyr His Pro Lys Cys Asp Val Cys Ser Leu Phe Ile Pro Thr Asn His
225                 230                 235                 240

Ala Gly Leu Ile Glu Tyr Arg Ala His Pro Phe Trp Val Gln Lys Tyr
                245                 250                 255

Cys Pro Ser His Glu His Asp Ala Thr Pro Arg Cys Cys Ser Cys Glu
            260                 265                 270

Arg Met Glu Pro Arg Asn Thr Gly Tyr Val Glu Leu Asn Asp Gly Arg
        275                 280                 285

Lys Leu Cys Leu Glu Cys Leu Asp Ser Ala Val Met Asp Thr Phe Gln
    290                 295                 300

Cys Gln Pro Leu Tyr Leu Gln Ile Gln Glu Phe Tyr Glu Gly Leu Phe
305                 310                 315                 320

Met Lys Val Glu Gln Asp Val Pro Leu Leu Val Glu Arg Gln Ala
                325                 330                 335

Leu Asn Glu Ala Arg Glu Gly Lys Asn Gly His Tyr His Met Pro
            340                 345                 350

Glu Thr Arg Gly Leu Cys Leu Ser Glu Glu Gln Thr Val Ser Thr Val
        355                 360                 365

Arg Lys Arg Ser Lys His Gly Thr Asn Trp Ala Gly Asn Met Ile
    370                 375                 380

Thr Glu Pro Tyr Lys Leu Thr Arg Gln Cys Glu Val Thr Ala Ile Leu
385                 390                 395                 400

Ile Leu Phe Gly Leu Pro Arg Leu Leu Thr Gly Ser Ile Leu Ala His
                405                 410                 415

Glu Met Met His Ala Trp Met Arg Leu Lys Gly Phe Arg Thr Leu Ser
            420                 425                 430

Gln Asp Val Glu Glu Gly Ile Cys Gln Val Met Ala His Lys Trp Leu
        435                 440                 445

Glu Ala Glu Leu Ala Ala Gly Ser Arg Asn Ser Asn Val Ala Ser Ser
    450                 455                 460

Ser Ser Ser Ser Gly Gly Leu Lys Lys Gly Pro Arg Ser Gln Tyr
465                 470                 475                 480

Glu Arg Lys Leu Gly Glu Phe Phe Lys His Gln Ile Glu Ser Asp Ala
                485                 490                 495

Ser Pro Val Tyr Gly Asp Gly Phe Arg Ala Gly Arg Leu Ala Val Asn
            500                 505                 510

Lys Tyr Gly Leu Pro Lys Thr Leu Glu His Ile His Met Thr Gly Arg
        515                 520                 525

Phe Pro Val
    530

<210> SEQ ID NO 70
<211> LENGTH: 2139
<212> TYPE: DNA
<213> ORGANISM: Brassica nigra
<220> FEATURE:
<221> NAME/KEY: exon
<222> LOCATION: (1)..(159)
```

```
<223> OTHER INFORMATION: Exon 1
<220> FEATURE:
<221> NAME/KEY: exon
<222> LOCATION: (240)..(535)
<223> OTHER INFORMATION: Exon 2-3
<220> FEATURE:
<221> NAME/KEY: exon
<222> LOCATION: (627)..(747)
<223> OTHER INFORMATION: Exon 4
<220> FEATURE:
<221> NAME/KEY: exon
<222> LOCATION: (836)..(919)
<223> OTHER INFORMATION: Exon 5
<220> FEATURE:
<221> NAME/KEY: exon
<222> LOCATION: (1013)..(1132)
<223> OTHER INFORMATION: Exon 6
<220> FEATURE:
<221> NAME/KEY: exon
<222> LOCATION: (1198)..(1410)
<223> OTHER INFORMATION: Exon 7
<220> FEATURE:
<221> NAME/KEY: exon
<222> LOCATION: (1495)..(1735)
<223> OTHER INFORMATION: Exon 8-9
<220> FEATURE:
<221> NAME/KEY: exon
<222> LOCATION: (1826)..(2139)
<223> OTHER INFORMATION: Exon 10

<400> SEQUENCE: 70 atg ggt tgg ttc aac aag atc ttc aaa ggc tcc tct aac caa agg ttc        48
Met Gly Trp Phe Asn Lys Ile Phe Lys Gly Ser Ser Asn Gln Arg Phe
1               5                   10                  15 ccg gtt ggg aat gag cac tat cat aat tac ggc tat tac gat ccc aat        96
Pro Val Gly Asn Glu His Tyr His Asn Tyr Gly Tyr Tyr Asp Pro Asn
            20                  25                  30 gcg cat tct gag cct agt gca gat aca gat gct gat cat acg cag gag        144
Ala His Ser Glu Pro Ser Ala Asp Thr Asp Ala Asp His Thr Gln Glu
        35                  40                  45 cca tct act tct gag gttgctatat gattgattat ggctattggt agctttgttt        199
Pro Ser Thr Ser Glu
    50 tatagttttt tttttctgag tttcttgtct tttactatag gat aca tgg aat ggc        254
                                            Asp Thr Trp Asn Gly
                                                        55 cag gaa aat gaa gaa gtg gac cgt gca att gca atg tct ctt cta gaa        302
Gln Glu Asn Glu Glu Val Asp Arg Ala Ile Ala Met Ser Leu Leu Glu
 60                  65                  70 gag aat caa gga cag act aat aaa ggg aag tat gca atg gtg gat gac        350
Glu Asn Gln Gly Gln Thr Asn Lys Gly Lys Tyr Ala Met Val Asp Asp
 75                  80                  85                  90 gat gag caa ctt gct aga gcc ata caa gaa agt atg ata gct agg aat        398
Asp Glu Gln Leu Ala Arg Ala Ile Gln Glu Ser Met Ile Ala Arg Asn
                 95                 100                 105 gga gct act tat gac aat att ggg gct ggt gat ttc tac ggg aat gga        446
Gly Ala Thr Tyr Asp Asn Ile Gly Ala Gly Asp Phe Tyr Gly Asn Gly
            110                 115                 120 cct atg cat gga gga gga gga gga aat gta tat gcc aat gga gat            494
Pro Met His Gly Gly Gly Gly Gly Asn Val Tyr Ala Asn Gly Asp
        125                 130                 135 att tat tat cca aaa cct att gct ttc tct atg gac ttc ag               535
Ile Tyr Tyr Pro Lys Pro Ile Ala Phe Ser Met Asp Phe Arg
    140                 145                 150 gtacttagat ggctaaacat ctttaaattt tggttgatgt gttatagttt cttttttaagg       595 cttttatcaa caacttgtcg tcactgaata g g att tgt gct ggc tgc aat atg        648
```

-continued

```
                            Ile Cys Ala Gly Cys Asn Met
                                            155 gag att ggc cat gga aga tat ctg aat tgt cta aat gcg cta tgg cat        696
Glu Ile Gly His Gly Arg Tyr Leu Asn Cys Leu Asn Ala Leu Trp His
160                 165                 170                 175 cca gaa tgt ttt cga tgt tat ggc tgt agt cac cct att tct gag tac        744
Pro Glu Cys Phe Arg Cys Tyr Gly Cys Ser His Pro Ile Ser Glu Tyr
                180                 185                 190 gag gtgtgaactc aaattctcat tctttccgtt gtagttaacc ttagaatcaa             797
Glu tgtaataaca tgttttcctc tctttttttc ttaaatag ttc tca acg tct ggg aac      853
                                        Phe Ser Thr Ser Gly Asn
                                                        195 tac cct ttt cac aaa gct tgt tac agg gag aga ttt cat cca aaa tgt        901
Tyr Pro Phe His Lys Ala Cys Tyr Arg Glu Arg Phe His Pro Lys Cys
        200                 205                 210 gat gtc tgc agc cac ttt gtatgtaaaa tctttacccc ttttccatcg               949
Asp Val Cys Ser His Phe
215                 220 tttaatgcgt tgttttgttt ggatatttca cttattttcg gttgctttct ttctttgtga      1009 cag att cca aca aac ctt gct ggt ctt att gaa tac aga gca cat cct        1057
Ile Pro Thr Asn Leu Ala Gly Leu Ile Glu Tyr Arg Ala His Pro
                225                 230                 235 ttt tgg gtc cag aag tat tgc cct tct cac gag cac gat gct act cca        1105
Phe Trp Val Gln Lys Tyr Cys Pro Ser His Glu His Asp Ala Thr Pro
                240                 245                 250 aga tgt tgc agt tgt gaa aga atg gag gtgagttttt cctcctctaa              1152
Arg Cys Cys Ser Cys Glu Arg Met Glu
                255                 260 acaagtttat gggcggaagt taacaagttt tcgttatttt tgcag cca cgg aat acg      1209
                                                Pro Arg Asn Thr gga tat gtt gaa ctc aac gat gga cgg aaa ctt tgc ctg gag tgt cta        1257
Gly Tyr Val Glu Leu Asn Asp Gly Arg Lys Leu Cys Leu Glu Cys Leu
265                 270                 275                 280 gac tct gca gtg atg gac act ttt caa tgc caa cct ctg tac ttg cag        1305
Asp Ser Ala Val Met Asp Thr Phe Gln Cys Gln Pro Leu Tyr Leu Gln
                285                 290                 295 ata caa gaa ttc tac gaa gga ctt aac atg aag gtg gag cag gaa gtt        1353
Ile Gln Glu Phe Tyr Glu Gly Leu Asn Met Lys Val Glu Gln Glu Val
                300                 305                 310 cct ctt ctc tta gtt gag agg caa gca ctc aac gaa gcc aga gaa ggt        1401
Pro Leu Leu Leu Val Glu Arg Gln Ala Leu Asn Glu Ala Arg Glu Gly
                315                 320                 325 gaa aag aat gtgagtaaaa aaacacacag ttttgcttga gaatacatca               1450
Glu Lys Asn
        330 cattttccca aagtgtttta gattttcatt ttgtgctctc ttag ggt cac tat cac       1506
                                                Gly His Tyr His
                                                            335 atg cca gag aca aga gga ctc tgc ctg tct gaa gaa caa act gtt cgc        1554
Met Pro Glu Thr Arg Gly Leu Cys Leu Ser Glu Glu Gln Thr Val Arg
                340                 345                 350 act gta aga aag aga tca aag cat agt aca gga aac tgg gct ggg aac        1602
Thr Val Arg Lys Arg Ser Lys His Ser Thr Gly Asn Trp Ala Gly Asn
                355                 360                 365 atg att aca gag cct ttc aag cta act cgt cga tgc gag gtt act gcc        1650
Met Ile Thr Glu Pro Phe Lys Leu Thr Arg Arg Cys Glu Val Thr Ala
                370                 375                 380
```

```
att ctc atc ttg ttt ggt ctc cct agg cta ctc act ggt tca att cta      1698
Ile Leu Ile Leu Phe Gly Leu Pro Arg Leu Leu Thr Gly Ser Ile Leu
385                 390                 395 gct cat gag atg atg cat gcg tgg atg cgg ctc aac g gtgagtttct         1745
Ala His Glu Met Met His Ala Trp Met Arg Leu Asn
400                 405                 410 tgctctctat ttgactctgc ttcttcttct cttgtttcac atttctttaa ccgtttaact    1805
acaatgtggt cttgaaaaag gg  ttc cgg aca ttg agc caa gac gtt gaa gag    1857
                         Gly Phe Arg Thr Leu Ser Gln Asp Val Glu Glu
                                         415                 420 gga ata tgt caa gtg atg gct cat aag tgg ttg gaa gct gag tta gat      1905
Gly Ile Cys Gln Val Met Ala His Lys Trp Leu Glu Ala Glu Leu Asp
    425                 430                 435 gct ggt tca gga aac agc aat gct gca tca tcg tca tct tct tct aga     1953
Ala Gly Ser Gly Asn Ser Asn Ala Ala Ser Ser Ser Ser Ser Ser Arg
440                 445                 450 gga gtg aag aag gga cca agg tcg cag tac gag agg aag ctt ggt gag     2001
Gly Val Lys Lys Gly Pro Arg Ser Gln Tyr Glu Arg Lys Leu Gly Glu
455                 460                 465                 470 ttt ttc aag cac caa att gag tct gat gcg tct ccg gtt tat gga gat     2049
Phe Phe Lys His Gln Ile Glu Ser Asp Ala Ser Pro Val Tyr Gly Asp
                475                 480                 485 ggg ttc agg gct ggg aag tta gcg gtt aac aag tat ggt ttg aga aga     2097
Gly Phe Arg Ala Gly Lys Leu Ala Val Asn Lys Tyr Gly Leu Arg Arg
            490                 495                 500 aca ctt gag cat ata cag atg act ggg aga ttc ccg gtt taa             2139
Thr Leu Glu His Ile Gln Met Thr Gly Arg Phe Pro Val
            505                 510                 515

<210> SEQ ID NO 71
<211> LENGTH: 1548
<212> TYPE: DNA
<213> ORGANISM: Brassica nigra
<220> FEATURE:
<221> NAME/KEY: CDS
<222> LOCATION: (1)..(1548)

<400> SEQUENCE: 71 atg ggt tgg ttc aac aag atc ttc aaa ggc tcc tct aac caa agg ttc      48
Met Gly Trp Phe Asn Lys Ile Phe Lys Gly Ser Ser Asn Gln Arg Phe
1               5                   10                  15 ccg gtt ggg aat gag cac tat cat aat tac ggc tat tac gat ccc aat      96
Pro Val Gly Asn Glu His Tyr His Asn Tyr Gly Tyr Tyr Asp Pro Asn
                20                  25                  30 gcg cat tct gag cct agt gca gat aca gat gct gat cat acg cag gag     144
Ala His Ser Glu Pro Ser Ala Asp Thr Asp Ala Asp His Thr Gln Glu
            35                  40                  45 cca tct act tct gag gat aca tgg aat ggc cag gaa aat gaa gaa gtg     192
Pro Ser Thr Ser Glu Asp Thr Trp Asn Gly Gln Glu Asn Glu Glu Val
        50                  55                  60 gac cgt gca att gca atg tct ctt cta gaa gag aat caa gga cag act     240
Asp Arg Ala Ile Ala Met Ser Leu Leu Glu Glu Asn Gln Gly Gln Thr
65                  70                  75                  80 aat aaa ggg aag tat gca atg gtg gat gac gat gag caa ctt gct aga     288
Asn Lys Gly Lys Tyr Ala Met Val Asp Asp Asp Glu Gln Leu Ala Arg
                85                  90                  95 gcc ata caa gaa agt atg ata gct agg aat gga gct act tat gac aat     336
Ala Ile Gln Glu Ser Met Ile Ala Arg Asn Gly Ala Thr Tyr Asp Asn
                100                 105                 110 att ggg gct ggt gat ttc tac ggg aat gga cct atg cat gga gga gga     384
Ile Gly Ala Gly Asp Phe Tyr Gly Asn Gly Pro Met His Gly Gly Gly
```

```
                115                    120                    125
gga gga gga aat gta tat gcc aat gga gat att tat tat cca aaa cct       432
Gly Gly Gly Asn Val Tyr Ala Asn Gly Asp Ile Tyr Tyr Pro Lys Pro
    130                    135                    140 att gct ttc tct atg gac ttc agg att tgt gct ggc tgc aat atg gag       480
Ile Ala Phe Ser Met Asp Phe Arg Ile Cys Ala Gly Cys Asn Met Glu
145                    150                    155                160 att ggc cat gga aga tat ctg aat tgt cta aat gcg cta tgg cat cca       528
Ile Gly His Gly Arg Tyr Leu Asn Cys Leu Asn Ala Leu Trp His Pro
                165                    170                    175 gaa tgt ttt cga tgt tat ggc tgt agt cac cct att tct gag tac gag       576
Glu Cys Phe Arg Cys Tyr Gly Cys Ser His Pro Ile Ser Glu Tyr Glu
            180                    185                    190 ttc tca acg tct ggg aac tac cct ttt cac aaa gct tgt tac agg gag       624
Phe Ser Thr Ser Gly Asn Tyr Pro Phe His Lys Ala Cys Tyr Arg Glu
        195                    200                    205 aga ttt cat cca aaa tgt gat gtc tgc agc cac ttt att cca aca aac       672
Arg Phe His Pro Lys Cys Asp Val Cys Ser His Phe Ile Pro Thr Asn
    210                    215                    220 ctt gct ggt ctt att gaa tac aga gca cat cct ttt tgg gtc cag aag       720
Leu Ala Gly Leu Ile Glu Tyr Arg Ala His Pro Phe Trp Val Gln Lys
225                    230                    235                240 tat tgc cct tct cac gag cac gat gct act cca aga tgt tgc agt tgt       768
Tyr Cys Pro Ser His Glu His Asp Ala Thr Pro Arg Cys Cys Ser Cys
                245                    250                    255 gaa aga atg gag cca cgg aat acg gga tat gtt gaa ctc aac gat gga       816
Glu Arg Met Glu Pro Arg Asn Thr Gly Tyr Val Glu Leu Asn Asp Gly
            260                    265                    270 cgg aaa ctt tgc ctg gag tgt cta gac tct gca gtg atg gac act ttt       864
Arg Lys Leu Cys Leu Glu Cys Leu Asp Ser Ala Val Met Asp Thr Phe
        275                    280                    285 caa tgc caa cct ctg tac ttg cag ata caa gaa ttc tac gaa gga ctt       912
Gln Cys Gln Pro Leu Tyr Leu Gln Ile Gln Glu Phe Tyr Glu Gly Leu
    290                    295                    300 aac atg aag gtg gag cag gaa gtt cct ctt ctc tta gtt gag agg caa       960
Asn Met Lys Val Glu Gln Glu Val Pro Leu Leu Leu Val Glu Arg Gln
305                    310                    315                320 gca ctc aac gaa gcc aga gaa ggt gaa aag aat ggt cac tat cac atg      1008
Ala Leu Asn Glu Ala Arg Glu Gly Glu Lys Asn Gly His Tyr His Met
                325                    330                    335 cca gag aca aga gga ctc tgc ctg tct gaa gaa caa act gtt cgc act      1056
Pro Glu Thr Arg Gly Leu Cys Leu Ser Glu Glu Gln Thr Val Arg Thr
            340                    345                    350 gta aga aag aga tca aag cat agt aca gga aac tgg gct ggg aac atg      1104
Val Arg Lys Arg Ser Lys His Ser Thr Gly Asn Trp Ala Gly Asn Met
        355                    360                    365 att aca gag cct ttc aag cta act cgt cga tgc gag gtt act gcc att      1152
Ile Thr Glu Pro Phe Lys Leu Thr Arg Arg Cys Glu Val Thr Ala Ile
    370                    375                    380 ctc atc ttg ttt ggt ctc cct agg cta ctc act ggt tca att cta gct      1200
Leu Ile Leu Phe Gly Leu Pro Arg Leu Leu Thr Gly Ser Ile Leu Ala
385                    390                    395                400 cat gag atg atg cat gcg tgg atg cgg ctc aac ggg ttc cgg aca ttg      1248
His Glu Met Met His Ala Trp Met Arg Leu Asn Gly Phe Arg Thr Leu
                405                    410                    415 agc caa gac gtt gaa gag gga ata tgt caa gtg atg gct cat aag tgg      1296
Ser Gln Asp Val Glu Glu Gly Ile Cys Gln Val Met Ala His Lys Trp
            420                    425                    430 ttg gaa gct gag tta gat gct ggt tca gga aac agc aat gct gca tca      1344
```

```
Leu Glu Ala Glu Leu Asp Ala Gly Ser Gly Asn Ser Asn Ala Ala Ser
            435                 440                 445 tcg tca tct tct tct aga gga gtg aag aag gga cca agg tcg cag tac      1392
Ser Ser Ser Ser Ser Arg Gly Val Lys Lys Gly Pro Arg Ser Gln Tyr
450                 455                 460 gag agg aag ctt ggt gag ttt ttc aag cac caa att gag tct gat gcg      1440
Glu Arg Lys Leu Gly Glu Phe Phe Lys His Gln Ile Glu Ser Asp Ala
465                 470                 475                 480 tct ccg gtt tat gga gat ggg ttc agg gct ggg aag tta gcg gtt aac      1488
Ser Pro Val Tyr Gly Asp Gly Phe Arg Ala Gly Lys Leu Ala Val Asn
                485                 490                 495 aag tat ggt ttg aga aga aca ctt gag cat ata cag atg act ggg aga      1536
Lys Tyr Gly Leu Arg Arg Thr Leu Glu His Ile Gln Met Thr Gly Arg
            500                 505                 510 ttc ccg gtt taa                                                      1548
Phe Pro Val
        515

<210> SEQ ID NO 72
<211> LENGTH: 515
<212> TYPE: PRT
<213> ORGANISM: Brassica nigra

<400> SEQUENCE: 72

Met Gly Trp Phe Asn Lys Ile Phe Lys Gly Ser Ser Asn Gln Arg Phe
1               5                   10                  15

Pro Val Gly Asn Glu His Tyr His Asn Tyr Gly Tyr Tyr Asp Pro Asn
            20                  25                  30

Ala His Ser Glu Pro Ser Ala Asp Thr Asp Ala Asp His Thr Gln Glu
        35                  40                  45

Pro Ser Thr Ser Glu Asp Thr Trp Asn Gly Gln Glu Asn Glu Glu Val
    50                  55                  60

Asp Arg Ala Ile Ala Met Ser Leu Leu Glu Glu Asn Gln Gly Gln Thr
65                  70                  75                  80

Asn Lys Gly Lys Tyr Ala Met Val Asp Asp Glu Gln Leu Ala Arg
                85                  90                  95

Ala Ile Gln Glu Ser Met Ile Ala Arg Asn Gly Ala Tyr Asp Asn
            100                 105                 110

Ile Gly Ala Gly Asp Phe Tyr Gly Asn Gly Pro Met His Gly Gly
        115                 120                 125

Gly Gly Gly Asn Val Tyr Ala Asn Gly Asp Ile Tyr Tyr Pro Lys Pro
    130                 135                 140

Ile Ala Phe Ser Met Asp Phe Arg Ile Cys Ala Gly Cys Asn Met Glu
145                 150                 155                 160

Ile Gly His Gly Arg Tyr Leu Asn Cys Leu Asn Ala Leu Trp His Pro
                165                 170                 175

Glu Cys Phe Arg Cys Tyr Gly Cys Ser His Pro Ile Ser Glu Tyr Glu
            180                 185                 190

Phe Ser Thr Ser Gly Asn Tyr Pro Phe His Lys Ala Cys Tyr Arg Glu
        195                 200                 205

Arg Phe His Pro Lys Cys Asp Val Cys Ser His Phe Ile Pro Thr Asn
    210                 215                 220

Leu Ala Gly Leu Ile Glu Tyr Arg Ala His Pro Phe Trp Val Gln Lys
225                 230                 235                 240

Tyr Cys Pro Ser His Glu His Asp Ala Thr Pro Arg Cys Cys Ser Cys
                245                 250                 255
```

```
Glu Arg Met Glu Pro Arg Asn Thr Gly Tyr Val Glu Leu Asn Asp Gly
            260                 265                 270

Arg Lys Leu Cys Leu Glu Cys Leu Asp Ser Ala Val Met Asp Thr Phe
        275                 280                 285

Gln Cys Gln Pro Leu Tyr Leu Gln Ile Gln Glu Phe Tyr Glu Gly Leu
    290                 295                 300

Asn Met Lys Val Glu Gln Glu Val Pro Leu Leu Val Glu Arg Gln
305                 310                 315                 320

Ala Leu Asn Glu Ala Arg Glu Gly Glu Lys Asn Gly His Tyr His Met
                325                 330                 335

Pro Glu Thr Arg Gly Leu Cys Leu Ser Glu Glu Gln Thr Val Arg Thr
            340                 345                 350

Val Arg Lys Arg Ser Lys His Ser Thr Gly Asn Trp Ala Gly Asn Met
        355                 360                 365

Ile Thr Glu Pro Phe Lys Leu Thr Arg Arg Cys Glu Val Thr Ala Ile
    370                 375                 380

Leu Ile Leu Phe Gly Leu Pro Arg Leu Leu Thr Gly Ser Ile Leu Ala
385                 390                 395                 400

His Glu Met Met His Ala Trp Met Arg Leu Asn Gly Phe Arg Thr Leu
                405                 410                 415

Ser Gln Asp Val Glu Glu Gly Ile Cys Gln Val Met Ala His Lys Trp
            420                 425                 430

Leu Glu Ala Glu Leu Asp Ala Gly Ser Gly Asn Ser Asn Ala Ala Ser
        435                 440                 445

Ser Ser Ser Ser Ser Arg Gly Val Lys Lys Gly Pro Arg Ser Gln Tyr
    450                 455                 460

Glu Arg Lys Leu Gly Glu Phe Phe Lys His Gln Ile Glu Ser Asp Ala
465                 470                 475                 480

Ser Pro Val Tyr Gly Asp Gly Phe Arg Ala Gly Lys Leu Ala Val Asn
                485                 490                 495

Lys Tyr Gly Leu Arg Arg Thr Leu Glu His Ile Gln Met Thr Gly Arg
            500                 505                 510

Phe Pro Val
        515

<210> SEQ ID NO 73
<211> LENGTH: 2327
<212> TYPE: DNA
<213> ORGANISM: Brassica nigra
<220> FEATURE:
<221> NAME/KEY: exon
<222> LOCATION: (1)..(180)
<223> OTHER INFORMATION: Exon 1
<220> FEATURE:
<221> NAME/KEY: exon
<222> LOCATION: (257)..(353)
<223> OTHER INFORMATION: Exon 2
<220> FEATURE:
<221> NAME/KEY: exon
<222> LOCATION: (452)..(680)
<223> OTHER INFORMATION: Exon 3
<220> FEATURE:
<221> NAME/KEY: exon
<222> LOCATION: (749)..(869)
<223> OTHER INFORMATION: Exon 4
<220> FEATURE:
<221> NAME/KEY: exon
<222> LOCATION: (969)..(1052)
<223> OTHER INFORMATION: Exon 5
<220> FEATURE:
<221> NAME/KEY: exon
<222> LOCATION: (1156)..(1275)
```

<223> OTHER INFORMATION: Exon 6
<220> FEATURE:
<221> NAME/KEY: exon
<222> LOCATION: (1370)..(1582)
<223> OTHER INFORMATION: Exon 7
<220> FEATURE:
<221> NAME/KEY: exon
<222> LOCATION: (1683)..(1923)
<223> OTHER INFORMATION: Exon 8-9
<220> FEATURE:
<221> NAME/KEY: exon
<222> LOCATION: (2011)..(2327)
<223> OTHER INFORMATION: Exon 10

<400> SEQUENCE: 73

```
atg ggt tgg ttt aac aag atc ttc aaa ggg tct act caa agg ttc cgg       48
Met Gly Trp Phe Asn Lys Ile Phe Lys Gly Ser Thr Gln Arg Phe Arg
1               5                   10                  15 ctt ggg aat gac cac ggt cac agt ggc tat tac cag agt tat cca cat       96
Leu Gly Asn Asp His Gly His Ser Gly Tyr Tyr Gln Ser Tyr Pro His
            20                  25                  30 tct tca cat gat gag cct agt gct gat aca gat cct gat cct gat cct      144
Ser Ser His Asp Glu Pro Ser Ala Asp Thr Asp Pro Asp Pro Asp Pro
        35                  40                  45 gat gaa act cat act cag gaa cca tct acc tct gag gttactatga           190
Asp Glu Thr His Thr Gln Glu Pro Ser Thr Ser Glu
    50                  55                  60 ctgattataa tacattagct ctggtttgca ctgttgcttc aactcttgct gtttctcttt    250 tactag gag gat aca tcg aac gac cag gag aat gaa gaa ata gac cgt       298
       Glu Asp Thr Ser Asn Asp Gln Glu Asn Glu Glu Ile Asp Arg
                       65                  70 gca atc gca ctg tct cta tta gaa gag agt caa gga cag aca aac aca      346
Ala Ile Ala Leu Ser Leu Leu Glu Glu Ser Gln Gly Gln Thr Asn Thr
75                  80                  85                  90 ggc gcc g gtgagtcctt tttccggaca gatgagcaaa gtacatttct tcattttccg     403
Gly Ala gttatatgaa aagatggttt agttatcaaa ctacattgaa ctttgcag gg  aaa tac     459
                                                    Gly Lys Tyr
                                                            95 gca atg gtg gat gat gac gag caa ctt gct aga gcc ata caa gaa agt      507
Ala Met Val Asp Asp Asp Glu Gln Leu Ala Arg Ala Ile Gln Glu Ser
                100                 105                 110 atg gta gtt ggg aat acg ccg cgt cag aag cat gga agt agt tat gat      555
Met Val Val Gly Asn Thr Pro Arg Gln Lys His Gly Ser Ser Tyr Asp
            115                 120                 125 att ggg aat gca tat ggg gct gga gac gta tac ggg aat gga cat atg      603
Ile Gly Asn Ala Tyr Gly Ala Gly Asp Val Tyr Gly Asn Gly His Met
        130                 135                 140 cat ggt gga ggt gga aat gta tat gcc aat gga gat att tat tat cca      651
His Gly Gly Gly Gly Asn Val Tyr Ala Asn Gly Asp Ile Tyr Tyr Pro
    145                 150                 155 aga cct act gct ttt cct atg gat ttc ag  gttcacttta atttggttga        700
Arg Pro Thr Ala Phe Pro Met Asp Phe Arg
160                 165 gatgtgttaa gtttctttcc agcttatcaa caacgtgtca atacatag g att tgt       755
                                                    Ile Cys
                                                        170 gct ggc tgc aat atg gag att ggc cat gga aga tat ctg aat tgc ttg      803
Ala Gly Cys Asn Met Glu Ile Gly His Gly Arg Tyr Leu Asn Cys Leu
            175                 180                 185 aat gca cta tgg cat cca gaa tgt ttt cga tgt tat ggc tgt agg cac      851
Asn Ala Leu Trp His Pro Glu Cys Phe Arg Cys Tyr Gly Cys Arg His
```

```
              190                 195                 200
cct att tct gag tac gag gtgaaatcaa gctcttccaa tatctcattc              899
Pro Ile Ser Glu Tyr Glu
    205 tttctgttgt agacttgtag ttaacctctg aaataatgca taacatgttt ttccttttt      959 tcttaatag ttc tca aca tct gga aat tac cct ttt cac aaa gct tgt tac    1010
           Phe Ser Thr Ser Gly Asn Tyr Pro Phe His Lys Ala Cys Tyr
               210                 215                 220 aga gag aga tac cat cca aaa tgt gat gtc tgc agc cac ttt               1052
Arg Glu Arg Tyr His Pro Lys Cys Asp Val Cys Ser His Phe
    225                 230                 235 gtatgtaaat cttttacctt tgctatcgtt atatgggtag tttcatcgga tattgcactt    1112
atcttctgtt gcttgttttt tcgaatgcaa atttgttgta cag att cca aca aac      1167
                                              Ile Pro Thr Asn
                                                          240 cat gct ggt ctt att gaa tat agg gca cat cct ttc tgg gtt cag aag      1215
His Ala Gly Leu Ile Glu Tyr Arg Ala His Pro Phe Trp Val Gln Lys
            245                 250                 255 tat tgc cct tct cac gaa cac gat gct acc cca aga tgt tgc agt tgc      1263
Tyr Cys Pro Ser His Glu His Asp Ala Thr Pro Arg Cys Cys Ser Cys
            260                 265                 270 gaa aga atg gag gtgagttttt ctcccctaag tctcccacaa caaacatcat          1315
Glu Arg Met Glu
    275 ctcaaagtca atactttttg ggaggaaagt tgacagcttc tctttatttt gtag cca      1372
                                                              Pro cgg aat acg gga tat gtt gaa ctt aac gat gga cgg aaa ctt tgt ctc      1420
Arg Asn Thr Gly Tyr Val Glu Leu Asn Asp Gly Arg Lys Leu Cys Leu
    280                 285                 290 gag tgt ctg gac tca gcg gtc atg gac act ttt caa tgc caa cct ctg      1468
Glu Cys Leu Asp Ser Ala Val Met Asp Thr Phe Gln Cys Gln Pro Leu
295                 300                 305                 310 tat ctg cag ata caa gca ttc tat gaa ggg ctt ttc atg aag gta gag      1516
Tyr Leu Gln Ile Gln Ala Phe Tyr Glu Gly Leu Phe Met Lys Val Glu
            315                 320                 325 cag gac gtt cca ctt ctt tta gtt gag agg caa gca ctt aac gaa gcc      1564
Gln Asp Val Pro Leu Leu Leu Val Glu Arg Gln Ala Leu Asn Glu Ala
            330                 335                 340 aga gaa ggg gaa aag aat gtgagtaaaa aaaaaaacaa ttattcttca             1612
Arg Glu Gly Glu Lys Asn
    345 gtgaacatat cacatttttg cttcttttt ttttccaaag tgttttagct tttggttgtg    1672 tgattcttag ggt cac tat cac atg cca gag aca aga gga ctc tgc ctt      1721
            Gly His Tyr His Met Pro Glu Thr Arg Gly Leu Cys Leu
                350                 355                 360 tca gaa gaa cag act gtt agc acc gta aga aag aga tcg aag cat ggc      1769
Ser Glu Glu Gln Thr Val Ser Thr Val Arg Lys Arg Ser Lys His Gly
            365                 370                 375 aca gga aac tgg ggt ggg aat atg att aca gag cct tac aag cta aca      1817
Thr Gly Asn Trp Gly Gly Asn Met Ile Thr Glu Pro Tyr Lys Leu Thr
            380                 385                 390 cgt cag tgc gag gtc act gcc att ctc atc tta ttt ggg ctc cct agg      1865
Arg Gln Cys Glu Val Thr Ala Ile Leu Ile Leu Phe Gly Leu Pro Arg
            395                 400                 405 cta ctc acc ggt tcg att ctg gct cat gag atg atg cac gcg tgg atg      1913
Leu Leu Thr Gly Ser Ile Leu Ala His Glu Met Met His Ala Trp Met
410                 415                 420                 425
```

| | |
|---|---|
| cgg ctc aaa g gtgagtttct tgttcctttc ttagttcact gcttcttctc<br>Arg Leu Lys | 1963 |
| ttgttacaca ttgttgaatc gtgttattac aatgtggtcg tggaaag ga ttc cgg<br>                                                                                                                                               Gly Phe Arg<br>                                                                                                                                               430 | 2018 |
| aca ctg agc caa gac gtt gaa gaa gga ata tgt caa gtg atg gct cat<br>Thr Leu Ser Gln Asp Val Glu Glu Gly Ile Cys Gln Val Met Ala His<br>               435                    440                     445 | 2066 |
| aag tgg tta gaa gcc gag tta gct gct ggt tca aga aac agc aat gtt<br>Lys Trp Leu Glu Ala Glu Leu Ala Ala Gly Ser Arg Asn Ser Asn Val<br>    450                        455                    460 | 2114 |
| gca tca tca tct tct tct tct gga gga gga ttg aag aag gga cca aga<br>Ala Ser Ser Ser Ser Ser Ser Gly Gly Gly Leu Lys Lys Gly Pro Arg<br>465                     470                    475 | 2162 |
| tcg cag tac gag agg aag ctc ggt gag ttt ttc aag cac caa atc gag<br>Ser Gln Tyr Glu Arg Lys Leu Gly Glu Phe Phe Lys His Gln Ile Glu<br>480                     485                    490                    495 | 2210 |
| tct gat gct tct ccg gtt tat gga gac ggg ttc agg gcg ggg agg tta<br>Ser Asp Ala Ser Pro Val Tyr Gly Asp Gly Phe Arg Ala Gly Arg Leu<br>                   500                    505                    510 | 2258 |
| gcg gtt aac aag tat ggt ttg ggg aaa aca ctt gag cat ata cag atg<br>Ala Val Asn Lys Tyr Gly Leu Gly Lys Thr Leu Glu His Ile Gln Met<br>               515                    520                    525 | 2306 |
| acc ggt aga ttc ccg gtt taa<br>Thr Gly Arg Phe Pro Val<br>          530 | 2327 |

```
<210> SEQ ID NO 74
<211> LENGTH: 1602
<212> TYPE: DNA
<213> ORGANISM: Brassica nigra
<220> FEATURE:
<221> NAME/KEY: CDS
<222> LOCATION: (1)..(1602)

<400> SEQUENCE: 74
```

| | |
|---|---|
| atg ggt tgg ttt aac aag atc ttc aaa ggg tct act caa agg ttc cgg<br>Met Gly Trp Phe Asn Lys Ile Phe Lys Gly Ser Thr Gln Arg Phe Arg<br>1                 5                    10                    15 | 48 |
| ctt ggg aat gac cac ggt cac agt ggc tat tac cag agt tat cca cat<br>Leu Gly Asn Asp His Gly His Ser Gly Tyr Tyr Gln Ser Tyr Pro His<br>             20                    25                    30 | 96 |
| tct tca cat gat gag cct agt gct gat aca gat cct gat cct gat cct<br>Ser Ser His Asp Glu Pro Ser Ala Asp Thr Asp Pro Asp Pro Asp Pro<br>       35                    40                    45 | 144 |
| gat gaa act cat act cag gaa cca tct acc tct gag gag gat aca tcg<br>Asp Glu Thr His Thr Gln Glu Pro Ser Thr Ser Glu Glu Asp Thr Ser<br>50                     55                    60 | 192 |
| aac gac cag gag aat gaa gaa ata gac cgt gca atc gca ctg tct cta<br>Asn Asp Gln Glu Asn Glu Glu Ile Asp Arg Ala Ile Ala Leu Ser Leu<br>65                 70                    75                    80 | 240 |
| tta gaa gag agt caa gga cag aca aac aca ggc gcc ggg aaa tac gca<br>Leu Glu Glu Ser Gln Gly Gln Thr Asn Thr Gly Ala Gly Lys Tyr Ala<br>                   85                    90                    95 | 288 |
| atg gtg gat gat gac gag caa ctt gct aga gcc ata caa gaa agt atg<br>Met Val Asp Asp Asp Glu Gln Leu Ala Arg Ala Ile Gln Glu Ser Met<br>                  100                   105                  110 | 336 |
| gta gtt ggg aat acg ccg cgt cag aag cat gga agt agt tat gat att<br>Val Val Gly Asn Thr Pro Arg Gln Lys His Gly Ser Ser Tyr Asp Ile<br>             115                    120                  125 | 384 |
| ggg aat gca tat ggg gct gga gac gta tac ggg aat gga cat atg cat | 432 |

```
Gly Asn Ala Tyr Gly Ala Gly Asp Val Tyr Gly Asn Gly His Met His
        130                 135                 140 ggt gga ggt gga aat gta tat gcc aat gga gat att tat tat cca aga      480
Gly Gly Gly Gly Asn Val Tyr Ala Asn Gly Asp Ile Tyr Tyr Pro Arg
145                 150                 155                 160 cct act gct ttt cct atg gat ttc agg att tgt gct ggc tgc aat atg      528
Pro Thr Ala Phe Pro Met Asp Phe Arg Ile Cys Ala Gly Cys Asn Met
                    165                 170                 175 gag att ggc cat gga aga tat ctg aat tgc ttg aat gca cta tgg cat      576
Glu Ile Gly His Gly Arg Tyr Leu Asn Cys Leu Asn Ala Leu Trp His
                180                 185                 190 cca gaa tgt ttt cga tgt tat ggc tgt agg cac cct att tct gag tac      624
Pro Glu Cys Phe Arg Cys Tyr Gly Cys Arg His Pro Ile Ser Glu Tyr
            195                 200                 205 gag ttc tca aca tct gga aat tac cct ttt cac aaa gct tgt tac aga      672
Glu Phe Ser Thr Ser Gly Asn Tyr Pro Phe His Lys Ala Cys Tyr Arg
    210                 215                 220 gag aga tac cat cca aaa tgt gat gtc tgc agc cac ttt att cca aca      720
Glu Arg Tyr His Pro Lys Cys Asp Val Cys Ser His Phe Ile Pro Thr
225                 230                 235                 240 aac cat gct ggt ctt att gaa tat agg gca cat cct ttc tgg gtt cag      768
Asn His Ala Gly Leu Ile Glu Tyr Arg Ala His Pro Phe Trp Val Gln
                    245                 250                 255 aag tat tgc cct tct cac gaa cac gat gct acc cca aga tgt tgc agt      816
Lys Tyr Cys Pro Ser His Glu His Asp Ala Thr Pro Arg Cys Cys Ser
                260                 265                 270 tgc gaa aga atg gag cca cgg aat acg gga tat gtt gaa ctt aac gat      864
Cys Glu Arg Met Glu Pro Arg Asn Thr Gly Tyr Val Glu Leu Asn Asp
            275                 280                 285 gga cgg aaa ctt tgt ctc gag tgt ctg gac tca gcg gtc atg gac act      912
Gly Arg Lys Leu Cys Leu Glu Cys Leu Asp Ser Ala Val Met Asp Thr
    290                 295                 300 ttt caa tgc caa cct ctg tat ctg cag ata caa gca ttc tat gaa ggg      960
Phe Gln Cys Gln Pro Leu Tyr Leu Gln Ile Gln Ala Phe Tyr Glu Gly
305                 310                 315                 320 ctt ttc atg aag gta gag cag gac gtt cca ctt ctt tta gtt gag agg     1008
Leu Phe Met Lys Val Glu Gln Asp Val Pro Leu Leu Leu Val Glu Arg
                    325                 330                 335 caa gca ctt aac gaa gcc aga gaa ggg gaa aag aat ggt cac tat cac     1056
Gln Ala Leu Asn Glu Ala Arg Glu Gly Glu Lys Asn Gly His Tyr His
                340                 345                 350 atg cca gag aca aga gga ctc tgc ctt tca gaa gaa cag act gtt agc     1104
Met Pro Glu Thr Arg Gly Leu Cys Leu Ser Glu Glu Gln Thr Val Ser
            355                 360                 365 acc gta aga aag aga tcg aag cat ggc aca gga aac tgg ggt ggg aat     1152
Thr Val Arg Lys Arg Ser Lys His Gly Thr Gly Asn Trp Gly Gly Asn
    370                 375                 380 atg att aca gag cct tac aag cta aca cgt cag tgc gag gtc act gcc     1200
Met Ile Thr Glu Pro Tyr Lys Leu Thr Arg Gln Cys Glu Val Thr Ala
385                 390                 395                 400 att ctc atc tta ttt ggg ctc cct agg cta ctc acc ggt tcg att ctg     1248
Ile Leu Ile Leu Phe Gly Leu Pro Arg Leu Leu Thr Gly Ser Ile Leu
                    405                 410                 415 gct cat gag atg atg cac gcg tgg atg cgg ctc aaa gga ttc cgg aca     1296
Ala His Glu Met Met His Ala Trp Met Arg Leu Lys Gly Phe Arg Thr
                420                 425                 430 ctg agc caa gac gtt gaa gaa gga ata tgt caa gtg atg gct cat aag     1344
Leu Ser Gln Asp Val Glu Glu Gly Ile Cys Gln Val Met Ala His Lys
            435                 440                 445
```

-continued

```
tgg tta gaa gcc gag tta gct gct ggt tca aga aac agc aat gtt gca    1392
Trp Leu Glu Ala Glu Leu Ala Ala Gly Ser Arg Asn Ser Asn Val Ala
    450             455                 460 tca tca tct tct tct tct gga gga gga ttg aag aag gga cca aga tcg    1440
Ser Ser Ser Ser Ser Ser Gly Gly Gly Leu Lys Lys Gly Pro Arg Ser
465                 470                 475                 480 cag tac gag agg aag ctc ggt gag ttt ttc aag cac caa atc gag tct    1488
Gln Tyr Glu Arg Lys Leu Gly Glu Phe Phe Lys His Gln Ile Glu Ser
                485                 490                 495 gat gct tct ccg gtt tat gga gac ggg ttc agg gcg ggg agg tta gcg    1536
Asp Ala Ser Pro Val Tyr Gly Asp Gly Phe Arg Ala Gly Arg Leu Ala
            500                 505                 510 gtt aac aag tat ggt ttg ggg aaa aca ctt gag cat ata cag atg acc    1584
Val Asn Lys Tyr Gly Leu Gly Lys Thr Leu Glu His Ile Gln Met Thr
        515                 520                 525 ggt aga ttc ccg gtt taa                                             1602
Gly Arg Phe Pro Val
    530

<210> SEQ ID NO 75
<211> LENGTH: 533
<212> TYPE: PRT
<213> ORGANISM: Brassica nigra

<400> SEQUENCE: 75

Met Gly Trp Phe Asn Lys Ile Phe Lys Gly Ser Thr Gln Arg Phe Arg
1               5                   10                  15

Leu Gly Asn Asp His Gly His Ser Gly Tyr Tyr Gln Ser Tyr Pro His
            20                  25                  30

Ser Ser His Asp Glu Pro Ser Ala Asp Thr Asp Pro Asp Pro Asp Pro
        35                  40                  45

Asp Glu Thr His Thr Gln Glu Pro Ser Thr Ser Glu Glu Asp Thr Ser
    50                  55                  60

Asn Asp Gln Glu Asn Glu Glu Ile Asp Arg Ala Ile Ala Leu Ser Leu
65                  70                  75                  80

Leu Glu Glu Ser Gln Gly Gln Thr Asn Thr Gly Ala Gly Lys Tyr Ala
                85                  90                  95

Met Val Asp Asp Asp Glu Gln Leu Ala Arg Ala Ile Gln Glu Ser Met
            100                 105                 110

Val Val Gly Asn Thr Pro Arg Gln Lys His Gly Ser Ser Tyr Asp Ile
        115                 120                 125

Gly Asn Ala Tyr Gly Ala Gly Asp Val Tyr Gly Asn Gly His Met His
    130                 135                 140

Gly Gly Gly Gly Asn Val Tyr Ala Asn Gly Asp Ile Tyr Tyr Pro Arg
145                 150                 155                 160

Pro Thr Ala Phe Pro Met Asp Phe Arg Ile Cys Ala Gly Cys Asn Met
                165                 170                 175

Glu Ile Gly His Gly Arg Tyr Leu Asn Cys Leu Asn Ala Leu Trp His
            180                 185                 190

Pro Glu Cys Phe Arg Cys Tyr Gly Cys Arg His Pro Ile Ser Glu Tyr
        195                 200                 205

Glu Phe Ser Thr Ser Gly Asn Tyr Pro Phe His Lys Ala Cys Tyr Arg
    210                 215                 220

Glu Arg Tyr His Pro Lys Cys Asp Val Cys Ser His Phe Ile Pro Thr
225                 230                 235                 240

Asn His Ala Gly Leu Ile Glu Tyr Arg Ala His Pro Phe Trp Val Gln
                245                 250                 255
```

```
Lys Tyr Cys Pro Ser His Glu His Asp Ala Thr Pro Arg Cys Cys Ser
            260                 265                 270

Cys Glu Arg Met Glu Pro Arg Asn Thr Gly Tyr Val Glu Leu Asn Asp
        275                 280                 285

Gly Arg Lys Leu Cys Leu Glu Cys Leu Asp Ser Ala Val Met Asp Thr
    290                 295                 300

Phe Gln Cys Gln Pro Leu Tyr Leu Gln Ile Gln Ala Phe Tyr Glu Gly
305                 310                 315                 320

Leu Phe Met Lys Val Glu Gln Asp Val Pro Leu Leu Leu Val Glu Arg
                325                 330                 335

Gln Ala Leu Asn Glu Ala Arg Glu Gly Glu Lys Asn Gly His Tyr His
            340                 345                 350

Met Pro Glu Thr Arg Gly Leu Cys Leu Ser Glu Glu Gln Thr Val Ser
        355                 360                 365

Thr Val Arg Lys Arg Ser Lys His Gly Thr Gly Asn Trp Gly Gly Asn
    370                 375                 380

Met Ile Thr Glu Pro Tyr Lys Leu Thr Arg Gln Cys Glu Val Thr Ala
385                 390                 395                 400

Ile Leu Ile Leu Phe Gly Leu Pro Arg Leu Leu Thr Gly Ser Ile Leu
                405                 410                 415

Ala His Glu Met Met His Ala Trp Met Arg Leu Lys Gly Phe Arg Thr
            420                 425                 430

Leu Ser Gln Asp Val Glu Glu Gly Ile Cys Gln Val Met Ala His Lys
            435                 440                 445

Trp Leu Glu Ala Glu Leu Ala Ala Gly Ser Arg Asn Ser Asn Val Ala
    450                 455                 460

Ser Ser Ser Ser Ser Ser Gly Gly Gly Leu Lys Lys Gly Pro Arg Ser
465                 470                 475                 480

Gln Tyr Glu Arg Lys Leu Gly Glu Phe Phe Lys His Gln Ile Glu Ser
                485                 490                 495

Asp Ala Ser Pro Val Tyr Gly Asp Gly Phe Arg Ala Gly Arg Leu Ala
            500                 505                 510

Val Asn Lys Tyr Gly Leu Gly Lys Thr Leu Glu His Ile Gln Met Thr
            515                 520                 525

Gly Arg Phe Pro Val
    530
```

BRASSICA PLANTS COMPRISING MUTANT DA1 ALLELES

CROSS-REFERENCE TO RELATED APPLICATION

This application is a 35 U.S.C 371 National Phase of PCT Application Serial No. PCT/EP2014/056628, filed Apr. 2, 2014, which claims priority to European Patent Application No. 13162447.0, filed Apr. 5, 2013.

FIELD OF THE INVENTION

The invention relates to the field of agricultural products, especially *Brassica* species, of which the seed weight is increased. More specifically, the invention relates to methods and means to modulate seed weight.

BACKGROUND OF THE INVENTION

Seed weight or seed size is an important agronomic trait in *Brassica* crop species.

For several crop species, Quantitative Trait Loci (QTLs) have been mapped for seed size and weight. In *Brassica*, several QTLs for seed weight have been mapped (Cai et al., 2012, BMC Genetics 13: 105; Zhang et al., 2011, Theor Appl Genet 122:21; Fan et al., 2010, Theor Appl Genet 121: 1289). Two candidate genes, BnMINI3a and BnTTG2a have, based on QTL mapping, been assigned as candidate genes (Fan et al., 2010, supra). BnMINI3a and BnTTG2a are *Brassica* homologs of WRKY transcription factors of *Arabidopsis* MINI3 and TTG2, respectively. Cai et al., 2012 (supra) mapped location of several candidate yield genes to yield QTLs and found localization of *Arabidopsis* genes TTG2 and GS5 close to yield QTL TSWA1; GW2 at the same position of TSWA2; CKI1 and MN1 nearby the peak of TSWA4; MINI3 in the confidence interval of TSWA5b; FIE in the confidence interval of TSWA5a; AHP3, AHP5 and MEA in the same confidence interval of TSWA10; and AGL62, GS3 and GASA4 on the peaks or in the confidence intervals of TSWC2a, TSWC2b, and TSWC2c, respectively. For two major QTLs, TSWA7a and TSWA7b, no known information about candidate genes could be inferred from the map.

In addition to the above genes, several other genes involved in seed size or weight regulation have been identified (see Cai et al., 2012 (supra) for an overview). It has further been described that *Brassica* plants overexpressing different variants of the REV gene have increased seed size and thousand seed weight (WO2007/079353, US2011/0271405). *Brassica* genes which increase seed weight when overexpressed in *Arabidopsis* are AOX1 (WO2012/100682) and a wri1-like gene (Liu et al., 2010, Plant Physiol Biochem 48: 9). Other genes affecting seed size or weight are MNT (WO2005/085453), Cytokinin Oxidase (US2005/0150012), CYP78A7 (US2010/0281576), sucrose isomerase (WO2012/119152), Polycomb group genes (WO2001/038551), Giberrelin 20-oxidase (US2009/0007295), and sorbitol dehydrogenase (WO2008/144653). In US2011/0265225, four rice genes have been described that increase seed size when overexpressed in rice. WO2003/096797 describes overexpression of several genes from several plant species and the effect on seed size and weight in *Arabidopsis* and soybeans.

Li et al (2008, Genes Dev 22:1331) and WO2009/047525 describe *Arabidopsis* DA1, encoding a predicted ubiquitin receptor, which sets final seed and organ size by restricting the period of cell proliferation. A da1-1 mutant has been identified in genetic screens in *Arabidopsis thaliana* that increases both seed and organ size. The increased seed mass was observed only when maternal plants were homozygous for the da1-1 mutation. The da1-1 mutant contains a single-nucleotide G to A transition in gene At1g19270, predicted to cause an arginine-to-lysine change in a conserved amino acid at position 358. The da1-1 phenotypes were complemented by the wild-type DA1 gene and by transgenic expression of a wild-type DA1 full length cDNA. Disruption of the DA1 gene did not cause an obvious growth phenotype. Lines heterozygous for the da1-1 mutation had a seed and organ size nearly similar to the wild type, whereas plants with the da1-1 mutation combined with the da1 knock-out allele displayed a similar phenotype to da1-1.

Two *Brassica rapa* DA1 orthologs, BrDA1a and BrDA1b have been identified (WO2009/047525). The amino acid sequence of BrDA1a is more close to the *Arabidopsis* DA1 (AtDA1) amino acid sequence, but BrDA1b was predicted to have more similar biochemical features to AtDA1. Transgenic *Arabidopsis* da1-1 plants expressing 35S-BrDA1a showed at least partial complementation of the da1-1 phenotype, whereas 35S-BrDA1b transgenic plants showed full complementation of the da1-1 phenotype. When the BrDA1a cDNA with a mutation equivalent to the R358K mutation of the *Arabidopsis* DA1 (BrDA1a$^{R358K}$) was overexpressed in wild-type *Arabidopsis*, typical da1-1 phenotypes were observed.

Cai et al, 2012 (supra) describe that *Brassica rapa* and *Brassica oleracea* each contain two copies of the DA1 gene. The homologous DA1 genes were positioned on a *B. napus* linkage map and aligned with Thousand Seed Weight (TSW) QTL loci. Whereas several candidate yield genes were linked to TSW QTLs by Cai et al. (see above), DA1 did not colocalize with one of the 11 tested TSW QTLs.

In order to use the DA1 gene to increase seed yield in *Brassica*, a need remains to understand the relative contribution of the different DA1 genes to seed weight. The isolation of mutant alleles corresponding to da1 in economically important Brassicaceae plants, such as oilseed rape, may be complicated by the amphidiploidy in oilseed rape and the consequent functional redundancy of the corresponding genes.

Thus, the prior art is deficient in teaching the identity of DA1 genes in amphidiploid *Brassica* species, as well as the contribution of the different DA1 genes to seed weight. As described hereinafter, this problem has been solved, allowing to modify DA1 with the aim to increase seed weight in *Brassica*, as will become apparent from the different embodiments and the claims.

SUMMARY OF THE INVENTION

It is one aspect of the invention to provide a *Brassica* plant or parts thereof comprising at least two DA1 genes, wherein at least one allele of a first DA1 gene is a mutant DA1 allele, said mutant DA1 allele encoding a mutant DA1 protein comprising at a position corresponding to position 358 of SEQ ID NO: 2 an amino acid other than Arginine. In another embodiment, said *Brassica* plant or parts thereof further comprises four DA1 genes, wherein at least one allele of a first DA1 gene is a mutant DA1 allele encoding a mutant DA1 protein comprising at a position corresponding to position 358 of SEQ ID NO: 2 an amino acid other than Arginine, and wherein at least one allele of a second DA1 gene is a mutant DA1 allele encoding a mutant DA1 protein comprising at a position corresponding to position 358 of SEQ ID NO: 2 an amino acid other than Arginine; or wherein the mutant DA1 allele of said second DA1 gene is a full knock-out DA1 allele. In a particular embodiment, the mutant DA1 allele of said first DA1 gene encodes a mutant DA1 protein comprising at a position corresponding to position 358 of SEQ ID NO: 2 a Lysine instead of an Arginine. In yet a further embodiment, the *Brassica* plant according to the invention is homozygous for the mutant DA1 alleles.

In yet a further embodiment, the mutant DA1 allele of the first DA1 gene of the *Brassica* plants according to the invention is a mutant DA1 allele which contains at least 80% sequence identity to SEQ ID NO: 6, such as a mutant DA1 allele containing at least 91% sequence identity to SEQ ID NO: 6, or a mutant DA1 allele which encodes a mutant DA1 protein containing at least 90% sequence identity to SEQ ID NO: 8. In another embodiment, the mutant DA1 allele of the second DA1 gene of the *Brassica* plants according to the invention is a mutant DA1 allele which contains at least 90% sequence identity to SEQ ID NO: 12, such as a mutant DA1 allele which contains at least 91% sequence identity to SEQ ID NO: 12; or a mutant DA1 allele of a DA1 gene, said DA1 gene encoding a DA1 protein containing at least 90% sequence identity to SEQ ID NO: 14. In a particular embodiment, the mutant DA1 allele of the first DA1 gene of the *Brassica* plants according to the invention encodes the protein of SEQ ID NO: 17, whereas in yet a further embodiment, the mutant DA1 allele of said second DA1 gene of the *Brassica* plants according to the invention is a full knock-out DA1 allele, said full knock-out DA1 allele comprising the sequence of SEQ ID NO: 12 with a C to T substitution at position 2011.

In a further embodiment, *Brassica* plants or parts thereof are provided comprising at least two DA1 genes, wherein at least one allele of a DA1 gene is a full knock-out DA1 allele. In yet another embodiment, said full knock-out DA1 allele contains at least 96% sequence identity to SEQ ID NO: 3, or contains at least 80% sequence identity to SEQ ID NO: 6, or contains at least 80% sequence identity to SEQ ID NO: 12, or encodes a protein containing at least 96% sequence identity to SEQ ID NO: 5, or at least 90% sequence identity to SEQ ID NO: 8, or at least 90% sequenc identity to SEQ ID NO: 14.

In another embodiment, the *Brassica* plant or parts thereof according to the invention are selected from the group consisting of *Brassica rapa, Brassica oleracea*, and *Brassica napus*.

It is a further embodiment to provide plants according to the invention comprising at least one mutant DA1 allele wherein the Thousand Seed Weight is significantly increased as compared to the Thousand Seed Weight of a corresponding plant not comprising a mutant DA1 allele.

In yet another embodiment, seeds from the *Brassica* plants according the invention are provided, such as seeds of which reference seed has been deposited at the NCIMB under accession number NCIMB 42114.

It is another embodiment to provide progeny of the *Brassica* plants according to the invention or of the seeds according to the invention.

In a further embodiment, a method is provided for identifying a mutant DA1 allele of the invention in a biological sample comprising subjecting the biological sample to an amplification reaction using a set of at least two primers, wherein one of said primers specifically recognizes the 5' or 3' flanking region of the mutant DA1 allele, and the other of said primers specifically recognizes the mutation region of the mutant DA1 allele; or wherein one of said primers specifically recognizes the 5' or 3' flanking region of the mutant DA1 allele and the other of said primers specifically recognizes the joining region between the 3' or 5' flanking region and the mutation region of the mutant DA1 allele, respectively; or wherein a specific probe specifically recognizes the joining region between the 5' or 3' flanking region and the mutation region of the mutant DA1 allele. In another embodiment, a method is provided for identifying a mutant DA1 allele of the invention in a biological sample comprising subjecting the biological sample to an amplification reaction using a set of at least two primers, further comprising subjecting the biological sample to a hybridization assay using a set of specific probes, comprising at least one specific probe, wherein said set of probes comprises one of said probes specifically recognizes the 5' or 3' flanking region of the mutant DA1 allele, and the other of said probes specifically recognizes the mutation region of the mutant DA1 allele; or wherein one of said probes specifically recognizes the 5' or 3' flanking region of the mutant DA1 allele and the other of said probes specifically recognizes the joining region between the 3' or 5' flanking region and the mutation region of the mutant DA1 allele, respectively; or comprising a specific probe which specifically recognizes the joining region between the 5' or 3' flanking region and the mutation region of the mutant DA1 allele.

It is a further object of the invention to provide a kit for identifying a mutant DA1 allele as described in claim 1 or 2 in a biological sample, comprising a set of primers or probes, wherein one of said primers specifically recognizes the 5' or 3' flanking region of the mutant DA1 allele, and the other of said primers specifically recognizes the mutation region of the mutant DA1 allele; or wherein one of said primers specifically recognizes the 5' or 3' flanking region of the mutant DA1 allele and the other of said primers specifically recognizes the joining region between the 3' or 5' flanking region and the mutation region of the mutant DA1 allele, respectively; or comprising a specific probe which specifically recognizes the joining region between the 5' or 3' flanking region and the mutation region of the mutant DA1 allele.

In another embodiment, a method is provided for producing hybrid seed, comprising crossing a first parent *Brassica* plant according to the invention with a second parent *Brassica* plant and harvesting a resultant hybrid seed.

In yet another embodiment, a method for breeding is provided, comprising crossing a first parent *Brassica* plant according to the invention with a second parent *Brassica* plant and, optionally, further comprising the step of identifying the presence or absence of a mutant DA1 allele according to the invention comprising subjecting the biological sample to an amplification reaction using a set of at least two primers according to the invention and, optionally, hybridizing with at least one probe according to the invention.

It is a further object of the invention to provide a method to increase Thousand Seed Weight of *Brassica* seeds, said method comprising introducing a mutant DA1 allele of a first DA1 gene according to the invention and, optionally, a mutant DA1 allele of a second DA1 gene according to the invention, into a *Brassica* plant.

In a further embodiment, a method for production of *Brassica* seeds is provided, said method comprising sowing the seeds according to claim 13 or 14, growing plants from said seeds, and harvesting seeds from said plants.

Further provided is the use of the plants according to the invention to produce seeds, or to produce a crop of oilseed rape, or to produce oilseed rape oil or oilseed rape seed cake. Further provided is oil or seed cake from the seed according to the invention.

It is a further object of the invention to provide a method for producing food or feed, such as oil, meal, grain, starch, flour, or protein, or an industrial such as biofuel, fiber, industrial chemicals, a pharmaceutical, or a neutraceutical product comprising obtaining the plant or a part thereof or the seed according to the invention, and preparing the food, feed or industrial product from the plant or part thereof.

BRIEF DESCRIPTION OF THE DRAWINGS

FIG. 1: Alignment of protein sequences of the *Arabidopsis* DA1 protein of SEQ ID NO: 2, and the *Brassica* DA1 proteins of SEQ ID NOs 5, 8, 11, 14, 56, 59, 62, 65, 69, 72, and 75. Underlined are the UIM1, UIM2 and LIM domains. The conserved Arginine residue (R) at a position corresponding to position 358 of the *Arabidopsis* DA1 protein of SEQ ID NO: 2 is indicates with a box.

GENERAL DEFINITIONS

Figure 2:
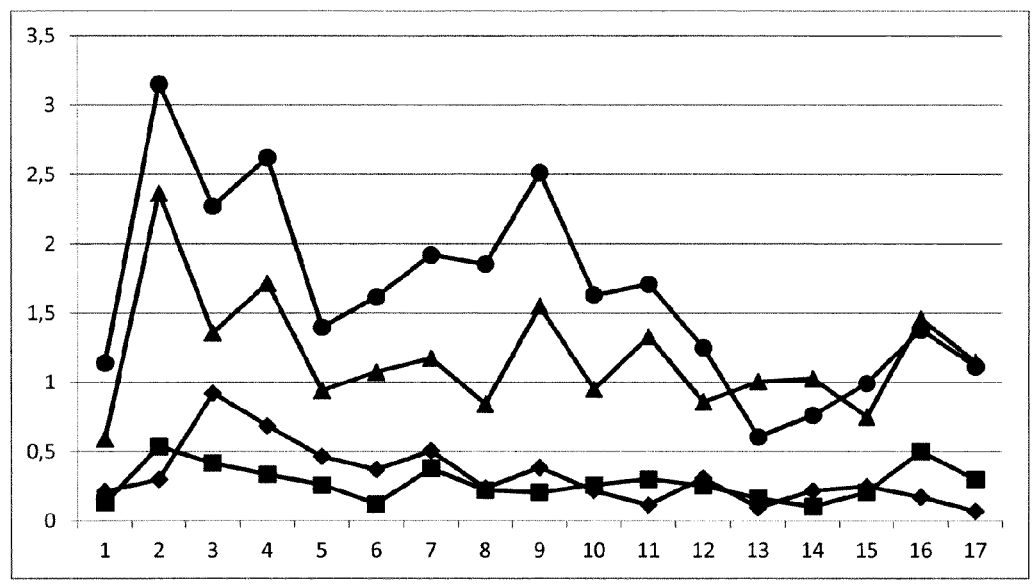
FIG. 2: Relative expression in silico in different tissues of the *Brassica* DA1-A1 (diamonds), DA1-A2 (circles), DA1-C1 (squares), and DA1-C2 (triangles) genes. 1: cotyledons; 2: root 2 weeks; 3: stem 2 weeks; 4: stem 5 weeks 33 days after sowing (DAS); 5: young leaf 33DAS; 6: apical meristem and youngest leaf 33DAS; 7: small flower buds (<5 mm) 42DAS; 8: big flower buds (>5 mm) 42DAS; 9: open flower 52DAS; 10: pod stage 2 14-20 days after flowering (DAF); 11: pod stage 3 21-25DAF; 12: seed stage 2 14-20DAS; 13: seed stage 3 21-25 DAF; 14: seed stage 4 26-30DAF; 15: seed stage 5 31-35DAF; 16: seed stage 6 42 DAF; 17: seed stage 7 49 DAF.

Thousand Seed Weight (TSW) refers to the weight in grams of 1000 seeds.

"Crop plant" refers to plant species cultivated as a crop, such as *Brassica napus* (AACC, 2n=38), *Brassica juncea* (AABB, 2n=36), *Brassica carinata* (BBCC, 2n=34), *Brassica rapa* (syn. *B. campestris*) (AA, 2n=20), *Brassica oleracea* (CC, 2n=18) or *Brassica nigra* (BB, 2n=16). The definition does not encompass weeds, such as *Arabidopsis thaliana*.

A "DA1 gene" or "DA1 allele", as used herein, is a gene or allele having a coding sequence comprising at least 80% sequence identity to the coding sequence of the DA1 gene of *Arabidopsis thaliana*, as described in At1g19270.1 and in SEQ ID NO: 1.

A DA1 gene or DA1 allele can, but does not need to encode a functional DA1 protein.

A "DA1 protein" or "DA1 polypeptide" as used herein, is a protein or polypeptide comprising at least 80% sequence identity to the amino acid sequence of the DA1 protein of *Arabidopsis thaliana*, as described in At1g19270.1 and in SEQ ID NO: 2.

A "mutant DA1 gene" or "mutant DA1 allele" as used herein refers to any DA1 gene or DA1 allele which is not found in plants in the natural population or breeding population, but which is produced by human intervention such as mutagenesis or gene targeting. A mutant DA1 allele comprises knock-out DA1 alleles, and functional DA1 alleles.

A "mutant DA1 protein" or "mutant DA1 polypeptide" is a DA1 protein or a DA1 polypeptide which is encoded by a mutant DA1 gene or a mutant DA1 allele.

A "full knock-out da1 gene" or "knock-out da1 allele" as used herein is a da1 gene or a da1 allele which encodes no functional DA1 protein or a significantly reduced amount of DA1 protein, or which encodes a DA1 protein with significantly reduced activity. Said "full knock-out DA1 gene" or "full knock-out DA1 allele" can be a mutant DA1 allele or a mutant DA1 gene, which may encode no DA1 protein, or which may encode a non-functional DA1 protein. The gene or allele may also be referred to as an inactivated gene or allele. Said "full knock-out DA1 gene" or "full knock-out DA1 allele" does not rescue the da1-1 phenotype when overexpressed in da1-1 mutant *Arabidopsis thaliana* as described in WO2009/047525 (incorporated herein by reference).

A "significantly reduced amount of DA1 protein" refers to a reduction in the amount of DA1 protein produced by the cell comprising a mutant DA1 allele by at least 30%, 40%, 50%, 60%, 70%, 80%, 90%, 95% or 100% (i.e. no DA1 protein is produced by the allele) as compared to the amount of the DA1 protein produced by the wild-type DA1 allele.

A "functional DA1 gene" or "functional DA1 allele" as used herein is a DA1 gene or a DA1 allele which encodes a functional DA1 protein. Said "functional DA1 gene" or "functional DA1 allele" rescues the da1-1 phenotype when overexpressed under control of a CaMV 35S promoter in da1-1 mutant *Arabidopsis thaliana* as described in WO2009/047525 (incorporated herein by reference).

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of a DA1 gene present within the nuclear genome of a *Brassica* cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operably linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The terms "protein" or "polypeptide" are used interchangeably and refer to molecules consisting of a chain of amino acids, without reference to a specific mode of action, size, 3-dimensional structure or origin. A "fragment" or "portion" of a DA1 protein may thus still be referred to as a "protein". An "isolated protein" is used to refer to a protein that is no longer in its natural environment, for example in vitro or in a recombinant bacterial or plant host cell.

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found.

"Wild type" (also written "wildtype" or "wild-type"), as used herein, refers to a typical form of a plant or a gene as it most commonly occurs in nature. A "wild type plant" refers to a plant in the natural population or in a breeding population. A "wild type allele" refers to an allele of a gene occurring in wild-type plants.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the seed weight), such as seed obtained by selfing or crossing, e.g. hybrid seed (obtained by crossing two inbred parental lines), hybrid plants and plant parts derived there from are encompassed herein, unless otherwise indicated.

A "molecular assay" (or test) refers herein to an assay that indicates (directly or indirectly) the presence or absence of one or more particular DA1 alleles at one or both DA1 loci. In one embodiment it allows one to determine whether a particular (wild type or mutant) allele is homozygous or heterozygous at the locus in any individual plant.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling, sexual reproduction (crossing with another plant) and asexual reproduction (e.g. apomixis, somatic hybridization).

"Mutagenesis", as used herein, refers to the process in which plant cells (e.g., a plurality of $Brassica$ seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), T-DNA insertion mutagenesis (Azpiroz-Leehan et al. (1997) Trends Genet 13:152-156), transposon mutagenesis (McKenzie et al. (2002) Theor Appl Genet 105:23-33), or tissue culture mutagenesis (induction of somaclonal variations), or a combination of two or more of these. Thus, the desired mutagenesis of one or more DA1 alleles may be accomplished by one of the above methods. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, $Brassica$ plants are regenerated from the treated cells using known techniques. For instance, the resulting $Brassica$ seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for $Brassica napus$. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant DA1 alleles. Several techniques are known to screen for specific mutant alleles, e.g., Delete-agene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant DA1 alleles are described in the Examples below.

The term "gene targeting" refers herein to directed gene modification that uses mechanisms such as homologous recombination, mismatch repair or site-directed mutagenesis. The method can be used to replace, insert and delete endogenous sequences or sequences previously introduced in plant cells. Methods for gene targeting can be found in, for example, WO 2006/105946 or WO2009/002150. Gene targeting can be used to create mutant DA1 alleles, such as knock-out DA1 alleles.

As used herein, the term "non-naturally occurring" or "cultivated" when used in reference to a plant, means a plant with a genome that has been modified by man. A transgenic plant, for example, is a non-naturally occurring plant that contains an exogenous nucleic acid molecule, e.g., a chimeric gene comprising a transcribed region which when transcribed yields a biologically active RNA molecule capable of reducing the expression of an endogenous gene, such as a DA1 gene, and, therefore, has been genetically modified by man. In addition, a plant that contains a mutation in an endogenous gene, for example, a mutation in an endogenous DA1 gene, (e.g. in a regulatory element or in the coding sequence) as a result of an exposure to a mutagenic agent is also considered a non-naturally plant, since it has been genetically modified by man. Furthermore, a plant of a particular species, such as *Brassica napus*, that contains a mutation in an endogenous gene, for example, in an endogenous DA1 gene, that in nature does not occur in that particular plant species, as a result of, for example, directed breeding processes, such as marker-assisted breeding and selection or introgression, with a plant of the same or another species, such as *Brassica juncea* or *rapa*, of that plant is also considered a non-naturally occurring plant. In contrast, a plant containing only spontaneous or naturally occurring mutations, i.e. a plant that has not been genetically modified by man, is not a "non-naturally occurring plant" as defined herein and, therefore, is not encompassed within the invention. One skilled in the art understands that, while a non-naturally occurring plant typically has a nucleotide sequence that is altered as compared to a naturally occurring plant, a non-naturally occurring plant also can be genetically modified by man without altering its nucleotide sequence, for example, by modifying its methylation pattern.

The term "ortholog" of a gene or protein refers herein to the homologous gene or protein found in another species, which has the same function as the gene or protein, but is (usually) diverged in sequence from the time point on when the species harboring the genes diverged (i.e. the genes evolved from a common ancestor by speciation). Orthologs of the *Brassica napus* DA1 genes may thus be identified in other plant species (e.g. *Brassica juncea*, etc.) based on both sequence comparisons (e.g. based on percentages sequence identity over the entire sequence or over specific domains) and/or functional analysis.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues ($\times 100$) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

DETAILED DESCRIPTION

*Brassica napus* (genome AACC, 2n=4x=38), which is an allotetraploid (amphidiploid) species containing essentially two diploid genomes (the A and the C genome) due to its origin from diploid ancestors. It was found by the inventors that *Brassica napus* comprises four DA1 genes in its genome, and that the A genome and the C genome contain DA1 genes which affect seed weight.

As in any diploid genome, two "alleles" can be present in vivo for each DA1 gene at each DA1 locus in the genome (one allele being the gene sequence found on one chromosome and the other on the homologous chromosome). The nucleotide sequence of these two alleles may be identical (homozygous plant) or different (heterozygous plant) in any given plant, although the number of different possible alleles existing for each DA1 gene may be much larger than two in the species population as a whole.

It is one aspect of the invention to provide a *Brassica* plant or parts thereof comprising at least two DA1 genes, wherein at least one allele of a first DA1 gene is a mutant DA1 allele, said mutant DA1 allele encoding a mutant DA1 protein comprising at a position corresponding to position 358 of SEQ ID NO: 2 an amino acid other than Arginine. In another embodiment, said *Brassica* plant or parts thereof further comprises four DA1 genes, wherein at least one allele of a first DA1 gene is a mutant DA1 allele encoding a mutant DA1 protein comprising at a position corresponding to position 358 of SEQ ID NO: 2 an amino acid other than Arginine, and wherein at least one allele of a second DA1 gene is a mutant DA1 allele encoding a mutant DA1 protein comprising at a position corresponding to position 358 of SEQ ID NO: 2 an amino acid other than Arginine; or wherein the mutant DA1 allele of said second DA1 gene is a full knock-out DA1 allele. In a particular embodiment, the mutant DA1 allele of said first DA1 gene encodes a mutant DA1 protein comprising at a position corresponding to position 358 of SEQ ID NO: 2 a Lysine instead of an Arginine. In yet a further embodiment, the *Brassica* plant according to the invention is homozygous for the mutant DA1 alleles.

In yet a further embodiment, the mutant DA1 allele of the first DA1 gene of the *Brassica* plants according to the invention is a mutant DA1 allele which contains at least 80% sequence identity to SEQ ID NO: 6, such as a mutant DA1 allele containing at least 91% sequence identity to SEQ ID NO: 6, or a mutant DA1 allele which encodes a mutant DA1 protein containing at least 90% sequence identity to SEQ ID NO: 8. In another embodiment, the mutant DA1 allele of the second DA1 gene of the *Brassica* plants according to the invention is a mutant DA1 allele which contains at least 90% sequence identity to SEQ ID NO: 12, such as a mutant DA1 allele which contains at least 91% sequence identity to SEQ ID NO: 12; or a mutant DA1 allele of a DA1 gene, said DA1 gene encoding a DA1 protein containing at least 90% sequence identity to SEQ ID NO: 14. In a particular embodiment, the mutant DA1 allele of the first DA1 gene of the *Brassica* plants according to the invention encodes the protein of SEQ ID NO: 8, whereas in yet a further embodiment, the mutant DA1 allele of said second DA1 gene of the *Brassica* plants according to the invention is a full knock-out DA1 allele, said full knock-out DA1 allele comprising the sequence of SEQ ID NO: 12 with a C to T substitution at position 2011.

In a further embodiment, *Brassica* plants or parts thereof are provided comprising at least two DA1 genes, wherein at least one allele of a DA1 gene is a full knock-out DA1 allele. In yet another embodiment, said full knock-out DA1 allele which contains at least 96% sequence identity to SEQ ID NO: 3, or which contains at least 80% sequence identity to SEQ ID NO: 6, or which contains at least 80% sequence identity to SEQ ID NO: 12, or which encodes a protein containing at least 96% sequence identity to SEQ ID NO: 5, or at least 90% sequence identity to SEQ ID NO: 8, or at least 90% sequenc identity to SEQ ID NO: 14.

In another embodiment, the *Brassica* plant or parts thereof according to the invention are selected from the group consisting of *Brassica rapa, Brassica oleracea*, and *Brassica napus*.

It is a further embodiment to provide plants according to the invention comprising at least one mutant DA1 allele wherein the Thousand Seed Weight is significantly increased as compared to the Thousand Seed Weight of a corresponding plant not comprising a mutant DA1 allele.

In yet another embodiment, seeds from the *Brassica* plants according the invention are provided, such as seeds of which reference seed has been deposited at the NCIMB under accession number NCIMB 42114, whereas in yet another embodiment progeny of the *Brassica* plants according to the invention or of the seeds according to the invention is provided.

Suitable are also plants obtainable or derivable from seeds as deposited at the NCIMB under accession number NCIMB 42114, such as plants obtainable or derivable by breeding from seeds as deposited at the NCIMB under accession number NCIMB 42114.

At least 80% sequence identity as used herein can be at least 80%, or at least 82%, or at least 84%, or at least 85%, or at least 88%, or at least 90%, or at least 91%, or at least 92%, or at least 93%, or at least 94%, or at least 95%, or at least 96%, or at least 97%, or at least 98%, or at least 99% sequence identity, or can be 100% sequence identity.

At least 90% sequence identity as used herein can be at least 90%, or at least 91%, or at least 92%, or at least 93%, or at least 94%, or at least 95%, or at least 96%, or at least 97%, or at least 98%, or at least 99% sequence identity, or can be 100% sequence identity.

At least 91% sequence identity as used herein can be at least 91%, or at least 92%, or at least 93%, or at least 94%, or at least 95%, or at least 96%, or at least 97%, or at least 98%, or at least 99% sequence identity, or can be 100% sequence identity.

At least 96% sequence identity as used herein can be at least 96%, or at least 97%, or at least 98%, or at least 99% sequence identity, or can be 100% sequence identity.

The Thousand Seed Weight, as used herein, is the weight in grams of thousand seeds. A significant increase in Thousand Seed Weight is an increase with at least 5%, or at least 8%, or at least 10%, or at least 13%, or at least 14%, or at least 15%, or at least 18%, or at least 20%, or at least 25%, or at least 30%, or at least 40%, or at least 50% as compared to the Thousand Seed Weight of *Brassica* plants not comprising mutant DA1 alleles according to the invention.

The plants according to the invention may further have an increased thickness of the pods. Increased thickness of the pods can be an increased average PODT value of at least 5%, or of at least 10%, or of at least 15%, or of at least 18%, or of at least 20%, or of at least 30% as compared to the values for Brassica plants not comprising mutant DA1 alleles according to the inventions using methods for measuring pod thickness as described herein.

The plants according to the invention may further have an increased Thousand Seed Oil Weight, i.e. increased amount of oil per 1000 seeds. Increased amount of oil per 1000 seeds can be an increase with at least 5%, or at least 8%, or at least 10%, or at least 13%, or at least 14%, or at least 15%, or at least 18%, or at least 20%, as compared to the amount of oil per 1000 seeds of Brassica plants not comprising mutant DA1 alleles according to the inventions using methods for measuring pod thickness as described herein.

It may be understood that seeds from the Brassica plants according to the invention can be seeds obtained by pollinating the Brassica plants according to the invention with pollen from the same Brassica plants according to the invention, such as seeds obtained by selfing Brassica plants according to the invention, or by pollinating with pollen from neighbouring Brassica plants according to the invention. Said seeds may also be obtained by pollinating the Brassica plants according to the invention with pollen from another Brassica plant, such as Brassica plants with different mutant DA1 alleles, or even with pollen from Brassica plants not comprising mutant DA1 alleles according to the invention.

The mutant DA1 allele according to the invention can be a mutant DA1 allele comprising one or more nucleotide deletions, insertions or substitutions relative to the wild type nucleic acid sequences. The mutation(s) can result in one or more changes (deletions, insertions and/or substitutions) in the amino acid sequence of the encoded protein.

Said full knock-out DA1 allele can be a mutant DA1 allele comprising one or more nucleotide deletions, insertions or substitutions relative to the wild type nucleic acid sequences. The mutation(s) can result in one or more changes (deletions, insertions and/or substitutions) in the amino acid sequence of the encoded protein, such that the encoded protein is not a functional DA1 protein.

The term "position" when used in accordance with the present invention means the position of either an amino acid within an amino acid sequence depicted herein or the position of a nucleotide within a nucleotide sequence depicted herein. The term "corresponding" as used herein also includes that a position is not only determined by the number of the preceding nucleotides/amino acids.

The position of a given nucleotide in accordance with the present invention which may be substituted may vary due to deletions or additional nucleotides elsewhere in the DA1 sequence, including the coding sequences or gene exons and introns. Similarly, the position of a given amino acid in accordance with the present invention which may be substituted may vary due to deletion or addition of amino acids elsewhere in the DA1 polypeptide.

Thus, under a "corresponding position" or "a position corresponding to position" in accordance with the present invention it is to be understood that nucleotides/amino acids may differ in the indicated number but may still have similar neighbouring nucleotides/amino acids. Said nucleotides/amino acids which may be exchanged, deleted or added are also comprised by the term "corresponding position".

In order to determine whether a nucleotide residue or amino acid residue in a given DA1 nucleotide/amino acid sequence corresponds to a certain position in the nucleotide sequence or amino acid sequence of another DA1 nucleotide/amino acid sequence, the skilled person can use means and methods well-known in the art, e.g., alignments, either manually or by using computer programs such as BLAST (Altschul et al. (1990), Journal of Molecular Biology, 215, 403-410), which stands for Basic Local Alignment Search Tool or ClustalW (Thompson et al. (1994), Nucleic Acid Res., 22, 4673-4680) or any other suitable program which is suitable to generate sequence alignments.

SEQ ID NO: 2 is the amino acid sequence of the *Arabidopsis thaliana* DA1 protein, whereas SEQ ID NOs 5, 8, 11, 14 and 17 are amino acid sequences of DA1 from *Brassica napus*, SEQ ID NOs 56 and 59 are amino acid sequences of DA1 from *Brassica rapa*, SEQ ID NOs 62, 65, 67, and 69 are amino acid sequences of DA1 from *Brassica oleracea*, and SEQ ID NOs 72 and 75 are amino acid sequences of DA1 from *Brassica nigra*. Accordingly, the amino acid at position 358 of SEQ ID NO: 2 corresponds to the amino acid at position 338 of SEQ ID NOs: 5 and 56, to the amino acid at position 353 of SEQ ID NOs 8 and 59, to the amino acid at position 341 of SEQ ID NOs: 11 and 62, to the amino acid at position 352 of SEQ ID NO: 14, to the amino acid at position 355 of SEQ ID NOs: 65 and 69, to the amino acid at position 340 of SEQ ID NO: 72, and to the amino acid at position 357 of SEQ ID NO: 75. An alignment of sequences of the DA1 proteins is shown in FIG. 1.

SEQ ID NO: 1 is the nucleotide sequence encoding an *A. thaliana* wild type DA1, whereas SEQ ID NO: 2 is the *A. thaliana* amino acid sequence derived from SEQ ID NO: 1. Accordingly, the codon at position 1072-1074 of the nucleotide sequence of SEQ ID NO: 1 encodes the amino acid at position 358 of SEQ ID NO: 2.

SEQ ID NO: 3 is a wild type genomic *B. napus* DA1-A1 sequence, SEQ ID NO: 4 is the coding sequence of a *B. napus* wild type DA1-A1, whereas SEQ ID NO: 5 is the *B. napus* amino acid sequence derived from SEQ ID NOs: 3 and 4. Accordingly, the codon at position 1012-1014 of the nucleotide sequence of SEQ ID NO: 4 and the corresponding codon at position 1618-1620 of SEQ ID NO: 3 encodes the amino acid at position 338 of SEQ ID NO: 5 (this position, again, corresponds to position 358 of SEQ ID NO: 2). In other words, the amino acid arginine ("Arg" (three letter code) or "R" (one letter code)) at position 338 of SEQ ID NO: 5 is encoded by the codon at positions 1618-1620 and 1012-1014 of the nucleotide sequence of SEQ ID NOs: 3 and 4, respectively.

SEQ ID NO: 6 is a wild type genomic *B. napus* DA1-A2 sequence, SEQ ID NO: 7 is the coding sequence of a *B. napus* wild type DA1-A2, whereas SEQ ID NO: 8 is the *B. napus* amino acid sequence derived from SEQ ID NOs: 6 and 7. Accordingly, the codon at position 1057-1059 of the nucleotide sequence of SEQ ID NO: 7 and the corresponding codon at position 1671-1673 of SEQ ID NO: 6 encodes the amino acid at position 353 of SEQ ID NO: 8 (this position, again, corresponds to position 358 of SEQ ID NO: 2). In other words, the amino acid arginine ("Arg" (three letter code) or "R" (one letter code)) at position 353 of SEQ ID NO: 8 is encoded by the codon at positions 1671-1673 and 1057-1059 of the nucleotide sequence of SEQ ID NOs: 6 and 7, respectively.

SEQ ID NO: 9 is a wild type genomic *B. napus* DA1-C1 sequence, SEQ ID NO: 10 is the coding sequence of a *B. napus* wild type DA1-C1, whereas SEQ ID NO: 11 is the *B. napus* amino acid sequence derived from SEQ ID NOs: 9 and 10. Accordingly, the codon at position 1021-1023 of the nucleotide sequence of SEQ ID NO: 10 and the corresponding codon at position 1646-1648 of SEQ ID NO: 9 encodes the amino acid at position 341 of SEQ ID NO: 11 (this position, again, corresponds to position 358 of SEQ ID NO: 2). In other words, the amino acid arginine ("Arg" (three letter code) or "R" (one letter code)) at position 341 of SEQ ID NO: 11 is encoded by the codon at positions 1646-1648 and 1021-1023 of the nucleotide sequence of SEQ ID NOs: 9 and 10, respectively.

SEQ ID NO: 12 is a wild type genomic *B. napus* DA1-C2 sequence, SEQ ID NO: 13 is the coding sequence of a *B. napus* wild type DA1-C2, whereas SEQ ID NO: 14 is the *B. napus* amino acid sequence derived from SEQ ID NOs: 12 and 13. Accordingly, the codon at position 1054-1056 of the nucleotide sequence of SEQ ID NO: 13 and the corresponding codon at position 1686-1688 of SEQ ID NO: 12 encodes the amino acid at position 352 of SEQ ID NO: 14 (this position, again, corresponds to position 358 of SEQ ID NO: 2). In other words, the amino acid arginine ("Arg" (three letter code) or "R" (one letter code)) at position 352 of SEQ ID NO: 14 is encoded by the codon at positions 1686-1688 and 1054-1056 of the nucleotide sequence of SEQ ID NOs: 12 and 13, respectively.

SEQ ID NO: 54 is a wild type genomic *B. rapa* DA1-A1 sequence, SEQ ID NO: 55 is the coding sequence of a *B. rapa* wild type DA1-A1, whereas SEQ ID NO: 56 is the *B. rapa* amino acid sequence derived from SEQ ID NOs: 54 and 55. Accordingly, the codon at position 1012-1014 of the nucleotide sequence of SEQ ID NO: 55 and the corresponding codon at position 1621-1623 of SEQ ID NO: 54 encodes the amino acid at position 338 of SEQ ID NO: 56 (this position, again, corresponds to position 358 of SEQ ID NO: 2). In other words, the amino acid arginine ("Arg" (three letter code) or "R" (one letter code)) at position 338 of SEQ ID NO: 56 is encoded by the codon at positions 1621-1623 and 1012-1014 of the nucleotide sequence of SEQ ID NOs: 54 and 55, respectively.

SEQ ID NO: 57 is a wild type genomic *B. rapa* DA1-A2 sequence, SEQ ID NO: 58 is the coding sequence of a *B. rapa* wild type DA1-A2, whereas SEQ ID NO: 59 is the *B. rapa* amino acid sequence derived from SEQ ID NOs: 57 and 58. Accordingly, the codon at position 1057-1059 of the nucleotide sequence of SEQ ID NO: 58 and the corresponding codon at position 1682-1684 of SEQ ID NO: 57 encodes the amino acid at position 353 of SEQ ID NO: 59 (this position, again, corresponds to position 358 of SEQ ID NO: 2). In other words, the amino acid arginine ("Arg" (three letter code) or "R" (one letter code)) at position 353 of SEQ ID NO: 59 is encoded by the codon at positions 1682-1684 and 1057-1059 of the nucleotide sequence of SEQ ID NOs: 57 and 58, respectively.

SEQ ID NO: 60 is a wild type genomic *B. oleracea* DA1-C1 sequence, SEQ ID NO: 61 is the coding sequence of a *B. oleracea* wild type DA1-C1, whereas SEQ ID NO: 62 is the *B. oleracea* amino acid sequence derived from SEQ ID NOs: 60 and 61. Accordingly, the codon at position 1021-1023 of the nucleotide sequence of SEQ ID NO: 61 and the corresponding codon at position 1646-1648 of SEQ ID NO: 60 encodes the amino acid at position 341 of SEQ ID NO: 62 (this position, again, corresponds to position 358 of SEQ ID NO: 2). In other words, the amino acid arginine ("Arg" (three letter code) or "R" (one letter code)) at position 341 of SEQ ID NO: 62 is encoded by the codon at positions 1646-1648 and 1021-1023 of the nucleotide sequence of SEQ ID NOs: 60 and 61, respectively.

SEQ ID NO: 63 is a wild type genomic *B. oleracea* DA1-C2 sequence, SEQ ID NO: 64 is isoform 1 of the coding sequence of a *B. oleracea* wild type DA1-C2, whereas SEQ ID NO: 65 is the isoform 1 *B. oleracea* amino acid sequence derived from SEQ ID NOs: 63 and 64. SEQ ID NO: 68 is isoform 3 of the coding sequence of a *B. oleracea* wild type DA1-C2, whereas SEQ ID NO: 69 is the isoform 3 *B. oleracea* amino acid sequence derived from SEQ ID NOs: 63 and 68. Accordingly, the codon at position 1063-1065 of the nucleotide sequence of SEQ ID NO: 64 and 68 and the corresponding codon at position 1658-1660 of SEQ ID NO: 63 encodes the amino acid at position 355 of SEQ ID NO: 65 and 69 (this position, again, corresponds to position 358 of SEQ ID NO: 2). In other words, the amino acid arginine ("Arg" (three letter code) or "R" (one letter code)) at position 355 of SEQ ID NO: 65 and 69 is encoded by the codon at positions 1658-1660 of the nucleotide sequence of SEQ ID NO: 63 and by the codon at positions 1063-1065 of the nucleotide sequence of SEQ ID NOs: 64 and 68.

SEQ ID NO: 70 is a wild type genomic *B. nigra* DA1-B1 sequence, SEQ ID NO: 71 is the coding sequence of a *B. nigra* wild type DA1-B1, whereas SEQ ID NO: 72 is the *B. nigra* amino acid sequence derived from SEQ ID NOs: 70 and 71. Accordingly, the codon at position 1018-1020 of the nucleotide sequence of SEQ ID NO: 71 and the corresponding codon at position 1519-1521 of SEQ ID NO: 70 encodes the amino acid at position 340 of SEQ ID NO: 72 (this position, again, corresponds to position 358 of SEQ ID NO: 2). In other words, the amino acid arginine ("Arg" (three letter code) or "R" (one letter code)) at position 340 of SEQ ID NO: 72 is encoded by the codon at positions 1519-1521 and 1018-1020 of the nucleotide sequence of SEQ ID NOs: 70 and 71, respectively.

SEQ ID NO: 73 is a wild type genomic *B. nigra* DA1-B2 sequence, SEQ ID NO: 74 is the coding sequence of a *B. nigra* wild type DA1-B2, whereas SEQ ID NO: 75 is the *B. nigra* amino acid sequence derived from SEQ ID NOs: 73 and 74. Accordingly, the codon at position 1069-1071 of the nucleotide sequence of SEQ ID NO: 74 and the corresponding codon at position 1707-1709 of SEQ ID NO: 73 encodes the amino acid at position 357 of SEQ ID NO: 75 (this position, again, corresponds to position 358 of SEQ ID NO: 2). In other words, the amino acid arginine ("Arg" (three letter code) or "R" (one letter code)) at position 357 of SEQ ID NO: 75 is encoded by the codon at positions 1707-1709 and 1069-1071 of the nucleotide sequence of SEQ ID NOs: 73 and 74, respectively.

In one embodiment, the amino acid at a position corresponding to position 358 of SEQ ID NO: 2 is a Lysine ("Lys" (three letter code) or "K" (one letter code)) instead of an Arginine ("Arg" (three letter code) or "R" (one letter code)).

In order to determine whether a nucleic acid sequence has a certain degree of identity to the nucleotide sequences of the present invention, the skilled person can use means and methods well-known in the art, e.g., alignments, either manually or by using computer programs such as those mentioned further down below in connection with the definition of the term "hybridization" and degrees of homology.

For the purpose of this invention, the "sequence identity" or "sequence homology" (the terms are used interchangeably herein) of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

Nucleic Acid Sequences Encoding DA1 Proteins

Nucleic acid sequences of DA1-A1, DA1-A2, DA1-C1, and DA1-C2 have been isolated from *Brassica napus*, nucleic acid sequences of DA1-A1, DA1-A2 have been isolated from *Brassica rapa*, nucleic acid sequences of DA1-C1, DA1-C2 have been isolated from *Brassica oleracea*, and nucleic acid sequences of DA1-B1, DA1-B2 have been isolated from *Brassica nigra*, as depicted in the sequence listing. The wild type DA1 sequences are depicted, while the mutant DA1 sequences of these sequences, and of sequences essentially similar to these, are described herein below and in the Examples, with reference to the wild type DA1 sequences. The genomic DA1 protein-encoding DNA from *Brassica napus, B. rapa, B. oleracea* and *B. nigra* do comprise any introns. The coding sequences or cDNA sequences, of the *Brassica* DA1 genes, not comprising the introns, are also depicted in the sequence listing.

A "*Brassica napus* DA1-A1 gene", "BnDA1-A1 gene", *Brassica napus* DA1-A1 allele", "BnRDA1-A1 allele" or "DA1-A1 from *Brassica napus*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 3.

A "*Brassica napus* DA1-A2 gene", "BnDA1-A2 gene", *Brassica napus* DA1-A2 allele", "BnDA1-A2 allele" or "DA1-A2 from *Brassica napus*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 6.

A "*Brassica napus* DA1-C1 gene", "BnDA1-C1 gene", *Brassica napus* DA1-C1 allele", "BnDA1-C1 allele" or "DA1-C1 from *Brassica napus*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 9.

A "*Brassica napus* DA1-C2 gene", "BnDA1-C2 gene", *Brassica napus* DA1-C2 allele", "BnDA1-C2 allele" or "DA1-C2 from *Brassica napus*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 12.

A "*Brassica rapa* DA1-A1 gene", "BrDA1-A1 gene", *Brassica rapa* DA1-A1 allele", "BrRDA1-A1 allele" or "DA1-A1 from *Brassica rapa*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 54.

A "*Brassica rapa* DA1-A2 gene", "BrDA1-A2 gene", *Brassica rapa* DA1-A2 allele", "BrDA1-A2 allele" or "DA1-A2 from *Brassica rapa*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 57.

A "*Brassica oleracea* DA1-C1 gene", "BoDA1-C1 gene", *Brassica oleracea* DA1-C1 allele", "BoDA1-C1 allele" or "DA1-C1 from *Brassica oleracea*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 60.

A "*Brassica oleracea* DA1-C2 gene", "BoDA1-C2 gene", *Brassica oleracea* DA1-C2 allele", "BoDA1-C2 allele" or "DA1-C2 from *Brassica oleracea*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 63.

A "*Brassica nigra* DA1-B1 gene", "BniDA1-B1 gene", *Brassica nigra* DA1-B1 allele", "BniDA1-B1 allele" or "DA1-B1 from *Brassica nigra*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 70.

A "*Brassica nigra* DA1-B2 gene", "BniDA1-B2 gene", *Brassica nigra* DA1-B2 allele", "BniDA1-B2 allele" or "DA1-B2 from *Brassica nigra*", or variant nucleic acid sequences thereof as used herein refers to a gene, allele or a sequence having at least 80%, or at least 85%, or at least 90%, or at least 95%, or at least 98%, or at least 99%, or 100% sequence identity SEQ ID No. 73.

A coding sequence of a "*Brassica napus* DA1-A1 gene", "BnDA1-A1 gene", *Brassica napus* DA1-A1 allele", "BnRDA1-A1 allele" or "DA1-A1 from *Brassica napus*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 4.

A coding sequence of a "*Brassica napus* DA1-A2 gene", "BnDA1-A2 gene", *Brassica napus* DA1-A2 allele", "BnDA1-A2 allele" or "DA1-A2 from *Brassica napus*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 7.

A coding sequence of a "*Brassica napus* DA1-C1 gene", "BnDA1-C1 gene", *Brassica napus* DA1-C1 allele", "BnDA1-C1 allele" or "DA1-C1 from *Brassica napus*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 10.

A coding sequence of a "*Brassica napus* DA1-C2 gene", "BnDA1-C2 gene", *Brassica napus* DA1-C2 allele", "BnDA1-C2 allele" or "DA1-C2 from *Brassica napus*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 13.

A coding sequence of a "*Brassica rapa* DA1-A1 gene", "BrDA1-A1 gene", *Brassica rapa* DA1-A1 allele", "BrRDA1-A1 allele" or "DA1-A1 from *Brassica rapa*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 55.

A coding sequence of a "*Brassica rapa* DA1-A2 gene", "BrDA1-A2 gene", *Brassica rapa* DA1-A2 allele", "BrDA1-A2 allele" or "DA1-A2 from *Brassica rapa*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 58.

A coding sequence of a "*Brassica oleracea* DA1-C1 gene", "BoDA1-C1 gene", *Brassica oleracea* DA1-C1 allele", "BoDA1-C1 allele" or "DA1-C1 from *Brassica oleracea*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 61.

An isoform 1 coding sequence of a "*Brassica oleracea* DA1-C2 gene", "BoDA1-C2 gene", *Brassica oleracea* DA1-C2 allele", "BoDA1-C2 allele" or "DA1-C2 from *Brassica oleracea*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 64.

An isoform 2 coding sequence of a "*Brassica oleracea* DA1-C2 gene", "BoDA1-C2 gene", *Brassica oleracea* DA1-C2 allele", "BoDA1-C2 allele" or "DA1-C2 from *Brassica oleracea*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 66.

An isoform 3 coding sequence of a "*Brassica oleracea* DA1-C2 gene", "BoDA1-C2 gene", *Brassica oleracea* DA1-C2 allele", "BoDA1-C2 allele" or "DA1-C2 from *Brassica oleracea*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 68.

A coding sequence of a "*Brassica nigra* DA1-B1 gene", "BniDA1-B1 gene", *Brassica nigra* DA1-B1 allele", "BniRDA1-B1 allele" or "DA1-B1 from *Brassica nigra*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 71.

A coding sequence of a "*Brassica nigra* DA1-B2 gene", "BniDA1-B2 gene", *Brassica nigra* DA1-B2 allele", "BniDA1-B2 allele" or "DA1-B2 from *Brassica nigra*", or variant nucleic acid sequences thereof as used herein refers to a coding sequence having at least 80%, or at least 85%, or at least 90%, or at least 95%, or at least 98%, or at least 99%, or 100% sequence identity SEQ ID No. 74.

A DA1-A1 gene or DA1-A1 allele or DA1-A1 coding sequence can comprise a *Brassica napus* DA1-A1 gene or allele or coding sequence and a *Brassica rapa* DA1-A1 gene or allele or coding sequence; a DA1-A2 gene or DA1-A2 allele or DA1-A2 coding sequence can comprise a *Brassica napus* DA1-A2 gene or allele or coding sequence and a *Brassica rapa* DA1-A2 gene or allele or coding sequence; a DA1-C1 gene or DA1-C1 allele or DA1-C1 coding sequence can comprise a *Brassica napus* DA1-C1 gene or allele or coding sequence and a *Brassica oleracea* DA1-C1 gene or allele or coding sequence; a DA1-C2 gene or DA1-C2 allele or DA1-C2 coding sequence can comprise a *Brassica napus* DA1-C2 gene or allele or coding sequence and a *Brassica oleracea* DA1-C2 gene or allele or coding sequence.

The nucleic acid sequences depicted in the sequence listing in SEQ ID NOs 3, 6, 9 and 12 (*B. napus*), SEQ ID NO: 54 and 57 (*B. rapa*), SEQ ID NO: 60 and 63 (*B. oleracea*) and SEQ ID NO: 70 and 73 (*B. nigra*) encode wild type DA1 proteins from the respective *Brassica* species. Thus, these sequences are endogenous to the *Brassica* plants from which they were isolated. Other *Brassica* crop species, varieties, breeding lines or wild accessions may be screened for other DA1 alleles, encoding the same DA1 proteins or variants thereof. For example, nucleic acid hybridization techniques (e.g. Southern blot analysis, using for example stringent hybridization conditions) or PCR-based techniques may be used to identify DA1 alleles endogenous to other *Brassica* plants, such as various *Brassica napus* varieties, lines or accessions, but also *Brassica juncea* (DA1 alleles on the A-genome and on the B-genome), *Brassica carinata* (DA1 alleles on the B-genome and the C-genome) plants, organs and tissues can be screened for other wild type DA1 alleles. To screen such plants, plant organs or tissues for the presence of DA1 alleles, the DA1 nucleic acid sequences provided in the sequence listing, or variants or fragments of any of these, may be used. For example whole sequences or fragments may be used as probes or primers. For example specific or degenerate primers may be used to amplify nucleic acid sequences encoding DA1 proteins from the genomic DNA of the plant, plant organ or tissue. These DA1 nucleic acid sequences may be isolated and sequenced using standard molecular biology techniques. Bioinformatics analysis may then be used to characterize the allele(s), for example in order to determine which DA1 allele the sequence corresponds to and which DA1 protein or protein variant is encoded by the sequence.

Whether a nucleic acid sequence encodes a functional DA1 protein can be analyzed by recombinant DNA techniques as known in the art, e.g., by a genetic complementation test using, e.g., an *Arabidopsis* plant, comprising a da1-1 allele such as described in WO2009/047525 (incorporated herewith by reference) or a *Brassica napus* plant, which is homozygous for a mutant DA1 allele of a DA1-A2 or a DA1-C2 gene.

In addition, it is understood that DA1 nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided.

Nucleic Acid Sequences Encoding Mutant DA1 Proteins

Nucleic acid sequences comprising one or more nucleotide deletions, insertions or substitutions relative to the wild type nucleic acid sequences are provided, as are fragments of such mutant nucleic acid molecules. Such mutant nucleic acid sequences can be generated and/or identified using various known methods, as described further below. The mutation(s) can result in one or more changes (deletions, insertions and/or substitutions) in the amino acid sequence of the encoded DA1 protein. Alternatively, the mutation(s) in the nucleic acid sequence result in a significantly reduced or completely abolished biological activity of the encoded DA1 protein relative to the wild type protein.

In one embodiment, the mutant DA1 allele encodes a mutant DA1 protein comprising at a position corresponding to position 358 of SEQ ID NO: 2 an amino acid other than Arginine, such as a Lysine.

Codons encoding Arginine are AGA, AGG, CGT, CGC, CGA, and CGG. The skilled person will immediately understand that different single, double, and triple mutations in these codons can result in codons that do not encode Arginine.

Lysine is encoded by the codons AAA and AAG. Single mutations in any of the codons encoding Arginine resulting in a codon encoding Lysine are therefore: AGA=>AAA and AGG=>AAG. Double mutations in any of the codons encoding Arginine resulting in a codon encoding Lysine are therefore: AGA=>AAG; AGG=>AAA; CGA=>AAA; and CGG=>AAG. Triple mutations in any of the codons encoding Arginine resulting in a codon encoding Lysine are therefore CGT=>AAA; CGT=>AAG; CGC=>AAA; CGC=>AAG; CGA=>AAG; and CGG=>AAG.

In the *Arabidopsis* DA1 protein, the Arginine at position 358 is encoded by the codon AGA (position 1072-1074 of SEQ ID NO: 1); in the BnDA1-A1 protein the Arginine at position 338 is encoded by the codon AGA (position 1012-1014 of SEQ ID NO: 4, position 1618-1620 of SEQ ID NO: 3); in the BnDA1-A2 protein the Arginine at position 353 is encoded by the codon AGA (position 1057-1059 of SEQ ID NO: 7, position 1671-1673 of SEQ ID NO: 6); in the BnDA1-C1 protein the Arginine at position 341 is encoded by the codon AGA (position 1021-1023 of SEQ ID NO: 10, position 1646-1648 of SEQ ID NO: 9); in the BnDA1-C2 protein the Arginine at position 352 is encoded by the codon AGA (position 1054-1056 of SEQ ID NO: 13, position 1686-1688 of SEQ ID NO: 12); in the BrDA1-A1 protein the Arginine at position 338 is encoded by the codon AGA (position 1012-1014 of SEQ ID NO: 55, position 1621-1623 of SEQ ID NO: 54); in the BrDA1-A2 protein the Arginine at position 353 is encoded by the codon AGA (position 1057-1059 of SEQ ID NO: 58, position 1682-1684 of SEQ ID NO: 57); in the BoDA1-C1 protein the Arginine at position 341 is encoded by the codon AGA (position 1021-1023 of SEQ ID NO: 61, position 1646-1648 of SEQ ID NO: 60); in the BoDA1-C2 protein (isoform 1 and 3) the Arginine at position 355 is encoded by the codon AGA (position 1063-1065 of SEQ ID NO: 64 and 68, position 1658-1660 of SEQ ID NO: 63); in the BniDA1-B1 protein the Arginine at position 340 is encoded by the codon AGA (position 1018-1020 of SEQ ID NO: 71, position 1519-1521 of SEQ ID NO: 70); in the BniDA1-B2 protein the Arginine at position 357 is encoded by the codon AGA (position 1069-1071 of SEQ ID NO: 74, position 1707-1709 of SEQ ID NO: 73).

It will be clear to the skilled person that the AGA codon of the *Brassica* DA1 genes can be mutated into an AAA codon (single nucleotide substitution) or an AAG codon (substitution of two nucleotides).

In a particular embodiment, the G at position 1672 of SEQ ID NO: 6 is mutated into an A, resulting in the mutation of the AGA codon at position 1671-1673 encoding Arginine into an AAA codon encoding Lysine. The sequence of a mutant DA1-A2 gene comprising this mutation is given in SEQ ID NO: 15; of a coding sequence of such a mutant DA1-A2 gene in SEQ ID NO: 16, and a protein encoded by such a mutated DA1-A2 gene in SEQ ID NO: 17.

Further provided are *Brassica* plants comprising a mutant allele of a second DA1 gene, wherein the mutant allele of said second DA1 gene is a full knock-out DA1 gene. Also provided are *Brassica* plants comprising a full knock-out DA1 gene wherein no DA1 allele is present which encodes a mutant DA1 protein comprising at a position corresponding to position 358 of SEQ ID NO: 2 an amino acid other than Arginine.

Basically, any mutation in the wild type DA1 nucleic acid sequences which results in an DA1 protein comprising at least one amino acid insertion, deletion and/or substitution relative to the wild type DA1 protein can lead to significantly reduced or no biological activity. It is, however, understood that certain mutations in the DA1 protein are more likely to result in a complete abolishment of the biological activity of the DA1 protein, such as mutations whereby significant portions of the functional domains, such as the UIM domain or the LIM domain are lacking.

The nucleic acid molecules may comprise one or more mutations, such as:
- a "missense mutation", which is a change in the nucleic acid sequence that results in the substitution of an amino acid for another amino acid;
- a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation;
- an "insertion mutation" of one or more amino acids, due to one or more codons having been added in the coding sequence of the nucleic acid;
- a "deletion mutation" of one or more amino acids, due to one or more codons having been deleted in the coding sequence of the nucleic acid;
- a "frameshift mutation", resulting in the nucleic acid sequence being translated in a different frame downstream of the mutation. A frameshift mutation can have various causes, such as the insertion, deletion or duplication of one or more nucleotides;
- a mutated splice site, resulting in altered splicing, which results in an altered mRNA processing and, consequently, in an altered encoded protein which contains either deletinos, substitutions, or insertions of various lengths, possibly combined with premature translation termination.

As defined in this application, a "full knock-out da1 gene" or "knock-out da1 allele" refers to a da1 gene or a da1 allele which does not rescue the da1-1 phenotype when overexpressed in da1-1 mutant *Arabidopsis thaliana* as described in WO2009/047525.

From this definition, it is thus clear that a knock-out DA1 protein can be provided by one or more missense, nonsense, insertion, deletion, frameshift, or splice site mutation.

Optimal alignment of the *Arabidopsis* DA1 nucleic acid (SEQ ID NO: 1) and amino acid (SEQ ID NO: 2) sequences with DA1 nucleic acid sequences, in particular the *Brassica* DA1 genomic sequences (SEQ ID NO: 3, 6, 9, 12, 54, 57, 60, 63, 70, and 73), coding sequences (SEQ ID NO: 4, 7, 10, 13, 55, 58, 61, 64, 66, 68, 71, and 74) and amino acid (SEQ ID NO: 5, 8, 11, 14, 56, 62, 65, 67, 69, 72, and 75) sequences of the present invention, allows to determine the positions of the corresponding conserved domains and amino acids in these *Brassica* sequences (see FIG. 1 for an alignment of the *Arabidopsis* DA1 protein sequence with the *Brassica* DA1 protein sequences of SEQ ID NOs: 5, 8, 11, 14, 56, 62, 65, 67, 69, 72, and 75).

A nonsense mutation in an DA1 allele, as used herein, is a mutation in an DA1 allele whereby one or more translation stop codons are introduced into the coding DNA and the corresponding mRNA sequence of the corresponding wild type DA1 allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. Thus, a full knockout mutant DA1 allele imay comprise a nonsense mutation wherein an in-frame stop codon is introduced in the DA1 codon sequence by a single nucleotide substitution, such as the mutation of CAG to TAG, TGG to TAG, TGG to TGA, or CAA to TAA. Alternatively, a full knockout mutant DA1 allele may comprise a nonsense mutation wherein an in-frame stop codon is introduced in the DA1 codon sequence by double nucleotide substitutions, such as the mutation of CAG to TAA, TGG to TAA, or CGG to TAG or TGA. A full knockout mutant DA1 allele may further comprise a nonsense mutation wherein an in-frame stop codon is introduced in the DA1 codon sequence by triple nucleotide substitutions, such as the mutation of CGG to TAA. The truncated protein lacks the amino acids encoded by the coding DNA downstream of the mutation (i.e. the C-terminal part of the DA1 protein) and maintains the amino acids encoded by the coding DNA upstream of the mutation (i.e. the N-terminal part of the DA1 protein).

The Tables herein below describe a range of possible nonsense mutations in the *Brassica napus* DA1 sequences provided herein:

TABLE 1a possible stop codon mutations in BnDA1-A1 (SEQ ID NO: 3)

| position relative to the genomic sequence (SEQ ID No. 3) | WT codon | AA | stop codon | AA |
|---|---|---|---|---|
| 37-39 | CAA | Gln | TAA | STOP |
| 400-402 | CAA | Gln | TAA | STOP |
| 558-560 | CAA | Gln | TAA | STOP |
| 576-578 | CAA | Gln | TAA | STOP |
| 881-883 | CAA | Gln | TAA | STOP |
| 1379-1381 | CAA | Gln | TAA | STOP |
| 1385-1387 | CAA | Gln | TAA | STOP |
| 1406-1408 | CAA | Gln | TAA | STOP |
| 1642-1644 | CAA | Gln | TAA | STOP |
| 1705-1707 | CAA | Gln | TAA | STOP |
| 1932-1934 | CAA | Gln | TAA | STOP |
| 1956-1958 | CAA | Gln | TAA | STOP |
| 136-138 | CAG | Gln | TAG | STOP |
|  |  |  | TAA | STOP |
| 839-841 | CAG | Gln | TAG | STOP |
|  |  |  | TAA | STOP |
| 1229-1231 | CAG | Gln | TAG | STOP |
|  |  |  | TAA | STOP |
| 1400-1402 | CAG | Gln | TAG | STOP |
|  |  |  | TAA | STOP |
| 1442-1444 | CAG | Gln | TAG | STOP |
|  |  |  | TAA | STOP |
| 1472-1474 | CAG | Gln | TAG | STOP |
|  |  |  | TAA | STOP |
| 2070-2072 | CAG | Gln | TAG | STOP |
|  |  |  | TAA | STOP |
| 2106-2108 | CAG | Gln | TAG | STOP |
|  |  |  | TAA | STOP |
| 2205-2207 | CAG | Gln | TAG | STOP |
|  |  |  | TAA | STOP |
| 890-892 | CGA | Arg | TGA | STOP |
|  |  |  | TAA | STOP |
| 1723-1725 | CGA | Arg | TGA | STOP |
|  |  |  | TAA | STOP |
| 1298-1300 | CGG | Arg | TAG | STOP |
|  |  |  | TGA | STOP |
|  |  |  | TAA | STOP |
| 1331-1333 | CGG | Arg | TAG | STOP |
|  |  |  | TGA | STOP |
|  |  |  | TAA | STOP |
| 1469-1471 | CGG | Arg | TAG | STOP |
|  |  |  | TGA | STOP |
|  |  |  | TAA | STOP |

TABLE 1a-continued possible stop codon mutations in BnDA1-A1 (SEQ ID NO: 3)

| position relative to the genomic sequence (SEQ ID No. 3) | WT codon | AA | stop codon | AA |
|---|---|---|---|---|
| 1816-1818 | CGG | Arg | TAG | STOP |
|  |  |  | TGA | STOP |
|  |  |  | TAA | STOP |
| 1920-1922 | CGG | Arg | TAG | STOP |
|  |  |  | TGA | STOP |
|  |  |  | TAA | STOP |
| 7-9 | TGG | Trp | TAG | STOP |
|  |  |  | TGA | STOP |
|  |  |  | TAA | STOP |
| 334-336 | TGG | Trp | TAG | STOP |
|  |  |  | TGA | STOP |
|  |  |  | TAA | STOP |
| 427, 529-530 | TGG | Trp | TAG | STOP |
|  |  |  | TGA | STOP |
|  |  |  | TAA | STOP |
| 872-874 | TGG | Trp | TAG | STOP |
|  |  |  | TGA | STOP |
|  |  |  | TAA | STOP |
| 1223-1225 | TGG | Trp | TAG | STOP |
|  |  |  | TGA | STOP |
|  |  |  | TAA | STOP |
| 1681-1683 | TGG | Trp | TAG | STOP |
|  |  |  | TGA | STOP |
|  |  |  | TAA | STOP |
| 1810-1812 | TGG | Trp | TAG | STOP |
|  |  |  | TGA | STOP |
|  |  |  | TAA | STOP |
| 1974-1976 | TGG | Trp | TAG | STOP |
|  |  |  | TGA | STOP |
|  |  |  | TAA | STOP |

TABLE 1b possible stop codon mutations in BnDA1-A2 (SEQ ID NO: 6)

| position relative to the genomic sequence (SEQ ID No. 6) | WT codon | AA | stop codon | AA |
|---|---|---|---|---|
| 37-39 | CAA | Gln | TAA | STOP |
| 313-315 | CAA | Gln | TAA | STOP |
| 450-452 | CAA | Gln | TAA | STOP |
| 468-470 | CAA | Gln | TAA | STOP |
| 1417-1419 | CAA | Gln | TAA | STOP |
| 1423-1425 | CAA | Gln | TAA | STOP |
| 1444-1446 | CAA | Gln | TAA | STOP |
| 1510-1512 | CAA | Gln | TAA | STOP |
| 1695-1697 | CAA | Gln | TAA | STOP |
| 1785-1787 | CAA | Gln | TAA | STOP |
| 1974-1976 | CAA | Gln | TAA | STOP |
| 1998-2000 | CAA | Gln | TAA | STOP |
| 2142-2144 | CAA | Gln | TAA | STOP |
| 82-84 | CAG | Gln | TAG | STOP |
|  |  |  | TAA | STOP |
| 151-153 | CAG | Gln | TAG | STOP |
|  |  |  | TAA | STOP |
| 259-261 | CAG | Gln | TAG | STOP |
|  |  |  | TAA | STOP |
| 319-321 | CAG | Gln | TAG | STOP |
|  |  |  | TAA | STOP |
| 501-503 | CAG | Gln | TAG | STOP |
|  |  |  | TAA | STOP |
| 1183-1185 | CAG | Gln | TAG | STOP |
|  |  |  | TAA | STOP |
| 1438-1440 | CAG | Gln | TAG | STOP |
|  |  |  | TAA | STOP |

TABLE 1b-continued possible stop codon mutations in BnDA1-A2 (SEQ ID NO: 6)

| position relative to the genomic sequence (SEQ ID No. 6) | WT codon | AA | stop codon | AA |
|---|---|---|---|---|
| 1480-1482 | CAG | Gln | TAG | STOP |
| | | | TAA | STOP |
| 2106-2108 | CAG | Gln | TAG | STOP |
| | | | TAA | STOP |
| 2241-2243 | CAG | Gln | TAG | STOP |
| | | | TAA | STOP |
| 819-821 | CGA | Arg | TGA | STOP |
| | | | TAA | STOP |
| 46-48 | CGG | Arg | TAG | STOP |
| | | | TGA | STOP |
| | | | TAA | STOP |
| 1369-1371 | CGG | Arg | TAG | STOP |
| | | | TGA | STOP |
| | | | TAA | STOP |
| 1878-1880 | CGG | Arg | TAG | STOP |
| | | | TGA | STOP |
| | | | TAA | STOP |
| 1962-1964 | CGG | Arg | TAG | STOP |
| | | | TGA | STOP |
| | | | TAA | STOP |
| 7-9 | TGG | Trp | TAG | STOP |
| | | | TGA | STOP |
| | | | TAA | STOP |
| 801-803 | TGG | Trp | TAG | STOP |
| | | | TGA | STOP |
| | | | TAA | STOP |
| 1177-1179 | TGG | Trp | TAG | STOP |
| | | | TGA | STOP |
| | | | TAA | STOP |
| 1743-1745 | TGG | Trp | TAG | STOP |
| | | | TGA | STOP |
| | | | TAA | STOP |
| 1872-1874 | TGG | Trp | TAG | STOP |
| | | | TGA | STOP |
| | | | TAA | STOP |
| 2016-2018 | TGG | Trp | TAG | STOP |
| | | | TGA | STOP |
| | | | TAA | STOP |

TABLE 1c possible stop codon mutations in BnDA1-C1 (SEQ ID NO: 9)

| position relative to the genomic sequence (SEQ ID No. 9) | WT codon | AA | stop codon | AA |
|---|---|---|---|---|
| 37-39 | CAA | Gln | TAA | STOP |
| 408-410 | CAA | Gln | TAA | STOP |
| 594-596 | CAA | Gln | TAA | STOP |
| 896-898 | CAA | Gln | TAA | STOP |
| 1404-1406 | CAA | Gln | TAA | STOP |
| 1431-1433 | CAA | Gln | TAA | STOP |
| 1497-1499 | CAA | Gln | TAA | STOP |
| 1670-1672 | CAA | Gln | TAA | STOP |
| 1733-1735 | CAA | Gln | TAA | STOP |
| 1960-1962 | CAA | Gln | TAA | STOP |
| 1984-1986 | CAA | Gln | TAA | STOP |
| 2224-2226 | CAA | Gln | TAA | STOP |
| 145-147 | CAG | Gln | TAG | STOP |
| | | | TAA | STOP |
| 351-353 | CAG | Gln | TAG | STOP |
| | | | TAA | STOP |
| 576-578 | CAG | Gln | TAG | STOP |
| | | | TAA | STOP |
| 1254-1256 | CAG | Gln | TAG | STOP |
| | | | TAA | STOP |

TABLE 1c-continued possible stop codon mutations in BnDA1-C1 (SEQ ID NO: 9)

| position relative to the genomic sequence (SEQ ID No. 9) | WT codon | AA | stop codon | AA |
|---|---|---|---|---|
| 1410-1412 | CAG | Gln | TAG | STOP |
| | | | TAA | STOP |
| 1425-1427 | CAG | Gln | TAG | STOP |
| | | | TAA | STOP |
| 1467-1469 | CAG | Gln | TAG | STOP |
| | | | TAA | STOP |
| 2089-2091 | CAG | Gln | TAG | STOP |
| | | | TAA | STOP |
| 2125-2127 | CAG | Gln | TAG | STOP |
| | | | TAA | STOP |
| 905-907 | CGA | Arg | TGA | STOP |
| | | | TAA | STOP |
| 1323-1325 | CGG | Arg | TAG | STOP |
| | | | TGA | STOP |
| | | | TAA | STOP |
| 1356-1358 | CGG | Arg | TAG | STOP |
| | | | TGA | STOP |
| | | | TAA | STOP |
| 1751-1753 | CGG | Arg | TAG | STOP |
| | | | TGA | STOP |
| | | | TAA | STOP |
| 1844-1846 | CGG | Arg | TAG | STOP |
| | | | TGA | STOP |
| | | | TAA | STOP |
| 1948-1950 | CGG | Arg | TAG | STOP |
| | | | TGA | STOP |
| | | | TAA | STOP |
| 7-9 | TGG | Trp | TAG | STOP |
| | | | TGA | STOP |
| | | | TAA | STOP |
| 342-344 | TGG | Trp | TAG | STOP |
| | | | TGA | STOP |
| | | | TAA | STOP |
| 435, 547-548 | TGG | Trp | TAG | STOP |
| | | | TGA | STOP |
| | | | TAA | STOP |
| 887-889 | TGG | Trp | TAG | STOP |
| | | | TGA | STOP |
| | | | TAA | STOP |
| 1248-1250 | TGG | Trp | TAG | STOP |
| | | | TGA | STOP |
| | | | TAA | STOP |
| 1709-1711 | TGG | Trp | TAG | STOP |
| | | | TGA | STOP |
| | | | TAA | STOP |
| 1838-1840 | TGG | Trp | TAG | STOP |
| | | | TGA | STOP |
| | | | TAA | STOP |
| 2002-2004 | TGG | Trp | TAG | STOP |
| | | | TGA | STOP |
| | | | TAA | STOP |

TABLE 1d possible stop codon mutations in BnDA1-C2 (SEQ ID NO: 12)

| position relative to the genomic sequence (SEQ ID No. 12) | WT codon | AA | stop codon | AA |
|---|---|---|---|---|
| 37-39 | CAA | Gln | TAA | STOP |
| 316-318 | CAA | Gln | TAA | STOP |
| 472-474 | CAA | Gln | TAA | STOP |
| 1440-1442 | CAA | Gln | TAA | STOP |
| 1446-1448 | CAA | Gln | TAA | STOP |
| 1467-1469 | CAA | Gln | TAA | STOP |
| 1533-1535 | CAA | Gln | TAA | STOP |

TABLE 1d-continued possible stop codon mutations in BnDA1-C2 (SEQ ID NO: 12)

| position relative to the genomic sequence (SEQ ID No. 12) | WT codon | AA | stop codon | AA |
|---|---|---|---|---|
| 1710-1712 | CAA | Gln | TAA | STOP |
| 1800-1802 | CAA | Gln | TAA | STOP |
| 1987-1989 | CAA | Gln | TAA | STOP |
| 2011-2013 | CAA | Gln | TAA | STOP |
| 2125-2127 | CAA | Gln | TAA | STOP |
| 2161-2163 | CAA | Gln | TAA | STOP |
| 82-84 | CAG | Gln | TAG | STOP |
|  |  |  | TAA | STOP |
| 151-153 | CAG | Gln | TAG | STOP |
|  |  |  | TAA | STOP |
| 262-264 | CAG | Gln | TAG | STOP |
|  |  |  | TAA | STOP |
| 454-456 | CAG | Gln | TAG | STOP |
|  |  |  | TAA | STOP |
| 505-507 | CAG | Gln | TAG | STOP |
|  |  |  | TAA | STOP |
| 1205-1207 | CAG | Gln | TAG | STOP |
|  |  |  | TAA | STOP |
| 1461-1463 | CAG | Gln | TAG | STOP |
|  |  |  | TAA | STOP |
| 1503-1505 | CAG | Gln | TAG | STOP |
|  |  |  | TAA | STOP |
| 817-819 | CGA | Arg | TGA | STOP |
|  |  |  | TAA | STOP |
| 46-48 | CGG | Arg | TAG | STOP |
|  |  |  | TGA | STOP |
|  |  |  | TAA | STOP |
| 1359-1361 | CGG | Arg | TAG | STOP |
|  |  |  | TGA | STOP |
|  |  |  | TAA | STOP |
| 1392-1394 | CGG | Arg | TAG | STOP |
|  |  |  | TGA | STOP |
|  |  |  | TAA | STOP |
| 1893-1895 | CGG | Arg | TAG | STOP |
|  |  |  | TGA | STOP |
|  |  |  | TAA | STOP |
| 1975-1977 | CGG | Arg | TAG | STOP |
|  |  |  | TGA | STOP |
|  |  |  | TAA | STOP |
| 7-9 | TGG | Trp | TAG | STOP |
|  |  |  | TGA | STOP |
|  |  |  | TAA | STOP |
| 799-801 | TGG | Trp | TAG | STOP |
|  |  |  | TGA | STOP |
|  |  |  | TAA | STOP |
| 1199-1201 | TGG | Trp | TAG | STOP |
|  |  |  | TGA | STOP |
|  |  |  | TAA | STOP |
| 1758-1760 | TGG | Trp | TAG | STOP |
|  |  |  | TGA | STOP |
|  |  |  | TAA | STOP |
| 1887-1889 | TGG | Trp | TAG | STOP |
|  |  |  | TGA | STOP |
|  |  |  | TAA | STOP |
| 2029-2031 | TGG | Trp | TAG | STOP |
|  |  |  | TGA | STOP |
|  |  |  | TAA | STOP |

TABLE 1e possible splice site mutations in BnDA1-A1 (SEQ ID NO: 3)

| position relative to the genomic sequence (SEQ ID No. 3) | Splice site | WT | mutant |
|---|---|---|---|
| 156 | Intron 1 - donor | g[gt | a[gt |
| 157 | Intron 1 - donor | g[gt | g[at |
| 324 | Intron 1 - acceptor | ag]g | aa]g |
| 325 | Intron 1 - acceptor | ag]g | ag]a |
| 428 | Intron 2 - donor | t[gt | t[at |
| 528 | Intron 2 - acceptor | ag]g | aa]g |
| 529 | Intron 2 - acceptor | ag]g | ag]a |
| 718 | Intron 3 - donor | g[gt | a[gt |
| 719 | Intron 3 - donor | g[gt | g[at |
| 807 | Intron 3 - acceptor | ag]g | aa]g |
| 808 | Intron 3 - acceptor | ag]g | ag]a |
| 928 | Intron 4 - donor | g[gt | a[gt |
| 929 | Intron 4 - donor | g[gt | g[at |
| 1014 | Intron 4 - acceptor | ag]t | aa]t |
| 1099 | Intron 5 - donor | t[gt | t[at |
| 1174 | Intron 5 - acceptor | ag]a | aa]a |
| 1508 | Intron 6 - donor | t[gt | t[at |
| 1593 | Intron 6 - acceptor | ag]g | aa]g |
| 1594 | Intron 6 - acceptor | ag]g | ag]a |
| 1825 | Intron 7 - donor | g[gt | a[gt |
| 1826 | Intron 7 - donor | g[gt | g[at |
| 1914 | Intron 7 - acceptor | ag]g | aa]g |
| 1915 | Intron 7 - acceptor | ag]g | ag]a |

TABLE 1f possible splice site mutations in BnDA1-A2 (SEQ ID NO: 6)

| position relative to the genomic sequence (SEQ ID No. 6) | Splice site | WT | mutant |
|---|---|---|---|
| 171 | Intron 1 - donor | g[gt | a[gt |
| 172 | Intron 1 - donor | g[gt | g[at |
| 243 | Intron 1 - acceptor | ag]g | aa]g |
| 244 | Intron 1 - acceptor | ag]g | ag]a |
| 340 | Intron 2 - donor | g[gt | a[gt |
| 341 | Intron 2 - donor | g[gt | g[at |
| 420 | Intron 2 - acceptor | ag]g | aa]g |
| 421 | Intron 2 - acceptor | ag]g | ag]a |
| 646 | Intron 3 - donor | g[gt | a[gt |
| 647 | Intron 3 - donor | g[gt | g[at |
| 736 | Intron 3 - acceptor | ag]g | aa]g |
| 737 | Intron 3 - acceptor | ag]g | ag]a |
| 857 | Intron 4 - donor | g[gt | a[gt |
| 858 | Intron 4 - donor | g[gt | g[at |
| 932 | Intron 4 - acceptor | ag]t | aa]t |
| 1017 | Intron 5 - donor | t[gt | t[at |
| 1128 | Intron 5 - acceptor | ag]a | aa]a |
| 1248 | Intron 6 - donor | g[gt | a[gt |
| 1249 | Intron 6 - donor | g[gt | g[at |
| 1332 | Intron 6 - acceptor | ag]c | aa]c |
| 1546 | Intron 7 - donor | t[gt | t[at |
| 1646 | Intron 7 - acceptor | ag]g | aa]g |
| 1647 | Intron 7 - acceptor | ag]g | ag]a |
| 1887 | Intron 8 - donor | g[gt | a[gt |
| 1888 | Intron 8 - donor | g[gt | g[at |
| 1956 | Intron 8 - acceptor | ag]g | aa]g |
| 1957 | Intron 8 - acceptor | ag]g | ag]a |

TABLE 1g possible splice site mutations in BnDA1-C1 (SEQ ID NO: 9)

| position relative to the genomic sequence (SEQ ID No. 9) | Splice site | WT | mutant |
|---|---|---|---|
| 165 | Intron 1 - donor | g[gt | a[gt |
| 166 | Intron 1 - donor | g[gt | g[at |
| 332 | Intron 1 - acceptor | ag]g | aa]g |
| 333 | Intron 1 - acceptor | ag]g | ag]a |
| 436 | Intron 2 - donor | t[gt | t[at |
| 546 | Intron 2 - acceptor | ag]g | aa]g |
| 547 | Intron 2 - acceptor | ag]g | ag]a |
| 736 | Intron 3 - donor | g[gt | a[gt |
| 737 | Intron 3 - donor | g[gt | g[at |
| 822 | Intron 3 - acceptor | ag]g | aa]g |
| 823 | Intron 3 - acceptor | ag]g | ag]a |
| 943 | Intron 4 - donor | g[gt | a[gt |
| 944 | Intron 4 - donor | g[gt | g[at |
| 1033 | Intron 4 - acceptor | ag]t | aa]t |
| 1118 | Intron 5 - donor | t[gt | t[at |
| 1199 | Intron 5 - acceptor | ag]a | aa]a |
| 1533 | Intron 6 - donor | t[gt | t[at |
| 1621 | Intron 6 - acceptor | ag]g | aa]g |
| 1622 | Intron 6 - acceptor | ag]g | ag]a |
| 1853 | Intron 7 - donor | g[gt | a[gt |
| 1854 | Intron 7 - donor | g[gt | g[at |
| 1942 | Intron 7 - acceptor | ag]g | aa]g |
| 1943 | Intron 7 - acceptor | ag]g | ag]a |

TABLE 1h possible splice site mutations in BnDA1-C2 (SEQ ID NO: 12)

| position relative to the genomic sequence (SEQ ID No. 12) | Splice site | WT | mutant |
|---|---|---|---|
| 171 | Intron 1 - donor | g[gt | a[gt |
| 172 | Intron 1 - donor | g[gt | g[at |
| 246 | Intron 1 - acceptor | ag]g | aa]g |
| 247 | Intron 1 - acceptor | ag]g | ag]a |
| 340 | Intron 2 - donor | g[gt | a[gt |
| 341 | Intron 2 - donor | g[gt | g[at |
| 424 | Intron 2 - acceptor | ag]g | aa]g |
| 425 | Intron 2 - acceptor | ag]g | ag]a |
| 650 | Intron 3 - donor | g[gt | a[gt |
| 651 | Intron 3 - donor | g[gt | g[at |
| 734 | Intron 3 - acceptor | ag]g | aa]g |
| 735 | Intron 3 - acceptor | ag]g | ag]a |
| 855 | Intron 4 - donor | g[gt | a[gt |
| 856 | Intron 4 - donor | g[gt | g[at |
| 938 | Intron 4 - acceptor | ag]t | aa]t |
| 1023 | Intron 5 - donor | t[gt | t[at |
| 1150 | Intron 5 - acceptor | ag]a | aa]a |
| 1270 | Intron 6 - donor | g[gt | a[gt |
| 1271 | Intron 6 - donor | g[gt | g[at |
| 1355 | Intron 6 - acceptor | ag]c | aa]c |
| 1569 | Intron 7 - donor | t[gt | t[at |
| 1661 | Intron 7 - acceptor | ag]g | aa]g |
| 1662 | Intron 7 - acceptor | ag]g | ag]a |
| 1902 | Intron 8 - donor | g[gt | a[gt |
| 1903 | Intron 8 - donor | g[gt | g[at |
| 1969 | Intron 8 - acceptor | ag]g | aa]g |
| 1970 | Intron 8 - acceptor | ag]g | ag]a |

Obviously, mutations are not limited to the ones shown in the above tables and it is understood that analogous STOP mutations may be present in DA1 alleles other than those depicted in the sequence listing and referred to in the tables above.

A missense mutation in a DA1 allele, as used herein, is any mutation (deletion, insertion or substitution) in a DA1 allele whereby one or more codons are changed into the coding DNA and the corresponding mRNA sequence of the corresponding wild type DA1 allele, resulting in the substitution of one or more amino acids in the wild type DA1 protein for one or more other amino acids in the mutant DA1 protein.

A frameshift mutation in a DA1 allele, as used herein, is a mutation (deletion, insertion, duplication, and the like) in a DA1 allele that results in the nucleic acid sequence being translated in a different frame downstream of the mutation.

A splice site mutation in a AD1 allele, as used herein, is a mutation (deletion, insertion, substitution, duplication, and the like) in an DA1 allele whereby a splice donor site or a splice acceptor site is mutated, resulting in altered processing of the mRNA and, consequently, an altered encoded protein, which can have insertions, deletions, substitutions of various lengths, or which can be truncated.

In specific embodiments, the C at position 1385 of SEQ ID NO: 3 is mutated into a T, resulting in the mutation of the CAA codon at position 1385-1387 encoding Glutamine into a TAA stopcodon; or the G at position 1683 of SEQ ID NO: 3 is mutated into an A, resulting in the mutation of the TGG codon at position 1681-1683 encoding Tryptophan into a TGA stopcodon; or the C at position 1932 of SEQ ID NO: 3 is mutated into a T, resulting in the mutation of the CAA codon at position 1932-1934 encoding Glutamine into a TAA stopcodon; or the G at position 1744 of SEQ ID NO: 6 is mutated into an A, resulting in the mutation of the TGG codon at position 1743-1745 encoding Tryptophan into a TAG stopcodon; or the C at position 1998 of SEQ ID NO: 6 is mutated into a T, resulting in the mutation of the CAA codon at position 1998-2000 encoding Glutamine into a TAA stopcodon; or the C at position 1974 of SEQ ID NO: 6 is mutated into a T, resulting in the mutation of the CAA codon at position 1974-1976 encoding Glutamine into a TAA stopcodon; or the G at position 1874 of SEQ ID NO: 6 is mutated into an A, resulting in the mutation of the TGG codon at position 1872-1874 encoding Tryptophan into a TGA stopcodon; or the C at position 1425 of SEQ ID NO: 9 is mutated into a T, resulting in the mutation of the CAG codon at position 1425-1427 encoding Glutamine into a TAG stopcodon; or the C at position 1960 of SEQ ID NO: 9 is mutated into a T, resulting in the mutation of the CAA codon at position 1960-1962 encoding Glutamine into a TAA stopcodon; or the C at position 1670 of SEQ ID NO: 9 is mutated into a T, resulting in the mutation of the CAA codon at position 1670-1672 encoding Glutamine into a TAA stopcodon; or the G at position 2004 of SEQ ID NO: 9 is mutated into an A, resulting in the mutation of the TGG codon at position 2002-2004 encoding Tryptophan into a TGA stopcodon; or the C at position 2011 of SEQ ID NO: 12 is mutated into a T, resulting in the mutation of the CAA codon at position 2011-2013 encoding Glutamine into a TAA stopcodon.

Amino Acid Sequences According to the Invention

The *A. thaliana* DA1 protein is predicted to encode a 532 amino acid protein containing two ubiquitin interaction motifs (UIMs) and one zinc-binding domain (LIM) at the N-terminus (WO2009/047525 and Li et al., 2008, supra). The IUM is a short peptide motif with the dual function of binding ubiquitin and promoting ubiquitination. The LIM domain is a protein-protein interaction motif critically involve din a variety of fundamental biological processes, including cytoskeleton organization, organ development and signal transduction. The position of the two UIM domains and the LIM domain is indicated in FIG. 1.

Provided are both wild type (functional) DA1 amino acid sequences and mutant DA1 amino acid sequences (comprising one or more mutations, such as mutations which result in a significantly reduced or no biological activity of the DA1 protein) from Brassicaceae, particularly from *Brassica* species, especially from *Brassica napus, Brassica rapa, Brassica oleracea* and *Brassica nigra*, but also from other *Brassica* crop species. For example, *Brassica* species comprising an A and/or a C genome may encode different DA1-A or DA1-C amino acids. In addition, mutagenesis methods can be used to generate mutations in wild type DA1 alleles, thereby generating mutant alleles which can encode further mutant DA1 proteins. In one embodiment the wild type and/or mutant DA1 amino acid sequences are provided within a *Brassica* plant (i.e. endogenously).

Amino acid sequences of DA1-A1 and DA1-A2 proteins have been isolated from *Brassica napus* and *Brassica rapa*; of DA1-B1 and DA1-B2 proteins from *Brassica nigra*, and DA1-C1 and DA1-C2 proteins from *Brassica napus* and *Brassica oleracea*; as depicted in the sequence listing. The wild type DA1 sequences are depicted, while the mutant DA1 sequences of these sequences, and of sequences essentially similar to these, are described herein below, with reference to the wild type DA1 sequences.

As described above, the DA1 proteins of *Brassica* described herein are about 511-533 amino acids in length and comprise a number of structural and functional domains.

"DA-A1 amino acid sequences" or "DA1-A1 variant amino acid sequences" according to the invention are amino acid sequences having at least 80%, at least 85%, at least 90%, at least 95%, 98%, 99% or 100% sequence identity with SEQ ID NO: 5. These amino acid sequences may also be referred to as being "essentially similar" or "essentially identical" to the DA1 sequences provided in the sequence listing.

"DA-A2 amino acid sequences" or "DA1-A2 variant amino acid sequences" according to the invention are amino acid sequences having at least 80%, at least 85%, at least 90%, at least 95%, 98%, 99% or 100% sequence identity with SEQ ID NO: 8. These amino acid sequences may also be referred to as being "essentially similar" or "essentially identical" to the DA1 sequences provided in the sequence listing.

DA-C1 amino acid sequences" or "DA1-C1 variant amino acid sequences" according to the invention are amino acid sequences having at least 80%, at least 85%, at least 90%, at least 95%, 98%, 99% or 100% sequence identity with SEQ ID NO: 11. These amino acid sequences may also be referred to as being "essentially similar" or "essentially identical" to the DA1 sequences provided in the sequence listing.

"DA1-C2 amino acid sequences" or "DA1-C2 variant amino acid sequences" according to the invention are amino acid sequences having at least 80%, at least 85%, at least 90%, at least 95%, 96%, 97%, 98%, 99% or 100% sequence identity with SEQ ID NO: 14. These amino acid sequences may also be referred to as being "essentially similar" or "essentially identical" the DA1 sequences provided in the sequence listing.

"*Brassica napus* DA-A1 amino acid sequences" or "*Brassica napus* DA1-A1 variant amino acid sequences" according to the invention are amino acid sequences having at least 80%, at least 85%, at least 90%, at least 95%, 98%, 99% or 100% sequence identity with SEQ ID NO: 5. These amino acid sequences may also be referred to as being "essentially similar" or "essentially identical" to the DA1 sequences provided in the sequence listing.

"*Brassica napus* DA-A2 amino acid sequences" or "*Brassica napus* DA1-A2 variant amino acid sequences" according to the invention are amino acid sequences having at least 80%, at least 85%, at least 90%, at least 95%, 98%, 99% or 100% sequence identity with SEQ ID NO: 8. These amino acid sequences may also be referred to as being "essentially similar" or "essentially identical" to the DA1 sequences provided in the sequence listing.

"*Brassica napus* DA-C1 amino acid sequences" or "*Brassica napus* DA1-C1 variant amino acid sequences" according to the invention are amino acid sequences having at least 80%, at least 85%, at least 90%, at least 95%, 98%, 99% or 100% sequence identity with SEQ ID NO: 11. These amino acid sequences may also be referred to as being "essentially similar" or "essentially identical" to the DA1 sequences provided in the sequence listing.

"*Brassica napus* DA1-C2 amino acid sequences" or "*Brassica napus* DA1-C2 variant amino acid sequences" according to the invention are amino acid sequences having at least 80%, at least 85%, at least 90%, at least 95%, 96%, 97%, 98%, 99% or 100% sequence identity with SEQ ID NO: 14. These amino acid sequences may also be referred to as being "essentially similar" or "essentially identical" the DA1 sequences provided in the sequence listing.

"*Brassica rapa* DA-A1 amino acid sequences" or "*Brassica rapa* DA1-A1 variant amino acid sequences" according to the invention are amino acid sequences having at least 80%, at least 85%, at least 90%, at least 95%, 98%, 99% or 100% sequence identity with SEQ ID NO: 56. These amino acid sequences may also be referred to as being "essentially similar" or "essentially identical" to the DA1 sequences provided in the sequence listing.

"*Brassica rapa* DA-A2 amino acid sequences" or "*Brassica rapa* DA1-A2 variant amino acid sequences" according to the invention are amino acid sequences having at least 80%, at least 85%, at least 90%, at least 95%, 98%, 99% or 100% sequence identity with SEQ ID NO: 59. These amino acid sequences may also be referred to as being "essentially similar" or "essentially identical" to the DA1 sequences provided in the sequence listing.

"*Brassica oleracea* DA-C1 amino acid sequences" or "*Brassica oleracea* DA1-C1 variant amino acid sequences" according to the invention are amino acid sequences having at least 80%, at least 85%, at least 90%, at least 95%, 98%, 99% or 100% sequence identity with SEQ ID NO: 62. These amino acid sequences may also be referred to as being "essentially similar" or "essentially identical" to the DA1 sequences provided in the sequence listing.

Isoform 1 "*Brassica oleracea* DA1-C2 amino acid sequences" or isoform 1 "*Brassica oleracea* DA1-C2 variant amino acid sequences" according to the invention are amino acid sequences having at least 80%, at least 85%, at least 90%, at least 95%, 96%, 97%, 98%, 99% or 100% sequence identity with SEQ ID NO: 65. These amino acid sequences may also be referred to as being "essentially similar" or "essentially identical" the DA1 sequences provided in the sequence listing.

Isoform 2 "*Brassica oleracea* DA1-C2 amino acid sequences" or isoform 2 "*Brassica oleracea* DA1-C2 variant amino acid sequences" according to the invention are amino acid sequences having at least 80%, at least 85%, at least 90%, at least 95%, 96%, 97%, 98%, 99% or 100% sequence identity with SEQ ID NO: 67. These amino acid sequences may also be referred to as being "essentially similar" or "essentially identical" the DA1 sequences provided in the sequence listing.

Isoform 3 "*Brassica oleracea* DA1-C2 amino acid sequences" or isoform 3 "*Brassica oleracea* DA1-C2 variant amino acid sequences" according to the invention are amino acid sequences having at least 80%, at least 85%, at least 90%, at least 95%, 96%, 97%, 98%, 99% or 100% sequence identity with SEQ ID NO: 69. These amino acid sequences may also be referred to as being "essentially similar" or "essentially identical" the DA1 sequences provided in the sequence listing.

"*Brassica nigra* DA-B1 amino acid sequences" or "*Brassica nigra* DA1-B1 variant amino acid sequences" according to the invention are amino acid sequences having at least 80%, at least 85%, at least 90%, at least 95%, 98%, 99% or 100% sequence identity with SEQ ID NO: 72. These amino acid sequences may also be referred to as being "essentially similar" or "essentially identical" to the DA1 sequences provided in the sequence listing.

"*Brassica nigra* DA-B2 amino acid sequences" or "*Brassica nigra* DA1-B2 variant amino acid sequences" according to the invention are amino acid sequences having at least 80%, at least 85%, at least 90%, at least 95%, 98%, 99% or 100% sequence identity with SEQ ID NO: 75. These amino acid sequences may also be referred to as being "essentially similar" or "essentially identical" to the DA1 sequences provided in the sequence listing.

DA1-A1 amino acid sequences can comprise *Brassica napus* DA1-A1 amino acid sequences and *Brassica rapa* DA1-A1 amino acid sequences; DA1-A2 amino acid sequences can comprise *Brassica napus* DA1-A2 amino acid sequences and *Brassica rapa* DA1-A2 amino acid sequences; DA1-C1 amino acid sequences can comprise *Brassica napus* DA1-C1 amino acid sequences and *Brassica oleracea* DA1-C1 amino acid sequences; DA1-C2 amino acid sequences can comprise *Brassica napus* DA1-C2 amino acid sequences and *Brassica oleracea* DA1-C2 amino acid sequences.

Thus, the invention provides both amino acid sequences of wild type, functional DA1 proteins, including variants and fragments thereof (as defined further below), as well as mutant amino acid sequences of any of these.

Further, the mutation in the amino acid sequence can result in a significant reduction in or a complete abolishment of the biological activity of the DA1 protein as compared to the biological activity of the corresponding wild type DA1 protein. A significant reduction in or complete abolishment of the biological activity of the DA1 protein.

Amino acid sequences of functional DA1 proteins.

The amino acid sequences depicted in the sequence listing are wild type DA1 proteins from *Brassica napus*. Thus, these sequences are endogenous to the *Brassica napus* plants from which they were isolated. Other *Brassica* crop species, varieties, breeding lines or wild accessions may be screened for other functional DA1 proteins with the same amino acid sequences or variants thereof, as described above.

In addition, it is understood that DA1 amino acid sequences and variants thereof (or fragments of any of these) may be identified in silico, by screening amino acid databases for essentially similar sequences. Fragments of amino acid molecules according to the invention are also provided.

Amino acid sequences of mutant DA1 proteins.

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutant DA1 protein comprises at a position corresponding to position 338 of SEQ ID NOs: 5 and 56, at position 353 of SEQ ID NOs 8 and 59, at position 341 of SEQ ID NOs: 11 and 62, at position 352 of SEQ ID NO: 14, at position 355 of SEQ ID NOs: 65 and 69, at position 340 of SEQ ID NO: 72, and at position 357 of SEQ ID NO: 75 an amino acid other than Argninine, such as Lysine.

In a particular embodiment, a DA1-A2 protein is provided which contains a Lysine instead of an Arginine at position 350 of SEQ ID NO: 8. A DA1-A2 protein containing this mutation is depicted in SEQ ID NO: 17.

In one embodiment, the mutation(s) in the amino acid sequence result in a significantly reduced or completely abolished biological activity of the DA1 protein relative to the wild type protein. As described above, basically, any mutation which results in a protein comprising at least one amino acid insertion, deletion and/or substitution relative to the wild type protein can lead to significantly reduced or no biological activity.

Thus in one embodiment, mutant DA1 proteins are provided comprising one or more deletion or insertion mutations, whereby the deletion(s) or insertion(s) result(s) in a mutant protein which has significantly reduced or no activity in vivo. Such mutant DA1 proteins are DA1 proteins wherein at least 1, at least 2, 3, 4, 5, 10, 20, 30, 50, 100, 100, 150, 175, 180 or more amino acids are deleted or inserted as compared to the wild type DA1 protein, whereby the deletion(s) or insertion(s) result(s) in a mutant protein which has significantly reduced or no activity in vivo.

In another embodiment, mutant DA1 proteins are provided which are truncated whereby the truncation results in a mutant protein that has significantly reduced or no activity in vivo. Such truncated DA1 proteins are DA1 proteins which lack functional domains in the C-terminal part of the corresponding wild type DA1 protein and which maintain the N-terminal part of the corresponding wild type DA1 protein.

In yet another embodiment, mutant DA1 proteins are provided comprising one or more substitution mutations, whereby the substitution(s) result(s) in a mutant protein that has significantly reduced or no activity in vivo. Such mutant DA1 proteins are DA1 proteins whereby conserved amino acid residues which have a specific function are substituted.

In one aspect of the invention, *Brassica* plants are provided comprising at least two DA1 genes, wherein at least one allele of a first DA1 gene is a mutant DA1 allele encoding a mutant DA1 protein comprising at a position corresponding to position 358 of SEQ ID NO: 1 an amino acid other than Arginine.

It was found that amphidiploid *Brassica napus*, comprising an A genome and a C genome, contains four DA1 genes, two DA1 genes on the A genome (DA1-A1 and DA1-A2), and two DA1 genes on the C-genome (DA1-C1 and DA1-C2), that diploid *Brassica rapa*, comprising an A genome, contains two DA1 genes, DA1-A1 and DA1-A2, that diploid *Brassica oleracea*, comprising a C genome, contains two DA1 genes, DA1-C1 and DA1-C2, and that diploid *Brassica nigra*, comprising a B genome, contains two DA1 genes, DA1-B1 and DA1-B2. Suitable for the invention are therefore diploid *Brassica* plants comprising two DA1 genes, wherein at least one allele a first DA1 gene is a mutant DA1 allele encoding a mutant DA1 protein comprising at a position corresponding to position 358 of SEQ ID NO: 1 an amino acid other than Arginine. Said mutant DA1 allele can be a mutant allele of a DA1-A1 gene, of a DA1-A2 gene, of a DA1-C1 gene, of a DA1-C2 gene, of a DA1-B1 gene, and of a DA1-B2 gene. More specifically, suitable are *Brassica rapa* plants comprising a mutant allele of a DA1-A2 gene, *Brassica oleracea* plants comprising a mutant allele of a DA1-C2 gene, and *Brassica nigra* plants comprising a mutant allele of a DA1-B2 gene. The second DA1 gene of said *Brassica* plants can comprise a wild-type allele, but can also comprise a mutant DA1 allele, such as a full knock-out DA1 allele.

The *Brassica* plants according to the invention can further be *Brassica* plants comprising four DA1 genes. Described herein are *Brassica napus* plants comprising four DA1 genes, two of which are on the A genome (DA1-A1 and DA1-A2), and two on the C-genome (DA1-C1 and DA1-C2). Further *Brassica* plants comprising four DA1 genes can be the allotetraploid *Brassica juncea* (A and B genome) and *Brassica carinata* (B and C genome), wherein the DA1 genes can be DA1-A1, DA1-A2, DA1-B1, DA1-B2 (for *B. juncea*), and DA1-B1, DA1-B2, DA1-C1 and DA1-C2 (for *B. carinata*). Suitable are *Brassica* plants comprising a mutant allele of a DA1-A2 gene, or a mutant allele of a DA1-C2 gene, or a mutant allele of a DA1-B2 gene, encoding a protein comprising at a position corresponding to position 358 of SEQ ID NO: 1 an amino acid other than Arginine, such as Lysine. Said *Brassica* plants can further comprise a mutant allele of a second DA1 gene, which can be a mutant DA1 allele encoding a protein comprising at a position corresponding to position 358 of SEQ ID NO: 1 an amino acid other than Arginine, such as Lysine, or said second mutant DA1 allele can be a full knock-out DA1 gene. Said mutant DA1 allele of said second DA1 gene can be an allele of any of the DA1 genes other than the first DA1 gene. Suitable second DA1 genes are DA1-A2, DA1-C2, and DA1-B2 genes. Suitable *Brassica* plants according to the invention comprising four DA1 genes are *Brassica napus* plants comprising a mutant allele of a first DA1-A2 gene, or a mutant allele of a first DA1-C2 gene, or a mutant allele of a first DA1-A2 gene and a mutant allele of a second DA1-C2 gene, or a mutant allele of a first DA1-C2 gene and a mutant allele of a second DA1-A2 gene, or *Brassica juncea* plants comprising a mutant allele of a first DA1-A2 gene, or a mutant allele of a first DA1-B2 gene, or a mutant allele of a first DA1-A2 gene and a mutant allele of a second DA1-B2 gene, or a mutant allele of a first DA1-B2 gene and a mutant allele of a second DA1-A2 gene, or *Brassica carinata* plants comprising a mutant allele of a first DA1-B2 gene, or a mutant allele of a first DA1-C2 gene, or a mutant allele of a first DA1-B2 gene and a mutant allele of a second DA1-C2 gene, or a mutant allele of a first DA1-C2 gene and a mutant allele of a second DA1-B2 gene, wherein said mutant allele of said first DA1 gene encodes a protein comprising at a position corresponding to position 358 of SEQ ID NO: 1 an amino acid other than Arginine, such as Lysine, and wherein said mutant allele of said second mutant DA1 gene is a mutant DA1 gene which encodes a protein comprising at a position corresponding to position 358 of SEQ ID NO: 1 an amino acid other than Arginine, such as Lysine, or is a full knock-out DA1 gene.

In another aspect of the invention, *Brassica* plants are provided comprising at least two DA1 genes, wherein at least one allele of a DA1 gene is a full knockout DA1 allele. Suitable for the invention are therefore *Brassica* plants comprising two DA1 genes, such as *Brassica rapa*, *Brassica oleracea*, and *Brassica nigra*, wherein at least one allele of a DA1 gene is a full knock-out DA1 allele. Said full knock-out DA1 allele can be a full knockout allele of a DA1-A1 gene, of a DA1-A2 gene, of a DA1-C1 gene, of a DA1-C2 gene, of a DA1-B1 gene, and of a DA1-B2 gene. More specifically, suitable are *Brassica rapa* plants comprising a full knockout allele of a DA1-A1 gene, DA1-A2 gene or both a DA1-A1 and a DA1-A2 gene, *Brassica oleracea* plants comprising a full knockout allele of a DA1-C2 gene, and *Brassica nigra* plants comprising a full knockout allele of a DA1-B1 gene, a DA1-B2 gene, or both a DA1-B1 and a DA1-B2 gene.

Also suitable are *Brassica* plants comprising four DA1 genes, such as *Brassica napus, Brassica juncea*, and *Brassica carinata* comprising a full knockout allele of a DA1-A1 gene, DA1-A2 gene, a DA1-C2 gene, or a DA1-C2 gene, or a full knockout allele of a DA1-B1 gene or a DA1-B2 gene, or any combination thereof. Suitable *Brassica* plants according to the invention comprising four DA1 genes are *Brassica napus* plants comprising a full knockout allele of a DA1-A1 gene, or a DA1-A2 gene, or a DA1-C2 gene, or any combination thereof; or *Brassica juncea* plants comprising a full knockout allele of a DA1-A1 gene, or a DA1-A2 gene, or a DA1-B1 gene, or a DA1-B2 gene, or any combination thereof; or *Brassica carinata* plants comprising a full knock-out allele of a DA1-B1 gene, or a DA1-B2 gene, or a DA1-C2 gene, or any combination thereof.

Methods According to the Invention

Mutant DA1 alleles may be generated (for example induced by mutagenesis) and/or identified using a range of methods, which are conventional in the art, for example using PCR based methods to amplify part or all of the DA1 genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant DA1 alleles, using techniques which are conventional in the art, for example polymerase chain reaction (PCR) based techniques (amplification of the DA1 alleles) or hybridization based techniques, e.g. Southern blot analysis, BAC library screening, and the like, and/or direct sequencing of DA1 alleles. To screen for the presence of point mutations (so called Single Nucleotide Polymorphisms or SNPs) in mutant DA1 alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type DA1 allele results in the presence of one or more deleted, inserted, or substituted nucleotides (hereinafter called "mutation region") in the resulting mutant DA1 allele. The mutant DA1 allele can thus be characterized by the location and the configuration of the one or more deleted, inserted, or substituted nucleotides in the wild type DA1 allele. The site in the wild type DA1 allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) DA1 allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) DA1 allele which is located either immediately upstream of and contiguous with (5' flanking region or sequence") or immediately downstream of and contiguous with (3' flanking region or sequence") the mutation region in the mutant DA1 allele (or in the corresponding wild type DA1 allele). A "joining region" as used herein refers to a DNA region in the mutant (or the corresponding wild type) DA1 allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

In one embodiment, a method is provided for identifying a mutant DA1 allele of the invention in a biological sample comprising subjecting the biological sample to an amplification reaction using a set of at least two primers, wherein one of said primers specifically recognizes the 5' or 3' flanking region of the mutant DA1 allele, and the other of said primers specifically recognizes the mutation region of the mutant DA1 allele; or wherein one of said primers specifically recognizes the 5' or 3' flanking region of the mutant DA1 allele and the other of said primers specifically recognizes the joining region between the 3' or 5' flanking region and the mutation region of the mutant DA1 allele, respectively; or wherein a specific probe specifically recognizes the joining region between the 5' or 3' flanking region and the mutation region of the mutant DA1 allele. In another embodiment, a method is provided for identifying a mutant DA1 allele of the invention in a biological sample comprising subjecting the biological sample to an amplification reaction using a set of at least two primers, further comprising subjecting the biological sample to a hybridization assay using a set of specific probes, comprising at least one specific probe, wherein said set of probes comprises one of said probes specifically recognizes the 5' or 3' flanking region of the mutant DA1 allele, and the other of said probes specifically recognizes the mutation region of the mutant DA1 allele; or wherein one of said probes specifically recognizes the 5' or 3' flanking region of the mutant DA1 allele and the other of said probes specifically recognizes the joining region between the 3' or 5' flanking region and the mutation region of the mutant DA1 allele, respectively; or comprising a specific probe which specifically recognizes the joining region between the 5' or 3' flanking region and the mutation region of the mutant DA1 allele.

The tools developed to identify a specific mutant DA1 allele or the plant or plant material comprising a specific mutant DA1 allele, or products which comprise plant material comprising a specific mutant DA1 allele are based on the specific genomic characteristics of the specific mutant DA1 allele as compared to the genomic characteristics of the corresponding wild type DA1 allele, such as, a specific restriction map of the genomic region comprising the mutation region, molecular markers or the sequence of the flanking and/or mutation regions.

Once a specific mutant DA1 allele has been sequenced, primers and probes can be developed which specifically recognize a sequence within the 5' flanking, 3' flanking and/or mutation regions of the mutant DA1 allele in the nucleic acid (DNA or RNA) of a sample by way of a molecular biological technique. For instance a PCR method can be developed to identify the mutant DA1 allele in biological samples (such as samples of plants, plant material or products comprising plant material). Such a PCR is based on at least two specific "primers": one recognizing a sequence within the 5' or 3' flanking region of the mutant DA1 allele and the other recognizing a sequence within the 3' or 5' flanking region of the mutant DA1 allele, respectively; or one recognizing a sequence within the 5' or 3' flanking region of the mutant DA1 allele and the other recognizing a sequence within the mutation region of the mutant DA1 allele; or one recognizing a sequence within the 5' or 3' flanking region of the mutant DA1 allele and the other recognizing a sequence spanning the joining region between the 3' or 5' flanking region and the mutation region of the specific mutant DA1 allele (as described further below), respectively.

The primers preferably have a sequence of between 15 and 35 nucleotides which under optimized PCR conditions "specifically recognize" a sequence within the 5' or 3' flanking region, a sequence within the mutation region, or a sequence spanning the joining region between the 3' or 5' flanking and mutation regions of the specific mutant DA1 allele, so that a specific fragment ("mutant DA1 specific fragment" or discriminating amplicon) is amplified from a nucleic acid sample comprising the specific mutant DA1 allele. This means that only the targeted mutant DA1 allele, and no other sequence in the plant genome, is amplified under optimized PCR conditions.

PCR primers suitable for the invention may be the following:
  oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant DA1 allele or the complement thereof (i.e., for example, the sequence 5' or 3' flanking the one or more nucleotides deleted, inserted or substituted in the mutant DA1 alleles of the invention, such as the sequence 5' or 3' flanking the non-sense, missense or frameshift mutations described above or the sequence 5' or 3' flanking the STOP codon mutations indicated in the above Tables or the sequences 5' or 3' flanking the splice site mutations as indicated above or the substitution mutations indicated above or the complement thereof) (primers recognizing 5' flanking sequences); or
  oligonucleotides ranging in length from 17 nt to about 200 nt, comprising a nucleotide sequence of at least 17 consecutive nucleotides, preferably 20 nucleotides selected from the sequence of the mutation region of a specific mutant DA1 allele or the complement thereof (i.e., for example, the sequence of nucleotides inserted or substituted in the DA1 genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant DA1 alleles of the invention and the sequence of the one or more nucleotides inserted or substituted or the sequence 3' or 5', respectively, flanking the one or more nucleotides deleted, such as the joining region between a sequence 5' or 3' flanking non-sense, missense or frameshift mutations in the DA1 genes of the invention described above and the sequence of the non-sense, missense or frameshift mutations, or the joining region between a sequence 5' or 3' flanking a potential STOP codon mutation as indicated in the above Tables, or the joining region between a sequence 5' or 3' flanking a splice site mutation as indicated above, or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A⇌T; G⇌C) and reading the sequence in the 5' to 3' direction, i.e. in opposite direction of the represented nucleotide sequence.

Examples of primers suitable to identify specific mutant DA1 alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant DA1 allele, provided the mismatches still allow specific identification of the specific mutant DA1 allele with these primers under optimized PCR conditions. The range of allowable mismatches however, can easily be determined experimentally and are known to a person skilled in the art.

Detection and/or identification of a "mutant DA1 specific fragment" can occur in various ways, e.g., via size estimation after gel or capillary electrophoresis or via fluorescence-based detection methods. The mutant DA1 specific fragments may also be directly sequenced. Other sequence specific methods for detection of amplified DNA fragments are also known in the art.

Standard PCR protocols are described in the art, such as in 'PCR Applications Manual" (Roche Molecular Biochemicals, 2nd Edition, 1999) and other references. The optimal conditions for the PCR, including the sequence of the specific primers, is specified in a "PCR identification protocol" for each specific mutant DA1 allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, MgCl2 concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of PCR identification protocols to identify specific mutant DA1 alleles are described in the Examples.

Alternatively, specific primers can be used to amplify a mutant DA1 specific fragment that can be used as a "specific probe" for identifying a specific mutant DA1 allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant DA1 allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant DA1 allele (hereinafter referred to as "mutant DA1 specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant DA1 allele.

Specific probes suitable for the invention may be the following:
  oligonucleotides ranging in length from 13 nt to about 1000 nt, comprising a nucleotide sequence of at least 13 consecutive nucleotides selected from the 5' or 3' flanking sequence of a specific mutant DA1 allele or the complement thereof (i.e., for example, the sequence 5' or 3' flanking the one or more nucleotides deleted, inserted or substituted in the mutant DA1 alleles of the invention, such as the sequence 5' or 3' flanking the non-sense, mis-sense or frameshift mutations described above or the sequence 5' or 3' flanking the potential STOP codon mutations indicated in the above Tables, or the sequence 5' or 3' flanking the splice site mutations as indicated above, or the substitution mutations indicated above), or a sequence having at least 80% sequence identity therewith (probes recognizing 5' flanking sequences); or
  oligonucleotides ranging in length from 13 nt to about 1000 nt, comprising a nucleotide sequence of at least 13 consecutive nucleotides selected from the mutation sequence of a specific mutant DA1 allele or the complement thereof (i.e., for example, the sequence of nucleotides inserted or substituted in the DA1 alleles of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be not longer than 50, more preferably not longer than 25 or even not longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant DA1 alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense or frameshift mutations in the DA1 alleles of the invention described above and the sequence of the non-sense, mis-sense or frameshift mutations, or the joining region between a sequence 5' or 3' flanking a potential STOP codon mutation as indicated in the above Tables, or the sequence 5' or 3' flanking the splice site mutations as indicated above, or the substitution mutations indicated above and the sequence of the potential STOP codon or substitution mutation, respectively), provided the mentioned nucleotide sequence is not derived exclusively from either the mutation region or flanking regions.

Examples of specific probes suitable to identify specific mutant DA1 alleles are described in the Examples.

Detection and/or identification of a "mutant DA1 specific region" hybridizing to a specific probe can occur in various ways, e.g., via size estimation after gel electrophoresis or via fluorescence-based detection methods. Other sequence specific methods for detection of a "mutant DA1 specific region" hybridizing to a specific probe are also known in the art.

Alternatively, plants or plant parts comprising one or more mutant DA1 alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant DA1 alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in DA1 alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant DA1 alleles. As for the mutagenesis techniques above, preferably Brassica species are screened which comprise an A and/or a C genome, so that the identified DA1 allele can subsequently be introduced into other Brassica species, such as Brassica napus, by crossing (inter- or intraspecific crosses) and selection. In ECOTILLING natural polymorphisms in breeding lines or related species are screened for by the TILLING methodology described above, in which individual or pools of plants are used for PCR amplification of the DA1 target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant DA1 alleles (and Brassica plants comprising one or more of these) can be identified. The desired mutant alleles can then be combined with the desired wild type alleles by crossing and selection methods as described further below. Finally a single plant comprising the desired number of mutant DA1 and the desired number of wild type DA1 alleles is generated.

Oligonucleotides suitable as PCR primers or specific probes for detection of a specific mutant DA1 allele can also be used to develop methods to determine the zygosity status of the specific mutant DA1 allele.

To determine the zygosity status of a specific mutant DA1 allele, a PCR-based assay can be developed to determine the presence of a mutant and/or corresponding wild type DA1 specific allele:

To determine the zygosity status of a specific mutant DA1 allele, two primers specifically recognizing the wild-type DA1 allele can be designed in such a way that they are directed towards each other and have the mutation region located in between the primers. These primers may be primers specifically recognizing the 5' and 3' flanking sequences, respectively. This set of primers allows simultaneous diagnostic PCR amplification of the mutant, as well as of the corresponding wild type DA1 allele.

Alternatively, to determine the zygosity status of a specific mutant DA1 allele, two primers specifically recognizing the wild-type DA1 allele can be designed in such a way that they are directed towards each other and that one of them specifically recognizes the mutation region. These primers may be primers specifically recognizing the sequence of the 5' or 3' flanking region and the mutation region of the wild type DA1 allele, respectively. This set of primers, together with a third primer which specifically recognizes the sequence of the mutation region in the mutant DA1 allele, allow simultaneous diagnostic PCR amplification of the mutant DA1 allele, as well as of the wild type DA1 allele.

Alternatively, to determine the zygosity status of a specific mutant DA1 allele, two primers specifically recognizing the wild-type DA1 allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type DA1 allele, respectively. This set of primers, together with a third primer which specifically recognizes the joining region between the mutation region and the 3' or 5' flanking region of the mutant DA1 allele, respectively, allow simultaneous diagnostic PCR amplification of the mutant DA1 allele, as well as of the wild type DA1 allele.

Alternatively, the zygosity status of a specific mutant DA1 allele can be determined by using alternative primer sets that specifically recognize mutant and wild type DA1 alleles.

If the plant is homozygous for the mutant DA1 allele or the corresponding wild type DA1 allele, the diagnostic PCR assays described above will give rise to a single PCR product typical, preferably typical in length, for either the mutant or wild type DA1 allele. If the plant is heterozygous for the mutant DA1 allele, two specific PCR products will appear, reflecting both the amplification of the mutant and the wild type DA1 allele.

Identification of the wild type and mutant DA1 specific PCR products can occur e.g. by size estimation after gel or capillary electrophoresis (e.g. for mutant DA1 alleles comprising a number of inserted or deleted nucleotides which results in a size difference between the fragments amplified from the wild type and the mutant DA1 allele, such that said fragments can be visibly separated on a gel); by evaluating the presence or absence of the two different fragments after gel or capillary electrophoresis, whereby the diagnostic PCR amplification of the mutant DA1 allele can, optionally, be performed separately from the diagnostic PCR amplification of the wild type DA1 allele; by direct sequencing of the amplified fragments; or by fluorescence-based detection methods.

Examples of primers suitable to determine the zygosity of specific mutant DA1 alleles are described in the Examples.

Alternatively, to determine the zygosity status of a specific mutant DA1 allele, a hybridization-based assay can be developed to determine the presence of a mutant and/or corresponding wild type DA1 specific allele:

To determine the zygosity status of a specific mutant DA1 allele, two specific probes recognizing the wild-type DA1 allele can be designed in such a way that each probe specifically recognizes a sequence within the DA1 wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type DA1 allele.

Alternatively, to determine the zygosity status of a specific mutant DA1 allele, two specific probes recognizing the wild-type DA1 allele can be designed in such a way that one of them specifically recognizes a sequence within the DA1 wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type DA1 allele, respectively. The use of one or, preferably, both of these probes, optionally, together with a third probe which specifically recognizes the sequence of the mutation region in the mutant DA1 allele, allow diagnostic hybridization of the mutant and of the wild type DA1 allele.

Alternatively, to determine the zygosity status of a specific mutant DA1 allele, a specific probe recognizing the wild-type DA1 allele can be designed in such a way that the probe specifically recognizes the joining region between the 5' or 3' flanking region, preferably the 5' flanking region, and the mutation region of the wild type DA1 allele. This probe, optionally, together with a second probe that specifically recognizes the joining region between the 5' or 3' flanking region, preferably the 5' flanking region, and the mutation region of the mutant DA1 allele, allows diagnostic hybridization of the mutant and of the wild type DA1 allele.

Alternatively, the zygosity status of a specific mutant DA1 allele can be determined by using alternative sets of probes that specifically recognize mutant and wild type DA1 alleles.

If the plant is homozygous for the mutant DA1 allele or the corresponding wild type DA1 allele, the diagnostic hybridization assays described above will give rise to a single specific hybridization product, such as one or more hybridizing DNA (restriction) fragments, typical, preferably typical in length, for either the mutant or wild type DA1 allele. If the plant is heterozygous for the mutant DA1 allele, two specific hybridization products will appear, reflecting both the hybridization of the mutant and the wild type DA1 allele.

Identification of the wild type and mutant DA1 specific hybridization products can occur e.g. by size estimation after gel or capillary electrophoresis (e.g. for mutant DA1 alleles comprising a number of inserted or deleted nucleotides which results in a size difference between the hybridizing DNA (restriction) fragments from the wild type and the mutant DA1 allele, such that said fragments can be visibly separated on a gel); by evaluating the presence or absence of the two different specific hybridization products after gel or capillary electrophoresis, whereby the diagnostic hybridization of the mutant DA1 allele can, optionally, be performed separately from the diagnostic hybridization of the wild type DA1 allele; by direct sequencing of the hybridizing DNA (restriction) fragments; or by fluorescence-based detection methods.

Examples of probes suitable to determine the zygosity of specific mutant DA1 alleles are described in the Examples.

Furthermore, detection methods specific for a specific mutant DA1 allele that differ from PCR- or hybridization-based amplification methods can also be developed using the specific mutant DA1 allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

It is a further object of the invention to provide a kit for identifying a mutant DA1 allele as described in claim 1 or 2 in a biological sample, comprising a set of primers or probes, wherein one of said primers specifically recognizes the 5' or 3' flanking region of the mutant DA1 allele, and the other of said primers specifically recognizes the mutation region of the mutant DA1 allele; or wherein one of said primers specifically recognizes the 5' or 3' flanking region of the mutant DA1 allele and the other of said primers specifically recognizes the joining region between the 3' or 5' flanking region and the mutation region of the mutant DA1 allele, respectively; or comprising a specific probe which specifically recognizes the joining region between the 5' or 3' flanking region and the mutation region of the mutant DA1 allele.

A "kit", as used herein, refers to a set of reagents for the purpose of performing the method of the invention, more particularly, the identification of a specific mutant DA1 allele in biological samples or the determination of the zygosity status of plant material comprising a specific mutant DA1 allele. More particularly, a preferred embodiment of the kit of the invention comprises at least two specific primers, as described above, for identification of a specific mutant DA1 allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant DA1 allele therein, as described above, for identification of a specific mutant DA1 allele, or at least two or three specific probes for the determination of the zygosity status. Optionally, the kit can further comprise any other reagent (such as but not limited to hybridizing buffer, label) for identification of a specific mutant DA1 allele in biological samples, using the specific probe.

The kit of the invention can be used, and its components can be specifically adjusted, for purposes of quality control (e.g., purity of seed lots), detection of the presence or absence of a specific mutant DA1 allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant DA1 allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant DA1 allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant DA1 allele, implying the presence of nucleic acids in the samples. Thus the methods referred to herein for identifying a specific mutant DA1 allele in biological samples, relate to the identification in biological samples of nucleic acids that comprise the specific mutant DA1 allele.

Specific DA1 alleles can be combined in one plant by transferring one or more specific mutant DA1 allele(s) from one plant to another plant, to the plants comprising one or more specific mutant DA1 allele(s), progeny can be obtained from these plants and plant cells, plant parts, and plant seeds can be derived from these plants.

Two or more selected mutant DA1 alleles can be combined in one plant is comprising the steps of:
  a. generating and/or identifying two or more plants each comprising one or more selected mutant DA1 alleles, as described above,
  b.—crossing a first plant comprising one or more selected mutant DA1 alleles with a second plant comprising one or more other selected mutant DA1 alleles, collecting F1 seeds from the cross, and, optionally, identifying an F1 plant comprising one or more selected mutant DA1 alleles from the first plant with one or more selected mutant DA1 alleles from the second plant, as described above,
  c.—optionally, repeating step (b) until an F1 plant comprising all selected mutant DA1 alleles is obtained,
  d.—optionally
    identifying an F1 plant, which is homozygous or heterozygous for a selected mutant DA1 allele by determining the zygosity status of the mutant DA1 alleles, as described above, or generating plants which are homozygous for one or more of the selected mutant DA1 alleles by performing one of the following steps:
  extracting doubled haploid plants from treated microspore or pollen cells of F1 plants comprising the one or more selected mutant DA1 alleles, as described above,
  selfing the F1 plants comprising the one or more selected mutant DA1 allele(s) for one or more generations (y), collecting F1 Sy seeds from the selfings, and identifying F1 Sy plants, which are homozygous for the one or more mutant DA1 allele, as described above.

One or more mutant DA1 alleles can be transferred from one plant to another plant using a method comprising the steps of:

a. generating and/or identifying a first plant comprising one or more selected mutant DA1 alleles, as described above, or generating the first plant by combining the one or more selected mutant DA1 alleles in one plant, as described above (wherein the first plant is homozygous or heterozygous for the one or more mutant DA1 alleles), b. crossing the first plant comprising the one or more mutant DA1 alleles with a second plant not comprising the one or more mutant DA1 alleles, collecting F1 seeds from the cross (wherein the seeds are heterozygous for a mutant DA1 allele if the first plant was homozygous for that mutant DA1 allele, and wherein half of the seeds are heterozygous and half of the seeds are azygous for, i.e. do not comprise, a mutant DA1 allele if the first plant was heterozygous for that mutant DA1 allele), and, optionally, identifying F1 plants comprising one or more selected mutant DA1 alleles, as described above, c. backcrossing F1 plants comprising one or more selected mutant DA1 alleles with the second plant not comprising the one or more selected mutant DA1 alleles for one or more generations (x), collecting BCx seeds from the crosses, and identifying in every generation BCx plants comprising the one or more selected mutant DA1 alleles, as described above, d. optionally, generating BCx plants which are homozygous for the one or more selected mutant DA1 alleles by performing one of the following steps:
  extracting doubled haploid plants from treated microspore or pollen cells of BCx plants comprising the one or more desired mutant DA1 allele(s), as described above,
  selfing the BCx plants comprising the one or more desired mutant DA1 allele(s) for one or more generations (y), collecting BCx Sy seeds from the selfings, and identifying BCx Sy plants, which are homozygous for the one or more desired mutant DA1 allele, as described above.

The first and the second plant can be *Brassica* plants, such as *Brassica napus* plants or plants from another *Brassica* crop species. The first plant can be a *Brassica* plant, such as a *Brassica napus* plant or a plant from another *Brassica* crop species, and the second plant can be a plant from a *Brassica* breeding line, such as from a *Brassica napus* breeding line or from a breeding line from another *Brassica* crop species. "Breeding line", as used herein, is a preferably homozygous plant line distinguishable from other plant lines by a preferred genotype and/or phenotype that is used to produce hybrid offspring.

It is another embodiment of the invention to provide a method for producing hybrid seed, comprising crossing a first parent *Brassica* plant according to the invention with a second parent *Brassica* plant and harvesting a resultant hybrid seed. Said second parent *Brassica* plant may, but does not need to have the mutant DA1 alleles according to the invention. Suitable second parent *Brassica* plants are plants having the same mutant DA1 alleles as the first parent *Brassica* plant.

In yet another embodiment, a method for breeding is provided, comprising crossing a first parent *Brassica* plant according to the invention with a second parent *Brassica* plant and, optionally, further comprising the step of identifying the presence or absence of a mutant DA1 allele according to the invention comprising subjecting the biological sample to an amplification reaction using a set of at least two primers according to the invention and, optionally, hybridizing with at least one probe according to the invention. Said second parent *Brassica* plant may, but does not need to have the mutant DA1 alleles according to the invention. Suitable second parent *Brassica* plants are plants having the same mutant DA1 alleles as the first parent *Brassica* plant.

It is a further object of the invention to provide a method to increase Thousand Seed Weight of *Brassica* seeds, said method comprising introducing a mutant DA1 allele of a first DA1 gene according to the invention and, optionally, a mutant DA1 allele of a second DA1 gene according to the invention, into a *Brassica* plant. Also suitable is a method to increase Thousand Seed Weight of *Brassica* seeds, said method comprising introducing one or more full knock-out DA1 alleles according to the invention into a *Brassica* plant. Said mutant DA1 alleles can, for example, be introduced by mutagenesis or gene targeting methods as described herein, or can be introduced by crossing with *Brassica* plants comprising said mutant DA1 allele.

In a further embodiment, a method for production of *Brassica* seeds is provided, said method comprising sowing the seeds according to the invention, growing plants from said seeds, and harvesting seeds from said plants. Seeds can be sown and plants can be grown using standard agricultural practices. Seeds can be harvested, for example, upon swathing or using a combine harvester.

Further provided is the use of the plants according to the invention to produce seeds, or to produce a crop of oilseed rape, or to produce oilseed rape oil or oilseed rape seed cake. Further provided is oil or seed cake from the seed according to the invention.

It is a further object of the invention to provide a method for producing food or feed, such as oil, meal, grain, starch, flour, or protein, or an industrial such as biofuel, fiber, industrial chemicals, a pharmaceutical, or a neutraceutical product comprising obtaining the plant or a part thereof or the seed according to the invention, and preparing the food, feed or industrial product from the plant or part thereof.

The plants according to the invention may contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EP0 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesteraseincrease to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants and seeds according to the invention may be further treated with a chemical compound, such as a chemical compound selected from the following lists:

Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin.

Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain I-1582, *Bacillus subtilis, Bacillus subtilis* strain GB03, *Bacillus subtilis* strain QST 713, *Bacillus pumulis, Bacillus. pumulis* strain GB34.

Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluoroethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, *Metarhizium anisopliae* F52.

All patents, patent applications, and publications or public disclosures (including publications on internet) referred to or cited herein are incorporated by reference in their entirety.

The sequence listing contained in the file named "BCS 13-2002_ST25.txt", which is 209 kilobytes (size as measured in Microsoft Windows®), contains 75 sequences SEQ ID NO: 1 through SEQ ID NO: 75 is filed herewith by electronic submission and is incorporated by reference herein.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

SEQUENCES

SEQ ID No.1: *Arabidopsis thaliana* DA1 coding sequence

SEQ ID No.2: *Arabidopsis thaliana* DA1 protein sequence

SEQ ID No.3: *Brassica napus* DA1-A1 genomic sequence

SEQ ID No.4: *Brassica napus* DA1-A1 coding sequence

SEQ ID No.5: *Brassica napus* DA1-A1 protein sequence

SEQ ID No.6: *Brassica napus* DA1-A2 genomic sequence

SEQ ID No.7: *Brassica napus* DA1-A2 coding sequence

SEQ ID No.8: *Brassica napus* DA1-A2 protein sequence

SEQ ID No.9: *Brassica napus* DA1-C1 genomic sequence

SEQ ID No.10: *Brassica napus* DA1-C1 coding sequence

SEQ ID No.11: *Brassica napus* DA1-C1 protein sequence

SEQ ID No.12: *Brassica napus* DA1-C2 genomic sequence

SEQ ID No.13: *Brassica napus* DA1-C2 coding sequence

SEQ ID No.14: *Brassica napus* DA1-C2 protein sequence

SEQ ID No. 15: *Brassica napus* DA1-A2 genomic sequence comprising a G to A substitution at position 1672

SEQ ID No.16: *Brassica napus* DA1-A2 coding sequence encoding a DA1 protein with a R to K substitution at position 353

SEQ ID No. 17: *Brassica napus* DA1-A2 protein sequence with an R to K substitution at position 353

SEQ ID No.18: Primer 1 for detection of the DA1-A1-EMS03 allele and its wild-type counterpart SEQ ID No.19: Primer 2 for detection of the DA1-A1-EMS03 allele and its wild-type counterpart SEQ ID No.20: FAM probe for detection of the DA1-A1-EMS03 allele SEQ ID No.21: VIC probe for detection of the wild-type counterpart of the DA1-A1-EMS03 allele SEQ ID No.22: Primer 1 for detection of the DA1-A2-EMS01 allele and its wild-type counterpart SEQ ID No.23: Primer 2 for detection of the DA1-A2-EMS01 allele and its wild-type counterpart SEQ ID No.24: FAM probe for detection of the DA1-A2-EMS01 allele SEQ ID No.25: VIC probe for detection of the wild-type counterpart of the DA1-A2-EMS01 allele
SEQ ID No.26: Primer 1 for detection of the DA1-A2-EMS05 allele and its wild-type counterpart
SEQ ID No.27: Primer 2 for detection of the DA1-A2-EMS05 allele and its wild-type counterpart
SEQ ID No.28: FAM probe for detection of the DA1-A2-EMS05 allele
SEQ ID No.29: VIC probe for detection of the wild-type counterpart of the DA1-A2-EMS05 allele
SEQ ID No.30: Primer 1 for detection of the DA1-C1-EMS02 allele and its wild-type counterpart
SEQ ID No.31: Primer 2 for detection of the DA1-C1-EMS02 allele and its wild-type counterpart
SEQ ID No.32: FAM probe for detection of the DA1-C1-EMS02 allele
SEQ ID No.33: VIC probe for detection of the wild-type counterpart of the DA1-C1-EMS02 allele
SEQ ID No.34: Primer 1 for detection of the DA1-C1-EMS03 allele and its wild-type counterpart
SEQ ID No.35: Primer 2 for detection of the DA1-C1-EMS03 allele and its wild-type counterpart
SEQ ID No.36: FAM probe for detection of the DA1-C1-EMS03 allele
SEQ ID No.37: VIC probe for detection of the wild-type counterpart of the DA1-C1-EMS03 allele
SEQ ID No.38: Primer 1 for detection of the DA1-C2-EMS02 allele and its wild-type counterpart
SEQ ID No.39: Primer 2 for detection of the DA1-C2-EMS02 allele and its wild-type counterpart
SEQ ID No.40: FAM probe for detection of the DA1-C2-EMS02 allele
SEQ ID No.41: VIC probe for detection of the wild-type counterpart of the DA1-C2-EMS02 allele
SEQ ID No.42: Primer 1 for detection of the DA1-C1-EMS04 allele and its wild-type counterpart
SEQ ID No.43: Primer 2 for detection of the DA1-C1-EMS04 allele and its wild-type counterpart
SEQ ID No.44: FAM probe for detection of the DA1-C1-EMS04 allele
SEQ ID No.45: VIC probe for detection of the wild-type counterpart of the DA1-C1-EMS04 allele
SEQ ID No.46: Primer 1 for detection of the DA1-A2-EMS02 allele and its wild-type counterpart
SEQ ID No.47: Primer 2 for detection of the DA1-A2-EMS02 allele and its wild-type counterpart
SEQ ID No.48: FAM probe for detection of the DA1-A2-EMS02 allele
SEQ ID No.49: VIC probe for detection of the wild-type counterpart of the DA1-A2-EMS02 allele
SEQ ID No.50: Primer 1 for detection of the DA1-A2-EMS03 allele and its wild-type counterpart
SEQ ID No.51: Primer 2 for detection of the DA1-A2-EMS03 allele and its wild-type counterpart
SEQ ID No.52: FAM probe for detection of the DA1-A2-EMS03 allele
SEQ ID No.53: VIC probe for detection of the wild-type counterpart of the DA1-A2-EMS03 allele
SEQ ID No.54: *Brassica rapa* DA1-A1 genomic sequence
SEQ ID No.55: *Brassica rapa* DA1-A1 coding sequence
SEQ ID No.56: *Brassica rapa* DA1-A1 protein sequence
SEQ ID No.57: *Brassica rapa* DA1-A2 genomic sequence
SEQ ID No.58: *Brassica rapa* DA1-A2 coding sequence
SEQ ID No.59: *Brassica rapa* DA1-A2 protein sequence
SEQ ID No.60: *Brassica oleracea* DA1-C1 genomic sequence
SEQ ID No.61: *Brassica oleracea* DA1-C1 coding sequence
SEQ ID No.62: *Brassica oleracea* DA1-C1 protein sequence
SEQ ID No.63: *Brassica oleracea* DA1-C2 genomic sequence
SEQ ID No.64: *Brassica oleracea* DA1-C2 coding sequence isoform 1
SEQ ID No.65: *Brassica oleracea* DA1-C2 protein sequence isoform 1
SEQ ID No.66: *Brassica oleracea* DA1-C2 coding sequence isoform 2
SEQ ID No.67: *Brassica oleracea* DA1-C2 protein sequence isoform 2
SEQ ID No.68: *Brassica oleracea* DA1-C2 coding sequence isoform 3
SEQ ID No.69: *Brassica oleracea* DA1-C2 protein sequence isoform 3
SEQ ID No.70: *Brassica nigra* DA1-B1 genomic sequence
SEQ ID No.71: *Brassica nigra* DA1-B1 coding sequence
SEQ ID No.72: *Brassica nigra* DA1-B1 protein sequence
SEQ ID No.73: *Brassica nigra* DA1-B2 genomic sequence
SEQ ID No.74: *Brassica nigra* DA1-B2 coding sequence
SEQ ID No.75: *Brassica nigra* DA1-B2 protein sequence

EXAMPLES

Example 1—Isolation of the DNA Sequences of the DA1 Genes

To determine the sequences of the DA1 genes of an elite spring oilseed rape breeding line, a Bacterial Artificial Chromosome (BAC) library of the line was screened as follows:
Isolation of BAC Clones Comprising a DA1 Sequence
To identify *Escherichia coli* colonies containing a BAC clone comprising a DA1 sequence of the elite spring oilseed rape breeding line, a BAC library of the line (average clone size of more than 120 kb) arrayed as individual duplicated clones on high density nylon filters were screened by standard Southern hybridization procedures:
  A probe with the sequence from *Arabidopsis thaliana* was labeled according to standard procedures used for hybridizing to the DNA on the nylon membrane.
  Pre-hybridization was performed for 2 hour at 65° C. in 30 mL of the following hybridization buffer: 6×SSC (20×SSC contains 3.0 M NaCl, 0.3 M Na citrate, pH 7.0), 5×Denhardt's (100×Denhardt's contains 2% Ficoll, 2% Polyvinyl pyrrolidone, 2% Bovine Serum Albumin), 0.5% SDS and 20 µg/mL denatured carrier DNA (single-stranded fish sperm DNA, with an average length of 120-3000 nucleotides).
  Hybridization was performed under the following conditions:
    The labeled probe (20 ng) was denaturated by heating for 5 minutes at 95° C. and chilling on ice for 5 minutes and added to 15 mL of hybridization buffer (same buffer as for the pre-hybridization),
    The hybridization was performed overnight at 65° C.
    The blots were washed three times for 30 minutes at 65° C. in the hybridization tubes (once with 30 mL 6×SSC with 0.1% SDS and twice with 30 mL 2×SSC with 0.1% SDS) and one time for 10 minutes at 65° C. with 500 mL 2×SSC with 0.1% SDS in a box.

Kodak BioMax MR films were exposed to the radioactive blots for 4 hours at −70° C.

Based on the positive signals, nine E. coli colonies containing a BAC clone comprising a DA1 sequence were picked up by screening the BAC library from the elite spring oilseed rape breeding line (total number of positives: 93) (hereinafter called "positive colonies").

Isolation of BAC Clones Comprising a Full-Length DA1 Sequence

To identify positive colonies comprising a BAC clone with a full-length genomic DNA sequence of one of the DA1 genes, a Southern blot analysis was performed on BAC clone DNA isolated from the positive colonies and on genomic DNA isolated from *Brassica napus*:

BAC clone DNA was isolated through alkaline lysis as described in the art from the positive colonies grown up in 25 mL Luria Broth medium containing 25 μm/mL chloramphenicol.

Genomic DNA was isolated from leaf tissue of *Brassica napus* according to the cetyltrimethylammoniumbromide (CTAB) method (Doyle and Doyle, 1987, Phytochemistry Bulletin 19:11-15).

The DNA concentration of each preparation was estimated by comparing the band intensity of 1 μL of each sample to the band intensity of 1, 2, 4, 8 and 20 μL of a solution containing 25 ng/μL Lambda DNA (Life Technologies®) on a 1% TBE (Invitrogen®) agarose gel (Roche®) containing ethidiumbromide (ICN Biochemicals®).

100-200 ng of BAC clone DNA and 1.7 μg genomic DNA were digested with restriction enzyme AseI in a final reaction volume of 20 μL, applying conditions proposed by the manufacturer (New England Biolabs). The time of digestion and/or amount of restriction enzyme were adjusted to ensure complete digestion of the genomic DNA samples without non-specific degradation.

After digestion, 2 μL of loading dye containing RNase (12.5 mL 1% xylene cyanol FF; 12.5 mL 1% bromophenol blue water soluble indicator; 25 mL glycerol; 100 μL 0.5M EDTA pH 8.0; 1 μL RNase (10 mg/mL)) was added to the digested DNA samples and the samples were incubated for 30 min at 37° C.

The samples were loaded on a 1% TAE agarose gel.

Phage Lambda DNA (Fermentas®) digested with PstI or 1 kbp DNA Ladder (Life Technologies) was included as size standard.

After electrophoresis, the DNA samples (digested BAC clone and genomic DNA) were transferred to a nylon membrane (Hybond-N+ Amersham Pharmacia Biotech®) by dry alkali capillary blotting.

The nylon membranes with digested BAC clone and genomic DNA were screened by standard Southern hybridization procedures as described above for the BAC library screenings, except that for the genomic DNA the Kodak BioMat MR films were exposed to the radioactive blots for 2 days at −70° C.

Based on a comparison between the hybridization patterns obtained after digestion of BAC clone DNA of the identified positive colonies and of genomic DNA isolated from *Brassica napus* with restriction enzyme AseI and hybridization with the probe, the BAC clones were grouped in four groups and for each of the four groups a BAC clone was selected containing a full-length DA1 sequence (named DA1_A1, DA1_A2, DA1_C1, DA1_C2).

The DA1 sequences comprised in the BAC clones of the selected positive colonies were determined by 454 BAC sequencing (Keygene Nev.).

Example 2—Characterization of DA1 Gene Sequences from *Brassica napus*

The genomic DNA fragments were sequenced, and the genes and coding regions of the DA1 sequences were determined with FGeneSH (Softberry, Inc. Mount Kisco, N.Y., USA). The BnDA1 sequences, as provided by FGeneSH, has nine exons.

SEQ ID NOs: 3, 6, 9 and 12 are the genomic sequences of DA1_A1, DA1_A2, DA1_C1, and DA1_C2, respectively. SEQ ID NOs: 4, 7, 10 and 13 are the coding sequences of DA1_A1, DA1_A2, DA1_C1, and DA1_C2, respectively. Proteins encoded by DA1_A1, DA1_A2, DA1_C1, and DA1_C2 are given in SEQ ID NOs: 5, 8, 11 and 14, respectively.

Subsequently, DA1 sequences were subsequently used as the query in a BLAST homology search of in-house databases of *Brassica rapa, Brassica nigra*, and *Brassica oleracea* sequences. The contigs in these databases were obtained by assembly of short sequence reads using the software package SOAPdenovo. The BLAST analyses resulted in the identification of 2 DA1 gene homologs for *B. rapa* (BrDA1-A1 (SEQ ID No. 54) and BrDA1-A2 (SEQ ID NO: 57)), 2 DA1 gene homologs for *B. oleracea* (BoDA1-C1 (SEQ ID No.60) and BoDA1-C2 (SEQ ID No. 63)), and 2 DA1 gene homologs for *B. nigra* (BniDA1-B1 (SEQ ID No: 70) and BniDA1-B2 (SEQ ID NO: 73)). cDNAs corresponding to these sequences were predicted using FgeneSH software, and are depicted in SEQ ID No. 55, SEQ ID No. 58, SEQ ID No. 61, SEQ ID No. 71 and SEQ ID NO: 74 for BrDA1-A1, BrDA1-A2, BoDA1-C1, BniDA1-B1 and BniDA1-B2, respectively. For BoDA1-C2, three isoforms were predicted, which are depicted in SEQ ID NOs 64, 66 and 68.

Example 3—Expression of *Brassica* DA1 Genes

In silico expression analysis (based on BGI Solexa mRNA data of *Brassica napus*) showed that BnDA1-A2 and BnDA1-C2 are most expressed, especially in root tissue of two-week-old plants (root 2 weeks) and in stem tissue of five-week-old plants (stem 5 weeks 33 DAS) (FIG. 2).

Example 4—Generation and Isolation of Mutant DA Alleles

Mutations in the DA1 genes of *Brassica napus* identified in Example 1 were generated and identified as follows:

30,000 seeds from an elite spring oilseed rape breeding line (M0 seeds) were pre-imbibed for 2 h on wet filter paper in deionized or distilled water. Half of the seeds were exposed to 0.8% EMS and half to 1% EMS (Sigma: M0880) and incubated for 4 h.

The mutagenized seeds (M1 seeds) were rinsed three times and dried in a fume hood overnight. 30,000 M1 plants were grown in soil and selfed to generate M2 seeds. M2 seeds were harvested for each individual M1 plant.

Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).

The DNA samples were screened for the presence of point mutations in the DA1 genes that cause the introduction of STOP codons and another amino acid in the protein-encoding regions of the DA1 genes, by direct sequencing by standard sequencing techniques (LGC) and analyzing the sequences for the presence of the point mutations using the NovoSNP software (VIB Antwerp).

The mutant DA1 alleles as depicted in Table 2 were thus identified.

TABLE 2

STOP codon and amino acid substitution mutations in DA1

| Position | Sample | Plant Name | WT seq | MUT seq | Allele | Type |
|---|---|---|---|---|---|---|
| EMS mutants for DA1-A1 (SEQ ID NO: 3) | | | | | | |
| 1385 | EMS_DS_0078_G09 | YIIN601 | C | T | DA1-A1-EMS01 | stop |
| 1385 | EMS_DS_0078_H12 | YIIN602 | C | T | DA1-A1-EMS02 | stop |
| 1683 | EMS_DS_0067_B11 | YIIN603 | G | A | DA1-A1-EMS03 | stop |
| 1932 | EMS_DS_0098_D01 | YIIN604 | C | T | DA1-A1-EMS04 | stop |
| EMS mutants for DA1-A2 (SEQ ID NO: 6) | | | | | | |
| 1744 | EMS_DS_0081_E03 | YIIN605 | G | A | DA1-A2-EMS01 | stop |
| 1998 | EMS_DS_0081_E11 | YIIN606 | C | T | DA1-A2-EMS02 | stop |
| 1974 | EMS_DS_0095_G01 | YIIN607 | C | T | DA1-A2-EMS03 | stop |
| 1874 | EMS_DS_0089_H02 | YIIN608 | G | A | DA1-A2-EMS04 | stop |
| 1672 | EMS_DS_0081_C08 | YIIN609 | G | A | DA1-A2-EMS05* | R→K |
| EMS mutants for DA1-C1 (SEQ ID NO: 9) | | | | | | |
| 1425 | EMS_DS_0098_H01 | YIIN610 | C | T | DA1-C1-EMS01 | stop |
| 1960 | EMS_DS_0067_G05 | YIIN611 | C | T | DA1-C1-EMS02 | stop |
| 1670 | EMS_DS_0078_G06 | YIIN612 | C | T | DA1-C1-EMS03 | stop |
| 2004 | EMS_DS_0090_F09 | YIIN613 | G | A | DA1-C1-EMS04 | stop |
| EMS mutants for DA1-C2 (SEQ ID NO: 12) | | | | | | |
| 2011 | EMS_DS_0080_D03 | YIIN614 | C | T | DA1-C2-EMS01 | stop |
| 2011 | EMS_DS_0084_C03 | YIIN615 | C | T | DA1-C2-EMS02* | stop |

*Seeds of plants comprising alleles DA1-A2-EMS05 and DA1-C2-EMS02 in homozygous state have been deposited at the the NCIMB, Ferguson Building, Craibstone Estate, Bucksburn, Aberdeen, AB 21 9YA UK, under the Budapest Treaty on 21 Feb., 2013, under accession number NCIMB 42114.

Example 5—Identification of a *Brassica* Plant Comprising a Mutant *Brassica* DA1 Allele

*Brassica* plants comprising the mutations in the DA1 genes identified in Example 4 were identified as follows:

For each mutant DA1 gene identified in the DNA sample of an M2 plant, at least 50 M2 plants derived from the same M1 plant as the M2 plant comprising the DA1 mutation, were grown and DNA samples were prepared from leaf samples of each individual M2 plant.

The DNA samples were screened for the presence of the identified point DA1 mutation as described above in Example 4.

Heterozygous and homozygous (as determined based on the electropherograms) M2 plants comprising the same mutation were selfed and M3 seeds were harvested.

Figure 3:
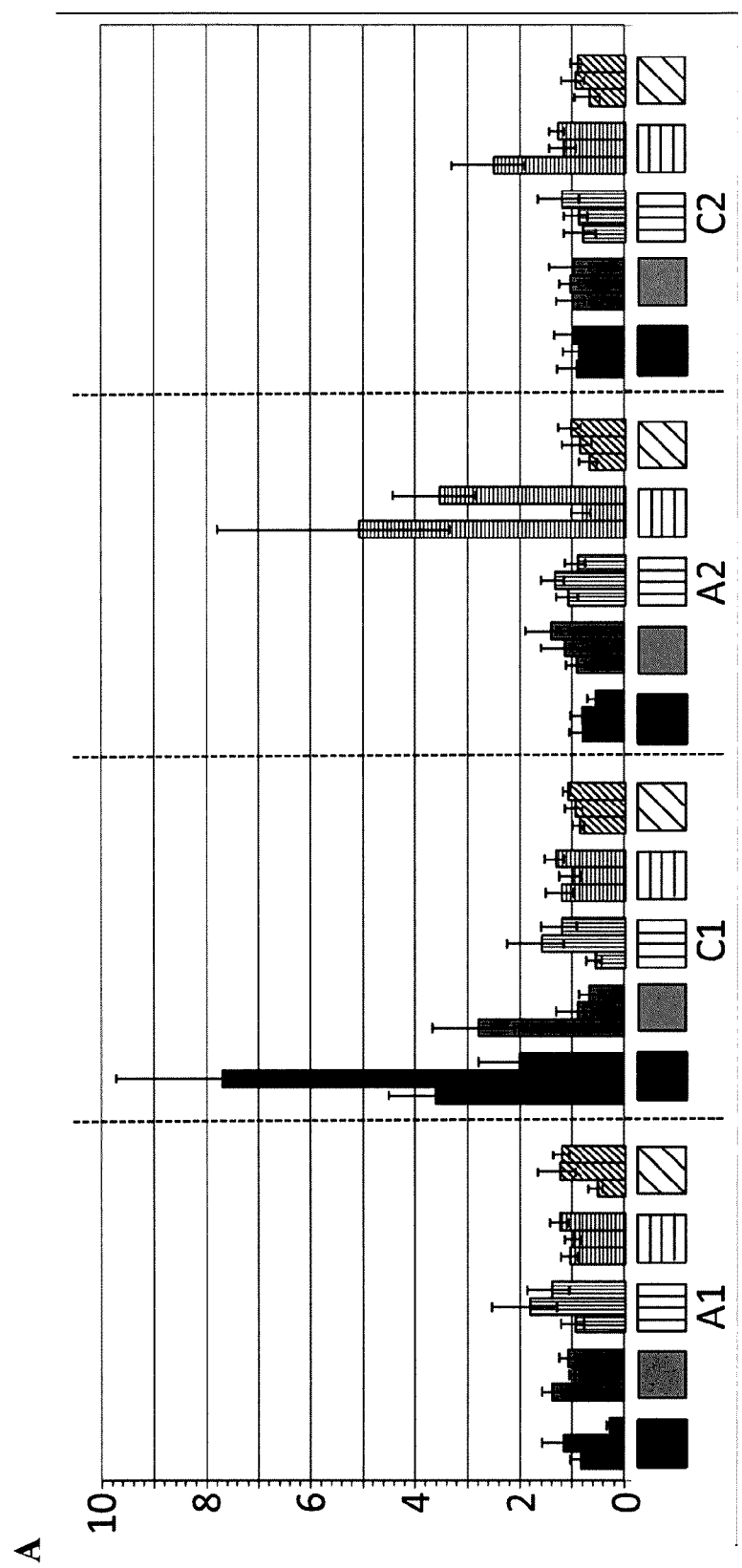
FIG. 3: Relative expression in young leaves 33 days after sowing (A) and stem 5 weeks 33 days after sowing (B) of the *Brassica* DA1 genes in tissues of different mutant lines. Values represent expression in mutant line over expression in wild-type. Black bars: relative expression in mutant line YIIN603; gray bars: relative expression in mutant line YIIN611; vertically striped bars: relative expression in mutant line YIIN612; horizontally striped bars: relative expression in mutant line YIIN609; diagonally striped bars: relative expression in mutant line YIIN615.

Expression of the different DA1 genes in different tissues of the mutant lines was analyzed using RT-PCR assays specific for each DA1 gene on total RNA isolated from *Brassica napus*. The results indicated that line YIIN603 showed no silencing of the A1 mutant allele, but an expression increase of C1 allele in young leaf and a decrease in stem. YIIN612 line showed silencing of the C1 allele in stem and no increased expression of the other alleles. In most mutant lines, all alleles have similar expression levels as in wild type plants. In general, there is no overexpression of the wild type alleles in the mutants. (FIG. 3).

Example 6—Analysis of the Seed Characteristics of *Brassica* Plants Comprising Mutant DA1 Genes

*Brassica* plants homozygous for different DA1 genes were grown in the greenhouse, and Thousand Seed Weight (TSW) and amount of seeds (g for 5 plants) was determined. The TSW values for two different greenhouse experiments and the amount of seeds are shown in Table 3.

TABLE 3

Amount of seeds (g for 5 plants) and Thousand Seed Weight (TSW) for plants homozygous for different mutant DA1 genes grown in the greenhouse

| Mutant Allele | Amount (g for 5plants) | TSW (I) | TSW (II) |
|---|---|---|---|
| (DA1-A1-EMS03)(DA1-A2-EMS05) | 59.50 | 4.67 | 3.65 |
| DA1-A1-EMS03 | 53.79 | 4.11 | 3.45 |
| DA1-A2-EMS05 | 61.21 | 4.58 | 3.47 |
| — | 68.22 | 4.23 | 3.13 |
| (DA1-A2-EMS05)(DA1-C1-EMS02) | 68.85 | 4.04 | 3.38 |
| DA1-A2-EMS05 | 75.50 | 4.23 | 3.46 |
| DA1-C1-EMS02 | 70.39 | 3.6 | 3.09 |
| — | 74.26 | 3.64 | 3.16 |
| (DA1-A2-EMS05)(DA1-C1-EMS03) | 61.25 | 4.32 | 3.29 |
| DA1-A2-EMS05 | 52.77 | 4.06 | 3.37 |
| DA1-C1-EMS03 | 70.65 | 3.92 | 3.18 |
| — | 61.08 | 4.16 | 3.16 |
| (DA1-A2-EMS05)(DA1-C2-EMS02) | 65.04 | 4.5 | 3.72 |
| DA1-A2-EMS05 | 65.00 | 4.07 | 3.45 |
| DA1-C2-EMS02 | 80.79 | 3.92 | 3.38 |
| — | 74.55 | 3.78 | 3.35 |

Figure 4A:
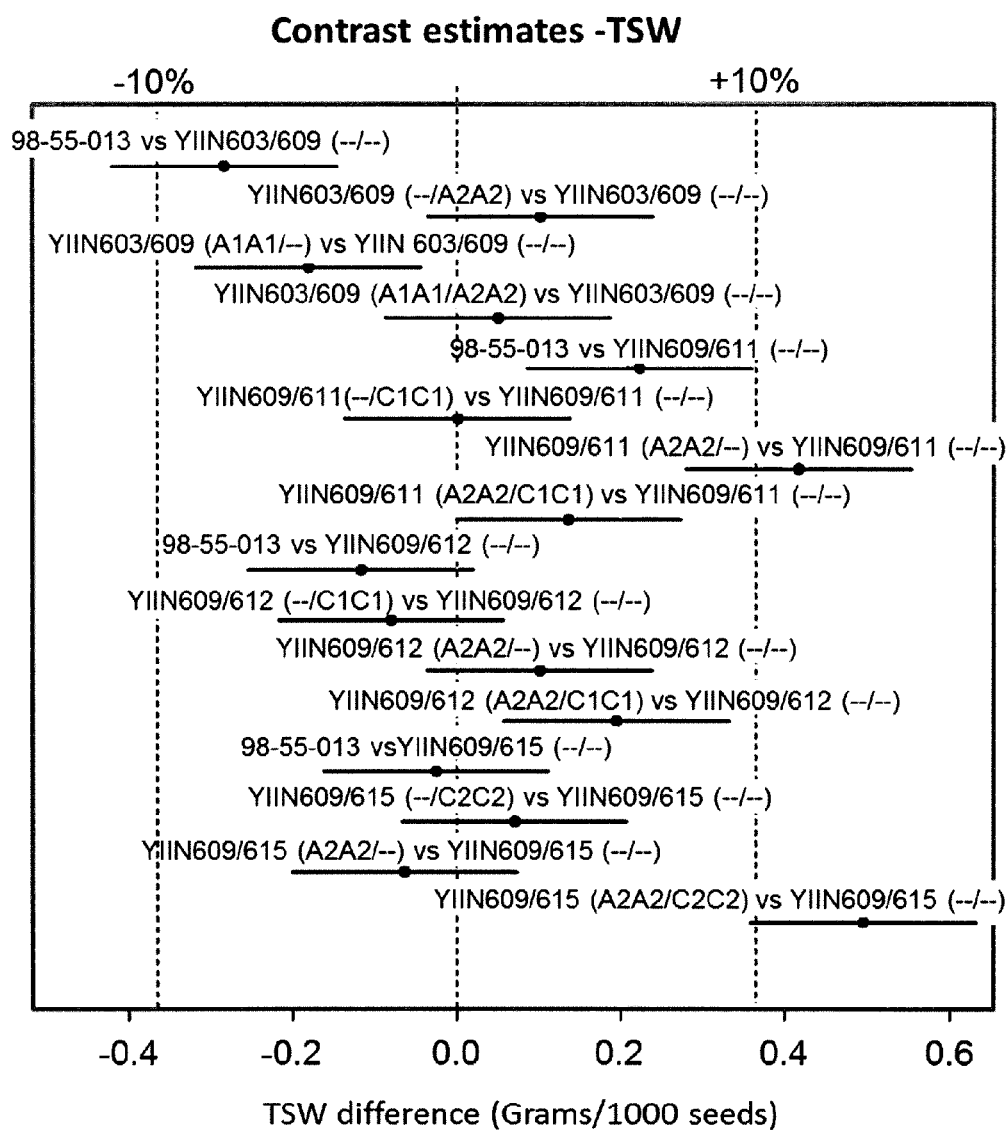
FIG. 4: Thousand seed weight (TSW) (A) and Pod Thickness (PODT) (B) in *Brassica* lines with different DA1 mutants. TSW and PODT values are expressed in difference as compared to the wild-type segregants.
Figure 4B:
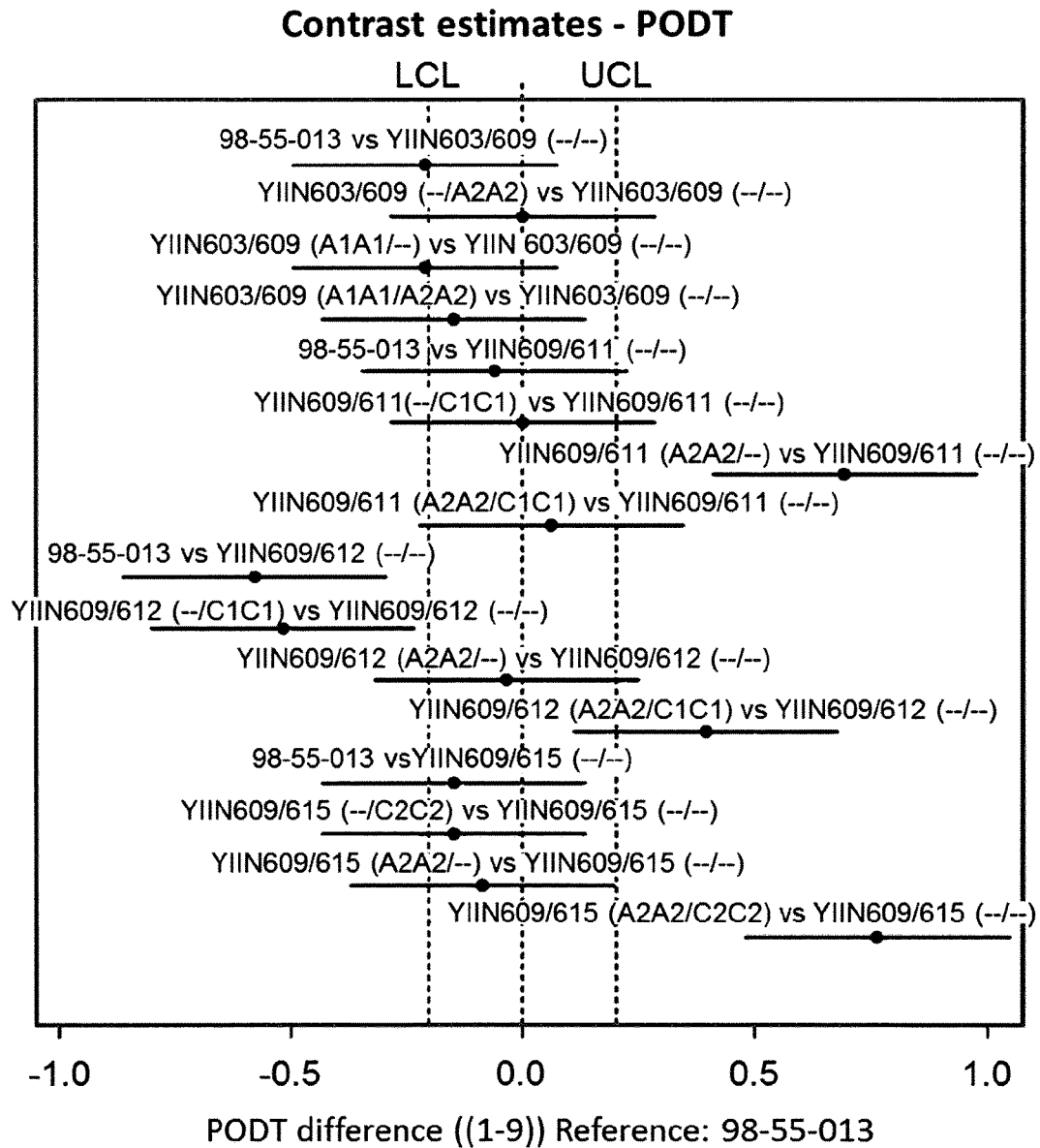

*Brassica* plants homozygous for different DA1 genes were grown in the field on three locations. Thousand Seed Weight (TSW) and Pod Thickness (PODT) were determined Pod Thickness is measured on a scale of 1-9, wherein 1=small, 5=average, 9=thick. The values for TSW and PODT are shown in Table 4. The differences in TSW and PODT of plants comprising mutant DA1 genes versus wild type segregants are graphically shown in FIGS. 4a and b, respectively.

TABLE 4

Averages of Thousand Seed Weight (TSW), SE, CI. lower and CI. upper for TSW, and averages for Pod Thickness (PODT) and LSD for PODT, for plants homozygous for different mutant DA1 genes grown in the field

| Genotype | TSW (g) | SE | CI. lower | CI. upper | PODT (1-9) |
|---|---|---|---|---|---|
| — | 3.937 | 0.050 | 3.839 | 4.034 | 5.22 |
| DA1-A2-EMS05 | 4.039 | 0.050 | 3.941 | 4.137 | 5.22 |
| DA1-A1-EMS03 | 3.756 | 0.050 | 3.658 | 3.854 | 4.89 |
| (DA1-A1-EMS03) (DA1-A2-EMS05) | 3.987 | 0.050 | 3.890 | 4.085 | 5.00 |
| — | 3.430 | 0.050 | 3.332 | 3.528 | 5.00 |
| DA1-C1-EMS02 | 3.431 | 0.050 | 3.334 | 3.529 | 5.00 |
| DA1-A2-EMS05 | 3.847 | 0.050 | 3.749 | 3.945 | 5.67 |
| (DA1-A2-EMS05) (DA1-C1-EMS02) | 3.567 | 0.050 | 3.469 | 3.664 | 5.11 |
| — | 3.769 | 0.050 | 3.672 | 3.867 | 5.44 |
| DA1-C1-EMS03 | 3.690 | 0.050 | 3.592 | 3.787 | 5.00 |
| DA1-A2-EMS05 | 3.871 | 0.050 | 3.773 | 3.969 | 5.56 |

TABLE 4-continued

Averages of Thousand Seed Weight (TSW), SE, CI. lower and CI. upper for TSW, and averages for Pod Thickness (PODT) and LSD for PODT, for plants homozygous for different mutant DA1 genes grown in the field

| Genotype | TSW (g) | SE | CI. lower | CI. upper | PODT (1-9) |
|---|---|---|---|---|---|
| (DA1-A2-EMS05) (DA1-C1-EMS03) | 3.965 | 0.050 | 3.867 | 4.062 | 5.89 |
| — | 3.678 | 0.050 | 3.580 | 3.776 | 5.11 |
| DA1-C2-EMS02 | 3.749 | 0.050 | 3.652 | 3.847 | 4.89 |
| DA1-A2-EMS05 | 3.615 | 0.050 | 3.517 | 3.713 | 5.00 |
| (DA1-A2-EMS05) (DA1-C2-EMS02) | 4.174 | 0.050 | 4.076 | 4.271 | 5.78 |
| wild-type | 3.653 | 0.050 | 3.556 | 3.751 | 4.89 |
| LSD (PODT) | | | | | 0.32 |

In a further field trial, *Brassica* plants homozygous for different DA1 genes were grown in the field at five locations in Canada and Belgium. The parameters scored were seed yield (g/plot; 7.5 m2/plot; seed at 8% moisture), thousand seed weight (TSW; g/1000 seeds), oil content (% of seed; NIR analysis), protein content (% of seed; NIR analysis) and thousand seed oil weight (TSOW; grams of oil in 1000 seeds (g/1000 seeds); calculated TWS*oil content (%)). The values for two different field experiments are shown in Tables 5a and 5b.

TABLE 5

Yield (YLD), Thousand Seed Weight (TSW), oil content (OILN), protein content (PRON) oil yield (OILYLD), and thousand seed oil weight (TSOW) of plants homozygous for different mutant DA1 genes grown in the field at five different locations in Canada (A) and Belgium (B).

| | YLD ram | TSW gram | OILN % | PRON % | OILYLD gram | TSOW gram |
|---|---|---|---|---|---|---|
| A. | | | | | | |
| GENOTYPES CA | | | | | | |
| YIIN603/YIIN609 (—/—) | 2717 | 4.13 | 45.72 | 48.36 | 1242.21 | 1.89 |
| YIIN603/YIIN609 (—/A2A2) | 2639 | 4.60* | 45.07 | 49.13 | 1189.40 | 2.07 |
| YIIN603/YIIN609 (A1A1/—) | 2605 | 4.40* | 45.20 | 48.99 | 1177.46 | 1.99 |
| YIIN603/YIIN609 (A1A1/A2A2) | 2559* | 4.52* | 44.68 | 48.86 | 1143.36 | 2.02 |
| YIIN609/YIIN611 (—/—) | 2563** | 4.25 | 45.56 | 48.45 | 1167.70 | 1.94 |
| YIIN609/YIIN611 (—/C1C1) | 2708 | 4.12 | 45.44 | 47.84 | 1230.52 | 1.87 |
| YIIN609/YIIN611 (A2A2/—) | 2629 | 4.28 | 45.42 | 48.01 | 1194.09 | 1.94 |
| YIIN609/YIIN611 (A2A2/C1C1) | 2551 | 4.36 | 45.14 | 48.17 | 1151.52 | 1.97 |
| YIIN609/YIIN612 (—/—) | 2567** | 3.89** | 45.73 | 47.99 | 1173.89 | 1.78 |
| YIIN609/YIIN612 (—/C1C1) | 2673 | 4.04 | 45.42 | 49.01 | 1214.08 | 1.83 |
| YIIN609/YIIN612 (A2A2/—) | 2472 | 4.18* | 44.62 | 47.98 | 1103.01 | 1.87 |
| YIIN609/YIIN612 (A2A2/C1C1) | 2655 | 4.16* | 44.98 | 48.15 | 1194.22 | 1.87 |
| YIIN609/YIIN615 (—/—) | 2695 | 4.18 | 45.18 | 48.37 | 1217.60 | 1.89 |
| YIIN609/YIIN615 (—/C2C2) | 2691 | 4.43* | 45.22 | 48.03 | 1216.87 | 2.00 |
| YIIN609/YIIN615 (A2A2/—) | 2683 | 4.44* | 44.58 | 48.04 | 1196.08 | 1.98 |
| YIIN609/YIIN615 (A2A2/C2C2) | 2496* | 4.74* | 43.99 | 48.51 | 1097.99 | 2.09 |
| 98-55-013 | 2827 | 4.15 | 46.09 | 48.59 | 1302.96 | 1.91 |
| B. | | | | | | |
| GENOTYPES BE | | | | | | |
| YIIN603/YIIN609 (—/—) | 2912.85 | 3.73 | 46.80 | 43.77 | 1363.21 | 1.75 |
| YIIN603/YIIN609 (—/A2A2) | 2939.11 | 3.94* | 46.55 | 44.20 | 1368.16 | 1.83 |
| YIIN603/YIIN609 (A1A1/—) | 2970.45 | 3.84 | 46.55 | 43.97 | 1382.74 | 1.79 |
| YIIN603/YIIN609 (A1A1/A2A2) | 2912.75 | 4.10* | 45.87 | 44.42 | 1336.08 | 1.88 |
| YIIN609/YIIN611 (—/—) | 3053.15 | 3.72 | 46.78 | 43.69 | 1428.26 | 1.74 |
| YIIN609/YIIN611 (—/C1C1) | 3080.2 | 3.66 | 46.80 | 43.71 | 1441.53 | 1.71 |
| YIIN609/YIIN611 (A2A2/—) | 2932.5 | 3.92* | 46.54 | 44.09 | 1364.79 | 1.82 |
| YIIN609/YIIN611 (A2A2/C1C1) | 2889.3 | 3.90* | 46.70 | 43.92 | 1349.30 | 1.82 |
| YIIN609/YIIN612 (—/—) | 2965.45 | 3.62 | 47.31 | 44.59 | 1402.95 | 1.71 |
| YIIN609/YIIN612 (—/C1C1) | 3105.4 | 3.67 | 46.91 | 44.33 | 1456.74 | 1.72 |
| YIIN609/YIIN612 (A2A2/—) | 2864.5 | 3.80* | 46.87 | 44.68 | 1342.59 | 1.78 |
| YIIN609/YIIN612 (A2A2/C1C1) | 2969.7 | 3.83* | 46.56 | 44.52 | 1382.69 | 1.78 |
| YIIN609/YIIN615 (—/—) | 3049.55 | 3.68 | 46.83 | 43.40 | 1428.10 | 1.72 |

TABLE 5-continued

Yield (YLD), Thousand Seed Weight (TSW), oil content (OILN), protein content (PRON) oil yield (OILYLD), and thousand seed oil weight (TSOW) of plants homozygous for different mutant DA1 genes grown in the field at five different locations in Canada (A) and Belgium (B).

|  | YLD ram | TSW gram | OILN % | PRON % | OILYLD gram | TSOW gram |
|---|---|---|---|---|---|---|
| YIIN609/YIIN615 (—/C2C2) | 3030.1 | 3.81 | 46.58 | 43.50 | 1411.42 | 1.77 |
| YIIN609/YIIN615 (A2A2/—) | 2966.35 | 3.94* | 46.42 | 43.33 | 1376.98 | 1.83 |
| YIIN609/YIIN615 (A2A2/C2C2) | 2855.2 | 4.32* | 46.00 | 43.89 | 1313.39 | 1.99 |
| 98-55-013 | 3096.59 | 3.69 | 47.25 | 44.03 | 1463.14 | 1.74 |

*mutant significant difference from wild-type segregant;
**wild-type segregant significantly different from wild-type control.

The greenhouse and field data show that the DA1-A2-EMS05 mutant (YIIN609), comprising a mutation at position 1683 of the DA1-A2 gene resulting in an Arginine to Lysine substitution of the encoded protein, gives rise to increased seed weight. This increase in seed weight is further increased when combined with the DA1-C2-EMS02 mutant (YIIN615), i.e. a full knock-out of the DA1-C2 gene. Moreover, the full knockout mutant DA1-A1 and DA1-C2 alleles have the potential to increase thousand seed weight and thousand seed oil weight in the absence of the DA1-A2-EMS05 mutant (Table 5A and B). The field data further show that plants comprising the DA1-A2-EMS05 mutant, especially when combined with the DA1-C2-EMS02 mutant, have increased pod thickness as compared to wild type plants not comprising said DA1 mutants, and have increased Thousand Seed Oil Weight.

Example 7—Detection and/or Transfer of Mutant DA1 Genes into (Elite) *Brassica* Lines To select for plants comprising a point mutation in a DA1 allele, direct sequencing by standard sequencing techniques known in the art, such as those described in Example 4, can be used. Alternatively, PCR assays can be developed to discriminate plants comprising a specific point mutation in an DA1 allele from plants not comprising that specific point mutation. The following discriminating Taqman PCR assays were thus developed to detect the presence or absence and the zygosity status of the mutant alleles identified in Example 4 (see Table 2):

Template DNA:
   Genomic DNA isolated from leaf material of homozygous or heterozygous mutant *Brassica* plants (comprising a mutant DA1 allele, called hereinafter "DA1-Xx-EMSXX").
   Wild type DNA control: Genomic DNA isolated from leaf material of wild type *Brassica* plants (comprising the wild type equivalent of the mutant DA1 allele, called hereinafter "WT").
   Positive DNA control: Genomic DNA isolated from leaf material of homozygous mutant *Brassica* plants known to comprise DA1-Xx-EMSXX.
Primers and probes for the mutant and corresponding wild type target DA1 gene are indicated in Table 6.
Generally, each primer set consists of two primers amplifying both the mutant and the wild type target gene, one probe specific for the nucleotide difference between mutant and wild type, in which the FAM probe contains the nucleotide for the mutant, and the VIC probe contains the nucleotide from wild type.

TABLE 6

Primers and probes for detection of wild type and mutant DA1 alleles

| | | | | SEQ ID NO |
|---|---|---|---|---|
| Plant: YIIN603_TQ2 | | | | |
| Primer 1 | ACGAGTTAGCTTGAATTGCTCTGTAA | | | 18 |
| Primer 2 | TCTGTCGGAAGAACAAACTGTTAGA | | | 19 |
| FAM probe | CCCACTTCAGTTTC | FAM allele | DA1-A1-EMS03 | 20 |
| VIC probe | ATATTCCCACTCCAGTTT | VIC allele | WT | 21 |
| Plant: YIIN605_TQ1 | | | | |
| Primer 1 | GAGCAAACTGTTAGCACTGTAAGAAAGA | | | 22 |
| Primer 2 | CCTCGCATTGACGTGTCAACT | | | 23 |
| FAM probe | CACAGGAAACTAGGCTG | FAM allele | DA1-A2-EMS01 | 24 |
| VIC probe | ACAGGAAACTGGGCTG | VIC allele | WT | 25 |
| Plant: YIIN609_TQ2 | | | | |
| Primer 1 | CCATGCTTCGATCTCTTTCTTACAG | | | 26 |
| Primer 2 | TAGGGTCACTATCACATGCCAGAG | | | 27 |
| FAM probe | AAGGCAGAGTCCTTTT | FAM allele | DA1-A2-EMS05 | 28 |
| VIC probe | AGGCAGAGTCCTCTT | VIC allele | WT | 29 |

TABLE 6 -continued

Primers and probes for detection of wild type and mutant DA1 alleles

| | | | | SEQ ID NO |
|---|---|---|---|---|
| Plant: YIIN611_TQ1 | | | | |
| Primer 1 | CCATCACTTGACATATCCCCTCTT | | | 30 |
| Primer 2 | ACTACAATGTGTGGTCTTGAAAAAGG | | | 31 |
| FAM probe | AACATCTTAGCTCAGTGT | FAM allele | DA1-C1-EMS02 | 32 |
| VIC probe | ACATCTTGGCTCAGTGTC | VIC allele | WT | 33 |
| Plant: YIIN612_TQ1 | | | | |
| Primer 1 | CTTTAGGGTCACTATCACATGCCA | | | 34 |
| Primer 2 | ATTCCCACTCCAGTTTCCCTTC | | | 35 |
| FAM probe | TTTCAGAGGAATAAAC | FAM allele | DA1-C1-EMS03 | 36 |
| VIC probe | TTTCAGAGGAACAAAC | VIC allele | WT | 37 |
| Plant: YIIN615_TQ1 | | | | |
| Primer 1 | CGCTGAGCCAAGACGTTGA | | | 38 |
| Primer 2 | CAACATTGCTGTTTCTTGAACCA | | | 39 |
| FAM probe | AGGAATATGTTTAAGTAATGG | FAM allele | DA1-C2-EMS02 | 40 |
| VIC probe | AGGAATATGTCAAGTAATG | VIC allele | WT | 41 |
| Plant: YIIN613_TQ1 | | | | |
| Primer 1 | ACACTGAGCCAAGATGTTGAAGAG | | | 42 |
| Primer 2 | TGCAGCGTTGCTGTTTCTAGA | | | 43 |
| FAM probe | ATGGCTCATAAGTGATT | FAM allele | DA1-C1-EMS04 | 44 |
| VIC probe | TCATAAGTGGTTAGAAGTTGAG | VIC allele | WT | 45 |
| Plant: YIIN606_TQ1 | | | | |
| Primer 1 | CCGGACGCTGAGCCAA | | | 46 |
| Primer 2 | CTTGAACCAGCAGCTAACTCTGC | | | 47 |
| FAM probe | AGAAGGAATATGTTTAAGTGATG | FAM allele | DA1-A2-EMS02 | 48 |
| VIC probe | AGAAGGAATATGTCAAGTGA | VIC allele | WT | 49 |
| Plant: YIIN607_TQ1 | | | | |
| Primer 1 | CTATTGTGGTCTTGAAAAGGATTCC | | | 50 |
| Primer 2 | ATGAGCCATCACTTGACATATTCC | | | 51 |
| FAM probe | CGCTGAGCTAAGAC | FAM allele | DA1-A2-EMS03 | 52 |
| VIC probe | ACGCTGAGCCAAGA | VIC allele | WT | 53 |

The invention claimed is:

1. A *Brassica* plant or parts thereof comprising at least two DA1 genes, wherein at least one allele of a first endogenous DA1 gene is a mutant DA1 allele, said mutant DA1 allele encoding a mutant DA1 protein comprising at a position corresponding to position 358 of SEQ ID NO: 2 a Lysine instead of an Arginine, and wherein the mutant DA1 allele of said first endogenous DA1 gene is:
   a. a mutant DA1 allele which comprises at least 80% sequence identity to SEQ ID NO: 6 or SEQ ID NO: 12; or
   b. a mutant DA1 allele which encodes a mutant DA1 protein comprising at least 90% sequence identity to SEQ ID NO: 8 or SEQ ID NO: 14,
   wherein said plant is homozygous for said mutant DA1 allele, and
   wherein said plant further comprises at least one wild-type DA1 allele.

2. The *Brassica* plant or parts thereof according to claim 1, wherein said plant comprises four DA1 genes, and wherein at least one allele of a first endogenous DA1 gene is a mutant DA1 allele encoding a mutant DA1 protein comprising at a position corresponding to position 358 of SEQ ID NO: 2 a Lysine instead of an Arginine, and wherein at least one allele of a second endogenous DA1 gene is
   a. a mutant DA1 allele encoding a mutant DA1 protein comprising at a position corresponding to position 358 of SEQ ID NO: 2 a Lysine instead of an Arginine; or
   b. a full knock-out DA1 allele,
   and wherein said wherein the mutant DA1 allele of said second endogenous DA1 gene is
   a. a mutant DA1 allele which comprises at least 80% sequence identity to SEQ ID NO: 6 or SEQ ID NO: 12; or
   b. a mutant DA1 allele of a DA1 gene, said DA1 gene encoding a DA1 protein comprising at least 90% sequence identity to SEQ ID NO: 8 or SEQ ID NO: 14,
   wherein said full knock-out DA1 allele is a mutant DA1 allele which encodes no DA1 protein or which encodes a non-functional DA1 protein, and wherein said full knock-out DA1 allele comprises a mutation that leads to the generation of an in-frame stop codon in the coding sequence on or upstream of a position corresponding to position 2011 of SEQ ID NO: 12; or said full knock-out DA1 allele comprises a frameshift mutation that results in the nucleic acid sequence being translated in a different frame downstream of the mutation; or said full knock-out DA1 allele comprises a splice site mutation whereby a splice donor site or a splice acceptor site is mutated, resulting in altered processing of the mRNA and, consequently, an altered encoded protein.

3. The *Brassica* plant or parts thereof according to claim 2, wherein said first endogenous DA1 gene comprises at least 91% sequence identity to SEQ ID NO: 6, and wherein said second endogenous DA1 gene comprises at least 91% sequence identity to SEQ ID NO: 12.

4. The *Brassica* plant or parts thereof according to claim 3, wherein the mutant DA1 allele of said first endogenous DA1 gene encodes the protein of SEQ ID NO: 17, and wherein the mutant DA1 allele of said second endogenous DA1 gene is a full knock-out DA1 allele, said full knock-out DA1 allele comprising the sequence of SEQ ID NO: 12 with a C to T substitution at position 2011.

5. Seeds, or seed cake of said seeds, from the *Brassica* plant according to claim 1, wherein the seeds comprise the mutant DA1 allele.

6. The seeds according to claim 5, wherein the mutant DA1 allele of said first endogenous DA1 gene encodes the protein of SEQ ID NO: 17, further comprising a mutant DA1 allele of a second endogenous DA1 gene, wherein the mutant DA1 allele of said second endogenous DA1 gene is a full knock-out DA1 allele, said full knock-out DA1 allele comprising the sequence of SEQ ID NO: 12 with a C to T substitution at position 2011, reference seed thereof having been deposited at the NCIMB under accession number NCIMB 42114.

7. Progeny of a *Brassica* plant according to claim 1, said progeny comprising at least two DA1 genes, wherein at least one allele of a first endogenous DA1 gene is a mutant DA1 allele as defined in claim 1, and further comprising at least one wild type allele.

8. A method for producing a *Brassica* plant according to claim 1, said method comprising crossing a first parent *Brassica* plant according to claim 1 with a second parent *Brassica* plant according to claim 1 and, optionally, further comprising the step of identifying the presence or absence of a mutant DA1 allele.

9. A method for production of *Brassica* seeds, said method comprising sowing the seeds according to claim 5, growing plants from said seeds, and harvesting seeds from said plants.

10. A method for producing food, feed, or an industrial product comprising preparing the food, feed or industrial product from the plant or part thereof of claim 1.

11. The method of claim 10, wherein
a. the food or feed is oil, meal, grain, starch, flour or protein; or
b. the industrial product is biofuel, fiber, industrial chemicals, a pharmaceutical or a nutraceutical.

12. The *Brassica* plant or parts thereof according to claim 1, wherein the mutant DA1 allele of said first endogenous DA1 gene is:

a. a mutant DA1 allele which comprises at least 90% sequence identity to SEQ ID NO: 6 or SEQ ID NO: 12; or
b. a mutant DA1 allele which encodes a mutant DA1 protein comprising at least 95% sequence identity to SEQ ID NO: 8 or SEQ ID NO: 14.

13. The *Brassica* plant or parts thereof according to claim 12, wherein said plant comprises four DA1 genes, and wherein at least one allele of a second endogenous DA1 gene is
a. a mutant DA1 allele encoding a mutant DA1 protein comprising at a position corresponding to position 358 of SEQ ID NO: 2 a Lysine instead of an Arginine; or
b. a full knock-out DA1 allele,
and wherein the mutant DA1 allele of said second endogenous DA1 gene is
a. a mutant DA1 allele which comprises at least 90% sequence identity to SEQ ID NO: 6 or SEQ ID NO: 12; or
b. a mutant DA1 allele of a DA1 gene, said DA1 gene encoding a DA1 protein comprising at least 95% sequence identity to SEQ ID NO: 8 or SEQ ID NO: 14,
wherein said full knock-out DA1 allele is a mutant DA1 allele which encodes no DA1 protein or which encodes a non-functional DA1 protein, and wherein
said full knock-out DA1 allele comprises a mutation that leads to the generation of an in-frame stop codon in the coding sequence on or upstream of a position corresponding to position 2011 of SEQ ID NO: 12; or
said full knock-out DA1 allele comprises a frameshift mutation that results in the nucleic acid sequence being translated in a different frame downstream of the mutation; or
said full knock-out DA1 allele comprises a splice site mutation whereby a splice donor site or a splice acceptor site is mutated, resulting in altered processing of the mRNA and, consequently, an altered encoded protein.

14. The *Brassica* plant or parts thereof according to claim 1, wherein the mutant DA1 allele of said first endogenous DA1 gene is:
a. a mutant DA1 allele which comprises a coding sequence having at least 95% sequence identity to SEQ ID NO: 7; or
b. a mutant DA1 allele which encodes a mutant DA1 protein comprising at least 95% sequence identity to SEQ ID NO: 8.

15. The *Brassica* plant or parts thereof according to claim 14, wherein said plant comprises four DA1 genes, and wherein at least one allele of a second endogenous DA1 gene is a full knock-out DA1 allele, wherein the mutant DA1 allele of said second endogenous DA1 gene is
a. a mutant DA1 allele which comprises a coding sequence having at least 95% sequence identity to SEQ ID NO: 13; or
b. a mutant DA1 allele of a DA1 gene, said DA1 gene encoding a DA1 protein comprising at least 95% sequence identity to SEQ ID NO: 14,
wherein said full knock-out DA1 allele is a mutant DA1 allele which encodes no DA1 protein or which encodes a non-functional DA1 protein, and wherein
said full knock-out DA1 allele comprises a mutation that leads to the generation of an in-frame stop codon in the coding sequence on or upstream of a position corresponding to position 2011 of SEQ ID NO: 12; or said full knock-out DA1 allele comprises a frameshift mutation that results in the nucleic acid sequence being translated in a different frame downstream of the mutation; or said full knock-out DA1 allele comprises a splice site mutation whereby a splice donor site or a splice acceptor site is mutated, resulting in altered processing of the mRNA and, consequently, an altered encoded protein.

* * * * *